United States Patent
Guo et al.

(10) Patent No.: US 10,428,069 B2
(45) Date of Patent: *Oct. 1, 2019

(54) 6-FUSED HETEROARYLDIHYDROPYRIMIDINES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Lei Guo, Shanghai (CN); Taishan Hu, Shanghai (CN); Buyu Kou, Shanghai (CN); Xianfeng Lin, Shanghai (CN); Hong Shen, Shanghai (CN); Houguang Shi, Shanghai (CN); Shixiang Yan, Shanghai (CN); Weixing Zhang, Shanghai (CN); Zhisen Zhang, Shanghai (CN); Mingwei Zhou, Shanghai (CN); Wei Zhu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/103,198

(22) Filed: Aug. 14, 2018

(65) Prior Publication Data

US 2018/0370969 A1 Dec. 27, 2018

Related U.S. Application Data

(63) Continuation of application No. 14/946,595, filed on Nov. 19, 2015, now Pat. No. 10,081,627, which is a continuation of application No. 14/640,397, filed on Mar. 6, 2015, now Pat. No. 9,233,978.

(51) Int. Cl.
| | |
|---|---|
| *C07D 471/04* | (2006.01) |
| *A61K 31/4985* | (2006.01) |
| *C07D 487/04* | (2006.01) |
| *C07D 498/04* | (2006.01) |
| *C07D 513/04* | (2006.01) |
| *A61K 31/517* | (2006.01) |
| *A61K 31/519* | (2006.01) |

(52) U.S. Cl.
CPC ........ *C07D 471/04* (2013.01); *A61K 31/4985* (2013.01); *C07D 487/04* (2013.01); *C07D 498/04* (2013.01); *C07D 513/04* (2013.01); *A61K 31/517* (2013.01); *A61K 31/519* (2013.01)

(58) Field of Classification Search
CPC .. C07D 471/04; C07D 487/04; C07D 498/04; C07D 513/04; A61K 31/4985; A61K 31/517; A61K 31/519
See application file for complete search history.

(56) References Cited

U.S. PATENT DOCUMENTS

| | | | |
|---|---|---|---|
| 9,233,978 B2 * | 1/2016 | Guo | ............... A61K 31/4985 |
| 10,081,627 B2 * | 9/2018 | Guo | ............... C07D 471/04 |
| 2007/0072934 A1 | 3/2007 | Liang et al. | |

FOREIGN PATENT DOCUMENTS

| | | | |
|---|---|---|---|
| CN | 104650069 | 5/2015 | |
| CN | 104650069 A | 5/2015 | |
| WO | 01/68642 A1 | 9/2001 | |
| WO | 2001/068641 | 9/2001 | |
| WO | 2001/068647 | 9/2001 | |
| WO | WO-0168641 A1 * | 9/2001 | ........... C07D 401/04 |
| WO | 2005/085462 A1 | 9/2005 | |
| WO | 2006/033995 A2 | 3/2006 | |
| WO | 2006/033995 A3 | 3/2006 | |
| WO | 2008/090115 A1 | 7/2008 | |
| WO | 2009/067547 A1 | 5/2009 | |

(Continued)

OTHER PUBLICATIONS

Allan et al., "Synthesis of analogs of GABA .15. preparation and resolution of some potent cyclopentene and cyclopentane derivatives" Aust. J. Chem 39:855-64 ( 1986).
Brezillon et al., "Antiviral actgivity of Bay 41-4109 on hepatitis B virus in humanized Alb-uPA/SCID mice" PLoSONE 6(12 Suppl 1-6):e25096 (Dec. 2011).
Deres et al., "Inhibition of hepatitis B virus replication by drug-induced depletion of nucleocapsids" Science 299(5608):893-6 ( 2003).

(Continued)

*Primary Examiner* — Alexander R Pagano
(74) *Attorney, Agent, or Firm* — Genentech, Inc.; Richard G. A. Bone

(57) ABSTRACT

The invention provides novel compounds having the general formula:

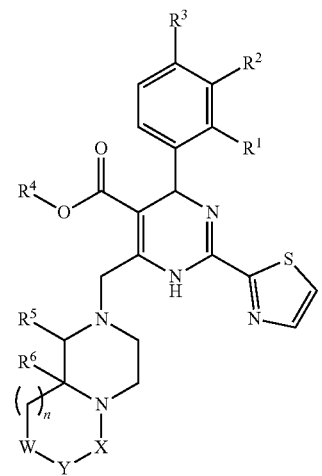

wherein $R^1$, $R^2$, $R^3$, $R^4$, $R^5$, $R^6$, X, Y, W and n are as described herein, compositions including the compounds and methods of using the compounds.

21 Claims, 1 Drawing Sheet

(56) References Cited

FOREIGN PATENT DOCUMENTS

| WO | 2009/103176 | A1 | 8/2009 |
| WO | 2010/023480 | | 3/2010 |
| WO | 2010/069147 | A1 | 6/2010 |
| WO | 2012/019426 | | 2/2012 |
| WO | 2014/029193 | A1 | 2/2014 |
| WO | 2014/184328 | A1 | 11/2014 |

OTHER PUBLICATIONS

Feld et al., "The phenylpropenamide derivative AT-130 blocks HBV replication at the level of viral RNA packaging" Antiviral Res 76:168-177 ( 2007).

Grygorenko et al., "Expedient synthesis of cis- and trans-3-aminocyclobutanecarboxylic acids" Synthetic Communications 41:1644-1649 ( 2011).

Guo et al., "Characterization of the intracellular deproteinized relaxed circular DNA of hepatitis B virus: an intermediate of covalently closed circular DNA formation" J Virol 81:12472-12484 ( 2007).

Mertin et al., "C-Alkylation of functionally substituted carbanions with cyclopropiminium ions: a new route to cyclopropane amino acids1" Synlett 2:87-89 ( 1991).

Sandstroem et al., "B-Amino acid substitutions and structure-based CoMFA modeling of hepatitis C virus NS3 protease inhibitors" Bioorgan Med Chem 16:5590-5605 ( 2008).

Sells et al., "Production of hepatitis B virus particles in Hep G2 cells transfected with cloned hepatitis B virus DNA" Proc. Natl. Acad. Sci USA 84:1005-1009 ( 1987).

Zlotnick et al., "A small molecule inhibits and misdirects assembly of hepatitis B virus capsids" J Virol 76(10):4848-4854 (May 2002).

* cited by examiner

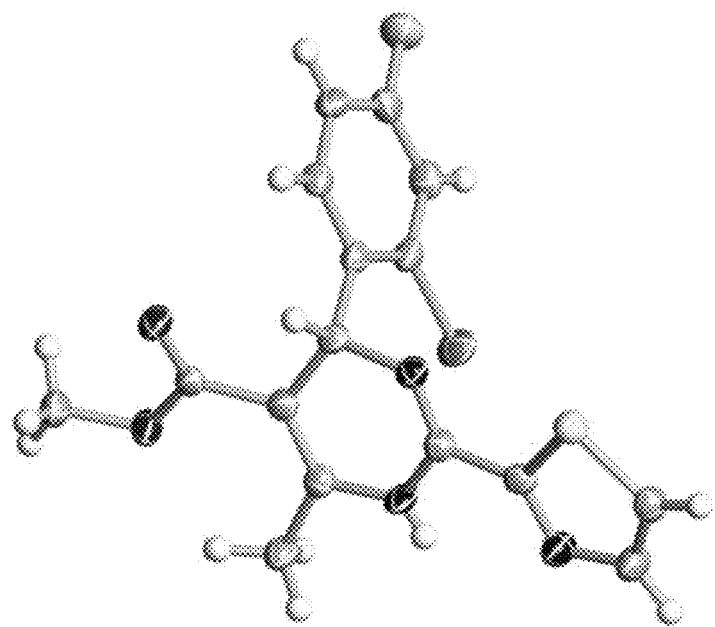

6-FUSED HETEROARYLDIHYDROPYRIMIDINES FOR THE TREATMENT AND PROPHYLAXIS OF HEPATITIS B VIRUS INFECTION

This application is a continuation of U.S. application Ser. No. 14/946,595, filed Nov. 19, 2015, (now U.S. Pat. No. 10,081,627), which is a continuation of U.S. application Ser. No. 14/640,397 (now U.S. Pat. No. 9,233,978), filed Mar. 6, 2015 which claims the benefit of priority to International Application No. PCT/CN2014/073068, filed Mar. 7, 2014, International Application No. PCT/CN2014/083027, filed Jul. 25, 2014, and International Application No. PCT/CN2015/070895, filed Jan. 16, 2015, each of which is incorporated herein by reference in its entirety.

The present invention relates to organic compounds useful for therapy and/or prophylaxis in a human, and in particular to Hepatitis B virus (HBV) inhibitors by targeting on HBV capsid for the treatment of HBV infection.

FIELD OF THE INVENTION

The present invention relates to novel 6-fused heteroaryl-dihydropyrimidines having pharmaceutical activity, their manufacture, pharmaceutical compositions containing them and their potential use as medicaments.

The present invention relates to compounds of formula (I)

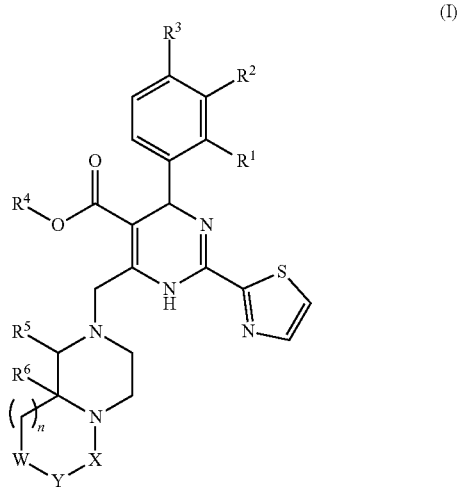

(I)

wherein $R^1$ to $R^6$, X, Y, W and n are as described below, or to pharmaceutically acceptable salts, or to enantiomers or diastereomers thereof.

HBV is a species of the hepadnaviridae family of viruses. HBV is a serious public health problem worldwide, with more than 400 million people especially in Asia-pacific regions chronically infected by this small enveloped DNA virus. Although most individuals seem to resolve the infection following acute symptoms, 15-40% of HBV patients will finally develop clinical diseases during their lifespan, most notably, hepatitis, liver cirrhosis, and hepatocellular carcinoma. Every year 500,000 to 1 million people die from the end stage of liver diseases caused by HBV infection.

HBV lifecycle begins with the binding of the "Dane" particle with an unidentified receptor on the surface of hepatocyte. Following entry, viral genome is delivered into nucleus where a covalently closed circular DNA (cccDNA) is formed through DNA repair of viral relaxed circular DNA. Unlike the mechanisms of most other DNA viruses, HBV cccDNA replicates through the retrotranscription of a 1.1-genome unit-length RNA copy (pregenomic RNA). Viral pregenomic RNA interacts with other two viral components, capsid protein and polymerase, as well as some host factors, to form capsid particles where viral DNA replication occurs. Most copies of the encapsidated genome then efficiently associate with the envelope proteins for virion assembly and secretion; a minority of these genomes is shunted to the nucleus, where they are converted to cccDNA.

Currently, there are two types of anti-HBV agents on the market, nucleoside (tide) analogs targeting viral polymerase (lamivudine, adefovir, tenofovir, telbivudine and entecavir) and interferon modulating host immune functions. Mutations in the primary sequence of the polymerase that confer resistance to lamivudine and adefovir have been identified clinically and underlie a rebound of serum virus titers that 70% of treated patients experience within 3 years of the start of lamivudine therapy. Although resistance to telbivudine, adefovir, and entecavir occurs more rarely, it has been recorded. Interferon alpha is the other major therapy available for hepatitis B, but it is limited by a poor long-term response and debilitating side effects. Some viral genotypes do not show good responses to interferon therapy. Now, the standard of clinic cure of HBV infection is the loss and/or seroconversion of HBsAg. The majority (around or more than 90%) of treated patients fail to achieve this goal. This drawback is mainly due to the presence of a stable pool of viral cccDNA in nucleus that doesn't replicate itself, therefore, shows no accessibility to nucleoside (tide) analogs.

Hence, there is certainly a medical need for treatments with improved characteristics and for a diversity of approaches in the development of therapies for HBV infection.

HBV capsid protein plays essential roles in HBV replication. HBV has an icosahedral core comprising of 240 copies of the capsid (or core) protein. The predominant biological function of capsid protein is to act as a structural protein to encapsidate pre-genomic RNA and form immature capsid particles in the cytoplasm. This step is prerequisite for viral DNA replication. The HBV capsid spontaneously self-assembles from many copies of core dimers present in the cytoplasm. It has been shown that the formation of a trimeric nucleus and the subsequent elongation reactions occur by adding one dimeric subunit at a time until it is complete. Besides this function, capsid protein regulates viral DNA synthesis through different phosphorylation status of its C-terminal phosphorylation sites. When a near full-length relaxed circular DNA is formed through reverse-transcription of viral pregenomic RNA, an immature capsid becomes a mature capsid. On one hand, capsid protein might facilitate the nuclear translocation of viral relaxed circular genome by means of the nuclear localization signals located in the Arginine-rich domain of the C-terminal region of capsid protein. In nucleus, as a component of viral cccDNA minichromosome, capsid protein could play a structural and regulatory role in the functionality of cccDNA minichromosomes. Capsid protein also interacts with viral large envelope protein in endoplasmic reticulum and triggers the release of intact viral particles from hepatocytes.

There has been a couple of capsid related anti-HBV inhibitors reported. For example, phenylpropenamide derivatives, including compounds named AT-61 and AT-130 (Feld J. et al. *Antiviral Research* 2007, 168-177), and a class of thiazolidin-4-ones from Valeant R&D (WO2006/033995), have been shown to inhibit pgRNA packaging. A recent study suggested that phenylpropenamides are, in fact, accelerators of HBV capsid assembly, and their actions result in the formation of empty capsids. These very interesting results illustrate the importance of the kinetic pathway in successful virus assembly.

Heteroaryldihydropyrimidines or HAP, including compounds named Bay 41-4109, Bay 38-7690 and Bay 39-5493, were discovered in a tissue culture-based screening (Deres K. et al. *Science* 2003, 893). These HAP analogs act as synthetic allosteric activators and are able to induce aberrant capsid formation that leads to degradation of the core protein. HAP analogs also reorganized core protein from preassembled capsids into noncapsid polymers, presumably by interaction of HAP with dimers freed during capsid 'breathing', the transitory breaking of individual intersubunit bonds. Bay 41-4109 was administered to HBV infected transgenic mouse or humanized mouse models and demonstrated in vivo efficacy with HBV DNA reduction (Deres K. et al. *Science* 2003, 893; Brezillon N. et al. *PLoS ONE* 2011, e25096). It was also shown that bis-ANS, a small molecule that acts as a molecular 'wedge' and interferes with normal capsid-protein geometry and capsid formation (Zlotnick A. et al. *J Virol.* 2002, 4848-4854).

SUMMARY OF THE INVENTION

The present invention relates to novel compounds of formula (I)

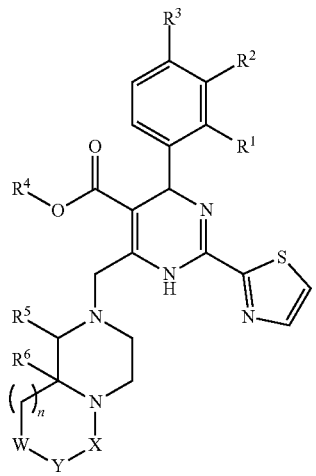

(I)

wherein

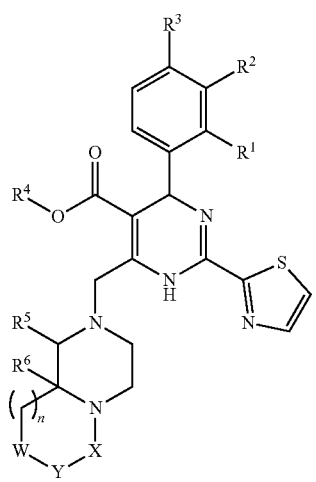

(I)

wherein
$R^1$ is hydrogen, halogen or $C_{1-6}$alkyl;
$R^2$ is hydrogen or halogen;
$R^3$ is hydrogen or halogen;
$R^4$ is $C_{1-6}$alkyl;
$R^5$ is hydrogen, hydroxy$C_{1-6}$alkyl, aminocarbonyl, $C_{1-6}$alkoxycarbonyl or carboxy;
$R^6$ is hydrogen, $C_{1-6}$alkoxycarbonyl or carboxy-$C_mH_{2m}$—;
X is carbonyl or sulfonyl;
Y is —$CH_2$—, —O— or —$N(R^7)$—,
  wherein $R^7$ is hydrogen, $C_{1-6}$alkyl, halo$C_{1-6}$alkyl, $C_{3-7}$cycloalkyl-$C_mH_{2m}$—, $C_{1-6}$alkoxycarbonyl-$C_mH_{2m}$—, —$C_tH_{2t}$—COOH, -halo$C_{1-6}$alkyl-COOH, —($C_{1-6}$alkoxy)$C_{1-6}$alkyl-COOH, —$C_{1-6}$alkyl-O—$C_{1-6}$alkyl-COOH, —$C_{3-7}$cycloalkyl-$C_mH_{2m}$—COOH, —$C_mH_{2m}$—$C_{3-7}$cycloalkyl-COOH, hydroxy-$C_tH_{2t}$—, carboxyspiro[3.3]heptyl or carboxyphenyl-$C_mH_{2m}$—, carboxypyridinyl-$C_mH_{2m}$—;
W is —$CH_2$—, —$C(C_{1-6}alkyl)_2$-, —O— or carbonyl;
n is 0 or 1;
m is 0-7;
t is 1-7;
or pharmaceutically acceptable salts, or enantiomers or diastereomers thereof.

The invention is also relates to their manufacture, medicaments based on a compound in accordance with the invention and their production as well as the use of compounds of formula (I) or other compounds of the present invention for the treatment or prophylaxis of HBV infection.

DETAILED DESCRIPTION OF THE INVENTION

Definitions

As used herein, the term "$C_{1-6}$alkyl" signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "—$C_mH_{2m}$—" alone or in combination signifies a saturated, linear or branched chain alkyl group containing m (m≠0) carbon atoms or a bond (m=0). In particular, "—$C_mH_{2m}$—" alone or in combination signifies a saturated, linear or branched chain alkyl group containing 1 to 4 carbon atoms.

The term "—$C_tH_{2t}$—" alone or in combination signifies a chemical link or a saturated, linear or branched chain alkyl group containing t (t≠0) carbon atoms or a bond (t=0). In particular, "—$C_tH_{2t}$—" alone or in combination signifies a saturated, linear or branched chain alkyl group containing 1 to 4 carbon atoms.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$ cycloalkyl" groups are cyclopropyl, cyclopentyl and cyclohexyl.

The term "carboxy" refers to the group —COOH.

The term "carbonyl" alone or in combination refers to the group —C(O)—.

The term "sulfonyl" alone or in combination refers to the group —S(O)$_2$—.

The term "halogen" and "halo" are used interchangeably herein and refer to fluoro, chloro, bromo, or iodo.

The term "haloC$_{1-6}$alkyl" refers to an alkyl group wherein at least one of the hydrogen atoms of the alkyl group has been replaced by same or different halogen atoms, particularly fluoro atoms. Examples of haloC$_{1-6}$alkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoroethyl or trifluoromethyl.

The term "C$_{1-6}$alkoxycarbonyl" refers to a group C$_{1-6}$alkoxy-C(O)—, wherein the "C$_{1-6}$alkoxy" is as defined above.

The term "carboxy-C$_m$H$_{2m}$—" refers to a group "—C$_m$H$_{2m}$—COOH", wherein the "—C$_m$H$_{2m}$—" is as defined above.

The term "C$_{3-7}$cycloalkyl-C$_m$H$_{2m}$—" refers to a "C$_{3-7}$cycloalkyl" group as defined above wherein one of the hydrogen atoms of the "C$_{3-7}$cycloalkyl" group is replaced by a "—C$_m$H$_{2m}$—" group.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and activities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) or other compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula (I).

Compounds of the general formula (I) or other compounds of the present invention which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

HBV Capsid Inhibitor

The present invention provides (i) novel compounds having the general formula (I):

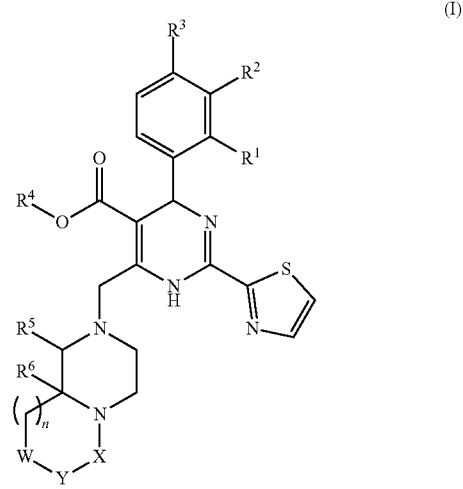

wherein
R$^1$ is hydrogen, halogen or C$_{1-6}$alkyl;
R$^2$ is hydrogen or halogen;
R$^3$ is hydrogen or halogen;
R$^4$ is C$_{1-6}$alkyl;
R$^5$ is hydrogen, hydroxyC$_{1-6}$alkyl, aminocarbonyl, C$_{1-6}$alkoxycarbonyl or carboxy;
R$^6$ is hydrogen, C$_{1-6}$alkoxycarbonyl or carboxy-C$_m$H$_{2m}$—;
X is carbonyl or sulfonyl;
Y is —CH$_2$—, —O— or —N(R$^7$)—,
  wherein R$^7$ is hydrogen, C$_{1-6}$alkyl, haloC$_{1-6}$alkyl, C$_{3-7}$cycloalkyl-C$_m$H$_{2m}$—, C$_{1-6}$alkoxycarbonyl-C$_m$H$_{2m}$—, —C$_t$H$_{2t}$—COOH, -haloC$_{1-6}$alkyl-COOH, —(C$_{1-6}$alkoxy)C$_{1-6}$alkyl-COOH, —C$_{1-6}$alkyl-O—C$_{1-6}$alkyl-COOH, —C$_{3-7}$cycloalkyl-C$_m$H$_{2m}$—COOH, —C$_m$H$_{2m}$—C$_{3-7}$cycloalkyl-COOH, hydroxy-C$_t$H$_{2t}$—, carboxyspiro[3.3]heptyl or carboxyphenyl-C$_m$H$_{2m}$—, carboxypyridinyl-C$_m$H$_{2m}$—;
W is —CH$_2$—, —C(C$_{1-6}$alkyl)$_2$-, —O— or carbonyl;
n is 0 or 1;
m is 0-7;
t is 1-7;
or pharmaceutically acceptable salts, or enantiomers or diastereomers thereof.

Another embodiment of present invention is (ii) a compound of formula I, wherein
R$^1$ is hydrogen, chloro, bromo or methyl;
R$^2$ is hydrogen or fluoro;
R$^3$ is hydrogen, chloro or fluoro;
R$^4$ is methyl, ethyl or propyl;
R$^5$ is hydrogen, hydroxymethyl, aminocarbonyl, methoxycarbonyl or carboxy;
R$^6$ is hydrogen, methyl-O-carbonyl or carboxymethyl;
X is carbonyl or sulfonyl;
Y is —CH$_2$—, —O—, —N(R$^7$)—,
  wherein R$^7$ is hydrogen, methyl, difluoroethyl, isopropyl, isobutyl, t-butyl, cyclopropyl, cyclopropylmethyl, methyl-O-carbonylisopropyl, carboxyethyl, carboxydifluoroethyl, carboxypropyl, carboxybutyl, carboxy(gemdimethyl)methyl, carboxy(gemdimethyl)ethyl, carboxy(gemdimethyl)propyl, carboxy(gemdimethyl)butyl, carboxy(methyl)ethyl, carboxy(ethyl)ethyl, carboxy(methoxy)ethyl, carboxycyclobutyl, carboxycyclobutylmethyl, carboxycyclopentyl, carboxycyclohexyl, carboxymethylcyclopropyl, carboxycyclopropylmethyl, carboxycyclobutylmethyl, carboxyspiro[3.3]heptyl, carboxymethoxyethyl, carboxymethoxypropyl, hydroxyethyl, hydroxymethyl (gemdimethyl)butyl, hydroxy(gemdimethyl)ethyl, carboxyphenyl, carboxypyridinyl or carboxyphenylmethyl;
W is —CH$_2$—, —C(CH$_3$)$_2$—, —O— or carbonyl;
n is 0 or 1;
or pharmaceutically acceptable salts, or enantiomers or diastereomers thereof.

Another embodiment of the present invention is (iii) a compound of formula (IA),

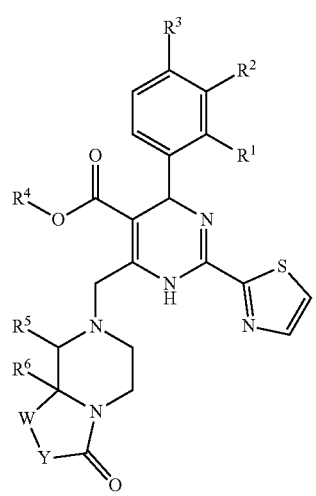

(IA)

wherein
R$^1$ is halogen or C$_{1-6}$alkyl;
R$^2$ is hydrogen or halogen;
R$^3$ is hydrogen or halogen;
R$^4$ is C$_{1-6}$alkyl;
R$^5$ is hydrogen, hydroxyC$_{1-6}$alkyl, aminocarbonyl, C$_{1-6}$alkoxycarbonyl or carboxy;
R$^6$ is hydrogen, C$_{1-6}$alkoxycarbonyl or carboxy-C$_m$H$_{2m}$—;
Y is —N(R$^7$)—,
  wherein R$^7$ is hydrogen, C$_{1-6}$alkyl, haloC$_{1-6}$alkyl, C$_{3-7}$cycloalkyl-C$_m$H$_{2m}$—, C$_{1-6}$alkoxycarbonyl-C$_m$H$_{2m}$—, —C$_t$H$_{2t}$—COOH, -haloC$_{1-6}$alkyl-COOH, —(C$_{1-6}$alkoxy)C$_{1-6}$alkyl-COOH, —C$_{1-6}$alkyl-O—C$_{1-6}$alkyl-COOH, —C$_{3-7}$cycloalkyl-C$_m$H$_{2m}$—COOH, —C$_m$H$_{2m}$—C$_{3-7}$cycloalkyl-COOH, hydroxy-C$_t$H$_{2t}$—, carboxyspiro[3.3]heptyl or carboxyphenyl-C$_m$H$_{2m}$—, carboxypyridinyl-C$_m$H$_{2m}$—;
W is —CH$_2$— or carbonyl;
m is 0-7;
t is 1-7;
or pharmaceutically acceptable salts, or enantiomers or diastereomers thereof.

A further embodiment of the present invention is (iv) a compound of formula (I) or (IA) or pharmaceutically acceptable salts, or enantiomers or diastereomers thereof, wherein
R$^1$ is chloro, bromo or methyl;
R$^2$ is hydrogen or fluoro;
R$^3$ is hydrogen, chloro or fluoro;
R$^4$ is methyl, ethyl or propyl;

R$^5$ is hydrogen, hydroxymethyl, aminocarbonyl, methoxycarbonyl or carboxy;
R$^6$ is hydrogen, methyl-O-carbonyl or carboxymethyl;
Y is —N(R$^7$)—,
  wherein R$^7$ is hydrogen, methyl, difluoroethyl, isopropyl, isobutyl, t-butyl, cyclopropyl, cyclopropylmethyl, methyl-O-carbonylisopropyl, carboxyethyl, carboxydifluoroethyl, carboxypropyl, carboxybutyl, carboxy(gemdimethyl)methyl, carboxy(gemdimethyl)ethyl, carboxy(gemdimethyl)propyl, carboxy(gemdimethyl)butyl, carboxy(methyl)ethyl, carboxy(ethyl)ethyl, carboxy(methoxy)ethyl, carboxycyclobutyl, carboxycyclobutylmethyl, carboxycyclopentyl, carboxycyclohexyl, carboxymethylcyclopropyl, carboxycyclopropylmethyl, carboxycyclobutylmethyl, carboxyspiro[3.3]heptyl, carboxymethoxyethyl, carboxymethoxypropyl, hydroxyethyl, hydroxymethyl (gemdimethyl)butyl, hydroxy(gemdimethyl)ethyl, carboxyphenyl, carboxypyridinyl or carboxyphenylmethyl;
W is —CH$_2$— or carbonyl.

Another embodiment of the present invention is (v) a compound of formula (IAA),

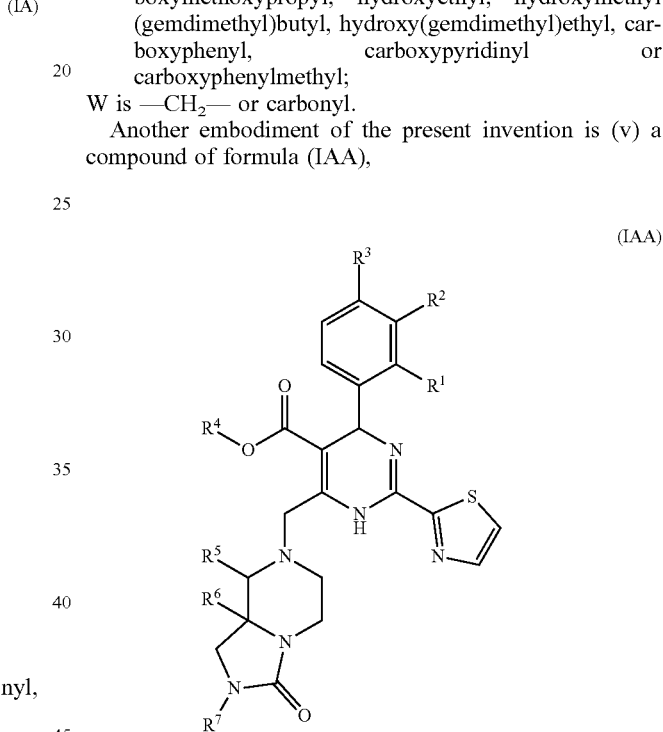

(IAA)

wherein
R$^1$ is halogen or C$_{1-6}$alkyl;
R$^2$ is hydrogen or halogen;
R$^3$ is hydrogen or halogen;
R$^4$ is C$_{1-6}$alkyl;
R$^5$ is hydrogen, aminocarbonyl or carboxy;
R$^6$ is hydrogen;
R$^7$ is C$_{1-6}$alkyl, haloC$_{1-6}$alkyl, C$_{3-7}$cycloalkyl, C$_{3-7}$cycloalkyl-C$_m$H$_{2m}$—, —C$_t$H$_{2t}$—COOH, —C$_m$H$_{2m}$—C$_{3-7}$cycloalkyl-COOH or carboxyphenyl;
m is 0-7;
t is 1-7;
or pharmaceutically acceptable salts, or enantiomers or diastereomers thereof.

A further embodiment of the present invention is (vi) a compound of formula (I), (IA) or (IAA) or pharmaceutically acceptable salts, or enantiomers or diastereomers thereof, wherein
R$^1$ is chloro or methyl;
R$^2$ is hydrogen or fluoro;
R$^3$ is hydrogen or fluoro;

$R^4$ is methyl or ethyl;

$R^5$ is hydrogen, aminocarbonyl or carboxy;

$R^6$ is hydrogen;

$R^7$ is methyl, isopropyl, isobutyl, t-butyl, difluoroethyl, cyclopropyl, cyclopropylmethyl, carboxy(gemdimethyl)ethyl, carboxy(gemdimethyl)propyl, carboxycyclopropylmethyl, carboxycyclobutylmethyl or carboxyphenyl.

Another embodiment of the present invention is (vii) a compound of formula (IB),

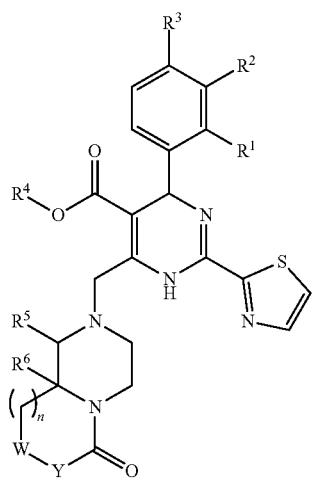

(IB)

wherein $R^1$ is hydrogen or halogen;

$R^2$ is hydrogen or halogen;

$R^3$ is hydrogen or halogen;

$R^4$ is $C_{1-6}$alkyl;

$R^5$ is hydrogen;

$R^6$ is hydrogen or carboxymethyl;

Y is —CH$_2$— or —O—;

W is —CH$_2$—, —C(C$_{1-6}$alkyl)$_2$- or —O—;

n is 0 or 1;

or pharmaceutically acceptable salts, or enantiomers or diastereomers thereof.

A further embodiment of the present invention is (viii) a compound according to formula (I) or (IB) or pharmaceutically acceptable salts, or enantiomers or diastereomers thereof, wherein $R^1$ is hydrogen, chloro or bromo;

$R^2$ is hydrogen or fluoro;

$R^3$ is hydrogen or fluoro;

$R^4$ is methyl or ethyl;

$R^5$ is hydrogen;

$R^6$ is hydrogen or carboxymethyl;

Y is —CH$_2$— or —O—;

W is —CH$_2$—, —C(CH$_3$)$_2$— or —O—;

n is 0 or 1.

Another embodiment of the present invention is (ix) a compound of formula (ID)

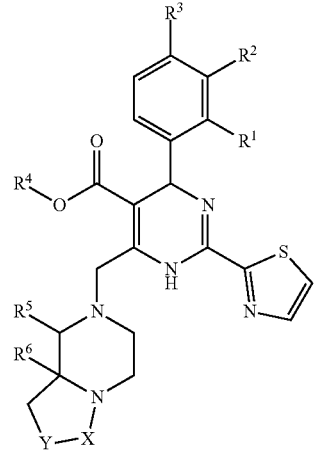

(ID)

wherein $R^1$ is halogen or $C_{1-6}$alkyl;

$R^2$ is hydrogen or halogen;

$R^3$ is hydrogen or halogen;

$R^4$ is $C_{1-6}$alkyl;

$R^5$ is hydrogen, aminocarbonyl or carboxy;

$R^6$ is hydrogen or $C_{1-6}$alkoxycarbonyl

X is carbonyl;

Y is —O— or —N($R^7$)— or —CH$_2$—, wherein $R^7$ is hydrogen, $C_{1-6}$alkyl, haloC$_{1-6}$alkyl, $C_{3-7}$cycloalkyl, $C_{3-7}$cycloalkyl-C$_m$H$_{2m}$—, —C$_t$H$_{2t}$—COOH—C$_m$H$_{2m}$—C$_{3-7}$cycloalkyl-COOH, hydroxy-C$_t$H$_{2t}$—, carboxyspiro[3.3]heptyl or carboxyphenyl-C$_m$H$_{2m}$—;

m is 0-7;

t is 1-7;

or pharmaceutically acceptable salts, or enantiomers or diastereomers thereof.

A further embodiment of the present invention is (x) a compound according to formula (I) or (ID), or pharmaceutically acceptable salts, or enantiomers or diastereomers thereof, wherein $R^1$ is chloro, bromo or methyl;

$R^2$ is hydrogen or fluoro;

$R^3$ is hydrogen or fluoro;

$R^4$ is methyl, ethyl or propyl;

$R^5$ is hydrogen, aminocarbonyl or carboxy;

$R^6$ is hydrogen or methyl-O-carbonyl;

X is carbonyl;

Y is —O—, —N($R^7$)— or —CH$_2$—, wherein $R^7$ is hydrogen, methyl, isopropyl, difluoroethyl, isobutyl, t-butyl, cyclopropyl, cyclopropylmethyl, carboxy(gemdimethyl)ethyl, carboxy(methyl)ethyl, carboxycyclopropylmethyl, carboxyphenyl, carboxycyclopentyl, carboxycyclohexyl, carboxy(gemdimethyl)propyl, carboxy(gemdimethyl)butyl, carboxycyclobutylmethyl, carboxyspiro[3.3]heptyl, hydroxyethyl, hydroxy(gemdimethyl)ethyl or carboxyphenylmethyl.

Another embodiment of the present invention is (xi) a compound of formula (IE),

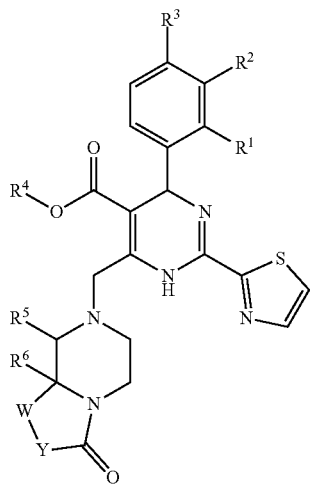

(IE)

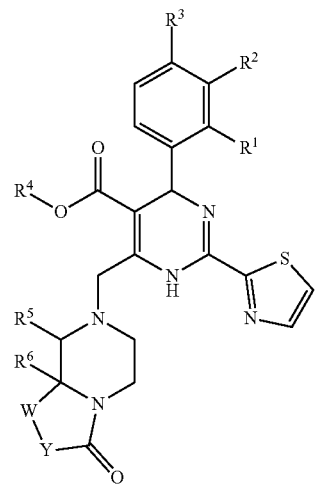

(IE)

wherein
R$^1$ is halogen or C$_{1-6}$alkyl;
R$^2$ is hydrogen or halogen;
R$^3$ is hydrogen or halogen;
R$^4$ is C$_{1-6}$alkyl;
R$^5$ is hydrogen or carboxy;
R$^6$ is hydrogen or carboxy-C$_m$H$_{2m}$—;
Y is —O—, —N(R$^7$)— or —CH$_2$—,
  wherein R$^7$ is C$_{1-6}$alkyl, C$_{3-7}$cycloalkyl, —C$_t$H$_{2t}$—COOH, —C$_{3-7}$cycloalkyl-C$_m$H$_{2m}$—COOH, —C$_m$H$_{2m}$—C$_{3-7}$cycloalkyl-COOH, —(C$_{1-6}$alkoxy)C$_{1-6}$alkyl-COOH, —C$_{1-6}$alkyl-O—C$_{1-6}$alkyl-COOH, carboxyspiro[3.3]heptyl or carboxyphenyl-C$_m$H$_{2m}$—;
W is —CH$_2$— or —C(C$_{1-6}$alkyl)$_2$-;
m is 0-7;
t is 1-7;
or pharmaceutically acceptable salts, or enantiomers or diastereomers thereof.

A further embodiment of the present invention is (xii) a compound of formula (I) or (IE) or pharmaceutically acceptable salts, or enantiomers or diastereomers thereof, wherein
R$^1$ is chloro or methyl;
R$^2$ is hydrogen or fluoro;
R$^3$ is hydrogen or fluoro;
R$^4$ is methyl or ethyl;
R$^5$ is hydrogen or carboxy;
R$^6$ is hydrogen or carboxymethyl;
Y is —O—, —N(R$^7$)— or —CH$_2$—,
  wherein R$^7$ is isopropyl, methyl, isobutyl, t-butyl, cyclopropyl, carboxyethyl, carboxypropyl, carboxybutyl, carboxy(gemdimethyl)methyl, carboxy(gemdimethyl)ethyl, carboxy(methyl)ethyl, carboxycyclobutyl, carboxycyclopropylmethyl, carboxycyclopentyl, carboxycyclohexyl, carboxymethylcyclopropyl, carboxy(gemdimethyl)propyl, carboxy(ethyl)ethyl, carboxy(methoxy)ethyl, carboxycyclobutylmethyl, carboxyspiro[3.3]heptyl, carboxymethoxyethyl, carboxymethoxypropyl, carboxyphenylmethyl or carboxyphenyl;
W is —CH$_2$— or —C(CH$_3$)$_2$—.

Another embodiment of the present invention is (xiii) a compound of formula (IE), wherein
R$^1$ is halogen or C$_{1-6}$alkyl;
R$^2$ is hydrogen or halogen;
R$^3$ is hydrogen or halogen;
R$^4$ is C$_{1-6}$alkyl;
R$^5$ is hydrogen or carboxy;
R$^6$ is hydrogen or carboxy-C$_m$H$_{2m}$—;
Y is —N(R$^7$)—,
  wherein R$^7$ is hydrogen, C$_{1-6}$alkyl, C$_{3-7}$cycloalkyl, —C$_t$H$_{2t}$—COOH, —C$_m$H$_{2m}$—C$_{3-7}$cycloalkyl-COOH or carboxyphenyl;
W is —CH$_2$—;
m is 0-7;
t is 1-7;
or pharmaceutically acceptable salts, or enantiomers or diastereomers thereof.

A further embodiment of the present invention is (xiv) a compound according to formula (I) or (IE), or pharmaceutically acceptable salts, or enantiomers or diastereomers thereof, wherein
R$^1$ is chloro or methyl;
R$^2$ is hydrogen or fluoro;
R$^3$ is hydrogen or fluoro;
R$^4$ is methyl or ethyl;
R$^5$ is hydrogen or carboxy;
R$^6$ is hydrogen or carboxymethyl;
Y is —N(R$^7$)—,
  wherein R$^7$ is hydrogen, methyl, t-butyl, cyclopropyl, carboxy(gemdimethyl)ethyl, carboxy(gemdimethyl)propyl, carboxy(methyl)ethyl, carboxycyclopropylmethyl, carboxycyclopentyl, carboxycyclohexyl, carboxycyclobutylmethyl or carboxyphenyl;
W is —CH$_2$—.

Another embodiment of the present invention is (xv) a compound of formula (I), (IA), (IAA), (IB), (ID) or (IE) or pharmaceutically acceptable salts, or enantiomers or diastereomers, wherein the 2-thiazolyl group is further substituted by C$_{1-6}$alkyl, and all the other substituents are defined as above.

A further embodiment of the present invention is (xvi) a compound of formula (I), (IA), (IAA), (IB), (ID) or (IE) or pharmaceutically acceptable salts, or enantiomers or diastereomers, wherein the 2-thiazolyl group is further substituted by methyl, and all the other substituents are defined as above.

Another embodiment of the present invention is (xvii) compounds having the general formula (I):

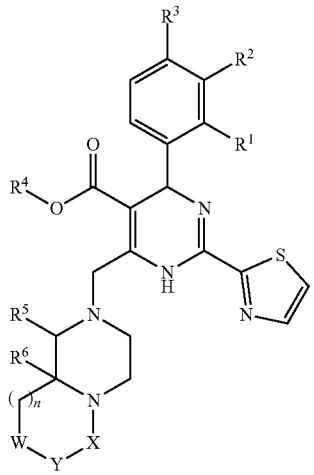

(I)

wherein
R$^1$ is hydrogen, halogen or C$_{1-6}$alkyl;
R$^2$ is hydrogen or halogen;
R$^3$ is hydrogen or halogen;
R$^4$ is C$_{1-6}$alkyl;
R$^5$ is hydrogen or carboxy;
R$^6$ is hydrogen, C$_{1-6}$alkoxycarbonyl or carboxy-C$_m$H$_{2m}$—;
X is carbonyl or sulfonyl;
Y is —CH$_2$—, —O— or —N(R$^7$)—,
   wherein R$^7$ is hydrogen, C$_{1-6}$alkyl, C$_{3-7}$cycloalkyl, C$_{1-6}$alkoxycarbonyl-C$_m$H$_{2m}$—, —C$_m$H$_{2m}$—COOH, —(C$_{1-6}$alkoxy)C$_{1-6}$alkyl-COOH, —C$_{1-6}$alkyl-O—C$_{1-6}$alkyl-COOH, —C$_{3-7}$ cycloalkyl-C$_m$H$_{2m}$—COOH, —C$_m$H$_{2m}$—C$_{3-7}$cycloalkyl-COOH, hydroxy-C$_m$H$_{2m}$—, carboxyspiro[3.3]heptyl or carboxyphenyl-C$_m$H$_{2m}$—;
W is —CH$_2$—, —C(C$_{1-6}$alkyl)$_2$-, —O— or carbonyl;
n is 0 or 1;
m is 0-7;
or pharmaceutically acceptable salts, or enantiomers or diastereomers thereof.

Further embodiment of present invention is (xviii) a compound of formula (I), wherein
R$^1$ is hydrogen, chloro, bromo or methyl;
R$^2$ is hydrogen or fluoro;
R$^3$ is hydrogen, chloro or fluoro;
R$^4$ is methyl or ethyl;
R$^5$ is hydrogen or carboxy;
R$^6$ is hydrogen, methyl-O-carbonyl or carboxymethyl;
X is carbonyl or sulfonyl;
Y is —CH$_2$—, —O—, —N(R$^7$)—,
   wherein R$^7$ is hydrogen, methyl, isopropyl, t-butyl, cyclopropyl, methyl-O-carbonylisopropyl, carboxyethyl, carboxypropyl, carboxybutyl, carboxy(gemdimethyl)methyl, carboxy(gemdimethyl)ethyl, carboxy(gemdimethyl)propyl, carboxy(gemdimethyl)butyl, carboxy(methyl)ethyl, carboxy(ethyl)ethyl, carboxy(methoxy)ethyl, carboxycyclobutyl, carboxycyclobutylmethyl, carboxycyclopentyl, carboxycyclohexyl, carboxymethylcyclopropyl, carboxycyclopropylmethyl, carboxycyclobutylmethyl, carboxyspiro[3.3]heptyl, carboxymethoxyethyl, carboxymethoxypropyl, hydroxyethyl, hydroxymethyl(gemdimethyl)butyl, carboxyphenyl or carboxyphenylmethyl;
W is —CH$_2$—, —C(CH$_3$)$_2$—, —O— or carbonyl;
n is 0 or 1;
or pharmaceutically acceptable salts, or enantiomers or diastereomers thereof.

Another embodiment of present invention is (xix) a compound of formula (IA)

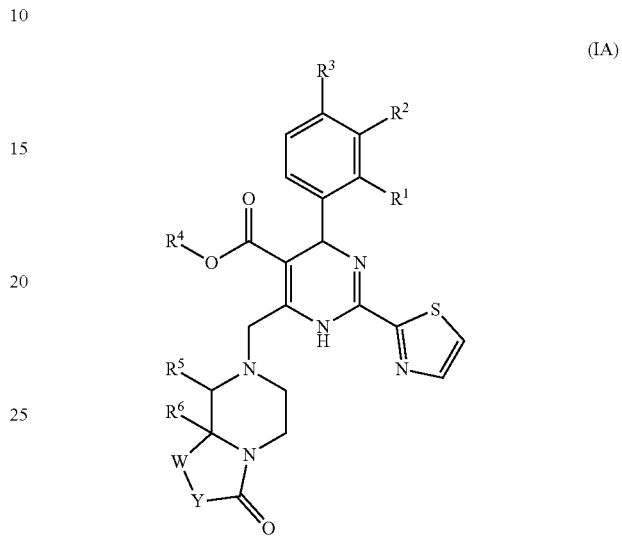

(IA)

wherein
R$^1$ is halogen or C$_{1-6}$alkyl;
R$^2$ is hydrogen or halogen;
R$^3$ is hydrogen or halogen;
R$^4$ is C$_{1-6}$alkyl;
R$^5$ is hydrogen or carboxy;
R$^6$ is hydrogen, C$_{1-6}$alkoxycarbonyl or carboxy-C$_m$H$_{2m}$—;
Y is —N(R$^7$)—,
   wherein R$^7$ is hydrogen, C$_{1-6}$alkyl, C$_{3-7}$cycloalkyl, C$_{1-6}$alkoxycarbonyl-C$_m$H$_{2m}$—, —C$_m$H$_{2m}$—COOH, —(C$_{1-6}$alkoxy)C$_{1-6}$alkyl-COOH, —C$_{1-6}$alkyl-O—C$_{1-6}$alkyl-COOH, —C$_{3-7}$ cycloalkyl-C$_m$H$_{2m}$—COOH, —C$_m$H$_{2m}$—C$_{3-7}$cycloalkyl-COOH, hydroxy-C$_m$H$_{2m}$—, carboxyspiro[3.3]heptyl or carboxyphenyl-C$_m$H$_{2m}$—;
W is —CH$_2$— or carbonyl;
m is 0-7;
or pharmaceutically acceptable salts, or enantiomers or diastereomers thereof.

Further embodiment of present invention is (xx) a compound of formula (IA) or pharmaceutically acceptable salts, or enantiomers or diastereomers thereof, wherein
R$^1$ is chloro, bromo or methyl;
R$^2$ is hydrogen or fluoro;
R$^3$ is hydrogen, chloro or fluoro;
R$^4$ is methyl or ethyl;
R$^5$ is hydrogen or carboxy;
R$^6$ is hydrogen, methyl-O-carbonyl or carboxymethyl;
Y is —N(R$^7$)—,
   wherein R$^7$ is hydrogen, methyl, isopropyl, t-butyl, cyclopropyl, methyl-O-carbonylisopropyl, carboxyethyl, carboxypropyl, carboxybutyl, carboxy(gemdimethyl)methyl, carboxy(gemdimethyl)ethyl, carboxy(gemdimethyl)propyl, carboxy(gemdimethyl)butyl, carboxy(methyl)ethyl, carboxy(ethyl)ethyl, carboxy(methoxy)ethyl, carboxycyclobutyl, carboxycyclobutylmethyl, carboxycyclopentyl, carboxycyclohexyl, carboxymethylcyclopropyl, carboxycyclopropylmethyl, carboxycyclobutylmethyl, carboxyspiro[3.3]heptyl, carboxymethoxyethyl, carboxymethoxypropyl, hydroxyethyl, hydroxymethyl(gemdimethyl)butyl, carboxyphenyl or carboxyphenylmethyl;

W is —CH$_2$— or carbonyl.

Another embodiment of present invention is (xxi) a compound of formula (IAA)

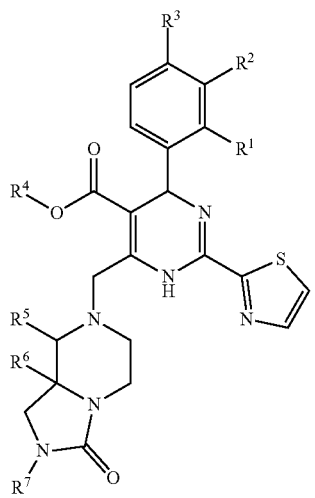

(IAA)

wherein

R$^1$ is halogen or C$_{1-6}$alkyl;

R$^2$ is hydrogen or halogen;

R$^3$ is hydrogen or halogen;

R$^4$ is C$_{1-6}$alkyl;

R$^5$ is hydrogen or carboxy;

R$^6$ is hydrogen;

R$^7$ is C$_{1-6}$alkyl, C$_{3-7}$cycloalkyl, —C$_m$H$_{2m}$—COOH, —C$_m$H$_{2m}$—C$_{3-7}$cycloalkyl-COOH or carboxyphenyl;

m is 1-6;

or pharmaceutically acceptable salts, or enantiomers or diastereomers thereof.

Further embodiment of present invention is (xxii) a compound of formula (IAA) or pharmaceutically acceptable salts, or enantiomers or diastereomers thereof, wherein R$^1$ is chloro or methyl;

R$^2$ is hydrogen or fluoro;

R$^3$ is hydrogen or fluoro;

R$^4$ is methyl or ethyl;

R$^5$ is hydrogen or carboxy;

R$^6$ is hydrogen;

R$^7$ is methyl, isopropyl, t-butyl, cyclopropyl, carboxy(gemdimethyl)ethyl, carboxy(gemdimethyl)propyl, carboxycyclopropylmethyl, carboxycyclobutylmethyl or carboxyphenyl.

Another embodiment of present invention is (xxiii) a compound of formula (IC)

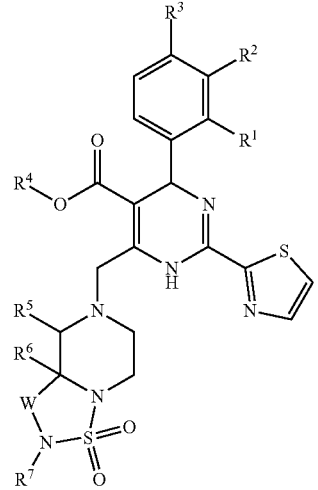

(IC)

wherein

R$^1$ is halogen;

R$^2$ is hydrogen;

R$^3$ is halogen;

R$^4$ is C$_{1-6}$alkyl;

R$^5$ is hydrogen;

R$^6$ is hydrogen;

R$^7$ is hydrogen;

W is —CH$_2$—;

or pharmaceutically acceptable salts, or enantiomers or diastereomers thereof.

Another embodiment of present invention is (xxiv) a compound of formula (ID)

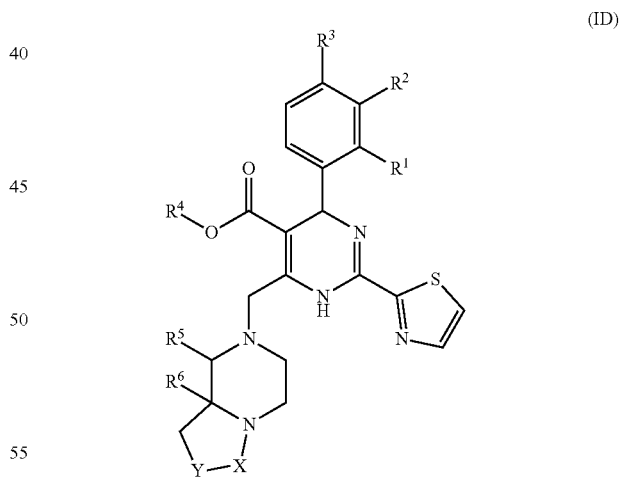

(ID)

wherein

R$^1$ is halogen or C$_{1-6}$alkyl;

R$^2$ is hydrogen or halogen;

R$^3$ is hydrogen or halogen;

R$^4$ is C$_{1-6}$alkyl;

R$^5$ is hydrogen or carboxy;

R$^6$ is hydrogen or C$_{1-6}$alkoxycarbonyl;

X is carbonyl;

Y is —O— or —N(R$^7$)—, wherein R⁷ is hydrogen, $C_{1-6}$alkyl, $C_{3-7}$cycloalkyl, —$C_mH_{2m}$—COOH, —$C_mH_{2m}$—$C_{3-7}$cycloalkyl-COOH, hydroxy-$C_mH_{2m}$—, carboxyspiro[3.3]heptyl or carboxyphenyl-$C_tH_{2t}$—;

m is 1-6;
t is 0-6;
or pharmaceutically acceptable salts, or enantiomers or diastereomers thereof.

Further embodiment of present invention is (xxv) a compound of formula (ID) or pharmaceutically acceptable salts, or enantiomers or diastereomers thereof, wherein
$R^1$ is chloro, bromo or methyl;
$R^2$ is hydrogen or fluoro;
$R^3$ is hydrogen or fluoro;
$R^4$ is methyl or ethyl;
$R^5$ is hydrogen or carboxy;
$R^6$ is hydrogen or methyl-O-carbonyl;
X is carbonyl;
Y is —O—, —N($R^7$)—,
wherein $R^7$ is hydrogen, methyl, isopropyl, t-butyl cyclopropyl, carboxy(gemdimethyl)ethyl, carboxy(methyl)ethyl, carboxycyclopropylmethyl, carboxyphenyl, carboxycyclopentyl, carboxycyclohexyl, carboxy(gemdimethyl)propyl, carboxy(gemdimethyl)butyl, carboxycyclobutylmethyl, carboxyspiro[3.3]heptyl, hydroxyethyl or carboxyphenylmethyl.

Another embodiment of present invention is (xxvi) a compound of formula (IE)

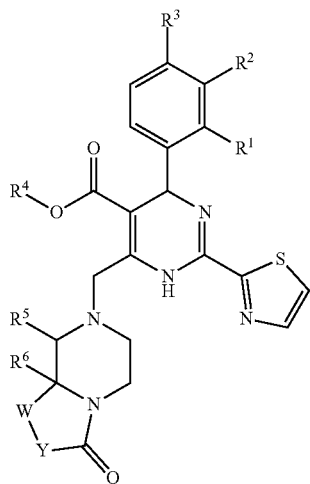

(IE)

wherein
$R^1$ is halogen or $C_{1-6}$alkyl;
$R^2$ is hydrogen or halogen;
$R^3$ is hydrogen or halogen;
$R^4$ is $C_{1-6}$alkyl;
$R^5$ is hydrogen or carboxy;
$R^6$ is hydrogen or carboxy-$C_mH_{2m}$—;
Y is —O— or —N($R^7$)—,
wherein $R^7$ is $C_{1-6}$alkyl, $C_{3-7}$cycloalkyl, —$C_mH_{2m}$—COOH, —$C_{3-7}$cycloalkyl-$C_mH_{2m}$—COOH, —$C_mH_{2m}$—$C_{3-7}$cycloalkyl-COOH, —($C_{1-6}$alkoxy)$C_{1-6}$alkyl-COOH, $C_{1-6}$alkyl-O—$C_{1-6}$alkyl-COOH, carboxyspiro[3.3]heptyl or carboxyphenyl-$C_mH_{2m}$—;
W is —$CH_2$— or —$C(C_{1-6}$alkyl$)_2$-;
m is 0-6;

or pharmaceutically acceptable salts, or enantiomers or diastereomers thereof.

Further embodiment of present invention is (xxvii) a compound of formula (IE) or pharmaceutically acceptable salts, or enantiomers or diastereomers thereof, wherein
$R^1$ is chloro or methyl;
$R^2$ is hydrogen or fluoro;
$R^3$ is hydrogen or fluoro;
$R^4$ is methyl or ethyl;
$R^5$ is hydrogen or carboxy;
$R^6$ is hydrogen or carboxymethyl;
Y is —O— or —N($R^7$)—,
wherein $R^7$ is isopropyl, methyl, t-butyl, cyclopropyl, carboxyethyl, carboxypropyl, carboxybutyl, carboxy(gemdimethyl)methyl, carboxy(gemdimethyl)ethyl, carboxy(methyl)ethyl, carboxycyclobutyl, carboxycyclopropylmethyl, carboxycyclopentyl, carboxycyclohexyl, carboxymethylcyclopropyl, carboxy(gemdimethyl)propyl, carboxy(ethyl)ethyl, carboxy(methoxy)ethyl, carboxycyclobutylmethyl, carboxyspiro[3.3]heptyl, carboxymethoxyethyl, carboxymethoxypropyl, carboxyphenylmethyl or carboxyphenyl;
W is —$CH_2$— or —$C(CH_3)_2$—.

Another embodiment of present invention is (xxviii) a compound of formula (IE)

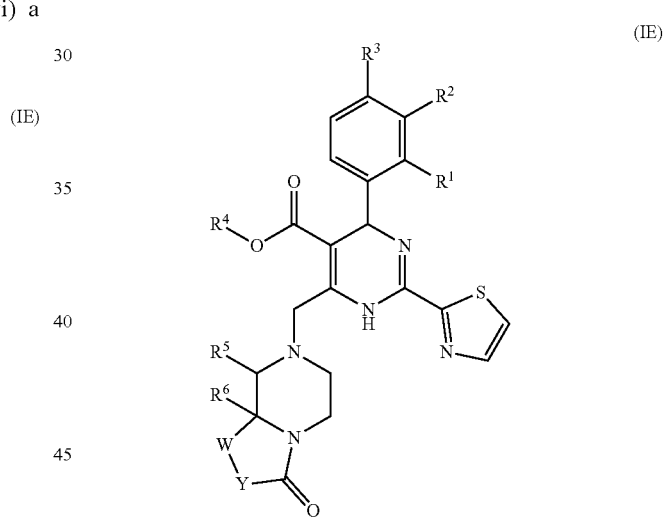

(IE)

wherein
$R^1$ is halogen or $C_{1-6}$alkyl;
$R^2$ is hydrogen or halogen;
$R^3$ is hydrogen or halogen;
$R^4$ is $C_{1-6}$alkyl;
$R^5$ is hydrogen or carboxy;
$R^6$ is hydrogen or carboxy-$C_mH_{2m}$—;
Y is —O—, —N($R^7$)— or —$CH_2$—,
wherein $R^7$ is $C_{1-6}$alkyl, $C_{3-7}$cycloalkyl, —$C_mH_{2m}$—COOH, —$C_{3-7}$cycloalkyl-$C_mH_{2m}$—COOH, —$C_mH_{2m}$—$C_{3-7}$cycloalkyl-COOH, carboxyspiro[3.3]heptyl, —($C_{1-6}$alkoxy)$C_{1-6}$alkyl-COOH, —$C_{1-6}$alkyl-O—$C_{1-6}$ alkyl-COOH, carboxypyridinyl-$C_mH_{2m}$— or carboxyphenyl-$C_mH_{2m}$—;
W is —$CH_2$— or —$C(C_{1-6}$alkyl$)_2$-;
m is 0-6;
or pharmaceutically acceptable salts, or enantiomers or diastereomers thereof.

Further embodiment of present invention is (xxix) a compound of formula (IE) or pharmaceutically acceptable salts, or enantiomers or diastereomers thereof, wherein
$R^1$ is chloro or methyl;
$R^2$ is hydrogen or fluoro;
$R^3$ is hydrogen or fluoro;
$R^4$ is methyl or ethyl;
$R^5$ is hydrogen or carboxy;
$R^6$ is hydrogen or carboxymethyl;
Y is —O—, —N($R^7$)— or —CH$_2$—,
  wherein $R^7$ is methyl, t-butyl, isopropyl, cyclopropyl, carboxyethyl, carboxypropyl, carboxybutyl, carboxy(gemdimethyl)methyl, carboxy(gemdimethyl)ethyl, carboxy(methyl)ethyl, carboxycyclobutyl, carboxycyclopentyl, carboxycyclohexyl, carboxycyclopropylmethyl, carboxy(gemdimethyl)propyl, carboxy(gemdimethyl)butyl, carboxy(ethyl)ethyl, carboxy(methoxy)ethyl, carboxycyclobutylmethyl, carboxymethylcyclopropyl, carboxyspiro[3.3]heptyl, carboxymethoxyethyl, carboxymethoxypropyl, carboxyphenylmethyl, carboxypyridinyl or carboxyphenyl;
W is —CH$_2$— or —C(CH$_3$)$_2$—.

The present invention provides (xxx) novel compounds having the general formula (I):

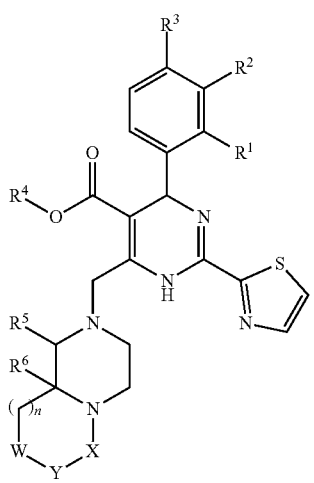

wherein
$R^1$ is hydrogen, halogen or $C_{1-6}$alkyl;
$R^2$ is hydrogen or halogen;
$R^3$ is hydrogen or halogen;
$R^4$ is $C_{1-6}$alkyl;
$R^5$ is hydrogen or carboxy;
$R^6$ is hydrogen, $C_{1-6}$alkoxycarbonyl or carboxy-$C_mH_{2m}$—;
X is carbonyl or sulfonyl;
Y is —CH$_2$—; —O—; —NR$^7$ or —N—R$^8$—COOH;
  wherein $R^7$ is hydrogen, $C_{1-6}$alkyl, $C_{3-7}$cycloalkyl or $C_{1-6}$alkoxycarbonyl-$C_mH_{2m}$—;
  $R^8$ is —$C_mH_{2m}$—, —$C_tH_{2t}$— $C_{3-7}$cycloalkyl-$C_tH_{2t}$— or phenyl;
W is —CH$_2$—, —O— or carbonyl;
n is 0 or 1;
m is 1-6;
t is 0-6;
or pharmaceutically acceptable salts, or enantiomers or diastereomers thereof.

Further embodiment of present invention is (xxxi) a compound of formula (I), wherein
$R^1$ is hydrogen, chloro, bromo or methyl;
$R^2$ is hydrogen or fluoro;
$R^3$ is hydrogen or fluoro;
$R^4$ is methyl or ethyl;
$R^5$ is hydrogen or carboxy;
$R^6$ is hydrogen, methyl-O-carbonyl or carboxymethyl;
X is carbonyl or sulfonyl;
Y is —CH$_2$—; —O—; —NR$^7$ or —N—R$^8$—COOH;
  wherein $R^7$ is hydrogen, isopropyl, cyclopropyl or methyl-O-carbonylisopropyl;
  $R^8$ is ethyl, propyl, (gemdimethyl)methyl, (gemdimethyl)ethyl, (methyl)ethyl, cyclobutyl, cyclopentyl, cyclohexyl, methylcyclopropyl, cyclopropylmethyl, cyclobutylmethyl or phenyl;
W is —CH$_2$—, —O— or carbonyl;
n is 0 or 1;
or pharmaceutically acceptable salts, or enantiomers or diastereomers thereof.

Another embodiment of present invention is (xxxii) a compound of formula (I), wherein
$R^1$ is hydrogen, halogen or $C_{1-6}$alkyl;
$R^2$ is hydrogen or halogen;
$R^3$ is hydrogen or halogen;
$R^4$ is $C_{1-6}$alkyl;
$R^5$ is hydrogen or carboxy;
$R^6$ is hydrogen, $C_{1-6}$alkoxycarbonyl or carboxy-$C_mH_{2m}$—;
X is carbonyl or sulfonyl;
Y is —CH$_2$—; —O—; —NR$^7$ or —N—R$^8$—COOH;
  wherein $R^7$ is hydrogen, $C_{1-6}$alkyl, $C_{3-7}$cycloalkyl or $C_{1-6}$alkoxycarbonyl-$C_mH_{2m}$—;
  $R^8$ is —$C_mH_{2m}$—, $C_{3-7}$cycloalkyl-$C_tH_{2t}$— or phenyl;
W is —CH$_2$—, —O— or carbonyl;
n is 0 or 1;
m is 1-6;
t is 0-6;
or pharmaceutically acceptable salts, or enantiomers or diastereomers thereof.

Further embodiment of present invention is (xxxiii) a compound of formula (I), wherein
$R^1$ is hydrogen, chloro, bromo or methyl;
$R^2$ is hydrogen or fluoro;
$R^3$ is hydrogen or fluoro;
$R^4$ is methyl or ethyl;
$R^5$ is hydrogen or carboxy;
$R^6$ is hydrogen, methyl-O-carbonyl or carboxymethyl;
X is carbonyl or sulfonyl;
Y is —CH$_2$—; —O—; —NR$^7$ or —N—R$^8$—COOH;
  wherein $R^7$ is hydrogen, isopropyl, cyclopropyl or methyl-O-carbonylisopropyl;
  $R^8$ is (gemdimethyl)methyl, (gemdimethyl)ethyl, (methyl)ethyl, cyclobutyl, cyclopropylmethyl or phenyl;
W is —CH$_2$—, —O— or carbonyl;
n is 0 or 1;
or pharmaceutically acceptable salts, or enantiomers or diastereomers thereof.

Another embodiment of present invention is (xxxiv) a compound of formula (IA)

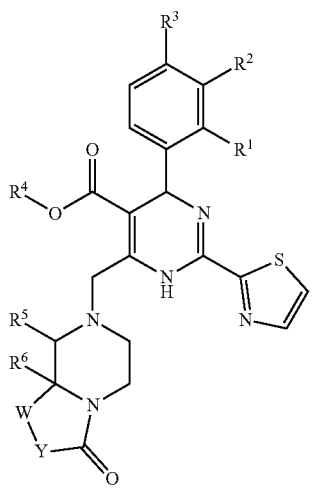

(IA)

wherein

R$^1$ is halogen or C$_{1-6}$alkyl;

R$^2$ is hydrogen or halogen;

R$^3$ is hydrogen or halogen;

R$^4$ is C$_{1-6}$alkyl;

R$^5$ is hydrogen or carboxy;

R$^6$ is hydrogen, C$_{1-6}$alkoxycarbonyl or carboxy-C$_m$H$_{2m}$—;

Y is —NR$^7$ or —N—R$^8$—COOH;

wherein R$^7$ is hydrogen, C$_{1-6}$alkyl, C$_{3-7}$cycloalkyl or C$_{1-6}$alkoxycarbonyl-C$_m$H$_{2m}$—;

R$^8$ is —C$_m$H$_{2m}$—, C$_{3-7}$cycloalkyl-C$_t$H$_{2t}$— or phenyl;

W is —CH$_2$— or carbonyl;

m is 1-6;

t is 0-6;

or pharmaceutically acceptable salts, or enantiomers or diastereomers thereof.

Further embodiment of present invention is (xxxv) a compound of formula (IA) or pharmaceutically acceptable salts, or enantiomers or diastereomers thereof, wherein R$^1$ is chloro, bromo or methyl;

R$^2$ is hydrogen or fluoro;

R$^3$ is hydrogen or fluoro;

R$^4$ is methyl or ethyl;

R$^5$ is hydrogen or carboxy;

R$^6$ is hydrogen, methyl-O-carbonyl or carboxymethyl;

Y is —NR$^7$ or —N—R$^8$—COOH;

wherein R$^7$ is hydrogen, isopropyl, cyclopropyl or methyl-O-carbonylisopropyl;

R$^8$ is (gemdimethyl)methyl, (gemdimethyl)ethyl, (methyl)ethyl, cyclobutyl, cyclopropylmethyl or phenyl;

W is —CH$_2$— or carbonyl.

Another embodiment of present invention is (xxxvi) a compound of formula (IAB)

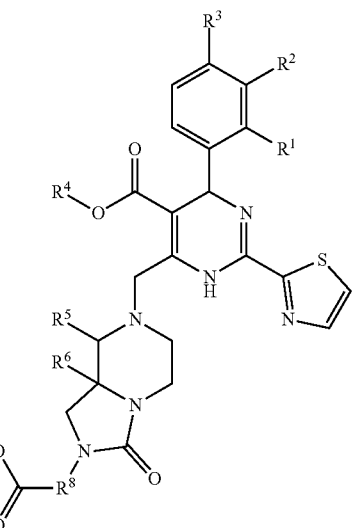

(IAB)

wherein

R$^1$ is halogen or C$_{1-6}$alkyl;

R$^2$ is hydrogen or halogen;

R$^3$ is hydrogen or halogen;

R$^4$ is C$_{1-6}$alkyl;

R$^5$ is hydrogen;

R$^6$ is hydrogen;

R$^8$ is —C$_m$H$_{2m}$—, C$_{3-7}$cycloalkyl-C$_m$H$_{2m}$— or phenyl;

m is 1-6;

or pharmaceutically acceptable salts, or enantiomers or diastereomers thereof.

Further embodiment of present invention is (xxxvii) a compound of formula (IAB) or pharmaceutically acceptable salts, or enantiomers or diastereomers thereof, wherein R$^1$ is chloro or methyl;

R$^2$ is hydrogen or fluoro;

R$^3$ is hydrogen or fluoro;

R$^4$ is methyl or ethyl;

R$^5$ is hydrogen;

R$^6$ is hydrogen;

R$^8$ is (gemdimethyl)ethyl, cyclopropylmethyl or phenyl.

Another embodiment of present invention is (xxxviii) a compound of formula (ID)

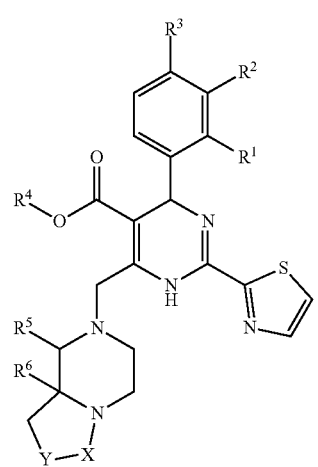

(ID)

wherein
R$^1$ is halogen or C$_{1-6}$alkyl;
R$^2$ is hydrogen or halogen;
R$^3$ is hydrogen or halogen;
R$^4$ is C$_{1-6}$alkyl;
R$^5$ is hydrogen or carboxy;
R$^6$ is hydrogen, C$_{1-6}$alkoxycarbonyl or carboxy-C$_m$H$_{2m}$—;
X is carbonyl or sulfonyl;
Y is —O—; —NR$^7$ or —N—R$^8$—COOH;
 wherein R$^7$ is hydrogen, C$_{1-6}$alkyl or C$_{3-7}$cycloalkyl;
 R$^8$ is —C$_m$H$_{2m}$—, C$_{3-7}$cycloalkyl-C$_t$H$_{2t}$— or phenyl;
m is 1-6;
t is 0-6;
or pharmaceutically acceptable salts, or enantiomers or diastereomers thereof.

Further embodiment of present invention is (xxxix) a compound of formula (ID) or pharmaceutically acceptable salts, or enantiomers or diastereomers thereof, wherein
R$^1$ is chloro, bromo or methyl;
R$^2$ is hydrogen or fluoro;
R$^3$ is hydrogen or fluoro;
R$^4$ is methyl or ethyl;
R$^5$ is hydrogen or carboxy;
R$^6$ is hydrogen, methyl-O-carbonyl or carboxymethyl;
X is carbonyl or sulfonyl;
Y is —O—; —NR$^7$ or —N—R$^8$—COOH;
 wherein R$^7$ is hydrogen, isopropyl or cyclopropyl;
 R$^8$ is (gemdimethyl)ethyl, (methyl)ethyl, cyclobutyl, cyclopropylmethyl or phenyl.

Another embodiment of present invention is (xl) a compound of formula (IF)

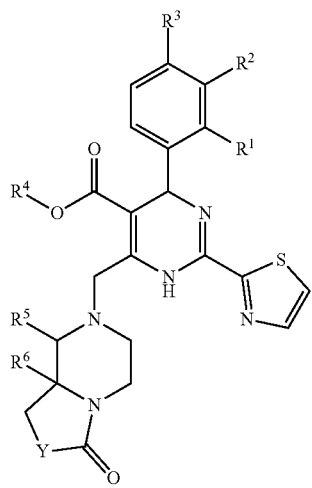

(IF)

wherein
R$^1$ is halogen or C$_{1-6}$alkyl;
R$^2$ is hydrogen or halogen;
R$^3$ is hydrogen or halogen;
R$^4$ is C$_{1-6}$alkyl;
R$^5$ is hydrogen or carboxy;
R$^6$ is hydrogen or carboxy-C$_m$H$_{2m}$—;
Y is —NR$^7$ or —N—R$^8$—COOH;
 wherein R$^7$ is C$_{1-6}$alkyl or C$_{3-7}$cycloalkyl;
 R$^8$ is —C$_m$H$_{2m}$—, C$_{3-7}$cycloalkyl-C$_t$H$_{2t}$— or phenyl;
m is 1-6;
t is 0-6;
or pharmaceutically acceptable salts, or enantiomers or diastereomers thereof.

Further embodiment of present invention is (xli) a compound of formula (IF) or pharmaceutically acceptable salts, or enantiomers or diastereomers thereof, wherein
R$^1$ is chloro or methyl;
R$^2$ is hydrogen or fluoro;
R$^3$ is hydrogen or fluoro;
R$^4$ is methyl or ethyl;
R$^5$ is hydrogen or carboxy;
R$^6$ is hydrogen or carboxymethyl;
Y is —NR$^7$ or —N—R$^8$—COOH;
 wherein R$^7$ is isopropyl or cyclopropyl;
 R$^8$ is (gemdimethyl)methyl, (gemdimethyl)ethyl, (methyl)ethyl, cyclobutyl, cyclopropylmethyl or phenyl.

Another embodiment of present invention is (xxxxii) a compound of formula (IF)

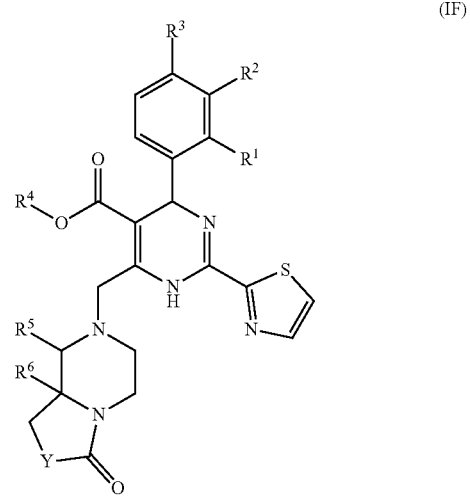

(IF)

wherein
R$^1$ is halogen or C$_{1-6}$alkyl;
R$^2$ is hydrogen or halogen;
R$^3$ is hydrogen or halogen;
R$^4$ is C$_{1-6}$alkyl;
R$^5$ is hydrogen or carboxy;
R$^6$ is hydrogen or carboxy-C$_m$H$_{2m}$—;
Y is —NR$^7$ or —N—R$^8$—COOH;
 wherein R$^7$ is hydrogen or C$_{3-7}$cycloalkyl;
 R$^8$ is —C$_m$H$_{2m}$—, C$_{3-7}$cycloalkyl-C$_m$H$_{2m}$— or phenyl;
m is 1-6;
or pharmaceutically acceptable salts, or enantiomers or diastereomers thereof.

Further embodiment of present invention is (xliii) a compound of formula (IE) or pharmaceutically acceptable salts, or enantiomers or diastereomers thereof, wherein
R$^1$ is chloro or methyl;
R$^2$ is hydrogen or fluoro;
R$^3$ is hydrogen or fluoro;
R$^4$ is methyl or ethyl;
R$^5$ is hydrogen or carboxy;
R$^6$ is hydrogen or carboxymethyl;
Y is —NR$^7$ or —N—R$^8$—COOH;
 wherein R$^7$ is hydrogen or cyclopropyl;
 R$^8$ is (gemdimethyl)ethyl, (methyl)ethyl, cyclopropylmethyl or phenyl.

Further embodiment of present invention is (xliv) a compound of formula (I), formula (IA), formula (IAA), formula (IB), formula (IC), formula (ID), formula (IE), formula (IAB), or formula (IF) or pharmaceutically acceptable salts, or enantiomers or diastereomers thereof, wherein chirality at 4-position of dihydropyrimidine core is the same as formula (I-R) below, and $R^1$, $R^2$, $R^3$, $R^4$, $R^5$, $R^6$, X, Y, W and n are as defined in any one of the above embodiment (i) to (xliii).

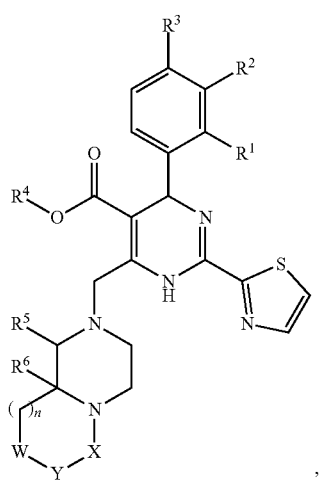

(I)

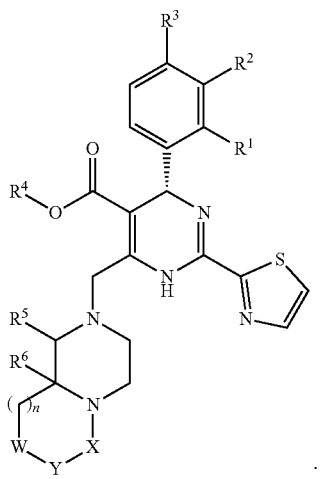

(I-R)

Particular compounds of the present invention according to the invention are the following:

Methyl (4R)-4-(2-chloro-4-fluoro-phenyl)-6-[(6-oxo-1,3,4,8,9,9a-hexahydropyrazino[1,2-c][1,3]oxazin-2-yl)methyl]-2-thiazol-2-yl-1,4-dihydropyrimidine-5-carboxylate;

Methyl (4R)-4-(2-chloro-4-fluoro-phenyl)-6-[(4-oxo-6,7,9,9a-tetrahydro-1H-pyrazino[2,1-c][1,4]oxazin-8-yl)methyl]-2-thiazol-2-yl-1,4-dihydropyrimidine-5-carboxylate;

Methyl (4R)-6-[[(8aR)-3-oxo-5,6,8,8a-tetrahydro-1H-oxazolo[3,4-a]pyrazin-7-yl]methyl]-4-(2-chloro-4-fluorophenyl)-2-thiazol-2-yl-1,4-dihydropyrimidine-5-carboxylate;

Methyl (4R)-6-[[(8aS)-3-oxo-5,6,8,8a-tetrahydro-1H-oxazolo[3,4-a]pyrazin-7-yl]methyl]-4-(2-chloro-4-fluorophenyl)-2-thiazol-2-yl-1,4-dihydropyrimidine-5-carboxylate;

Methyl (4R)-6-[[(8aS)-6-oxo-1,3,4,7,8,8a-hexahydropyrrolo[1,2-a]pyrazin-2-yl]methyl]-4-(2-chloro-4-fluorophenyl)-2-thiazol-2-yl-1,4-dihydropyrimidine-5-carboxylate;

Methyl (4R)-6-[[(8aR)-6-oxo-1,3,4,7,8,8a-hexahydropyrrolo[1,2-a]pyrazin-2-yl]methyl]-4-(2-chloro-4-fluorophenyl)-2-thiazol-2-yl-1,4-dihydropyrimidine-5-carboxylate;

Methyl (4R)-6-[[(8aR)-6-oxo-1,3,4,7,8,8a-hexahydropyrrolo[1,2-a]pyrazin-2-yl]methyl]-4-(2-bromo-4-fluorophenyl)-2-thiazol-2-yl-1,4-dihydropyrimidine-5-carboxylate;

Ethyl (4R)-6-[[(8aR)-6-oxo-1,3,4,7,8,8a-hexahydropyrrolo[1,2-a]pyrazin-2-yl]methyl]-4-(2-bromo-4-fluoro-phenyl)-2-thiazol-2-yl-1,4-dihydropyrimidine-5-carboxylate;

Ethyl (4S)-6-[[(8aR)-6-oxo-1,3,4,7,8,8a-hexahydropyrrolo[1,2-a]pyrazin-2-yl]methyl]-4-(3,4-difluorophenyl)-2-thiazol-2-yl-1,4-dihydropyrimidine-5-carboxylate;

Ethyl (4R)-4-(2-chloro-3-fluoro-phenyl)-6-[(6-oxo-3,4,7,8,9,9a-hexahydro-1H-pyrido[1,2-a]pyrazin-2-yl)methyl]-2-thiazol-2-yl-1,4-dihydropyrimidine-5-carboxylate;

Methyl (4R)-6-[[(8aR)-3-oxo-1,2,5,6,8,8a-hexahydroimidazo[1,5-a]pyrazin-7-yl]methyl]-4-(2-chloro-4-fluorophenyl)-2-thiazol-2-yl-1,4-dihydropyrimidine-5-carboxylate;

Methyl (4R)-6-[[(8aS)-3-oxo-1,2,5,6,8,8a-hexahydroimidazo[1,5-a]pyrazin-7-yl]methyl]-4-(2-chloro-4-fluorophenyl)-2-thiazol-2-yl-1,4-dihydropyrimidine-5-carboxylate;

Ethyl (4R)-6-[[(8aS)-3-oxo-1,2,5,6,8,8a-hexahydroimidazo[1,5-a]pyrazin-7-yl]methyl]-4-(2-bromo-4-fluoro-phenyl)-2-thiazol-2-yl-1,4-dihydropyrimidine-5-carboxylate;

Ethyl (4R)-6-[[(8aR)-3-oxo-1,2,5,6,8,8a-hexahydroimidazo[1,5-a]pyrazin-7-yl]methyl]-4-(2-bromo-4-fluoro-phenyl)-2-thiazol-2-yl-1,4-dihydropyrimidine-5-carboxylate;

Methyl (4R)-6-[[(8aR)-1,3-dioxo-5,6,8,8a-tetrahydroimidazo[1,5-a]pyrazin-7-yl]methyl]-4-(2-chloro-4-fluorophenyl)-2-thiazol-2-yl-1,4-dihydropyrimidine-5-carboxylate;

Methyl (4R)-6-[[(8aS)-1,3-dioxo-5,6,8,8a-tetrahydroimidazo[1,5-a]pyrazin-7-yl]methyl]-4-(2-chloro-4-fluorophenyl)-2-thiazol-2-yl-1,4-dihydropyrimidine-5-carboxylate;

Methyl (4R)-6-[[(3aS)-1,1-dioxo-2,3,3a,4,6,7-hexahydro-[1,2,5]thiadiazolo[2,3-a]pyrazin-5-yl]methyl]-4-(2-chloro-4-fluoro-phenyl)-2-thiazol-2-yl-1,4-dihydropyrimidine-5-carboxylate;

Methyl (4R)-6-[[(3aR)-1,1-dioxo-2,3,3a,4,6,7-hexahydro-[1,2,5]thiadiazolo[2,3-a]pyrazin-5-yl]methyl]-4-(2-chloro-4-fluoro-phenyl)-2-thiazol-2-yl-1,4-dihydropyrimidine-5-carboxylate;

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[(4R)-4-(2-chlorophenyl)-5-ethoxycarbonyl-2-thiazol-2-yl-1,4-dihydropyrimidin-6-yl]methyl]-3-oxo-5,6,8,8a-tetrahydro-H-imidazo[1,5-a]pyrazin-2-yl]-2-methyl-propanoic acid;

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-H-imidazo[1,5-a]pyrazin-2-yl]-2-methyl-propanoic acid;

3-[(8aS)-7-[[(4S)-4-(3,4-difluoro-2-methyl-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

Ethyl (4R)-4-(2-chloro-3-fluoro-phenyl)-6-[[2-(2-methoxyl-1,1-dimethyl-2-oxo-ethyl)-3-oxo-5,6,8,8a-tetrahydro-1H-imidazo[1,5-a]pyrazin-7-yl]methyl]-2-thiazol-2-yl-1,4-dihydropyrimidine-5-carboxylate;

Methyl 7-[[(4R)-4-(2-chloro-3-fluoro-phenyl)-5-ethoxycarbonyl-2-thiazol-2-yl-1,4-dihydropyrimidin-6-yl]methyl]-3-oxo-2,5,6,8-tetrahydro-1H-imidazo[1,5-a]pyrazine-8a-carboxylate;

(R)-6-[(S)-2-(4-Carboxy-phenyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester;

(R)-6-[(S)-2-(4-Carboxy-phenyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

(R)-6-[(S)-2-(3-Carboxy-phenyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

(R)-6-[(S)-2-(2-Carboxy-phenyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

(R)-6-[(S)-2-(3-Carboxy-phenyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester;

2-[(8aS)-7-[[(4R)-4-(2-chloro-4-fluoro-phenyl)-5-methoxycarbonyl-2-thiazol-2-yl-1,4-dihydropyrimidin-6-yl]methyl]-2-cyclopropyl-3-oxo-1,5,6,8-tetrahydroimidazo[1,5-a]pyrazin-8a-yl]acetic acid;

2-[(8aS)-7-[[(4R)-4-(2-chloro-4-fluoro-phenyl)-5-methoxycarbonyl-2-thiazol-2-yl-1,4-dihydropyrimidin-6-yl]methyl]-2-isopropyl-3-oxo-1,5,6,8-tetrahydroimidazo[1,5-a]pyrazin-8a-yl]acetic acid;

(R)-6-[(S)-2-(1-Carboxyl-1-methyl-ethyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

3-[(8aS)-7-[[(4R)-4-(2-chloro-4-fluoro-phenyl)-5-methoxycarbonyl-2-thiazo-2-yl-1,4-dihydropyrimidin-6-yl]methyl]-3-oxo-5,6,8,8a-tetrahydro-1H-imidazo[1,5-a]pyrazin-2-yl]-3-methyl-butanoic acid;

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3-methyl-butanoic acid;

1-[[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]cyclopropanecarboxylic acid;

1-[[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]cyclopropanecarboxylic acid;

3-[(8aS)-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3-methyl-butanoic acid;

1-[[(8aS)-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]cyclopropanecarboxylic acid;

3-[(2S,8aR)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclobutanecarboxylic acid;

3-[(8aR)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclobutanecarboxylic acid;

3-[(8aS)-7-[[(4R)-4-(2-chloro-3-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[(4S)-4-(3-fluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; and 7-[[(4R)-4-(2-chloro-4-fluoro-phenyl)-5-methoxycarbonyl-2-thiazol-2-yl-1,4-dihydropyrimidin-6-yl]methyl]-2-cyclopropyl-3-oxo-5,6,8,8a-tetrahydro-1H-imidazo[1,5-a]pyrazine-8-carboxylic acid.

2-[1-[(8aR)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopropyl]acetic acid;

2-[1-[(8aR)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopropyl]acetic acid;

2-[1-[(8aR)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopropyl]acetic acid;

(1R,2R)-2-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopentanecarboxylic acid;

(1S,2R)-2-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopentanecarboxylic acid;

(1R,2S)-2-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopentanecarboxylic acid;

(1S,2S)-2-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopentanecarboxylic acid;

4-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]butanoic acid;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-butanoic acid;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid;

(R)-6-[(S)-2-(2-Carboxy-ethyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

(R)-6-[(S)-2-((R)-2-Carboxyl-1-methyl-ethyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

(R)-6-[(S)-2-((S)-2-Carboxyl-1-methyl-ethyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

(R)-6-[(S)-2-(1-Carboxy-cyclobutylmethyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester;

6-[(S)-2-(1-Carboxy-cyclobutylmethyl)-3-oxo-hexahydro-imidazo[1,5-a]pyrazin-7-ylmethyl]-4-((R)-2-chloro-3-fluoro-phenyl)-2-thiazol-2-yl-1,4-dihydro-pyrimidine-5-carboxylic acid ethyl ester;

(R)-6-[(S)-2-((1R,3S)-3-Carboxy-cyclopentyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester;

(R)-6-[(S)-2-((R)-(S)-3-Carboxy-cyclopentyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

(R)-6-[(S)-2-((1R,3R)-3-Carboxy-cyclopentyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester;

(R)-6-[(S)-2-((1R,3R)-3-Carboxy-cyclopentyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

(R)-6-[2-(4-Carboxy-benzyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester;

(R)-6-[2-(4-Carboxy-benzyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

2-[2-[7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]ethoxy]acetic acid;

2-[3-[7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]propoxy]acetic acid;

methyl (4R)-4-(2-chloro-4-fluoro-phenyl)-6-[[2-(5-hydroxy-4,4-dimethyl-pentyl)-3-oxo-5,6,8,8a-tetrahydro-1H-imidazo[1,5-a]pyrazin-7-yl]methyl]-2-thiazol-2-yl-1,4-dihydropyrimidine-5-carboxylate;

ethyl (4R)-4-(2-chloro-3-fluoro-phenyl)-6-[[2-(2-hydroxy-ethyl)-3-oxo-5,6,8,8a-tetrahydro-1H-imidazo[1,5-a]pyrazin-7-yl]methyl]-2-thiazol-2-yl-1,4-dihydropyrimidine-5-carboxylate;

ethyl (4R)-4-(2-chloro-3-fluoro-phenyl)-6-[[2-(2-hydroxy-ethyl)-3-oxo-5,6,8,8a-tetrahydro-1H-imidazo[1,5-a]pyrazin-7-yl]methyl]-2-thiazol-2-yl-1,4-dihydropyrimidine-5-carboxylate;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclohexanecarboxylic acid;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclohexanecarboxylic acid;

3-[(8aS)-7-[[(4R)-4-(2-chlorophenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

2-[[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]butanoic acid;

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[4-(4-chlorophenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2-methoxy-propanoic acid;

2-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]spiro[3.3]heptane-6-carboxylic acid;

5-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]pentanoic acid;

3-[[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]cyclobutanecarboxylic acid;

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-cyclopropyl-3-oxo-5,6,8,8a-tetrahydro-1H-imidazo[1,5-a]pyrazine-8-carboxylic acid;

(8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-cyclopropyl-3-oxo-5,6,8,8a-tetrahydro-1H-imidazo[1,5-a]pyrazine-8-carboxylic acid;

(8R,8aS)-2-cyclopropyl-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

(8S,8aR)-2-cyclopropyl-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-isopropyl-3-oxo-5,6,8,8a-tetrahydro-1H-imidazo[1,5-a]pyrazine-8-carboxylic acid;

(8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-isopropyl-3-oxo-5,6,8,8a-tetrahydro-1H-imidazo[1,5-a]pyrazine-8-carboxylic acid;

(8R,8aS)-7-[[(4S)-4-(3,4-difluoro-2-methyl-phenyl)-5-methoxycarbonyl-2-thiazol-2-yl-1,4-dihydropyrimidin-6-yl]methyl]-2-isopropyl-3-oxo-5,6,8,8a-tetrahydro-1H-imidazo[1,5-a]pyrazine-8-carboxylic acid;

(8S,8aR)-7-[[(4S)-4-(3,4-difluoro-2-methyl-phenyl)-5-methoxycarbonyl-2-thiazol-2-yl-1,4-dihydropyrimidin-6-yl]methyl]-2-isopropyl-3-oxo-5,6,8,8a-tetrahydro-1H-imidazo[1,5-a]pyrazine-8-carboxylic acid;

(8R,8aS)-2-tert-butyl-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

(8S,8aR)-2-tert-butyl-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

(8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

(8R,8aS)-2-tert-butyl-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

(8S,8aR)-2-tert-butyl-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

methyl (8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-2,5,6,8-tetrahydro-1H-imidazo[1,5-a]pyrazine-8a-carboxylate;

2-[(8aS)-7-[[(4R)-4-(2-chloro-4-fluoro-phenyl)-5-methoxycarbonyl-2-thiazol-2-yl-1,4-dihydropyrimidin-6-yl]methyl]-1,1-dimethyl-3-oxo-6,8-dihydro-5H-oxazolo[3,4-a]pyrazin-8a-yl]acetic acid;

2-[(8aR)-7-[[(4R)-4-(2-chloro-4-fluoro-phenyl)-5-methoxycarbonyl-2-thiazol-2-yl-1,4-dihydropyrimidin-6-yl]methyl]-1,1-dimethyl-3-oxo-6,8-dihydro-5H-oxazolo[3,4-a]pyrazin-8a-yl]acetic acid;

(8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-methyl-3-oxo-5,6,8,8a-tetrahydro-1H-imidazo[1,5-a]pyrazine-8-carboxylic acid;

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-methyl-3-oxo-5,6,8,8a-tetrahydro-1H-imidazo[1,5-a]pyrazine-8-carboxylic acid;

Methyl (4R)-6-[[(8R,8aS)-2-tert-butyl-8-carbamoyl-3-oxo-5,6,8,8a-tetrahydro-1H-imidazo[1,5-a]pyrazin-7-yl]methyl]-4-(2-chloro-4-fluoro-phenyl)-2-thiazol-2-yl-1,4-dihydropyrimidine-5-carboxylate;

Methyl (4R)-6-[[(8S,8aR)-2-tert-butyl-8-carbamoyl-3-oxo-5,6,8,8a-tetrahydro-1H-imidazo[1,5-a]pyrazin-7-yl]methyl]-4-(2-chloro-4-fluoro-phenyl)-2-thiazol-2-yl-1,4-dihydropyrimidine-5-carboxylate;

3-[(8aS)-7-[[(4R)-4-(2-chloro-3-fluoro-phenyl)-5-propoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

4-[(8aS)-7-[[(4R)-4-(2-chloro-4-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-butanoic acid;

5-[7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]pyridine-2-carboxylic acid;

(S)-6-[(S)-2-(2-Carboxy-2,2-difluoro-ethyl)-3-oxo-hexahydro-imidazo[1,5-a]pyrazin-7-ylmethyl]-4-(3,4-difluoro-2-methyl-phenyl)-2-thiazol-2-yl-1,4-dihydro-pyrimidine-5-carboxylic acid ethyl ester;

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-(cyclopropylmethyl)-3-oxo-5,6,8,8a-tetrahydro-1H-imidazo[1,5-a]pyrazine-8-carboxylic acid;

(8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-(cyclopropylmethyl)-3-oxo-5,6,8,8a-tetrahydro-1H-imidazo[1,5-a]pyrazine-8-carboxylic acid;

3-[(8aS)-7-[[(4R)-4-(2-chloro-3-fluoro-phenyl)-5-ethoxycarbonyl-2-(4-methylthiazol-2-yl)-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

2-[[(4R)-4-(2-chloro-3-fluoro-phenyl)-5-ethoxycarbonyl-2-thiazol-2-yl-1,4-dihydropyrimidin-6-yl]methyl]-6-oxo-1,3,4,7,8,8a-hexahydropyrrolo[1,2-a]pyrazine-1-carboxylic acid;

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-isobutyl-3-oxo-5,6,8,8a-tetrahydro-1H-imidazo[1,5-a]pyrazine-8-carboxylic acid;

(8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-isobutyl-3-oxo-5,6,8,8a-tetrahydro-1H-imidazo[1,5-a]pyrazine-8-carboxylic acid;

(8R,8aR)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-oxazolo[3,4-a]pyrazine-8-carboxylic acid;

(8S,8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-oxazolo[3,4-a]pyrazine-8-carboxylic acid;

Ethyl (4R)-6-[[(8R,8aS)-2-tert-butyl-8-(hydroxymethyl)-3-oxo-5,6,8,8a-tetrahydro-1H-imidazo[1,5-a]pyrazin-7-yl]methyl]-4-(2-chloro-3-fluoro-phenyl)-2-thiazol-2-yl-1,4-dihydropyrimidine-5-carboxylate;

Ethyl (4R)-6-[[(8S,8aR)-2-tert-butyl-8-(hydroxymethyl)-3-oxo-5,6,8,8a-tetrahydro-1H-imidazo[1,5-a]pyrazin-7-yl]methyl]-4-(2-chloro-3-fluoro-phenyl)-2-thiazol-2-yl-1,4-dihydropyrimidine-5-carboxylate;

Ethyl (4R)-6-[[(8aR)-2-isopropyl-3-oxo-5,6,8,8a-tetrahydro-1H-imidazo[1,5-a]pyrazin-7-yl]methyl]-4-(2-chloro-3-fluoro-phenyl)-2-thiazol-2-yl-1,4-dihydropyrimidine-5-carboxylate; and Ethyl (4R)-6-[[(8aS)-2-isopropyl-3-oxo-5,6,8,8a-tetrahydro-1H-imidazo[1,5-a]pyrazin-7-yl]methyl]-4-(2-chloro-3-fluoro-phenyl)-2-thiazol-2-yl-1,4-dihydropyrimidine-5-carboxylate;

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-(2,2-difluoroethyl)-3-oxo-5,6,8,8a-tetrahydro-1H-imidazo[1,5-a]pyrazine-8-carboxylic acid;

(8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-(2,2-difluoroethyl)-3-oxo-5,6,8,8a-tetrahydro-1H-imidazo[1,5-a]pyrazine-8-carboxylic acid;

Ethyl (4R)-6-[[(8aR)-2-(2-hydroxy-2-methyl-propyl)-3-oxo-5,6,8,8a-tetrahydro-1H-imidazo[1,5-a]pyrazin-7-yl]

methyl]-4-(2-chloro-3-fluoro-phenyl)-2-thiazol-2-yl-1,4-dihydropyrimidine-5-carboxylate;
and Ethyl (4R)-6-[[(8aS)-2-(2-hydroxy-2-methyl-propyl)-3-oxo-5,6,8,8a-tetrahydro-1H-imidazo[1,5-a]pyrazin-7-yl]methyl]-4-(2-chloro-3-fluoro-phenyl)-2-thiazol-2-yl-1,4-dihydropyrimidine-5-carboxylate;
or pharmaceutically acceptable salts, or enantiomers or diastereomers thereof.

More particular compounds of the present invention are the following:

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[(4S)-4-(3,4-difluoro-2-methyl-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

(R)-6-[(S)-2-(4-Carboxy-phenyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester;

(R)-6-[(S)-2-(4-Carboxy-phenyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

(R)-6-[(S)-2-(3-Carboxy-phenyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester;

(R)-6-[(S)-2-(3-Carboxy-phenyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester;

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3-methyl-butanoic acid;

1-[[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]cyclopropanecarboxylic acid;

1-[[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]cyclopropanecarboxylic acid;

1-[[(8aS)-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]cyclopropanecarboxylic acid;

3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; and 3-[(8aS)-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-butanoic acid;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid;

(R)-6-[(S)-2-(1-Carboxy-cyclobutylmethyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester;

6-[(S)-2-(1-Carboxy-cyclobutylmethyl)-3-oxo-hexahydro-imidazo[1,5-a]pyrazin-7-ylmethyl]-4-((R)-2-chloro-3-fluoro-phenyl)-2-thiazol-2-yl-1,4-dihydro-pyrimidine-5-carboxylic acid ethyl ester;

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

(8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-cyclopropyl-3-oxo-5,6,8,8a-tetrahydro-1H-imidazo[1,5-a]pyrazine-8-carboxylic acid;

(8S,8aR)-2-cyclopropyl-7-[[(4S)-4-(3,4-difluoro-2-methyl-phenyl)-5-methoxycarbonyl-2-thiazol-2-yl-1,4-dihydro-pyrimidin-6-yl]methyl]-3-oxo-5,6,8,8a-tetrahydro-1H-imidazo[1,5-a]pyrazine-8-carboxylic acid;

(8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-isopropyl-3-oxo-5,6,8,8a-tetrahydro-1H-imidazo[1,5-a]pyrazine-8-carboxylic acid;

(8S,8aR)-7-[[(4S)-4-(3,4-difluoro-2-methyl-phenyl)-5-methoxycarbonyl-2-thiazol-2-yl-1,4-dihydropyrimidin-6-yl]methyl]-2-isopropyl-3-oxo-5,6,8,8a-tetrahydro-1H-imidazo[1,5-a]pyrazine-8-carboxylic acid;

(8S,8aR)-2-tert-butyl-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

(8S,8aR)-2-tert-butyl-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-methyl-3-oxo-5,6,8,8a-tetrahydro-1H-imidazo[1,5-a]pyrazine-8-carboxylic acid;

Methyl (4R)-6-[[(8R,8aS)-2-tert-butyl-8-carbamoyl-3-oxo-5,6,8,8a-tetrahydro-1H-imidazo[1,5-a]pyrazin-7-yl]methyl]-4-(2-chloro-4-fluoro-phenyl)-2-thiazol-2-yl-1,4-dihydropyrimidine-5-carboxylate;

Methyl (4R)-6-[[(8S,8aR)-2-tert-butyl-8-carbamoyl-3-oxo-5,6,8,8a-tetrahydro-1H-imidazo[1,5-a]pyrazin-7-yl]methyl]-4-(2-chloro-4-fluoro-phenyl)-2-thiazol-2-yl-1,4-dihydropyrimidine-5-carboxylate;

4-[(8aS)-7-[[(4R)-4-(2-chloro-4-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-butanoic acid;

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-(cyclopropylmethyl)-3-oxo-5,6,8,8a-tetrahydro-1H-imidazo[1,5-a]pyrazine-8-carboxylic acid;

(8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-(cyclopropylmethyl)-3-oxo-5,6,8,8a-tetrahydro-1H-imidazo[1,5-a]pyrazine-8-carboxylic acid;

2-[[(4R)-4-(2-chloro-3-fluoro-phenyl)-5-ethoxycarbonyl-2-thiazol-2-yl-1,4-dihydropyrimidin-6-yl]methyl]-6-oxo-1,3,4,7,8,8a-hexahydropyrrolo[1,2-a]pyrazine-1-carboxylic acid;

(8R,8aR)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-oxazolo[3,4-a]pyrazine-8-carboxylic acid;

(8S,8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-oxazolo[3,4-a]pyrazine-8-carboxylic acid;

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-(2,2-difluoroethyl)-3-oxo-5,6,8,8a-tetrahydro-1H-imidazo[1,5-a]pyrazine-8-carboxylic acid; and (8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-(2,2-difluoroethyl)-3-oxo-5,6,8,8a-tetrahydro-1H-imidazo[1,5-a]pyrazine-8-carboxylic acid;

or pharmaceutically acceptable salts, or enantiomers or diastereomers.

Synthesis

The compounds of the present invention can be prepared by any conventional means. Suitable processes for synthesizing these compounds as well as their starting materials are provided in the schemes below and in the examples. All substituents, in particular, $R^1$ to $R^6$, X, Y, W and n are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Compound I (Scheme 1)

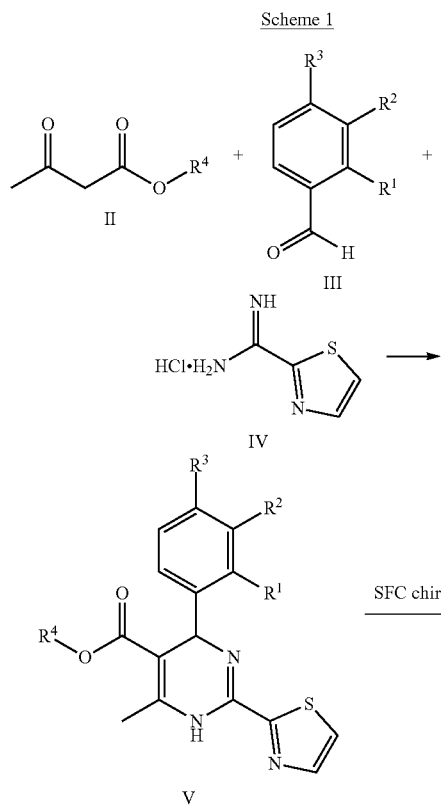

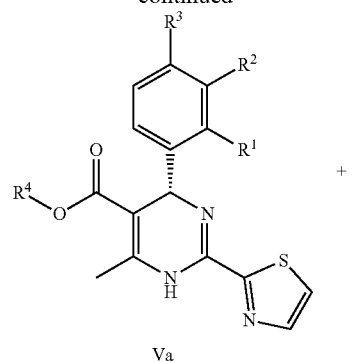

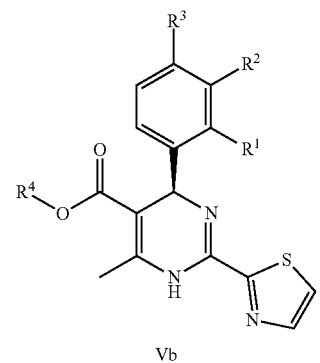

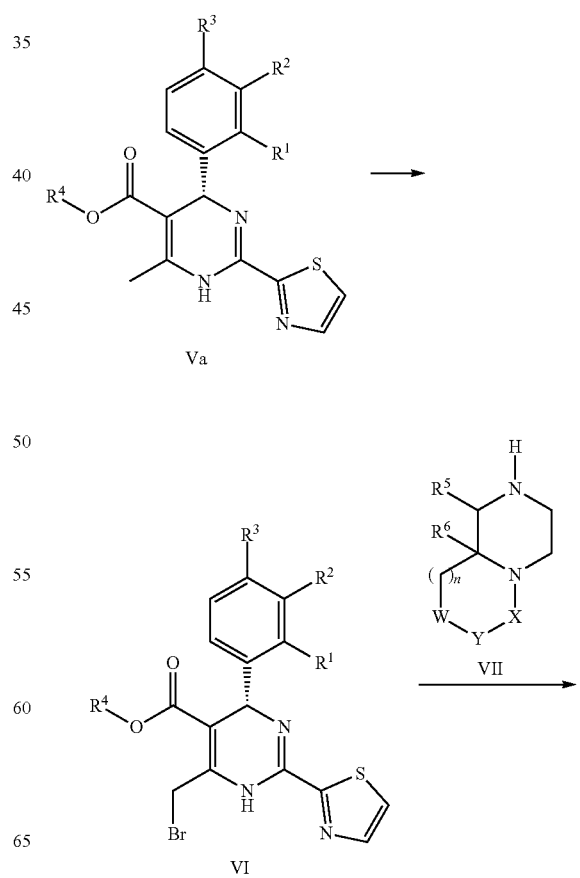

-continued

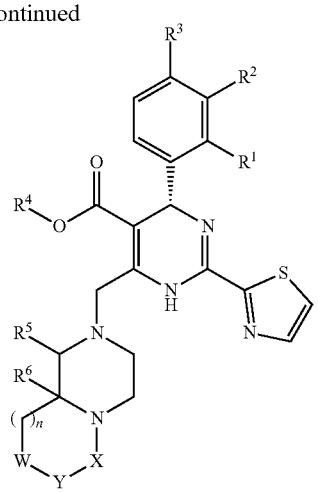

I

Compound of interest I can be prepared according to Scheme 1. A one-pot reaction between acetyl acetate II, benzaldehyde III and thiazole amidine IV gives dihydropyrimidine V. (−)-Enantiomer Va is then obtained by SFC chiral separation of V and its stereochemistry is determined by comparing its SFC retention time with one of its particular Compound B1 which stereochemistry is determined by X-ray diffraction study (FIG. 1). Bromination of Va affords VI. Coupling VI with a suitable fused amine VII gives the compound of interest I.

Dihydropyrimidine V can be prepared from condensation and cyclization sequence of acetyl acetate II, aldehyde III and thiazole amidine IV. The reaction can be carried out in a suitable alcoholic solvent such as trifluoroethanol in the presence of a base such as potassium acetate under a heating condition over several hours.

(−)-Enantiomer Va is obtained by SFC chiral separation of V.

Bromide VI can be prepared by reaction of Va with a bromination reagent such as N-bromosuccinimide, in a suitable inert solvent such as carbon tetrachloride at 80-100 degrees Celsius.

Compound of interest I can be obtained by coupling bromide VI with a fused amine VII. The reaction is typically performed in a suitable solvent such as 1,2-dichloroethane at room temperature over several hours in the presence of an organic base such as N,N-diisopropylethylamine.

General Synthetic Route for the Diastereoisomer Mixture of Compound I-I (Scheme 1-1)

Scheme 1-1

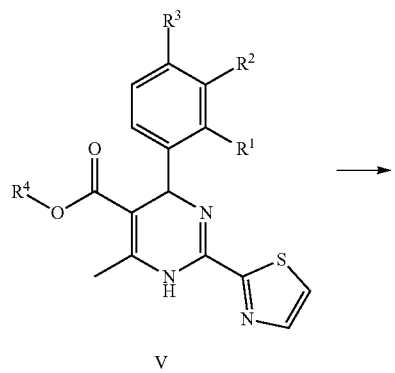

V

-continued

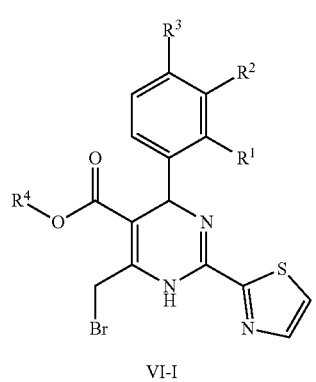 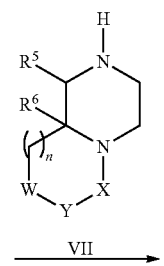

VI-I

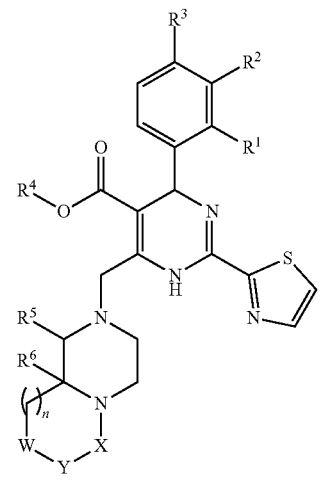

I-I

Compound of interest I-I can be prepared in analogy to compound of interest I without SFC chiral separation of dihydropyrimidine V.

For scheme 1 or scheme 1-1, the 2-thiazolyl group of general formula (I), (V), (Va), (Vb), (VI), (VI-I), (I-I) and any other compounds of this invention can be further substituted by $C_{1-6}$ alkyl, such as methyl.

This invention also relates to a process for the preparation of a compound of formula (I) or other compounds of the present invention comprising the reaction of (a) a compound of formula (A)

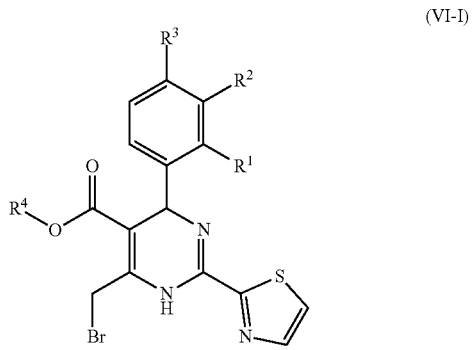

(VI-I)

with

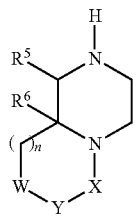

in the presence of a base;
wherein $R^1$ to $R^6$, X, Y, W and n are defined above unless otherwise indicated.

In step (a), the base can be for example N,N-diisopropylethylamine.

A compound of formula (I) or other compounds of the present invention when manufactured according to the above process is also an object of the invention.

Pharmaceutical Compositions and Administration

The invention also relates to a compound of formula (I) or other compounds of the present invention for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) or other compounds of the present invention may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) or a compound of the present invention is formulated in an acetate buffer, at pH 5. In another embodiment, the compounds of formula (I) and other compounds of the present invention are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular human being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to the suppression of serum HBV DNA levels, or HBeAg seroconversion to HBeAb, or HBsAg loss, or normalization of alanine aminotransferase levels and improvement in liver histology. For example, such amount may be below the amount that is toxic to normal cells, or the human as a whole.

In one example, the pharmaceutically effective amount of the compound of the invention administered parenterally per dose will be in the range of about 0.01 to 100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 mg to 1000 mg of the compound of the invention compounded with about 30 mg to 90 mg anhydrous lactose, about 5 mg to 40 mg sodium croscarmellose, about 5 mg to 30 mg polyvinylpyrrolidone (PVP) K30, and about 1 mg to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I), or a stereoisomer or pharmaceutically acceptable salt thereof. In a further embodiment includes a pharmaceutical composition comprising a compound of formula (I), or a stereoisomer or pharmaceutically acceptable salt thereof, together with a pharmaceutically acceptable carrier or excipient.

The following example A and B illustrate typical compositions of the present invention, but serve merely as representative thereof.

EXAMPLE A

A compound of the present invention can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

EXAMPLE B

A compound of the present invention can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBV's de novo DNA synthesis and reduce HBV DNA levels. Accordingly, the compounds of the invention are useful for the treatment or prophylaxis of HBV infection.

The compounds of inventions are useful as HBV capsid inhibitors.

The invention relates to the use of a compound of formula (I) or a compound of the present invention for the treatment or prophylaxis of HBV infection.

The use of a compound of formula (I) or a compound of the present invention for the preparation of medicaments useful in the treatment or prophylaxis diseases that are related to HBV infection is an object of the invention.

The invention relates in particular to the use of a compound of formula (I) or a compound of the present invention for the preparation of a medicament for the treatment or prophylaxis of HBV infection.

Another embodiment includes a method for the treatment or prophylaxis of HBV infection which method comprises administering an effective amount of a compound of formula (I), a stereoisomer, tautomer, prodrug or pharmaceutically acceptable salt thereof.

Combination Therapy

The compounds of the invention can be used together with interferon, pegylated interferons, Lamivudine, Adefovir dipivoxil, Entecavir, Telbivudine, and Tenofovir disoproxil for the treatment or prophylaxis of HBV.

BRIEF DESCRIPTION OF THE FIGURE

FIG. 1. X-ray crystal structure of Compound B1

EXAMPLES

The invention will be more fully understood by reference to the following examples. They should not, however, be construed as limiting the scope of the invention.

Abbreviations used herein are as follows:

$[\alpha]_D^{20}$: optical rotation at 20 degrees Celsius
BOMCl benzylchloromethyl ester
calc'd: calculated
$CC_{50}$: concentration results in the death of 50 percent of the cells
CCK-8: cell counting kit-8
$CCl_4$: carbon tetrachloride
Ct: cycle threshold
d: day
DIPEA: N,N-diisopropylethylamine
DCM: dichloromethylene
PE: petroleum ether
DMSO: dimethylsulfoxide
DEA: diethyl amine
DNA: deoxyribonucleic acid
EtOH: ethanol
EtOAc or EA: ethyl acetate
g: gram
$EC_{50}$: half maximal effective concentration
h or hr: hour
hrs: hours
HAP: heteroaryldihydropyrimidine
HATU: 1-[Bis(dimethylamino)methylene]-1H-1,2,3-triazolo[4,5-b]pyridinium 3-oxid hexafluorophosphate
HBeAb: hepatitis B e antibody
HBeAg: hepatitis B e antigen
HBsAg: hepatitis B surface antigen
HCl: hydrogen chloride
HPLC: high performance liquid chromatography
HPLC-UV: high performance liquid chromatography with ultraviolet detector
Hz: hertz
IPA: isopropanol
LDA: lithium diisopropylamide
METHANOL-$d_4$: deuterated methanol
MeOH: methanol
mg: milligram
MHz: megahertz
min: minute
mins: minutes
mL: milliliter
mm: millimeter
mM: mmol/L
mmol: millimole
MS: mass spectrometry
MW: molecular weight
$Na_2SO_4$: sodium sulfate
NaOH: sodium hydroxide
NBS: N-bromosuccinimide
NMR: nuclear magnetic resonance PBS: phosphate buffered saline
PD: pharmacodynamics
PK: pharmacokinetics
prep-HPLC: preparative high performance liquid chromatography
rt: room temperature
sat. saturated
SFC: supercritical fluid chromatography
TEA: triethylamine
Tet: tetracycline
TFA: trifluoroacetic acid
THF: tetrahydrofuran
μg: microgram
μL: microliter
μM: micromole
UV: ultraviolet detector
OD: optical density
pgRNA: pre-genomic RNA
qPCR: quantitative polymerase chain reaction
qRT-PCR: quantitative real-time polymerase chain reaction
CYP: cytochromes P450
[Ir(COD)$_2$Cl]$_2$: bis(1,5-cyclooctadiene)diiridium(I) dichloride
Cs$_2$CO$_3$: cesium carbonate
Pd(OAc)$_2$: palladium(II) acetate
NaBH$_4$: sodium borohydride
RuCl$_3$: ruthenium(III) chloride General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 μm, OBD™ 30×100 mm) column or SunFire™ Prep-C18 (5 μm, OBD™ 30×100 mm) column. Waters AutoP purification System (Column: XBridge™ Prep-C18, 30×100 mm, Sample Manager 2767, Pump 2525, Detector: Micromass ZQ and UV 2487, solvent system: acetonitrile and 0.1% ammonium hydroxide in water). For SFC chiral separation, intermediates were separated by chiral column (Daicel chiralpak IC, 5 μm, 30×250 mm) column using Mettler Toledo SFC-Multigram III system, solvent system: 95% CO$_2$ and 5% IPA (0.5% TEA in IPA), back pressure 100 bar, detection UV@ 254 nm.

LC/MS spectra of compounds were obtained using a LC/MS (Waters™ Alliance 2795-Micromass ZQ), LC/MS conditions were as follows (running time 6 min):

Acidic condition: A: 0.1% formic acid in H$_2$O; B: 0.1% formic acid in acetonitrile;

Basic condition: A: 0.1% NH$_3$.H$_2$O in H$_2$O; B: acetonitrile;

Neutral condition: A: H$_2$O; B: acetonitrile.

Mass spectra (MS): generally only ions which indicate the parent mass are reported, and unless otherwise stated the mass ion quoted is the positive mass ion (MH)$^+$.

NMR Spectra were obtained using Bruker Avance 400 MHz.

A single crystal was mounted in a loop and cooled to 160 K in a nitrogen stream. Data were collected on a Gemini R Ultra diffractometer (Oxford Diffraction, UK) with Cu-K-alpha-radiation (1.54178 Å) and processed with the Crysalis-package. Structure solution and refinement was performed using the ShelXTL software (Bruker AXS, Karlsruhe)

The microwave assisted reactions were carried out in a Biotage Initiator Sixty microwave synthesizer.

All reactions involving air-sensitive reagents were performed under an argon atmosphere. Reagents were used as received from commercial suppliers without further purification unless otherwise noted.

Preparative Examples

The invention will be more fully understood by reference to the following examples. They should not, however, be construed as limiting the scope of the invention.

Example 1

Methyl (4R)-4-(2-chloro-4-fluoro-phenyl)-6-[(6-oxo-1,3,4,8,9,9a-hexahydropyrazino[1,2-c][1,3]oxazin-2-yl)methyl]-2-thiazol-2-yl-1,4-dihydropyrimidine-5-carboxylate

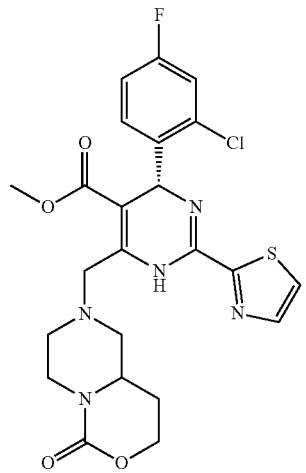

The title compound was prepared according to the general synthetic routes shown in Scheme 1. A detailed synthetic route is provided in Scheme 2.

Scheme 2

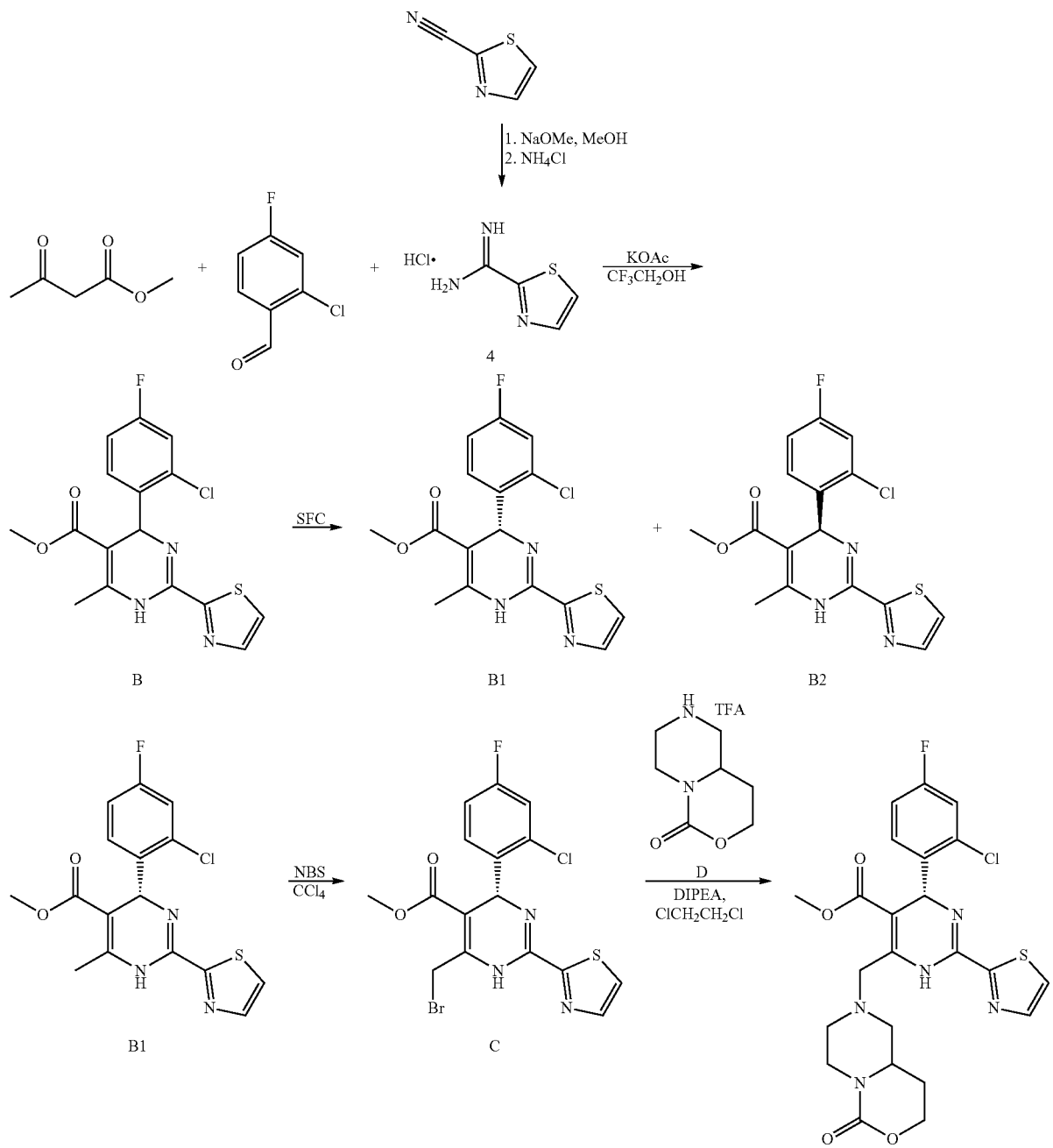

Preparation of Compound A

To a stirred solution of thiazole-2-carbonitrile (1.5 g, 14 mmol) in 5 mL of dry MeOH was added dropwise a solution of sodium methoxide (0.74 g, 14 mmol) in 10 mL of dry methanol. The reaction mixture was stirred at room temperature until the disappearance of starting material. After that, ammonium chloride (1.5 g, 28 mmol) was added in one portion and the reaction mixture was stirred overnight. The undissolved material was removed by filtration and the filtrate was concentrated to afford thiazole-2-carboxamidine hydrochloride (Compound A) as a grey solid which was used directly in the next step without further purification. MS: calc'd 128 (MH$^+$), measured 128 (MH$^+$).

Preparation of Compound B

To a stirred solution of thiazole-2-carboxamidine hydrochloride (0.13 g, 1.0 mmol), methyl acetoacetate (0.12 g, 1.0 mmol) and 2-chloro-4-fluorobenzaldehyde (0.16 g, 1.0 mmol) in trifluoroethanol (8 mL) was added potassium acetate (0.20 g, 2.0 mmol). The reaction mixture was refluxed for 16 hours. After it was cooled to room temperature, the reaction mixture was concentrated and the residue was dissolved in ethyl acetate and then washed with brine. The organic layer was dried over sodium sulfate. The solvent was concentrated, and the residue was purified by column chromatography (ethyl acetate/petroleum ether is from 1/4 to 1/2) to afford 4-(2-chloro-4-fluoro-phenyl)-6-methyl-2-thiazol-2-yl-1,4-dihydro-pyrimidine-5-carb oxylic acid methyl ester (Compound B) as a yellow solid. MS: calc'd (MH$^+$) 366, measured (MH$^+$) 366.

Preparation of Compound B1

The enantiomer (R)-4-(2-chloro-4-fluoro-phenyl)-6-methyl-2-thiazol-2-yl-1,4-dihydro-pyrimidine-5-carboxylic acid methyl ester (Compound B1) was obtained through SFC (SFC-Multigram; IC: 5×250 mm, 5µ) chiral separation of 4-(2-chloro-4-fluoro-phenyl)-6-methyl-2-oxazol-2-yl-1,4-dihydro-pyrimidine-5-carboxylic acid methyl ester (Compound B) eluting with a mixed solvent of 85% supercritical CO$_2$/15% EtOH at 100 mL/min rate. The desired (−)-enantiomer B1 was eluted out before (+)-enantiomer B2. The absolute configuration of (−)-enantiomer B1 was determined by X-ray diffraction study (FIG. 1).

Compound B1: $[\alpha]_D^{20}$ −55.0 (c 0.845, MeOH).
Compound B2: $[\alpha]_D^{20}$ +44.6 (c 0.175, MeOH).

Preparation of Compound C

To a stirred solution of (R)-4-(2-chloro-4-fluoro-phenyl)-6-methyl-2-thiazol-2-yl-1,4-dihydro-pyrimidine-5-carboxylic acid methyl ester (0.37 g, 1.0 mmol) in CCl$_4$ (5 mL) was added NBS (0.20 g, 1.1 mmol) in portions. After the reaction mixture was stirred at room temperature for 1 hour, the solvent was removed in vacuo and the residue was purified by column chromatography to give (R)-6-bromomethyl-4-(2-chloro-4-fluoro-phenyl)-2-thiazol-2-yl-1,4-dihydro-pyrimidine-5-carboxylic acid methyl ester (Compound C) as a yellow solid. MS: calc'd 445 (MH$^+$), measured 445 (MH$^+$).

Preparation of hexahydro-pyrazino[1,2-c][1,3]oxazin-6-one (Compound D)

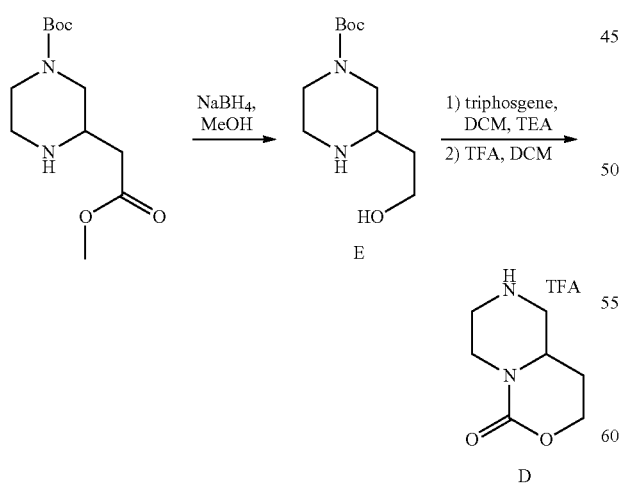

Step 1: Methyl 4-boc-piperazine-2-acetate (CAS number: 183742-33-8, Chemfinder) (1.0 g, 4 mmol) was dissolved in 10 mL of MeOH, then NaBH$_4$ (1.5 g, 40 mmol) was added portion wise and stirred overnight. The solvent was removed in vacuo and the residue was partitioned between EtOAC and water. The organic layer was separated, and then dried over Na$_2$SO$_4$ and concentrated to give 3-(2-hydroxy-ethyl)-piperazine-1-carboxylic acid tert-butyl ester as crude oil (compound E), which was used directly without further purification.

Step 2: 3-(2-Hydroxy-ethyl)-piperazine-1-carboxylic acid tert-butyl ester (58 mg, 0.25 mmol) was dissolved in 4 mL of dichloromethane and 1 mL of DIPEA, and then triphosgene (27 mg, 0.09 mmol) was added at room temperature. The reaction mixture was stirred for 30 minutes, and the solvent was removed in vacuo. The residue was dissolved in 3 mL of dichloromethane and 1 mL of TFA. After the reaction mixture was stirred for 1 hour, the solvent was removed in vacuo to give hexahydro-pyrazino[1,2-c][1,3]oxazin-6-one trifluoro acetitic acid salt (Compound D) as a crude product which was used directly without further purification. LC/MS: calc'd 157 (MH$^+$), exp 157 (MH$^+$).

Preparation of Example 1

To a stirred solution of (R)-6-bromomethyl-4-(2-chloro-4-fluoro-phenyl)-2-thiazol-2-yl-1,4-dihydro-pyrimidine-5-carboxylic acid methyl ester (0.072 g, 0.16 mmol) and hexahydro-pyrazino[1,2-c][1,3]oxazin-6-one trifluoro acetitic acid salt (Compound D, crude, 0.25 mmol) in 1,2-dichloroethane (5 mL) was added dropwise DIPEA (0.078 mL, 0.45 mmol). The reaction mixture was stirred at room temperature until the disappearance of starting material. The mixture was diluted with EtOAc (50 mL) and washed successively with saturated aqueous NH$_4$Cl solution and brine. The organic layer was separated and then dried over Na$_2$SO$_4$. The solvent was concentrated in vacuo and the crude product was purified by prep-HPLC to give methyl (4R)-4-(2-chloro-4-fluoro-phenyl)-6-[(6-oxo-1,3,4,8,9,9a-hexahydropyrazino[1,2-c][1,3]oxazin-2-yl)methyl]-2-thiazol-2-yl-1,4-dihydropyrimidine-5-carboxylate (Example 1) as a light yellow solid (11 mg). $^1$H NMR (400 MHz, METHANOL-d$_4$) d ppm 7.97 (dd, J=3.01, 1.00 Hz, 1H), 7.81 (d, J=3.01 Hz, 1H), 7.46 (dd, J=8.66, 6.15 Hz, 1H), 7.26 (dd, J=8.78, 2.51 Hz, 1H), 7.00-7.13 (m, 1H), 6.19 (d, J=1.76 Hz, 1H), 4.19-4.48 (m, 4H), 4.11 (d, J=16.06 Hz, 1H), 3.76-3.94 (m, 1H), 3.62 (s, 3H), 3.18-3.31 (m, 2H), 2.37-2.80 (m, 3H), 2.11-2.30 (m, 1H), 1.90 (qdd, J=14.37, 14.37, 14.37, 9.22, 5.40 Hz, 1 H). MS: calc'd 520 (MH$^+$), measured 520 (MH$^+$).

Example 2

Methyl (4R)-4-(2-chloro-4-fluoro-phenyl)-6-[(4-oxo-6,7,9,9a-tetrahydro-1H-pyrazino[2,1-c][1,4]oxazin-8-yl)methyl]-2-thiazol-2-yl-1,4-dihydropyrimidine-5-carboxylate

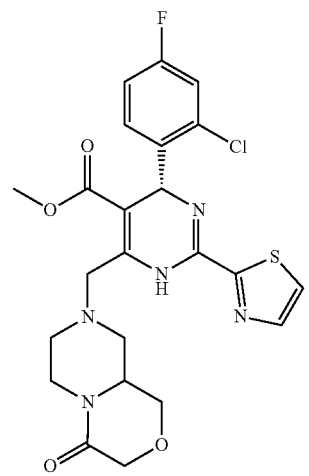 [SMILES: COC(=O)C1=C(CN2CCN3C(=O)COCC3C2)NC(c2nccs2)=N[C@H]1c1ccc(F)cc1Cl]

The title compound was prepared in analogy to Example 1 by using 1,6,7,8,9,9a-hexahydropyrazino[2,1-c][1,4]oxazin-4-one (WuXi AppTec (Wuhan) Co., Ltd, catalog number: WX111240; for its synthesis, please refer to: Tang, Pengcho et al., PCT Int. Appl., 2012019426) instead of hexahydro-pyrazino[1,2-c][1,3]oxazin-6-one (Compound D). Example 2 was obtained as a light yellow solid (9 mg). $^1$H NMR (400 MHz, METHANOL-$d_4$) d ppm 7.96 (d, J=3.14 Hz, 1H), 7.76 (d, J=3.14 Hz, 1H), 7.43 (dd, J=8.72, 6.09 Hz, 1H), 7.24 (dd, J=8.72, 2.57 Hz, 1H), 6.96-7.12 (m, 1H), 6.18 (d, J=2.26 Hz, 1H), 4.46-4.66 (m, 1H), 4.05-4.22 (m, 3H), 3.77-4.05 (m, 3H), 3.53-3.73 (m, 4H), 2.94-3.13 (m, 2H), 2.81-2.94 (m, 1H), 2.15-2.52 (m, 2 H). MS: calc'd 520 (MH$^+$), measured 520 (MH$^+$).

Example 3

Methyl (4R)-6-[[(8aR)-3-oxo-5,6,8,8a-tetrahydro-1H-oxazolo[3,4-a]pyrazin-7-yl]methyl]-4-(2-chloro-4-fluoro-phenyl)-2-thiazol-2-yl-1,4-dihydropyrimidine-5-carboxylate

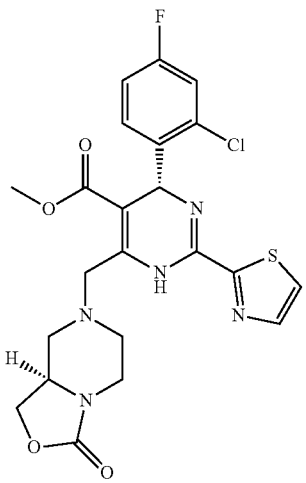 [SMILES: COC(=O)C1=C(CN2CCN3C(=O)OC[C@H]3C2)NC(c2nccs2)=N[C@H]1c1ccc(F)cc1Cl]

The title compound was prepared in analogy to Example 1 by using (S)-4-N-Boc-2-hydroxymethyl-piperazine (CAS number: 314741-40-7, Bepharm) instead of 3-(2-hydroxyethyl)-piperazine-1-carboxylic acid tert-butyl ester (Compound E). Example 3 was obtained as a light yellow solid (21 mg). $^1$H NMR (400 MHz, METHANOL-$d_4$) d ppm 7.93-8.00 (m, 1H), 7.73-7.84 (m, 1H), 7.40-7.50 (m, 1H), 7.25 (dd, J=8.66, 2.64 Hz, 1H), 7.00-7.12 (m, 1H), 6.15-6.22 (m, 1H), 4.42-4.57 (m, 1H), 4.25 (d, J=16.81 Hz, 1H), 4.13-4.22 (m, 1H), 3.99-4.13 (m, 2H), 3.78-3.90 (m, 1H), 3.56-3.67 (m, 3H), 3.29-3.39 (m, 1H), 3.25 (d, J=9.03 Hz, 1H), 2.96 (d, J=11.04 Hz, 1H), 2.30-2.61 (m, 2 H). MS: calc'd 506 (MH$^+$), measured 506 (MH$^+$).

Example 4

Methyl (4R)-6-[[(8aS)-3-oxo-5,6,8,8a-tetrahydro-1H-oxazolo[3,4-a]pyrazin-7-yl]methyl]-4-(2-chloro-4-fluoro-phenyl)-2-thiazol-2-yl-1,4-dihydropyrimidine-5-carboxylate

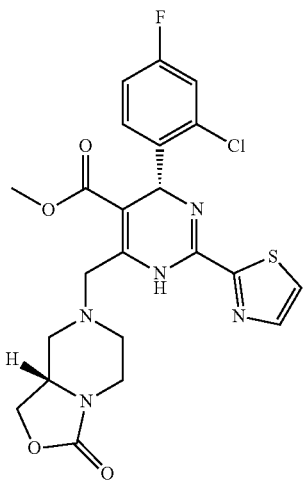 [SMILES: COC(=O)C1=C(CN2CCN3C(=O)OC[C@@H]3C2)NC(c2nccs2)=N[C@H]1c1ccc(F)cc1Cl]

The title compound was prepared in analogy to Example 1 by using (R)-4-N-boc-2-hydroxymethyl-piperazine (CAS number: 278788-66-2, Bepharm) instead of 3-(2-hydroxyethyl)-piperazine-1-carboxylic acid tert-butyl ester (Compound E). Example 4 was obtained as a light yellow solid (20 mg). $^1$H NMR (400 MHz, METHANOL-$d_4$) d ppm 7.92-8.00 (m, 1H), 7.78 (d, J=3.26 Hz, 1H), 7.44 (dd, J=8.78, 6.02 Hz, 1H), 7.25 (dd, J=8.66, 2.64 Hz, 1H), 7.01-7.12 (m, 1H), 6.14-6.21 (m, 1H), 4.46 (t, J=8.53 Hz, 1H), 4.18-4.26 (m, 1H), 4.08-4.18 (m, 1H), 3.97-4.08 (m, 2H), 3.82-3.93 (m, 1H), 3.53-3.67 (m, 3H), 3.34-3.40 (m, 1H), 3.08 (d, J=10.54 Hz, 2H), 2.46-2.60 (m, 1H), 2.28-2.44 (m, 1 H). MS: calc'd 506 (MH$^+$), measured 506 (MH$^+$).

Example 5

Methyl (4R)-6-[[(8aS)-6-oxo-1,3,4,7,8,8a-hexahydropyrrolo[1,2-a]pyrazin-2-yl]methyl]-4-(2-chloro-4-fluoro-phenyl)-2-thiazol-2-yl-1,4-dihydropyrimidine-5-carboxylate

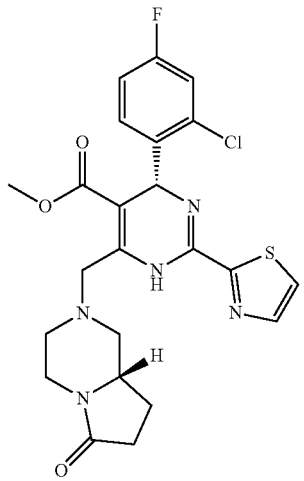 [SMILES: COC(=O)C1=C(CN2CCN3C(=O)CC[C@H]3C2)NC(c2nccs2)=N[C@H]1c1ccc(F)cc1Cl]

The title compound was prepared by SFC chiral separation of methyl (4R)-4-(2-chloro-4-fluoro-phenyl)-6-[(6-oxo-1,3,4,7,8,8a-hexahydropyrrolo[1,2-a]pyrazin-2-yl)methyl]-2-thiazol-2-yl-1,4-dihydropyrimidine-5-carboxylate (Compound F). Example 5 was obtained as a light yellow solid (14 mg). ¹H NMR (400 MHz, METHANOL-$d_4$) d ppm 7.90-7.99 (m, 1H), 7.72-7.82 (m, 1H), 7.36-7.52 (m, 1H), 7.20-7.31 (m, 1H), 7.06 (td, J=8.41, 2.76 Hz, 1H), 6.18 (s, 1H), 4.18 (d, J=17.07 Hz, 1H), 3.97-4.04 (m, 2H), 3.86-3.97 (m, 1H), 3.61 (s, 3H), 3.21 (d, J=9.29 Hz, 1H), 3.03-3.16 (m, 1H), 2.83-2.95 (m, 1H), 2.36-2.56 (m, 2H), 2.19-2.35 (m, 3H), 1.66-1.82 (m, 1 H). MS: calc'd 504 (MH⁺), measured 504 (MH⁺).

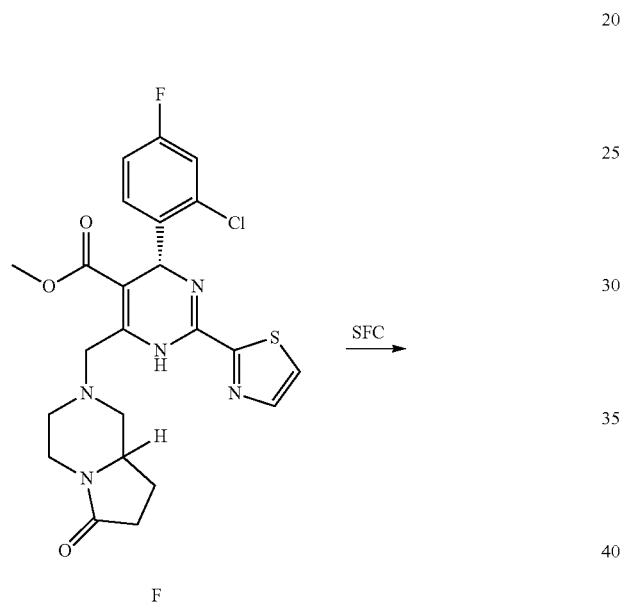

F

SFC →

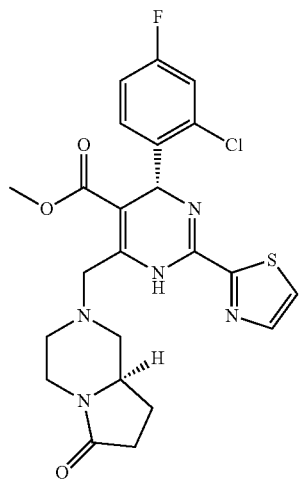

Example 6

Preparation of methyl (4R)-4-(2-chloro-4-fluoro-phenyl)-6-[(6-oxo-1,3,4,7,8,8a-hexahydropyrrolo[1,2-a]pyrazin-2-yl)methyl]-2-thiazol-2-yl-1,4-dihydropyrimidine-5-carboxylate (Compound F)

Compound F was prepared in analogy to Example 1 by using hexahydropyrrolo[1,2-a]pyrazin-6(2H)-one (CAS number: 117810-52-3, Bepharm; for its synthesis, please refer to: Alvaro G., Large C. *PCT Int. Appl.*, 2008090115) instead of hexahydro-pyrazino[1,2-c][1,3]oxazin-6-one (Compound D).

Example 6

Methyl (4R)-6-[[(8aR)-6-oxo-1,3,4,7,8,8a-hexahydropyrrolo[1,2-a]pyrazin-2-yl]methyl]-4-(2-chloro-4-fluoro-phenyl)-2-thiazol-2-yl-1,4-dihydropyrimidine-5-carboxylate

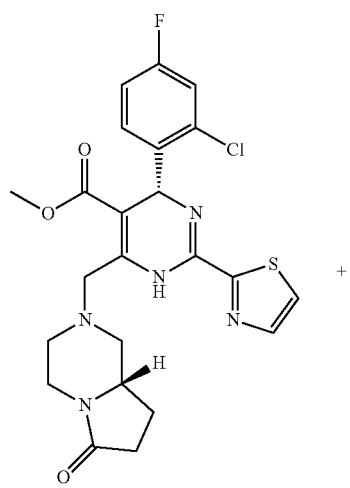

Example 5

+

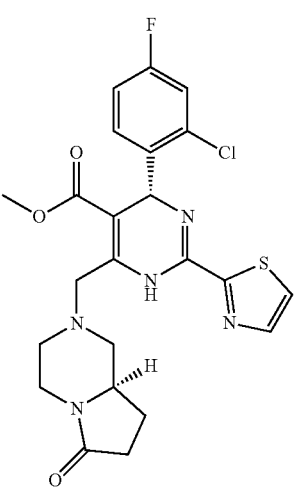 [SMILES: COC(=O)C1=C(CN2CCN3C(=O)CC[C@@H]3C2)NC(c2nccs2)=N[C@H]1c1ccc(F)cc1Cl]

The title compound was prepared by SFC chiral separation of methyl (4R)-4-(2-chloro-4-fluoro-phenyl)-6-[(6-oxo-1,3,4,7,8,8a-hexahydropyrrolo[1,2-a]pyrazin-2-yl)methyl]-2-thiazol-2-yl-1,4-dihydropyrimidine-5-carboxylate (Compound F) in Example 5. Example 6 was obtained as a light yellow solid (14 mg). $^1$H NMR (400 MHz, METHANOL-$d_4$) d ppm 7.87-8.01 (m, 1H), 7.71-7.81 (m, 1H), 7.36-7.49 (m, 1H), 7.19-7.29 (m, 1H), 7.06 (td, J=8.41, 2.51 Hz, 1H), 6.18 (s, 1H), 4.11-4.21 (m, 1H), 4.06 (dd, J=12.55, 3.01 Hz, 1H), 3.95-4.02 (m, 1H), 3.89 (dtd, J=10.73, 7.25, 7.25, 3.64 Hz, 1H), 3.53-3.65 (m, 3H), 3.01-3.19 (m, 3H), 2.33-2.54 (m, 3H), 2.22 (dddd, J=13.08, 9.38, 7.65, 4.02 Hz, 1H), 2.12 (t, J=10.92 Hz, 1H), 1.61-1.76 (m, 1 H). MS: calc'd 504 (MH$^+$), measured 504 (MH$^+$).

Example 7

Methyl (4R)-6-[[(8aR)-3-oxo-5,6,8,8a-tetrahydro-1H-oxazolo[3,4-a]pyrazin-7-yl]methyl]-4-(2-chloro-4-fluoro-phenyl)-2-thiazol-2-yl-1,4-dihydropyrimidine-5-carboxylate

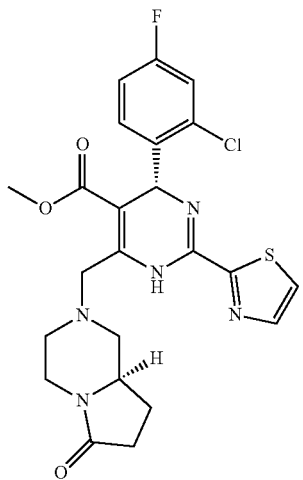 [SMILES: COC(=O)C1=C(CN2CCN3C(=O)CC[C@@H]3C2)NC(c2nccs2)=N[C@H]1c1ccc(F)cc1Cl]

The title compound was prepared in analogy to Example 1 by using 2-bromo-4-fluorobenzaldehyde and (8aR)-2,3,4,7,8,8a-hexahydro-1H-pyrrolo[1,2-a]pyrazin-6-one (for its synthesis, refer to: Tang P., et al, *PCT Int. Appl.*, 2012019426) instead of 2-chloro-4-fluorobenzaldehyde and hexahydro-pyrazino[1,2-c][1,3]oxazin-6-one (Compound D). Example 7 was obtained as a light yellow solid (19 mg). $^1$H NMR (400 MHz, METHANOL-$d_4$) d ppm 7.95 (d, J=3.26 Hz, 1H), 7.76 (d, J=3.01 Hz, 1H), 7.35-7.48 (m, 2H), 7.11 (td, J=8.41, 2.76 Hz, 1H), 6.17 (s, 1H), 4.09-4.19 (m, 1H), 4.05 (dd, J=12.80, 2.76 Hz, 1H), 3.93-4.01 (m, 1H), 3.89 (dtd, J=10.63, 7.23, 7.23, 3.76 Hz, 1H), 3.61 (s, 3H), 2.95-3.18 (m, 3H), 2.31-2.54 (m, 3H), 2.15-2.28 (m, 1H), 2.08 (t, J=10.92 Hz, 1H), 1.61-1.75 (m, 1 H). MS: calc'd 548 (MH$^+$), measured 548 (MH$^+$).

Example 8

Ethyl (4R)-6-[[(8aR)-6-oxo-1,3,4,7,8,8a-hexahydro-pyrrolo[1,2-a]pyrazin-2-yl]methyl]-4-(2-bromo-4-fluoro-phenyl)-2-thiazol-2-yl-1,4-dihydropyrimidine-5-carboxylate

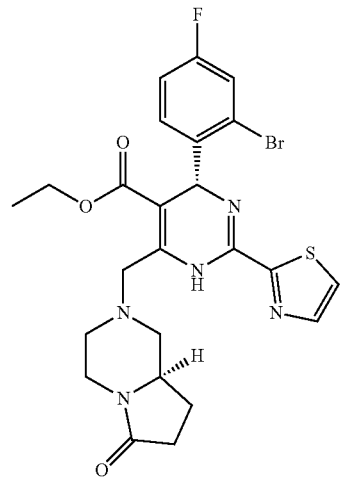 [SMILES: CCOC(=O)C1=C(CN2CCN3C(=O)CC[C@@H]3C2)NC(c2nccs2)=N[C@H]1c1ccc(F)cc1Br]

The title compound was prepared in analogy to Example 1 by using 2-bromo-4-fluorobenzaldehyde, ethyl acetoacetate and (8aR)-2,3,4,7,8,8a-hexahydro-1H-pyrrolo[1,2-a]pyrazin-6-one (for its synthesis, refer to: Tang P., et al, *PCT Int. Appl.*, 2012019426) instead of 2-chloro-4-fluorobenzaldehyde, methyl acetoacetate and hexahydro-pyrazino[1,2-c][1,3]oxazin-6-one (Compound D). Example 8 was obtained as a light yellow solid (8 mg). $^1$H NMR (400 MHz, METHANOL-$d_4$) d ppm 7.95 (d, J=3.01 Hz, 1H), 7.76 (d, J=3.26 Hz, 1H), 7.36-7.53 (m, 2H), 7.12 (td, J=8.34, 2.64 Hz, 1H), 6.18 (s, 1H), 4.11-4.17 (m, 1H), 4.05 (q, J=6.86 Hz, 2H), 3.97 (d, J=16.81 Hz, 1H), 3.83-3.93 (m, 1H), 2.94-3.19 (m, 3H), 2.30-2.53 (m, 3H), 2.22 (ddd, J=16.75, 12.86, 3.51 Hz, 1H), 2.07 (t, J=10.67 Hz, 1H), 1.61-1.75 (m, 1H), 1.15 (t, J=7.15 Hz, 3 H). MS: calc'd 562 (MH$^+$), measured 562 (MH$^+$).

Example 9

Ethyl (4S)-6-[[(8aR)-6-oxo-1,3,4,7,8,8a-hexahydro-pyrrolo[1,2-a]pyrazin-2-yl]methyl]-4-(3,4-difluoro-phenyl)-2-thiazol-2-yl-1,4-dihydropyrimidine-5-carboxylate

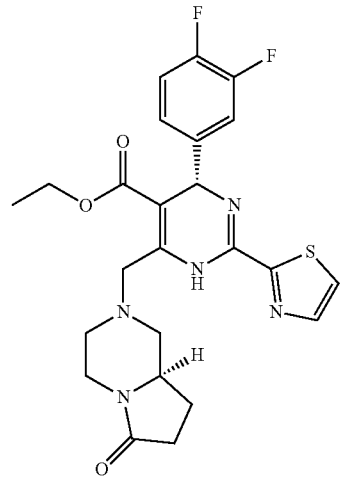 [SMILES: CCOC(=O)C1=C(CN2CCN3C(=O)CC[C@@H]3C2)NC(c2nccs2)=N[C@H]1c1ccc(F)c(F)c1]

The title compound was prepared in analogy to Example 1 by using 3,4-difluorobenzaldehyde, ethyl acetoacetate and (8aR)-2,3,4,7,8,8a-hexahydro-1H-pyrrolo[1,2-a]pyrazin-6-one (for its synthesis, refer to: Tang P., et al, *PCT Int. Appl.*, 2012019426) instead of 2-chloro-4-fluorobenzaldehyde, methyl acetoacetate and hexahydro-pyrazino[1,2-c][1,3]oxazin-6-one (Compound D). Example 9 was obtained as a light yellow solid (11 mg). $^1$H NMR (400 MHz, METHANOL-$d_4$) d ppm 7.94-8.05 (m, 1H), 7.81 (d, J=3.01 Hz, 1H), 7.14-7.33 (m, 3H), 5.74 (s, 1H), 4.07-4.23 (m, 3H), 4.03 (dd, J=13.05, 2.51 Hz, 1H), 3.83-3.94 (m, 2H), 3.09 (t, J=12.55 Hz, 1H), 2.98 (d, J=10.54 Hz, 2H), 2.28-2.52 (m, 3H), 2.20 (ddt, J=17.00, 9.29, 3.80, 3.80 Hz, 1H), 2.05 (t, J=10.92 Hz, 1H), 1.59-1.73 (m, 1H), 1.24 (t, J=7.15 Hz, 3 H). MS: calc'd 502 (MH$^+$), measured 502 (MH$^+$).

Example 10

Ethyl (4R)-4-(2-chloro-3-fluoro-phenyl)-6-[(6-oxo-3,4,7,8,9,9a-hexahydro-1H-pyrido[1,2-a]pyrazin-2-yl)methyl]-2-thiazol-2-yl-1,4-dihydropyrimidine-5-carboxylate

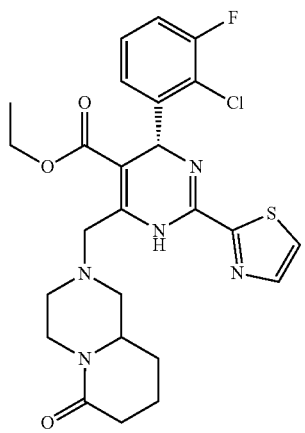 [SMILES: CCOC(=O)C1=C(CN2CCN3C(=O)CCCC3C2)NC(c2nccs2)=N[C@H]1c1cccc(F)c1Cl]

The title compound was prepared in analogy to Example 1 by using 2-chloro,3-fluorobenzaldehyde, ethyl acetoacetate and 1,2,3,4,7,8,9,9a-octahydropyrido[1,2-a]pyrazin-6-one hydrochloride salt (J & W Pharm Lab, CAS number: 151665-85-9; for its synthesis, please refer to: Ghelardini C. et al. *PCT Int. Appl.*, 2009103176) instead of 2-chloro-4-fluorobenzaldehyde, methyl acetoacetate and hexahydro-pyrazino[1,2-c][1,3]oxazin-6-one (Compound D). Example 10 was obtained as a light yellow solid (6 mg). $^1$H NMR (400 MHz, METHANOL-$d_4$) d ppm 8.02 (d, J=3.26 Hz, 1 H), 7.96 (d, J=3.26 Hz, 1H), 7.23-7.38 (m, 2H), 7.10-7.21 (m, 1H), 6.23 (s, 1 H), 4.56-4.78 (m, 2H), 3.82-4.21 (m, 5H), 3.05-3.28 (m, 4H), 2.40 (m, 2H), 1.5-2.21 (m, 4 H), 1.21 (m, 3 H). MS: calc'd 532 (MH$^+$), measured 532 (MH$^+$).

Example 11

Methyl (4R)-6-[[(8aR)-3-oxo-1,2,5,6,8,8a-hexahydroimidazo[1,5-a]pyrazin-7-yl]methyl]-4-(2-chloro-4-fluoro-phenyl)-2-thiazol-2-yl-1,4-dihydropyrimidine-5-carboxylate

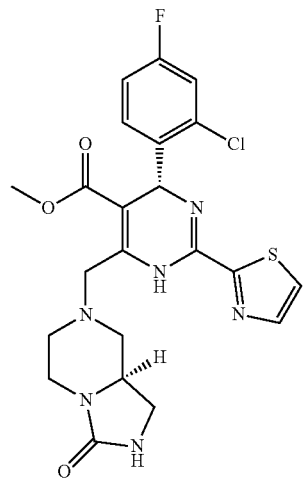 [SMILES: COC(=O)C1=C(CN2CCN3C(=O)NC[C@@H]3C2)NC(c2nccs2)=N[C@H]1c1ccc(F)cc1Cl]

The title compound was prepared in analogy to Example 1 by using (8aS)-2,5,6,7,8,8a-hexahydro-1H-imidazo[1,5-a]pyrazin-3-one (Compound H) instead of hexahydro-pyrazino[1,2-c][1,3]oxazin-6-one (Compound D). Example 11 was obtained as a light yellow solid (11 mg). $^1$H NMR (400 MHz, METHANOL-$d_4$) d ppm 7.93-8.01 (m, 1H), 7.72-7.81 (m, 1H), 7.38-7.49 (m, 1H), 7.24 (dd, J=8.66, 2.64 Hz, 1H), 7.06 (td, J=8.47, 2.64 Hz, 1H), 6.18 (s, 1H), 4.04-4.17 (m, 1H), 3.95-4.02 (m, 1H), 3.89-3.95 (m, 1H), 3.84 (dd, J=13.43, 2.38 Hz, 1H), 3.61 (s, 3H), 3.53 (t, J=8.91 Hz, 1H), 3.11-3.21 (m, 1H), 3.06 (dd, J=9.41, 4.64 Hz, 1H), 2.92 (dd, J=9.79, 1.51 Hz, 1H), 2.84 (dd, J=11.17, 2.64 Hz, 1H), 2.38 (td, J=11.67, 3.51 Hz, 1H), 2.19-2.29 (m, 1 H). MS: calc'd 505 (MH$^+$), measured 505 (MH$^+$).

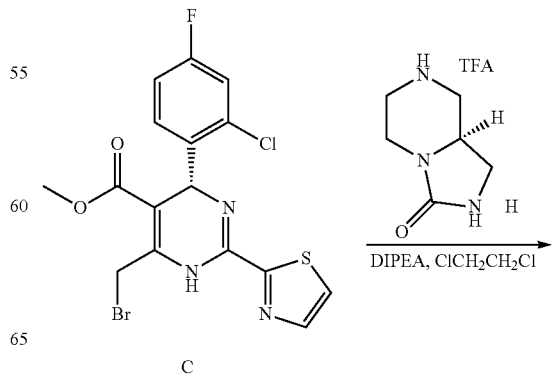

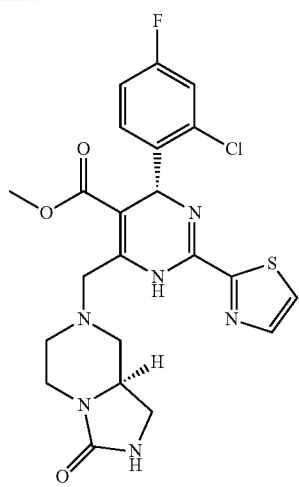

11

Preparation of (8aS)-2,5,6,7,8,8a-hexahydro-1H-imidazo[1,5-a]pyrazin-3-one (Compound H)

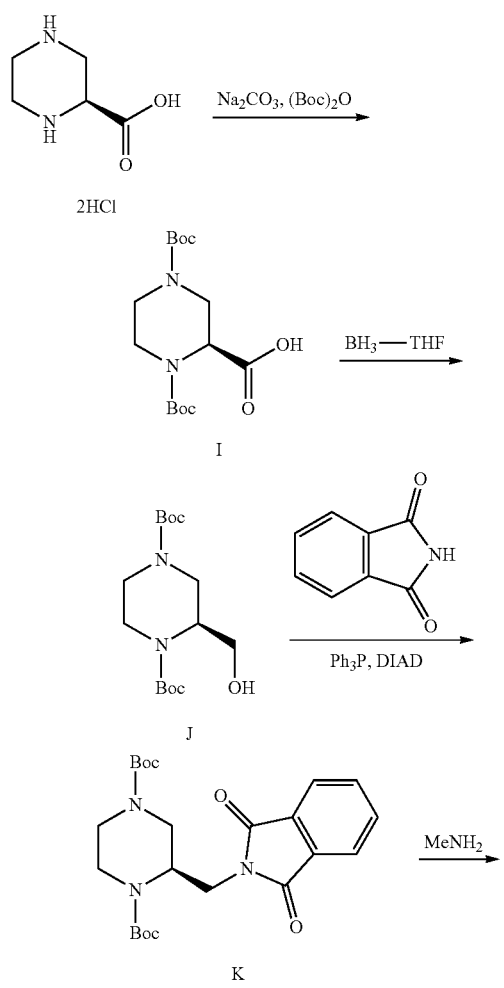

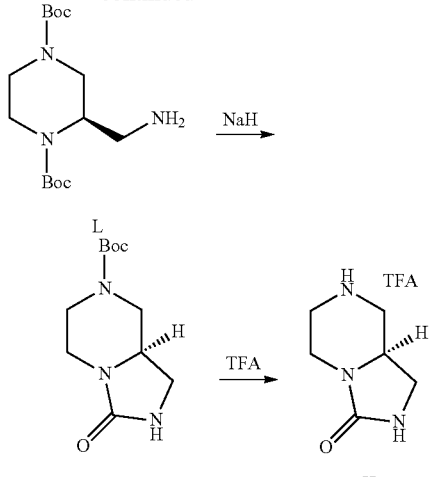

Step 1: To a stirred solution of Na$_2$CO$_3$ (118 g, 1.11 mol) in water (600 mL) was added (2S)-piperazine-2-carboxylic acid dihydrochloride salts (30 g, 0.15 mol) at 25° C., followed by di-tert-butyl dicarbonate (112 g, 0.56 mol) and tetrahydrofuran (300 mL). Then the mixture was stirred for additional 20 hours at room temperature. The reaction mixture was concentrated in vacuo and the resulting solution was extracted with methyl tert-butyl ether (200 mL) three times to remove nonpolar species. The aqueous layer was cooled to below 0° C. and then treated with 3.0 M HCl until to pH 2 to 3. Then it was extracted with ethyl acetate (500 mL) three times. The combined organic layer was dried over Na$_2$SO$_4$, and then filtered and concentrated under vacuum to give Compound I (39 g).

Step 2: To a solution of Compound I (39 g, 0.12 mol) in tetrahydrofuran (200 mL) was added dropwise BH$_3$.THF complex (240 mL, 0.24 mol) at 0° C. under N$_2$ atmosphere. Then the mixture was warmed to room temperature and heated to reflux for 2~3 hours. The mixture was quenched with MeOH (100 mL) at 0° C. and the obtained solution was concentrated in vacuo. The residue was re-dissolved into MeOH (200 mL) and the solution was refluxed for 3 to 4 hours. Then the solvent was removed to give the crude product (45 g). The crude product was purified by column chromatography on silica (petroleum ether/EtOAc=10:1 to 1:1) to give Compound J (31 g).

Step 3: To a solution of Compound J (15 g, 47.41 mmol), Ph$_3$P (16.17 g, 61.63 mmol) and phthalimide (9.07 g, 61.63 mmol) in anhydrous tetrahydrofuran (230 mL) was added a solution of diisopropyl azodicarboxylate (12.46 g, 61.63 mmol) in tetrahydrofuran (20 mL) at 10° C. under N$_2$ atmosphere. Then the mixture was stirred for additional 2 hours at 10° C. The mixture was quenched with 1N HCl (100 mL) and then extracted with EtOAc (300 mL). The organic layer was dried over Na$_2$SO$_4$, filtered, and then concentrated in vacuo to give the crude product (50 g). The crude product was triturated with petroleum ether/EtOAc (200 mL, V/V=5:1) to get crude product (25 g) with removal of triphenylphosphine oxide and other impurities. The crude product was purified by column chromatography on silica (petroleum ether/EtOAc=20:1) to get the pure product K (12 g) as a white solid and some impure compound K (4 g).

Step 4: To a stirred solution of Compound K (12 g, 26.9 mmol) in ethanol (85 mL) was added methylamine alcohol solution (85 mL) at room temperature. Then the mixture was heated to reflux for additional 3 hours. The mixture was cooled to room temperature and then concentrated. The resulting residue was dissolved in water (50 mL), then acidified to pH 3 with 1N HCl solution, and then extracted with methyl-tert-butyl ether (50 mL) three times. The pH was adjusted to 10 with solid NaOH and the mixture was extracted with ethyl acetate (150 mL) three times. The organic layer was dried and filtered and the solvent was removed under reduced pressure to give Compound L (6 g crude).

Step 5: To a stirred suspension of sodium hydride (1.0 g, 25 mmol) in tetrahydrofuran (50 mL) was added Compound L (6 g, 19 mmol, crude) at 0° C. Then the mixture was heated to reflux for 2 hours. And then additional NaH (1.0 g, 25 mmol) was added into the mixture at room temperature. After the reaction mixture was refluxed for 1 hour, the reaction was quenched with ice-water (100 mL) and then extracted with EtOAc (300 mL). The organic layer was evaporated in vacuo to give the crude product (5 g). The crude product was purified by column chromatography on silica gel (EtOAc/MeOH=200:1) to give Compound M (2.2 g, 40%).

Step 6: To a stirred solution of Compound M (2.2 g, 9.1 mmol) in 30 mL of dichloromethane was added dropwise 10 mL of TFA. After the reaction mixture was stirred for 1 hour, the solvent was removed in vacuo to give (8aS)-2,5,6,7,8, 8a-hexahydro-1H-imidazo[1,5-a]pyrazin-3-one trifluoro acetitic acid salt (Compound H) as a crude product which was used directly without further purification.

Example 12

Methyl (4R)-6-[[(8aS)-3-oxo-1,2,5,6,8,8a-hexahydroimidazo[1,5-a]pyrazin-7-yl]methyl]-4-(2-chloro-4-fluoro-phenyl)-2-thiazol-2-yl-1,4-dihydropyrimidine-5-carboxylate

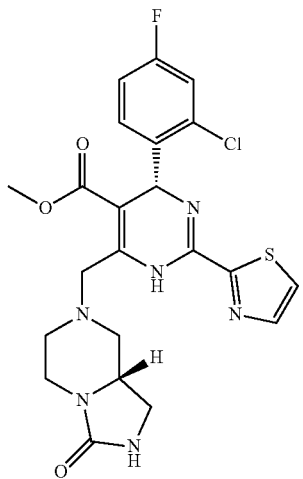 [SMILES: COC(=O)C1=C(CN2CCN3C(=O)NC[C@H]3C2)NC(c2nccs2)=N[C@H]1c1ccc(F)cc1Cl]

The title compound was prepared in analogy to Example 11 by using (2R)-piperazine-2-carboxylic acid instead of (2S)-piperazine-2-carboxylic acid. Example 12 was obtained as a light yellow solid (13 mg). $^1$H NMR (400 MHz, METHANOL-d$_4$) d ppm 7.91-8.01 (m, 1H), 7.71-7.81 (m, 1H), 7.42 (dd, J=8.66, 6.15 Hz, 1H), 7.24 (dd, J=8.66, 2.64 Hz, 1H), 7.05 (td, J=8.41, 2.51 Hz, 1H), 6.18 (s, 1H), 4.12 (d, J=17.32 Hz, 1H), 3.95-4.05 (m, 1H), 3.91 (d, J=17.32 Hz, 1H), 3.77 (dd, J=13.18, 1.88 Hz, 1H), 3.61 (s, 3H), 3.56-3.60 (m, 1H), 3.08-3.21 (m, 2H), 3.01 (dd, J=10.79, 2.76 Hz, 1H), 2.74 (d, J=11.29 Hz, 1H), 2.39 (t, J=10.92 Hz, 1H), 2.24 (td, J=11.67, 3.26 Hz, 1 H). MS: calc'd 505 (MH$^+$), measured 505 (MH$^+$).

Example 13

Ethyl (4R)-6-[[(8aS)-3-oxo-1,2,5,6,8,8a-hexahydroimidazo[1,5-a]pyrazin-7-yl]methyl]-4-(2-bromo-4-fluoro-phenyl)-2-thiazol-2-yl-1,4-dihydropyrimidine-5-carboxylate

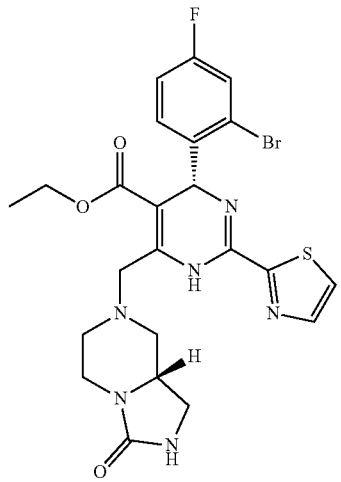 [SMILES: CCOC(=O)C1=C(CN2CCN3C(=O)NC[C@H]3C2)NC(c2nccs2)=N[C@H]1c1ccc(F)cc1Br]

The title compound was prepared in analogy to Example 11 by using 2-bromo-4-fluorobenzaldehyde and ethyl acetoacetate instead of 2-chloro-4-fluorobenzaldehyde and methyl acetoacetate. Example 13 was obtained as a light yellow solid (34 mg). $^1$H NMR (400 MHz, METHANOL-d$_4$) d ppm 7.91-8.02 (m, 1H), 7.78 (d, J=3.01 Hz, 1H), 7.34-7.53 (m, 2H), 7.12 (td, J=8.41, 2.76 Hz, 1H), 6.18 (s, 1H), 4.15-4.31 (m, 1H), 3.93-4.13 (m, 4H), 3.76-3.89 (m, 1H), 3.61 (t, J=8.91 Hz, 1H), 3.07-3.25 (m, 3H), 2.83-3.03 (m, 1H), 2.55 (br. s., 1H), 2.40 (br. s., 1H), 1.14 (t, J=7.15 Hz, 3 H). MS: calc'd 563 (MH$^+$), measured 563 (MH$^+$).

Example 14

Ethyl (4R)-6-[[(8aR)-3-oxo-1,2,5,6,8,8a-hexahydroimidazo[1,5-a]pyrazin-7-yl]methyl]-4-(2-bromo-4-fluoro-phenyl)-2-thiazol-2-yl-1,4-dihydropyrimidine-5-carboxylate

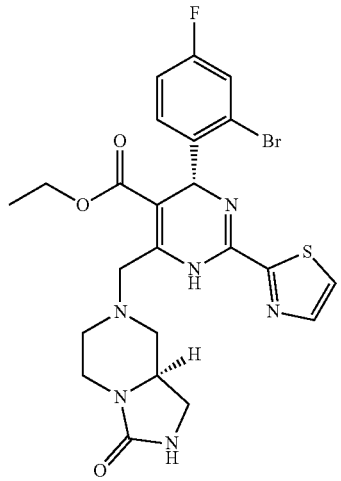 [SMILES: CCOC(=O)C1=C(CN2CCN3C(=O)NC[C@@H]3C2)NC(c2nccs2)=N[C@H]1c1ccc(F)cc1Br]

The title compound was prepared in analogy to Example 12 by using 2-bromo-4-fluorobenzaldehyde and ethyl acetoacetate instead of 2-chloro-4-fluorobenzaldehyde and methyl acetoacetate. Example 14 was obtained as a light yellow solid (34 mg). $^1$H NMR (400 MHz, METHANOL-$d_4$) d ppm 7.92-8.01 (m, 1H), 7.78 (d, J=3.26 Hz, 1H), 7.35-7.56 (m, 2H), 7.12 (td, J=8.41, 2.76 Hz, 1H), 6.18 (s, 1H), 4.17-4.32 (m, 1H), 3.96-4.16 (m, 4H), 3.89 (dd, J=13.55, 2.51 Hz, 1H), 3.49-3.64 (m, 1H), 3.17-3.28 (m, 1H), 2.97-3.17 (m, 3H), 2.31-2.68 (m, 2H), 1.14 (t, J=7.15 Hz, 3 H). MS: calc'd 563 (MH$^+$), measured 563 (MH$^+$).

Example 15

Methyl (4R)-6-[[(8aR)-1,3-dioxo-5,6,8,8a-tetrahydroimidazo[1,5-a]pyrazin-7-yl]methyl]-4-(2-chloro-4-fluoro-phenyl)-2-thiazol-2-yl-1,4-dihydropyrimidine-5-carboxylate

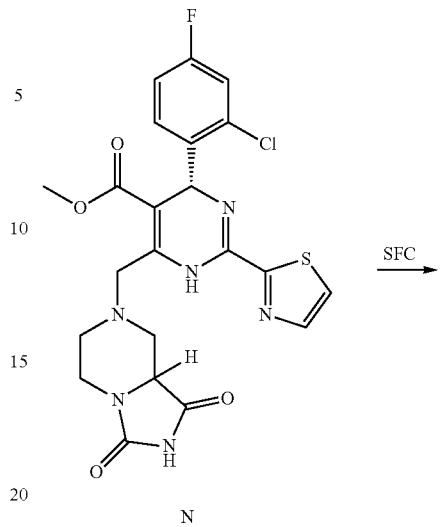

SFC →

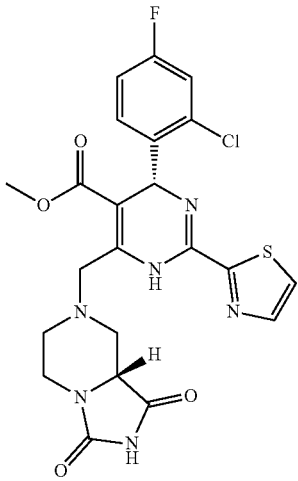 [SMILES: COC(=O)C1=C(CN2CCN3C(=O)NC(=O)[C@H]3C2)NC(c2nccs2)=N[C@H]1c1ccc(F)cc1Cl]

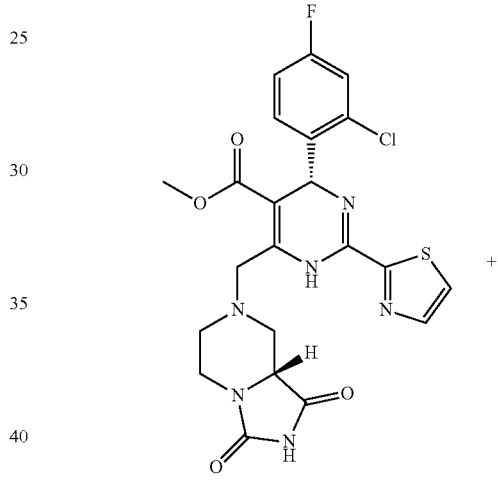

Example 15

The title compound was prepared by SFC chiral separation of methyl (4R)-4-(2-chloro-4-fluoro-phenyl)-6-[(1,3-dioxo-5,6,8,8a-tetrahydroimidazo[1,5-a]pyrazin-7-yl) methyl]-2-thiazol-2-yl-1,4-dihydropyrimidine-5-carboxylate (Compound N). Example 15 was obtained as a yellow solid (11 mg). $^1$H NMR (400 MHz, METHANOL-$d_4$) d ppm 7.89-7.97 (m, 1H), 7.71-7.81 (m, 1H), 7.38-7.53 (m, 1H), 7.24 (dd, J=8.78, 2.76 Hz, 1H), 7.07 (td, J=8.41, 2.76 Hz, 1H), 6.19 (s, 1H), 4.28-4.40 (m, 1H), 4.15-4.26 (m, 1H), 3.92-4.07 (m, 2H), 3.61 (s, 3H), 3.36 (d, J=4.77 Hz, 1H), 3.20-3.29 (m, 1H), 2.78-2.86 (m, 1H), 2.42 (t, J=11.17 Hz, 1H), 2.29 (td, J=11.86, 3.64 Hz, 1 H). MS: calc'd 519 (MH$^+$), measured 519 (MH$^+$).

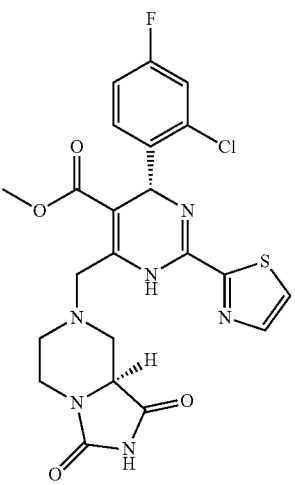

Example 16

63

Preparation of methyl (4R)-4-(2-chloro-4-fluoro-phenyl)-6-[(1,3-dioxo-5,6,8,8a-tetrahydroimidazo[1,5-a]pyrazin-7-yl)methyl]-2-thiazol-2-yl-1,4-dihydro-pyrimidine-5-carboxylate (Compound N)

The title compound was prepared in analogy to Example 1 by using 6,7,8,8a-tetrahydro-5H-imidazo[1,5-a]pyrazine-1,3-dione (For its synthesis, please refer to: WO2010/23480) instead of hexahydro-pyrazino[1,2-c][1,3]oxazin-6-one (Compound D).

Example 16

Methyl (4R)-6-[[(8aS)-1,3-dioxo-5,6,8,8a-tetrahydroimidazo[1,5-a]pyrazin-7-yl]methyl]-4-(2-chloro-4-fluoro-phenyl)-2-thiazol-2-yl-1,4-dihydropyrimidine-5-carboxylate

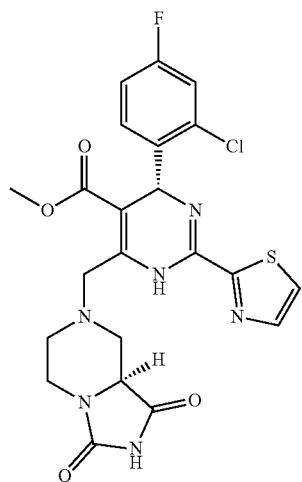 [SMILES: COC(=O)C1=C(CN2CCN3C(=O)NC(=O)[C@@H]3C2)NC(c2nccs2)=N[C@H]1c1ccc(F)cc1Cl]

The title compound was prepared by SFC chiral separation of methyl (4R)-4-(2-chloro-4-fluoro-phenyl)-6-[(1,3-dioxo-5,6,8,8a-tetrahydroimidazo[1,5-a]pyrazin-7-yl)methyl]-2-thiazol-2-yl-1,4-dihydropyrimidine-5-carboxylate (Compound N) in Example 15. Example 16 was obtained as a yellow solid (10 mg). $^1$H NMR (400 MHz, METHANOL-d$_4$) d ppm 7.90-7.97 (m, 1H), 7.76 (d, J=3.26 Hz, 1H), 7.37-7.49 (m, 1H), 7.24 (dd, J=8.78, 2.76 Hz, 1H), 7.06 (td, J=8.41, 2.76 Hz, 1H), 6.19 (s, 1H), 4.24-4.36 (m, 1H), 4.13-4.22 (m, 1H), 4.09 (dd, J=13.43, 2.89 Hz, 1H), 3.98-4.06 (m, 1H), 3.61 (s, 3H), 3.27 (td, J=12.67, 3.76 Hz, 1H), 3.18 (dd, J=11.04, 4.27 Hz, 1H), 2.97-3.04 (m, 1H), 2.44 (td, J=11.80, 3.76 Hz, 1H), 2.29 (t, J=11.17 Hz, 1 H). MS: calc'd 519 (MH$^+$), measured 519 (MH$^+$).

64

Example 17

Methyl (4R)-6-[[(3aS)-1,1-dioxo-2,3,3a,4,6,7-hexahydro-[1,2,5]thiadiazolo[2,3-a]pyrazin-5-yl]methyl]-4-(2-chloro-4-fluoro-phenyl)-2-thiazol-2-yl-1,4-dihydropyrimidine-5-carboxylate

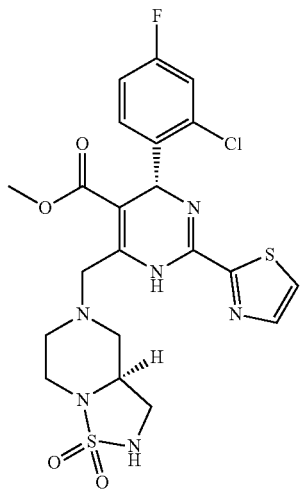 [SMILES: COC(=O)C1=C(CN2CCN3[C@H](CNS3(=O)=O)C2)NC(c2nccs2)=N[C@H]1c1ccc(F)cc1Cl]

The title compound was prepared by SFC chiral separation of methyl (4R)-4-(2-chloro-4-fluoro-phenyl)-6-[(1,1-dioxo-2,3,3a,4,6,7-hexahydro-[1,2,5]thiadiazolo[2,3-a]pyrazin-5-yl)methyl]-2-thiazol-2-yl-1,4-dihydropyrimidine-5-carboxylate (Compound O). Example 17 was obtained as a yellow solid (14 mg). $^1$H NMR (400 MHz, METHANOL-d$_4$) d ppm 7.93-8.00 (m, 1H), 7.77 (d, J=3.01 Hz, 1H), 7.44 (dd, J=8.78, 6.02 Hz, 1H), 7.25 (dd, J=8.66, 2.64 Hz, 1H), 7.06 (td, J=8.41, 2.76 Hz, 1H), 6.18 (s, 1H), 4.12-4.26 (m, 1H), 3.97-4.10 (m, 1H), 3.58-3.70 (m, 4H), 3.42-3.55 (m, 2H), 3.03-3.20 (m, 4H), 2.63-2.76 (m, 1H), 2.42 (t, J=10.54 Hz, 1 H). MS: calc'd 541 (MH$^+$), measured 541 (MH$^+$).

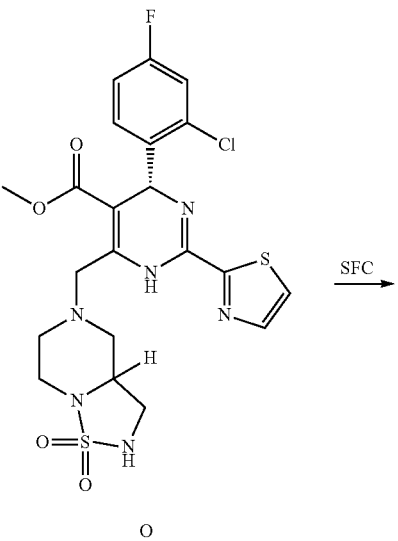

SFC →

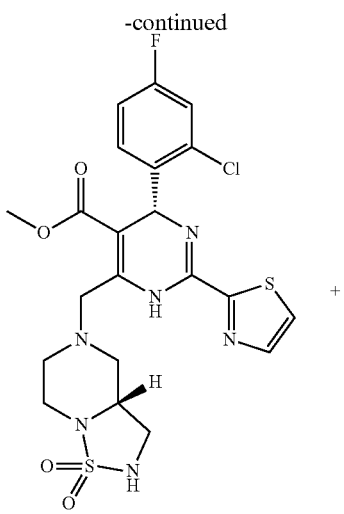

Example 17

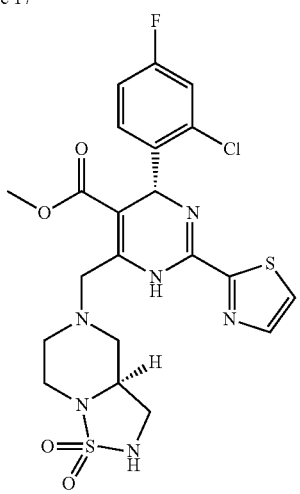

Example 18

Preparation of methyl (4R)-4-(2-chloro-4-fluoro-phenyl)-6-[(1,1-dioxo-2,3,3a,4,6,7-hexahydro-[1,2,5]thiadiazolo[2,3-a]pyrazin-5-yl)methyl]-2-thiazol-2-yl-1,4-dihydropyrimidine-5-carboxylate (Compound O)

The title compound was prepared in analogy to Example 1 by using hexahydro-1-thia-2,5,7a-triaza-indene 1,1-dioxide (Compound P) instead of hexahydro-pyrazino[1,2-c][1,3]oxazin-6-one (Compound D).

Preparation of hexahydro-1-thia-2,5,7a-triaza-indene 1,1-dioxide (Compound P)

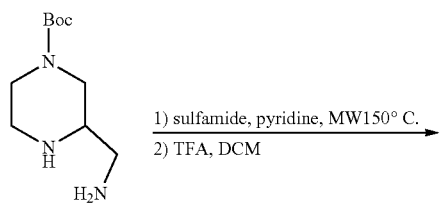

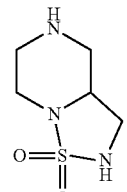

P

To a stirred solution of 3-aminomethyl-piperazine-1-carboxylic acid tert-butyl ester (CAS number: 1376099-80-7, Bepharm) (215 mg, 1.0 mmol) in 2 mL of pyridine was added sulfamide (1.5 mmol). The reaction mixture was heated to 150° C. for 6 hours under microwave. The solvent was removed in vacuo, and the residue was dissolved in 3 mL of dichloromethane and 1 mL of TFA. The reaction mixture was stirred for 1 hour, and the solvent was removed in vacuo to give the crude Compound P which was used directly without further purification. LC/MS: calc'd 178 (MH$^+$), measured 178 (MH$^+$).

Example 18

Methyl (4R)-6-[[(3aR)-1,1-dioxo-2,3,3a,4,6,7-hexahydro-[1,2,5]thiadiazolo[2,3-a]pyrazin-5-yl]methyl]-4-(2-chloro-4-fluoro-phenyl)-2-thiazol-2-yl-1,4-dihydropyrimidine-5-carboxylate

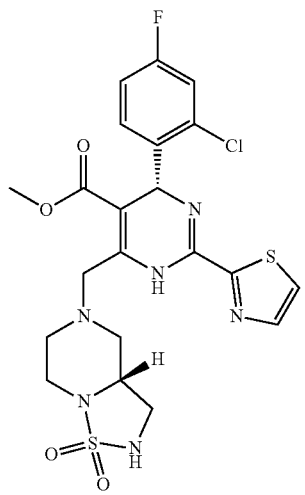 [SMILES: COC(=O)C1=C(CN2CCN3[C@@H](CNS3(=O)=O)C2)NC(c2nccs2)=N[C@H]1c1ccc(F)cc1Cl]

The title compound was prepared by SFC chiral separation of methyl (4R)-4-(2-chloro-4-fluoro-phenyl)-6-[(1,1-dioxo-2,3,3a,4,6,7-hexahydro-[1,2,5]thiadiazolo[2,3-a]pyrazin-5-yl)methyl]-2-thiazol-2-yl-1,4-dihydropyrimidine-5-carboxylate (Compound O) in Example 17. Example 18 was obtained as a yellow solid (28 mg). $^1$H NMR (400 MHz, METHANOL-d$_4$) d ppm 7.97 (d, J=3.26 Hz, 1H), 7.79 (d, J=3.26 Hz, 1H), 7.45 (dd, J=8.78, 6.02 Hz, 1H), 7.25 (dd, J=8.78, 2.51 Hz, 1H), 7.07 (td, J=8.41, 2.76 Hz, 1H), 6.19 (s, 1H), 4.32 (d, J=16.81 Hz, 1H), 4.09 (d, J=16.81 Hz, 1H), 3.67-3.81 (m, 1H), 3.58-3.66 (m, 3H), 3.46-3.58 (m, 2H), 3.29-3.31 (m, 1H), 3.23 (dd, J=9.79, 8.78 Hz, 1H), 3.02-3.19 (m, 2H), 2.69 (q, J=10.79 Hz, 2 H). MS: calc'd 541 (MH$^+$), measured 541 (MH$^+$).

Example 19

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid

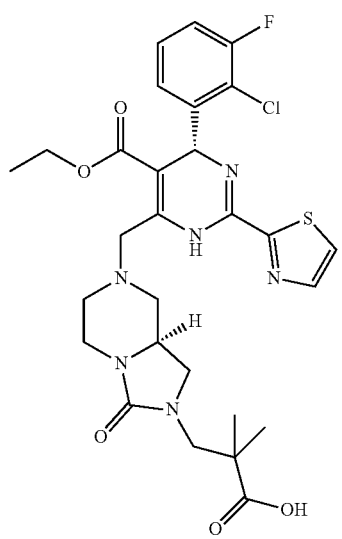 [SMILES: CCOC(=O)C1=C(CN2CCN3C(=O)N(CC(C)(C)C(=O)O)C[C@@H]3C2)NC(c2nccs2)=N[C@H]1c1cccc(F)c1Cl]

The title compound was prepared in analogy to Example 1 by using 2-chloro,3-fluorobenzaldehyde, ethyl acetoacetate and 3-[(8aS)-3-oxo-1,5,6,7,8,8a-hexahydroimidazo[1,5-a]pyrazin-2-yl]-2,2-dimethyl-propanoic acid (Compound Q) instead of 2-chloro-4-fluorobenzaldehyde, methyl acetoacetate and hexahydro-pyrazino[1,2-c][1,3]oxazin-6-one (Compound D). Example 19 was obtained as a light yellow solid (12 mg). ¹H NMR (400 MHz, METHANOL-d₄) d ppm 7.92-8.02 (m, 1H), 7.70-7.80 (m, 1H), 7.21-7.36 (m, 2H), 7.10-7.21 (m, 1H), 6.19-6.28 (m, 1H), 3.99-4.14 (m, 3H), 3.81-3.96 (m, 3H), 3.47-3.56 (m, 1H), 3.38-3.44 (m, 1H), 3.27-3.32 (m, 1H), 3.15-3.25 (m, 1H), 3.07-3.14 (m, 1H), 2.79-2.96 (m, 2H), 2.30-2.41 (m, 1H), 2.13-2.23 (m, 1H), 1.20 (d, J=2.76 Hz, 6H), 1.13 (m, 3H). MS: calc'd 619 (MH⁺), measured 619 (MH⁺).

Preparation of 3-[(8aS)-3-oxo-1,5,6,7,8,8a-hexahydroimidazo[1,5-a]pyrazin-2-yl]-2,2-dimethyl-propanoic acid (Compound Q)

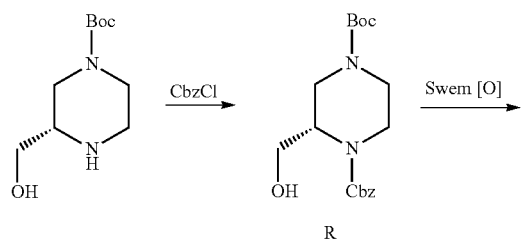

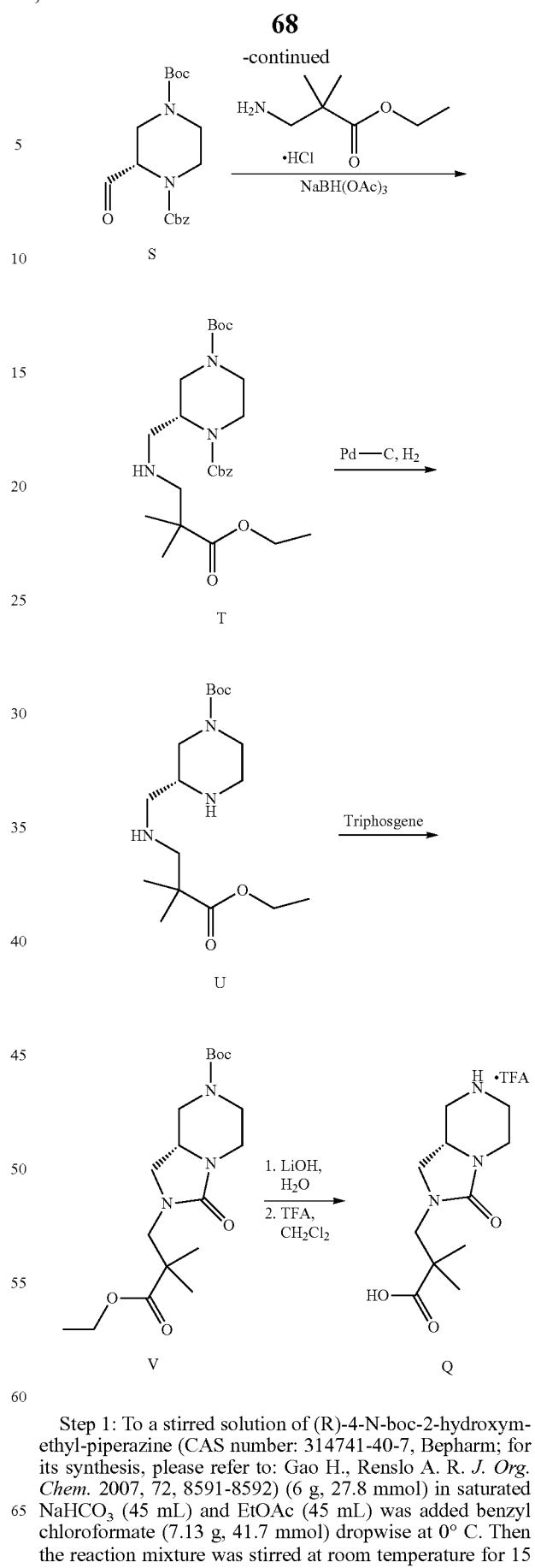

Step 1: To a stirred solution of (R)-4-N-boc-2-hydroxymethyl-piperazine (CAS number: 314741-40-7, Bepharm; for its synthesis, please refer to: Gao H., Renslo A. R. *J. Org. Chem.* 2007, 72, 8591-8592) (6 g, 27.8 mmol) in saturated NaHCO₃ (45 mL) and EtOAc (45 mL) was added benzyl chloroformate (7.13 g, 41.7 mmol) dropwise at 0° C. Then the reaction mixture was stirred at room temperature for 15 hours. The reaction was diluted with EtOAc (60 mL), and the organic layer was separated and aqueous layer was extracted with EtOAc (35 mL). The combined organic layer was dried over Na$_2$SO$_4$ and the solution was concentrated to give a crude product. The crude product was purified by column chromatography on silica (Petroleum ether:EtOAc=10:1 to 1:1) to give Compound R (6.7 g).

Step 2: To a stirred solution of oxalyl chloride (3.64 g, 28.65 mmol) in anhydrous dichloromethane (80 mL) at −78° C. was added dimethyl sulfoxide (4.47 g, 57.3 mmol) dropwise. After 10 minutes, a solution of Compound R (6.7 g, 19.1 mmol) in dichloromethane (20 mL) was added dropwise. After the mixture was stirred for 30 minutes at −78° C., N,N-diisopropylethylamine (14.78 g, 114.6 mmol) was added and the reaction mixture was stirred for 30 minutes. After the reaction mixture was slowly warmed to 0° C. over 30 minutes, it was diluted with dichloromethane (80 mL), washed with 5% aqueous citric acid (10 mL), brine and then dried over Na$_2$SO$_4$. After filtration, the mixture was concentrated in vacuo to get the crude product S (7 g).

Step 3: To a stirred solution of ethyl 3-amino-2,2-dimethyl-propanoate hydrochloride salt (3.4 g, 18.6 mmol) in anhydrous DCM (100 mL) was added DIPEA (2.6 g, 27.3 mmol) at room temperature. Then Compound S (7 g, 20 mmol) was added, followed by NaBH(OAc)$_3$ (6.3 g, 29.8 mmol) and AcOH (1.5 mL). The reaction mixture was stirred for 16 hours at room temperature. Water (100 mL) was added and the mixture was extracted with DCM (100 mL). The organic layer was dried and concentrated in vacuo to dryness to give crude Compound T (7.3 g).

Step 4: To the solution of Compound T (3.3 g, 6.9 mmol) in EtOH (100 mL) was added Pd/C (1 g). Then the mixture was stirred at 50° C. for 3 hours under hydrogen atmosphere (50 Psi). The reaction mixture was filtered and the filtrate was concentrated in vacuo to get the Compound U (1.8 g).

Step 5: To the solution of Compound U (1.8 g, 5.24 mmol) in anhydrous dichloromethane (60 mL) was added N,N-diisopropylethylamine (3.4 g, 26.2 mmol) at 0° C. Then triphosgene (783 mg, 2.62 mmol) was added at 0° C. and the mixture was stirred at 10-15° C. for 16 hours. Water (50 mL) was added and the mixture was extracted with dichloromethane (60 mL), and then dried over Na$_2$SO$_4$. The solvent was removed in vacuo to give the crude product. The crude product was purified by column chromatography on silica (petroleum ether:EtOAc=5:1 to 1:1) to obtain Compound V (1.3 g).

Step 6: To a stirred solution of Compound V (240 mg, 0.64 mmol) in THF (3 ml) was added a solution of LiOH.H$_2$O (215 mg, 5.10 mmol) in H$_2$O (1 mL) at room temperature. After the reaction mixture was stirred at room temperature overnight, it was acidified to PH 3 to 4 with 1 N HCl at 0° C. The mixture was then concentrated and azeotropically dried with toluene to give the crude product which was dissolved in dichloromethane (2 mL) and treated with trifluoroacetic acid (2 mL) at room temperature. After the reaction mixture was stirred at room temperature for 1 hour, the solvent was removed in vacuo to give 3-[(8aS)-3-oxo-1,5,6,7,8,8a-hexahydroimidazo[1,5-a]pyrazin-2-yl]-2,2-dimethyl-propanoic acid (Compound Q) which was used directly.

Example 20

3-[(8aS)-7-[[(4R)-4-(2-chlorophenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2-methyl-propanoic acid

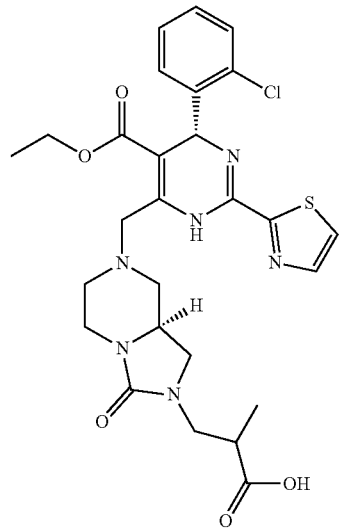 [SMILES: CCOC(=O)C1=C(CN2CCN3C(=O)N(CC(C)C(=O)O)C[C@@H]3C2)NC(c2nccs2)=N[C@H]1c1ccccc1Cl]

The title compound was prepared in analogy to Example 19 by using 2-chlorobenzaldehyde and methyl 3-amino-2-methyl-propanoate hydrochloride salt (Compound W) instead of 2-chloro-4-fluorobenzaldehyde and ethyl 3-amino-2,2-dimethyl-propanoate hydrochloride salt. Example 20 was obtained as a light yellow solid (20 mg). $^1$H NMR (400 MHz, METHANOL-d$_4$) d ppm 7.96 (d, J=3.01 Hz, 1H), 7.75 (d, J=3.01 Hz, 1H), 7.42 (d, J=7.78 Hz, 2H), 7.14-7.36 (m, 2H), 6.22 (s, 1H), 3.97-4.16 (m, 3H), 3.79-3.97 (m, 3H), 3.43-3.59 (m, 2H), 3.26-3.43 (m, 2H), 3.05-3.26 (m, 2H), 2.80-2.99 (m, 2H), 2.65-2.80 (m, 1H), 2.35 (t, J=10.79 Hz, 1H), 2.19 (q, J=10.46 Hz, 1H), 1.06-1.24 (m, 5 H). MS: calc'd 587 (MH$^+$), measured 587 (MH$^+$).

Preparation of methyl 3-amino-2-methyl-propanoate hydrochloride salt (Compound W)

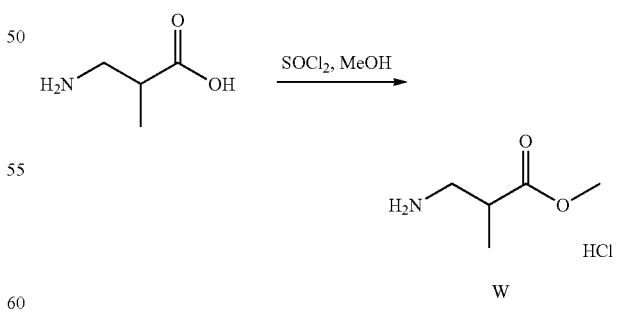

To the solution of DL-3-aminoisobutyric acid (CAS number: 144-90-1, Aldrich) (2.7 g, 26.4 mmol) in MeOH (50 mL) was added SOCl$_2$ (6.17 g, 52.8 mmol) dropwise at 0° C. under N$_2$ atmosphere. The reaction was refluxed for 18 hours. The solvent was removed in vacuo to give crude Compound W which was used directly in the next step.

Example 21

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2-methyl-propanoic acid

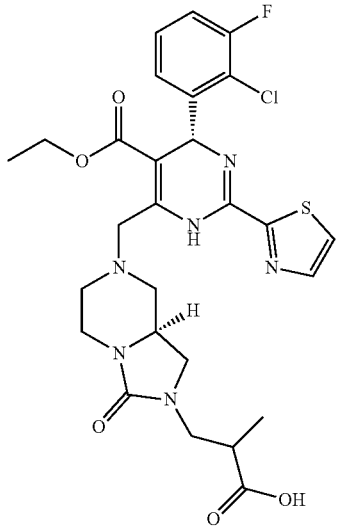 [SMILES: CCOC(=O)C1=C(CN2CCN3C(=O)N(CC(C)C(=O)O)C[C@@H]3C2)NC(c2nccs2)=N[C@H]1c1cccc(F)c1Cl]

The title compound was prepared in analogy to Example 19 by using methyl 3-amino-2-methyl-propanoate hydrochloride salt (Compound W) instead of ethyl 3-amino-2,2-dimethyl-propanoate hydrochloride salt. Example 21 was obtained as a light yellow solid (10 mg). $^1$H NMR (400 MHz, METHANOL-$d_4$) d ppm 7.96 (d, J=3.26 Hz, 1H), 7.76 (d, J=3.26 Hz, 1H), 7.21-7.36 (m, 2H), 7.10-7.21 (m, 1H), 6.24 (s, 1H), 3.98-4.17 (m, 3H), 3.79-3.98 (m, 3H), 3.42-3.58 (m, 2H), 3.24-3.42 (m, 2H), 3.08-3.24 (m, 2H), 2.79-2.96 (m, 2H), 2.73 (ddt, J=10.63, 7.00, 3.73, 3.73 Hz, 1H), 2.30-2.43 (m, 1H), 2.13-2.27 (m, 1H), 1.08-1.24 (m, 5 H). MS: calc'd 605 (MH$^+$), measured 605 (MH$^+$).

Example 22

3-[(8aS)-7-[[(4S)-4-(3,4-difluoro-2-methyl-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid The title compound was prepared in analogy to Example 19 by using 2-methyl-3,4-difluorobenzaldehyde instead of 2-chloro-4-fluorobenzaldehyde. Example 22 was obtained as a light yellow solid (2 mg). $^1$H NMR (400 MHz, METHANOL-$d_4$) d ppm 7.88-8.00 (m, 1H), 7.69-7.80 (m, 1H), 6.95-7.13 (m, 2H), 5.88-5.99 (m, 1H), 4.03-4.16 (m, 2H), 3.79-3.97 (m, 3H), 3.47-3.54 (m, 1H), 3.36-3.44 (m, 2H), 3.28-3.31 (m, 1 H), 3.07-3.24 (m, 2H), 2.76-2.94 (m, 2H), 2.57 (d, J=2.26 Hz, 3H), 2.31-2.42 (m, 1H), 2.12-2.22 (m, 1H), 1.10-1.24 (m, 9 H). MS: calc'd 617 (MH$^+$), measured 617 (MH$^+$).

Example 23

Ethyl (4R)-4-(2-chloro-3-fluoro-phenyl)-6-[[2-(2-methoxyl-1,1-dimethyl-2-oxo-ethyl)-3-oxo-5,6,8,8a-tetrahydro-1H-imidazo[1,5-a]pyrazin-7-yl]methyl]-2-thiazol-2-yl-1,4-dihydropyrimidine-5-carboxylate The title compound was prepared in analogy to Example 19 by using methyl 3-amino-2-methyl-propanoate hydrochloride salt instead of ethyl 3-amino-2,2-dimethyl-propanoate hydrochloride salt. Example 23 was obtained as a light yellow solid (4 mg). $^1$H NMR (400 MHz, METHANOL-$d_4$) d ppm 7.94-8.03 (m, 1H), 7.72-7.82 (m, 1H), 7.22-7.38 (m, 2H), 7.11-7.20 (m, 1H), 6.25 (s, 1H), 4.10-4.22 (m, 1H), 3.85-4.02 (m, 2H), 3.76-3.84 (m, 1H), 3.74 (d, J=1.00 Hz, 2H), 3.59-3.71 (m, 1H), 3.12-3.30 (m, 2H), 2.76-3.03 (m, 2H), 2.20-2.52 (m, 2H), 1.50 (t, J=7.78 Hz, 6H), 1.14 (t, J=7.03 Hz, 3 H). MS: calc'd 619 (MH$^+$), measured 619 (MH$^+$).

Example 24

Methyl 7-[[(4R)-4-(2-chloro-3-fluoro-phenyl)-5-ethoxycarbonyl-2-thiazol-2-yl-1,4-dihydropyrimidin-6-yl]methyl]-3-oxo-2,5,6,8-tetrahydro-1H-imidazo[1,5-a]pyrazine-8a-carboxylate

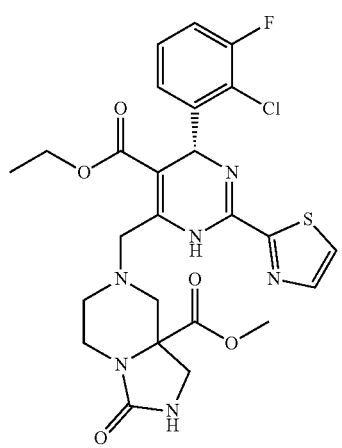 [SMILES: CCOC(=O)C1=C(CN2CCN3C(=O)NCC3(C(=O)OC)C2)NC(c2nccs2)=N[C@H]1c1cccc(F)c1Cl]

The title compound was prepared in analogy to Example 1 by using 2-chloro,3-fluorobenzaldehyde, ethyl acetoacetate and methyl 3-oxo-1,2,5,6,7,8-hexahydroimidazo[1,5-a]pyrazine-8a-carboxylate (Compound X) instead of 2-chloro-4-fluorobenzaldehyde, methyl acetoacetate and hexahydro-pyrazino[1,2-c][1,3]oxazin-6-one (Compound D). Example 24 was obtained as a light yellow solid (5 mg). $^1$H NMR (400 MHz, METHANOL-d$_4$) d ppm 7.96 (d, J=3.26 Hz, 1H), 7.76 (d, J=3.26 Hz, 1H), 7.27-7.35 (m, 1H), 7.26 (s, 1H), 7.16 (s, 1H), 6.22 (s, 1H), 3.97-4.14 (m, 3H), 3.87-3.95 (m, 1H), 3.78-3.85 (m, 1H), 3.67 (s, 3H), 3.46 (d, J=9.79 Hz, 2H), 3.35-3.42 (m, 2H), 2.87-2.99 (m, 1H), 2.45-2.55 (m, 1H), 2.29-2.42 (m, 1H), 1.12 (t, J=7.15 Hz, 3 H). MS: calc'd 577 (MH$^+$), measured 577 (MH$^+$).

Preparation of methyl 3-oxo-1,2,5,6,7,8-hexahydroimidazo[1,5-a]pyrazine-8a-carboxylate (Compound X)

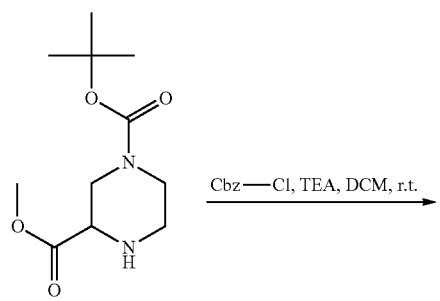

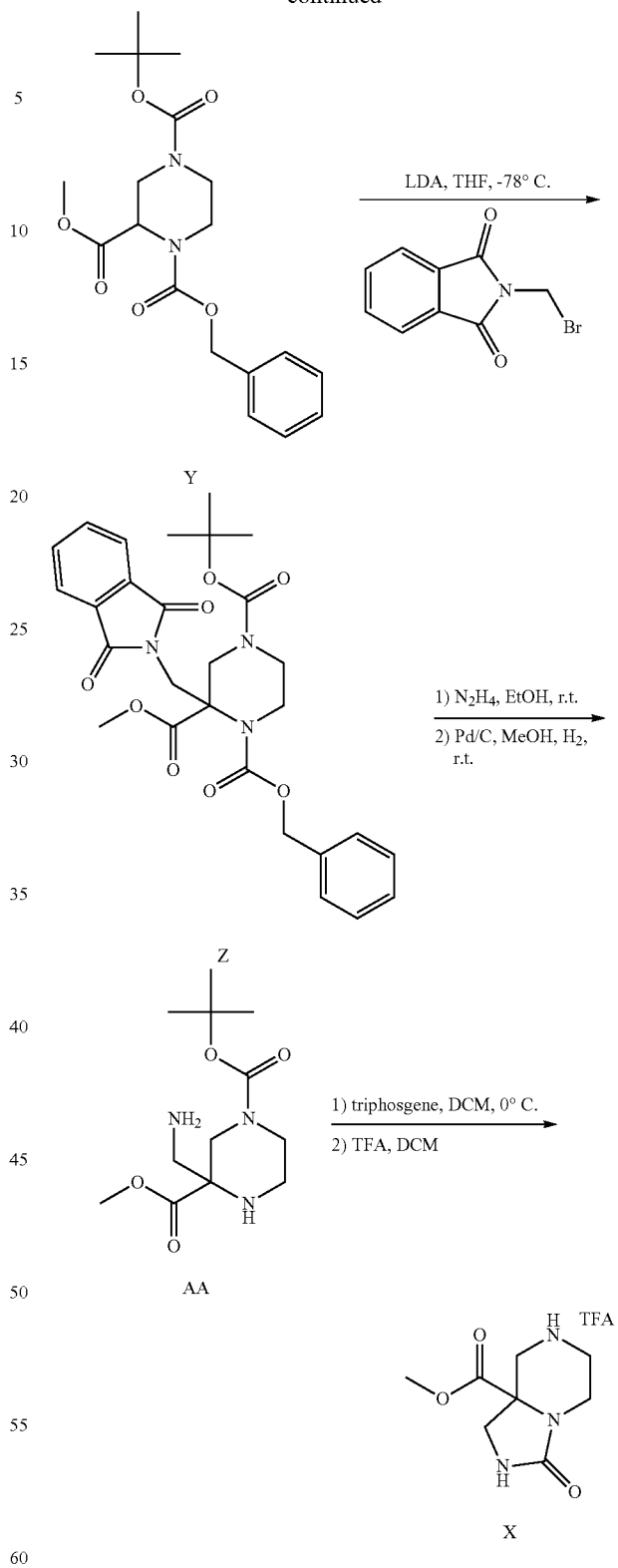

Step 1: Piperazine-1,3-dicarboxylic acid 1-tert-butyl ester 3-methyl ester (244 mg, 1.0 mmol) was dissolved in 5 mL of dichloromethane followed by sequential addition of TEA (202 mg, 2.0 mmol) and benzyl chloroformate (170 mg, 1.0 mmol) at room temperature. After the reaction was stirred for 1 hour, it was diluted with dichloromethane, and then washed with water and brine. The solvent was concentrated to give crude Compound Y, which was used directly without further purification.

Step 2: Piperazine-1,2,4-tricarboxylic acid 1-benzyl ester 4-tert-butyl ester 2-methyl ester (Compound Y) from previous step was dissolved in 5 mL of THF at −78° C., then LDA (2 M, 1 mL, 2 mmol) was added dropwise. After the reaction mixture was stirred for 2 hours at −78° C., 2-bromomethyl-isoindole-1,3-dione (239 mg, 1 mmol) in 2 mL of THF was added. The reaction mixture was stirred overnight. The solvent was removed in vacuo and the residue was triturate with petroleum ether. The solid was collected by filtration, washed with water and then dried in vacuo to give Compound Z.

Step 3: 2-(1,3-Dioxo-1,3-dihydro-isoindol-2-ylmethyl)-piperazine-1,2,4-tricarboxylic acid 1-benzyl ester 4-tert-butyl ester 2-methyl ester (Compound Z) from Step 2 was dissolved in 3 mL of EtOH and 1 mL of $N_2H_4$ solution. The reaction mixture was stirred at room temperature overnight. The solid was filtered off and the filtrate was concentrated in vacuo. The crude oil was dissolved in 10 mL of MeOH and stirred with 50 mg of Pd/C under $H_2$ atmosphere overnight. After filtration, the solvent was concentrated in vacuo to give 100 mg of crude Compound AA as oil, which was used directly without further purification in the next step.

Step 4: 3-Aminomethyl-piperazine-1,3-dicarboxylic acid 1-tert-butyl ester 3-methyl ester (Compound AA) from Step 3 was dissolved in 4 mL of dichloromethane and 1 mL of DIPEA, then triphosgene (108 mg, 0.36 mmol) was added at room temperature. After the reaction mixture was stirred for 30 minutes, the solvent was removed in vacuo. The residue was dissolved in 3 mL of dichloromethane and 1 mL of TFA. The reaction mixture was stirred for 1 hour at room temperature, and the solvent was removed in vacuo to give the crude Compound X which was used directly without further purification.

Example 25

(R)-6-[(S)-2-(4-Carboxy-phenyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester

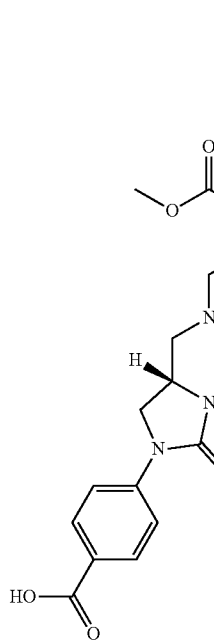

The title compound was prepared in analogy to Example 1 by using 4-[(8aS)-3-oxo-1,5,6,7,8,8a-hexahydroimidazo[1,5-a]pyrazin-2-yl]benzoic acid (Compound AB) instead of hexahydro-pyrazino[1,2-c][1,3]oxazin-6-one (Compound D). Example 25 was obtained as a light yellow solid (45 mg). $^1$H NMR (400 MHz, METHANOL-$d_4$) d ppm 7.93-8.06 (m, 3H), 7.79 (d, 1H), 7.64-7.75 (m, 2H), 7.45 (m, 1H), 7.25 (m, 1H), 7.08 (m, 1H), 6.19 (s, 1H), 4.22 (d, 1H), 3.95-4.15 (m, 4H), 3.53-3.66 (m, 4H), 3.29 (d, 1H), 3.09 (d, 2H), 3.03-3.17 (m, 2H), 2.50-2.63 (m, 1H), 2.35 (br. s., 1H). MS: calc'd 625 (MH$^+$), measured 625 (MH$^+$).

Preparation of 4-[(8aS)-3-oxo-1,5,6,7,8,8a-hexahydroimidazo[1,5-a]pyrazin-2-yl]benzoic acid (Compound AB)

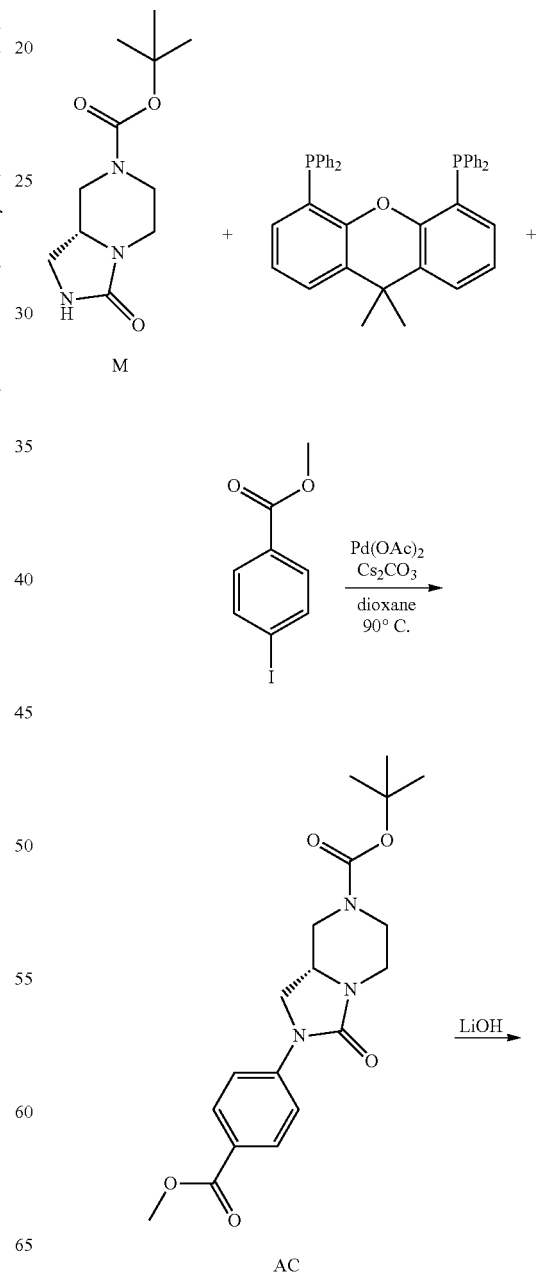

-continued

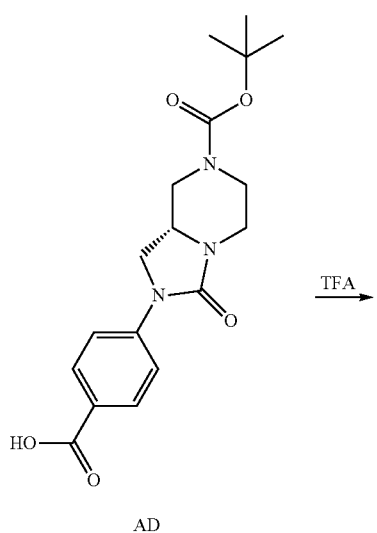

AD

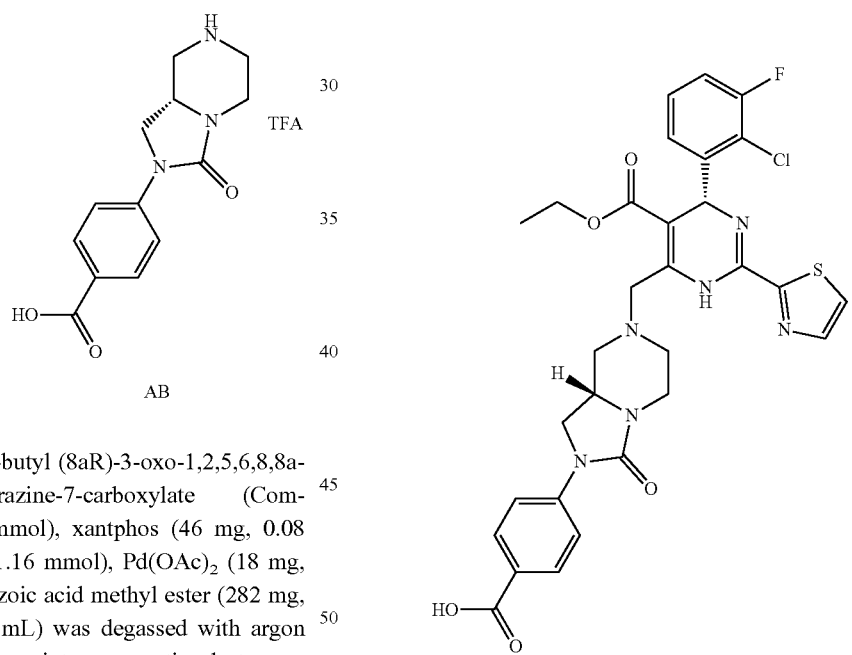

AB

Step 1: A mixture of tert-butyl (8aR)-3-oxo-1,2,5,6,8,8a-hexahydroimidazo[1,5-a]pyrazine-7-carboxylate (Compound M, 200 mg, 0.83 mmol), xantphos (46 mg, 0.08 mmol), $Cs_2CO_3$ (378 mg, 1.16 mmol), $Pd(OAc)_2$ (18 mg, 0.08 mmol) and 4-iodo-benzoic acid methyl ester (282 mg, 1.08 mmol) in dioxane (6 mL) was degassed with argon atmosphere three times. The mixture was stirred at room temperature for 5 minutes under argon atmosphere, and then heated at 90° C. overnight. The mixture was diluted with EtOAc (20 mL), and filtered through celite. The filtrate was concentrated and purified on silica gel to give Compound AC (240 mg).

Step 2: To a solution of Compound AC (240 mg, 0.64 mmol) in THF (3 mL) was added a solution of $LiOH·H_2O$ (215 mg, 5.10 mmol) in $H_2O$ (1 mL) at room temperature. After the reaction mixture was stirred at room temperature overnight, it was acidified to PH 3 to 4 with 1 N HCl at 0° C. The mixture was then concentrated and azeotropically dried with toluene to give Compound AD (231 mg) which was used directly without further purification in the next step.

Step 3: To a solution of Compound AD (231 mg, 0.64 mmol) in dichloromethane (2 mL) was added TFA (2 mL) at room temperature. The mixture was stirred at room temperature for 1 hour, then concentrated to give methyl 4-(3-oxo-1,5,6,7,8,8a-hexahydroimidazo[1,5-a]pyrazin-2-yl)benzoic acid (Compound AB) (240 mg).

Example 26

(R)-6-[(S)-2-(4-Carboxy-phenyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester The title compound was prepared in analogy to Example 25 by using 2-chloro,3-fluorobenzaldehyde and ethyl acetoacetate instead of 2-chloro-4-fluorobenzaldehyde and methyl acetoacetate. Example 26 was obtained as a light yellow solid (76 mg). $^1$H NMR (400 MHz, METHANOL-$d_4$) d ppm 7.85-7.96 (m, 3H), 7.79 (d, 1H), 7.61 (d, 2H), 7.23-7.30 (m, 2H), 7.08-7.19 (m, 1H), 6.16 (s, 1H), 4.62 (d, 1H), 4.43 (d, 1H), 4.22 (m, 1H), 4.02-4.16 (m, 2H), 3.97 (m, 2H), 3.57-3.73 (m, 3H), 3.36-3.49 (m, 1H), 3.02-3.16 (m, 2H), 0.95-1.08 (m, 3H). MS: calc'd 639 (MH$^+$), measured 639 (MH$^+$).

Example 27

(R)-6-[(S)-2-(3-Carboxy-phenyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester

Example 28

(R)-6-[(S)-2-(2-Carboxy-phenyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester

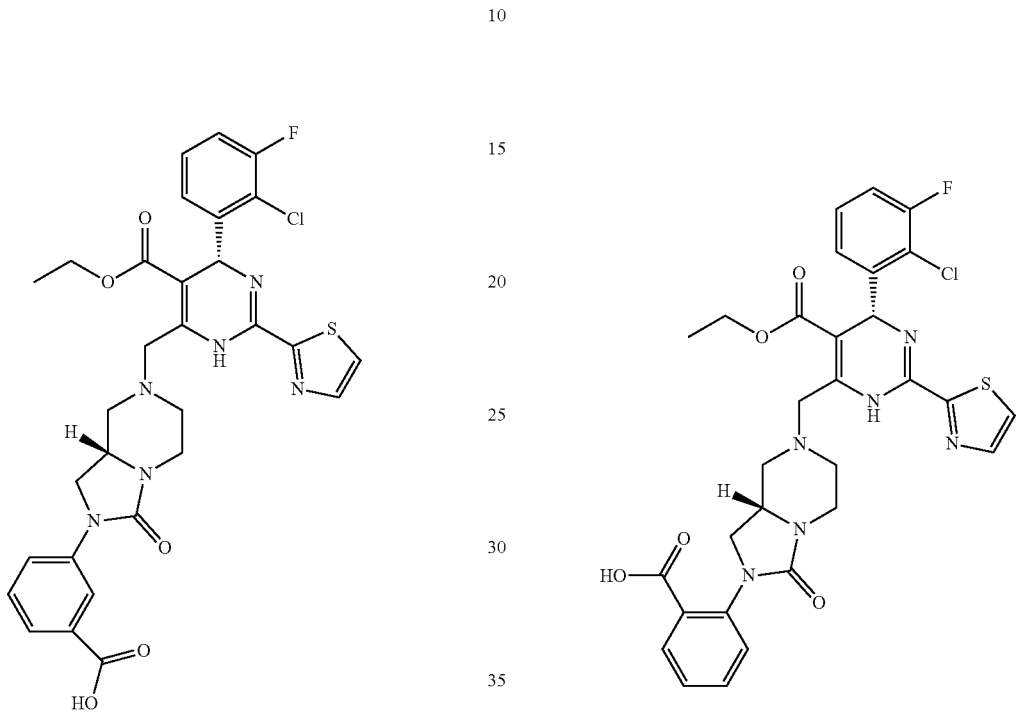

The title compound was prepared in analogy to Example 25 by using 2-chloro,3-fluorobenzaldehyde, ethyl acetoacetate and 3-[(8aS)-3-oxo-1,5,6,7,8,8a-hexahydroimidazo[1,5-a]pyrazin-2-yl]benzoic acid (Compound AE) instead of 2-chloro-4-fluorobenzaldehyde, methyl acetoacetate and 4-[(8aS)-3-oxo-1,5,6,7,8,8a-hexahydroimidazo[1,5-a]pyrazin-2-yl]benzoic acid (Compound AB). Example 27 was obtained as a light yellow solid (20 mg). $^1$H NMR (400 MHz, METHANOL-d$_4$) d ppm 8.11 (s, 1H), 7.90 (d, 1H), 7.75-7.82 (m, 2H), 7.66 (d, 1H), 7.37 (m, 1H), 7.23-7.29 (m, 2H), 7.07-7.17 (m, 1H), 6.16 (s, 1H), 4.59 (d, 1H), 4.34-4.45 (m, 1H), 4.15-4.25 (m, 1H), 4.01-4.13 (m, 2H), 3.97 (m, 2H), 3.52-3.67 (m, 3H), 3.36-3.46 (m, 1H), 3.02-3.16 (m, 2H), 1.01 (m, 3H). MS: calc'd 639 (MH$^+$), measured 639 (MH$^+$).

The title compound was prepared in analogy to Example 25 by using 2-chloro,3-fluorobenzaldehyde and ethyl acetoacetate and 2-[(8aS)-3-oxo-1,5,6,7,8,8a-hexahydroimidazo[1,5-a]pyrazin-2-yl]benzoic acid (Compound AF) instead of 2-chloro-4-fluorobenzaldehyde and methyl acetoacetate and 4-[(8aS)-3-oxo-1,5,6,7,8,8a-hexahydroimidazo[1,5-a]pyrazin-2-yl]benzoic acid (Compound AB). Example 28 was obtained as a light yellow solid (95 mg). $^1$H NMR (400 MHz, METHANOL-d$_4$) d ppm 7.83-7.93 (m, 2H), 7.80 (d, 1H), 7.53 (m, 1H), 7.24-7.35 (m, 4H), 7.08-7.19 (m, 1H), 6.16 (s, 1H), 4.66 (d, 1H), 4.48 (d, 1H), 4.20-4.29 (m, 1H), 4.06-4.11 (m, 1H), 3.92-4.04 (m, 3H), 3.65 (d, 2H), 3.29-3.55 (m, 3H), 3.13 (m, 1H), 1.02 (m, 3H). MS: calc'd 639 (MH$^+$), measured 639 (MH$^+$).

Preparation of 3-[(8aS)-3-oxo-1,5,6,7,8,8a-hexahydroimidazo[1,5-a]pyrazin-2-yl]benzoic acid (Compound AE)

Compound AE was prepared in analogy to Compound AB in Example 25 by using 3-iodo-benzoic acid methyl ester instead of 4-iodo-benzoic acid methyl ester.

Preparation of 2-[(8aS)-3-oxo-1,5,6,7,8,8a-hexahydroimidazo[1,5-a]pyrazin-2-yl]benzoic acid (Compound AF)

The title compound was prepared in analogy to Compound AB in Example 25 by using 2-iodo-benzoic acid methyl ester instead of 4-iodo-benzoic acid methyl ester.

Example 29

(R)-6-[(S)-2-(3-Carboxy-phenyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester

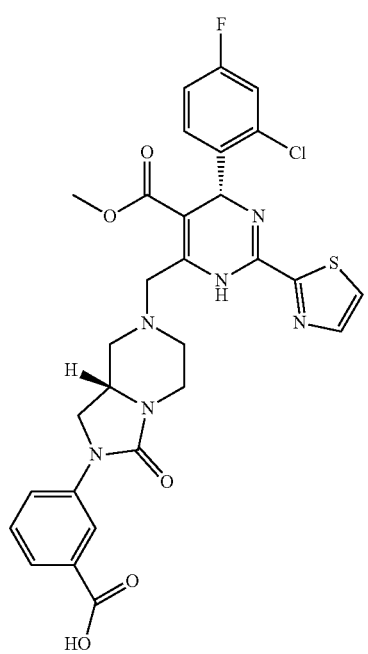 [SMILES: COC(=O)C1=C(CN2CCN3C(=O)N(c4cccc(C(=O)O)c4)C[C@@H]3C2)NC(c2nccs2)=N[C@H]1c1ccc(F)cc1Cl]

The title compound was prepared in analogy to Example 25 by using 3-[(8aS)-3-oxo-1,5,6,7,8,8a-hexahydroimidazo[1,5-a]pyrazin-2-yl]benzoic acid (Compound AE) instead of 4-[(8aS)-3-oxo-1,5,6,7,8,8a-hexahydroimidazo[1,5-a]pyrazin-2-yl]benzoic acid (Compound AB). Example 29 was obtained as a light yellow solid (220 mg). $^1$H NMR (400 MHz, METHANOL-d$_4$) d ppm 8.20-8.26 (m, 1H), 8.03 (d, 1H), 7.85-7.96 (m, 2H), 7.78 (m, 1H), 7.56 (m, 1H), 7.49 (m, 1H), 7.30 (m, 1H), 7.13 (m, 1H), 6.21 (s, 1H), 4.78 (d, 1H), 4.55-4.63 (m, 1H), 4.36 (dm, 1H), 4.13-4.29 (m, 2H), 3.72-3.90 (m, 3H), 3.65 (s, 3H), 3.51-3.61 (m, 1H), 3.35-3.40 (m, 1H), 3.26-3.31 (m, 1H). MS: calc'd 625 (MH$^+$), measured 625 (MH$^+$).

Example 30

2-[7-[[(4R)-4-(2-chloro-4-fluoro-phenyl)-5-methoxycarbonyl-2-thiazol-2-yl-1,4-dihydropyrimidin-6-yl]methyl]-2-cyclopropyl-3-oxo-1,5,6,8-tetrahydroimidazo[1,5-a]pyrazin-8a-yl]acetic acid

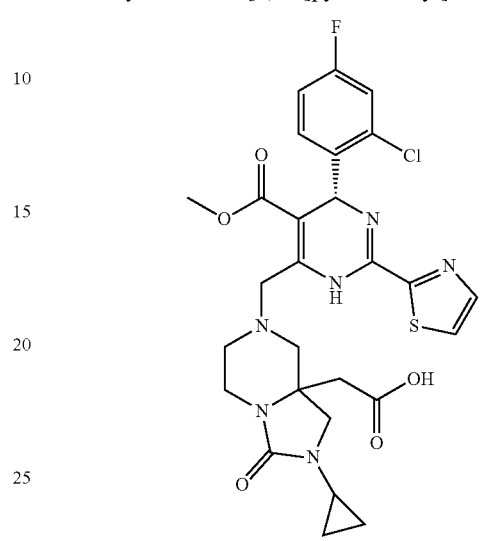

The title compound was prepared in analogy to Example 1 by using 4-[(8aS)-3-oxo-1,5,6,7,8,8a-hexahydroimidazo[1,5-a]pyrazin-2-yl]benzoic acid (Compound AG) instead of hexahydro-pyrazino[1,2-c][1,3]oxazin-6-one (Compound D). Example 30 was obtained as a light yellow solid (48 mg). $^1$H NMR (400 MHz, METHANOL-d$_4$) d ppm 7.93 (d, J=3.0 Hz, 1H), 7.73 (d, J=3.0 Hz, 1H), 7.43 (dd, J=6.1, 8.7 Hz, 1H), 7.24 (dd, J=2.5, 8.8 Hz, 1H), 7.06 (d, J=2.8 Hz, 1H), 6.16 (s, 1H), 4.14 (d, J=16.6 Hz, 1H), 3.85-3.71 (m, 2H), 3.60 (s, 3H), 3.46 (d, J=9.8 Hz, 1H), 3.30-3.15 (m, 3H), 3.06 (d, J=11.3 Hz, 1H), 2.95-2.82 (m, 2H), 2.45 (d, J=5.0 Hz, 1H), 2.39-2.29 (m, 1H), 2.22 (d, J=11.5 Hz, 1H), 0.83-0.53 (m, 4H). MS: calc'd 604 (MH$^+$), measured 604 (MH$^+$).

Preparation of 4-[(8aS)-3-oxo-1,5,6,7,8,8a-hexahydroimidazo[1,5-a]pyrazin-2-yl]benzoic acid (Compound AG)

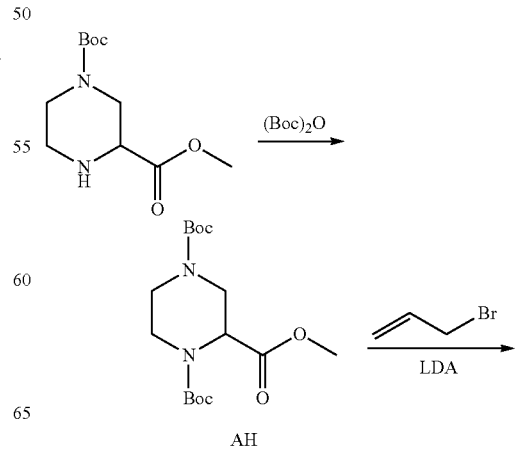

-continued

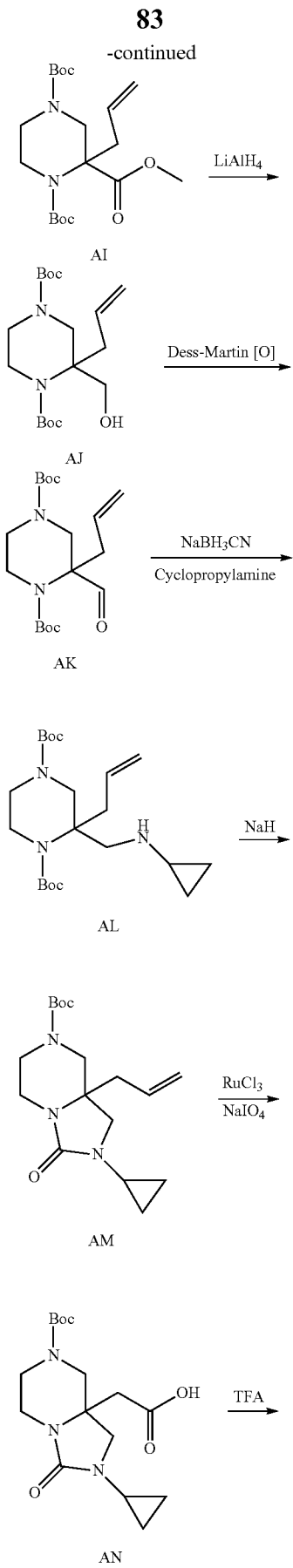

AI

AJ

AK

AL

AM

AN

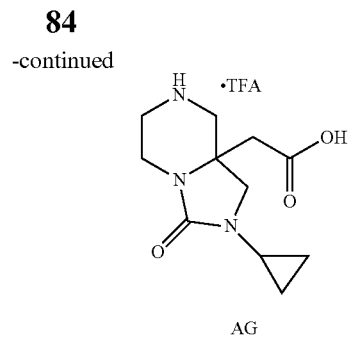

AG

Step 1: To a solution of piperazine-1,3-dicarboxylic acid 1-tert-butyl ester 3-methyl ester (10.6 g, 43 mmol) in 250 mL of dichloromethane was added (Boc)$_2$O (19 g, 86 mmol) at 0° C. The reaction mixture stirred for 4 hours at room temperature, and then quenched with water and then extracted with dichloromethane. After the organic layer was dried over anhydrous Na$_2$SO$_4$, the filtrate was concentrated. The residue was purified by silica gel column chromatography to give Compound AH (yield 13.6 g, 92%).

Step 2: To a solution of Compound AH (13.4 g, 38.9 mmol) in 200 mL of anhydrous THF was added freshly prepared LDA (2M in THF, 38 mL) at −78° C. The reaction mixture was stirred for 30 minutes at −78° C. and then warmed to room temperature for 30 minutes. The mixture was cooled down to −78° C. and a solution of allyl bromide (6.7 mL, 77.9 mmol) in 10 mL of THF was added. After the mixture was warmed to room temperature and stirred overnight, the solvent was removed under reduced pressure. The residue was purified by silica gel column chromatography to afford Compound AI (yield 13.6 g, 91%).

Step 3: To a solution of Compound AI (1.0 g, 2.6 mmol) in 20 mL of anhydrous THF was added LAH (2M in THF, 1.3 mL) at −78° C. The reaction mixture was stirred for 30 minutes at −78° C. and then warmed to room temperature and stirred overnight. Anhydrous Na$_2$SO$_4$ was added.

After 1 hour, the filtrate was concentrated. The residue was purified by silica gel column chromatography to afford Compound AJ (yield 0.7 g, 75%).

Step 4: To a solution of Compound AJ (3 g, 8.4 mmol) in 50 mL of anhydrous dichloromethane was added Dess-Martin periodinane (6 g, 14.1 mmol) at 0° C. The reaction mixture was stirred for 2 hours at room temperature, and then quenched with water. The filtrate was extracted with dichloromethane, and then dried over anhydrous Na$_2$SO$_4$, and the filtrate was concentrated to give Compound AK without further purification.

Step 5: To a stirred solution of Compound AK (1.5 g, 4.2 mmol) in dichloromethane (15 mL) was added successively acetic acid and cyclopropylamine (0.29 mL, 4.2 mmol). The reaction mixture was stirred for 2 hours at room temperature, then sodium triacetoxyborohydride (520 mg, 8.4 mmol) was added and the reaction mixture was stirred for 3 hours at room temperature. The reaction mixture was quenched with saturated NH$_4$Cl. Then water (20 mL) was added followed by dichloromethane (40 mL). The organic layer was separated and then washed with brine, and then dried over Na$_2$SO$_4$. The filtrate was concentrated to give Compound AL without further purification.

Step 6: To a solution of Compound AL (1.5 g, 3.8 mmol) in 20 mL of anhydrous THF was added NaH (0.26 g, 9.4 mmol) at 0° C. The reaction mixture was stirred over night at 85° C. Then the reaction was cooled to room temperature, quenched with water and extracted with dichloromethane. The organic layer was dried over anhydrous Na$_2$SO$_4$ and then concentrated in vacuo. The residue was purified by silica gel column chromatography to give Compound AM (yield 1.0 g, 82%).

Step 7: To a solution of Compound AM (700 mg, 2.2 mmol) in H$_2$O (1 mL) and CH$_3$CN (6 mL) under nitrogen atmosphere was added RuCl$_3$.H$_2$O (18 mg, 0.086 mmol), followed by NaIO$_4$ (2.7 g, 12.6 mmol). The reaction was stirred at room temperature overnight. The mixture was diluted with water and ethyl ether, filtered through a celite pad, and the pad was washed with ethyl ether. The aqueous layer was extracted with dichloromethane. The combined organic layers were dried over Na$_2$SO$_4$, and concentrated to give Compound AN (yield 450 mg, 60%).

Step 8: To a solution of Compound AN (600 mg, 1.76 mmol) in dichloromethane (8 mL) was added TFA (2 mL) at 0° C. After the reaction mixture was stirred for 2 hours at room temperature, it was concentrated to give Compound AG without further purification.

Example 31

2-[7-[[(4R)-4-(2-chloro-4-fluoro-phenyl)-5-methoxycarbonyl-2-thiazol-2-yl-1,4-dihydropyrimidin-6-yl]methyl]-2-isopropyl-3-oxo-1,5,6,8-tetrahydroimidazo[1,5-a]pyrazin-8a-yl]acetic acid

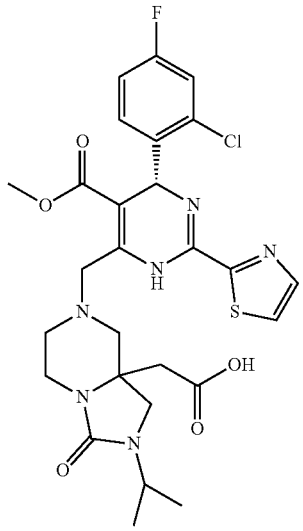 [SMILES: COC(=O)C1=C(CN2CCN3C(=O)N(C(C)C)CC3(CC(=O)O)C2)NC(c2nccs2)=N[C@H]1c1ccc(F)cc1Cl]

The title compound was prepared in analogy to Example 30 by using 2-(2-isopropyl-3-oxo-5,6,7,8-tetrahydro-1H-imidazo[1,5-a]pyrazin-8a-yl)acetic acid (Compound AO) instead of 4-[(8aS)-3-oxo-1,5,6,7,8,8a-hexahydroimidazo[1,5-a]pyrazin-2-yl]benzoic acid (Compound AG). Example 31 was obtained as a light yellow solid (8 mg). $^1$H NMR (400 MHz, METHANOL-d$_4$) d ppm 7.94 (d, J=3.0 Hz, 1H), 7.73 (d, J=3.3 Hz, 1H), 7.43 (dd, J=6.0, 8.8 Hz, 1H), 7.24 (dd, J=2.8, 8.8 Hz, 1H), 7.11-7.02 (m, 1H), 6.16 (s, 1H), 4.18-4.04 (m, 2H), 3.79 (d, J=16.6 Hz, 2H), 3.61 (s, 3H), 3.47 (d, J=9.5 Hz, 1H), 3.29-3.24 (m, 1H), 3.20 (d, J=9.5 Hz, 1H), 3.09 (d, J=11.5 Hz, 1H), 2.90 (d, J=15.6 Hz, 2H), 2.38-2.12 (m, 3H), 1.18 (d, J=7.0 Hz, 3H), 1.12 (d, J=6.8 Hz, 3H). MS: calc'd 606 (MH$^+$), measured 606 (MH$^+$).

Preparation of 2-(2-isopropyl-3-oxo-5,6,7,8-tetrahydro-1H-imidazo[1,5-a]pyrazin-8a-yl)acetic acid (Compound AO)

The title compound was prepared in analogy to Compound AG in Example 30 by using iso-propyl amine instead of cyclopropyl amine.

Example 32

(R)-6-[(S)-2-(1-Carboxyl-1-methyl-ethyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester

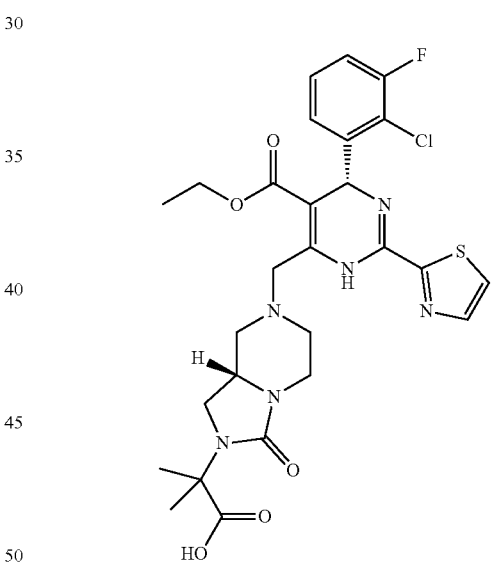

The title compound was prepared in analogy to Example 19 by using methyl 2-amino-2-methyl-propanoate hydrochloride salt instead of ethyl 3-amino-2,2-dimethyl-propanoate hydrochloride salt. Example 32 was obtained as a light yellow solid (60 mg). $^1$H NMR (400 MHz, METHANOL-d$_4$) d ppm 7.98 (d, 1H), 7.79 (d, 1H), 7.23-7.38 (m, 2H), 7.09-7.23 (m, 1H), 6.25 (s, 1H), 4.23 (br. s., 1H), 4.06 (m, 3H), 3.78-3.97 (m, 2H), 3.59-3.71 (m, 1H), 3.14-3.29 (m, 2H), 2.89-3.14 (m, 2H), 2.54 (br. s., 2H), 1.40-1.57 (m, 6H), 1.04-1.19 (m, 3H). MS: calc'd 605 (MH$^+$), measured 605 (MH$^+$).

Example 33

3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3-methyl-butanoic acid

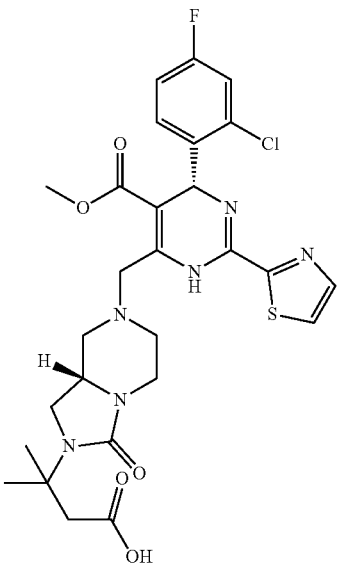 [SMILES: COC(=O)C1=C(CN2CCN3C(=O)N(C(C)(C)CC(=O)O)C[C@@H]3C2)NC(c2nccs2)=N[C@H]1c1ccc(F)cc1Cl]

The title compound was prepared in analogy to Example 19 by using 2-chloro-4-fluorobenzaldehyde, methyl acetoacetate and 3-[(8aS)-3-oxo-1,5,6,7,8,8a-hexahydroimidazo[1,5-a]pyrazin-2-yl]-3-methyl-butanoic acid (Compound AP) instead of 2-chloro-3-fluorobenzaldehyde, ethyl acetoacetate and 3-[(8aS)-3-oxo-1,5,6,7,8,8a-hexahydroimidazo[1,5-a]pyrazin-2-yl]-2,2-dimethyl-propanoic acid (Compound Q). Example 33 was obtained as a light yellow solid (381 mg). $^1$H NMR (400 MHz, METHANOL-$d_4$) d ppm 8.00-8.01 (d, J=4.0Hz, 1H), 7.90-7.91 (d, J=4.0Hz, 1H), 7.55 (m, 1H), 7.29 (m, 1H), 7.13 (m, 1H), 6.20 (s, 1H), 4.76 (d, J=16.0 Hz, 1H), 4.60 (d, J=16.0 Hz, 1H), 4.12 (m, 1H), 4.02-4.06 (m, 1H), 3.70-3.80 (m, 3H), 3.65 (s, 3H), 3.32-3.44 (m, 2H), 3.20 (m, 2H), 3.09-3.05 (d, J=16.0Hz, 1H), 2.79-2.83 (d, J=16.0Hz, 1H), 1.47 (s, 6H). MS: calc'd 605 (MH$^+$), measured 605 (MH$^+$).

Preparation of 3-[(8aS)-3-oxo-1,5,6,7,8,8a-hexahydroimidazo[1,5-a]pyrazin-2-yl]-3-methyl-butanoic acid (Compound AP)

The title compound was prepared in analogy to Compound Q in Example 19 by using methyl 3-amino-3-methyl-butanoate hydrochloride salt (Compound AP-1) instead of ethyl 3-amino-2,2-dimethyl-propanoate hydrochloride salt.

Preparation of methyl 3-amino-3-methyl-butanoate hydrochloride salt (Compound AP-1)

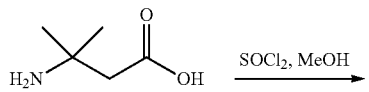

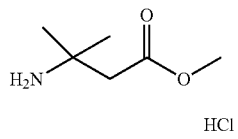

Compound AP-1 was prepared in analogy to Compound W in Example 20 by using 3-amino-3-methyl-butyric acid instead of DL-3-aminoisobutyric acid.

Example 34

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3-methyl-butanoic acid

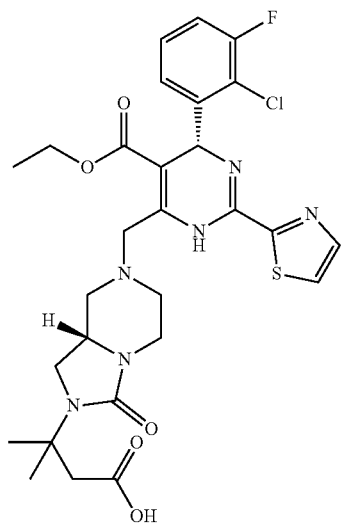 [SMILES: CCOC(=O)C1=C(CN2CCN3C(=O)N(C(C)(C)CC(=O)O)C[C@@H]3C2)NC(c2nccs2)=N[C@H]1c1cccc(F)c1Cl]

The title compound was prepared in analogy to Example 19 by using 3-[(8aS)-3-oxo-1,5,6,7,8,8a-hexahydroimidazo[1,5-a]pyrazin-2-yl]-3-methyl-butanoic acid (Compound AP) instead of 3-[(8aS)-3-oxo-1,5,6,7,8,8a-hexahydroimidazo[1,5-a]pyrazin-2-yl]-2,2-dimethyl-propanoic acid (Compound Q). Example 34 was obtained as a light yellow solid (26 mg). $^1$H NMR (400 MHz, METHANOL-$d_4$) d ppm 7.99-8.00 (d, J=4.0Hz, 1H), 7.83-7.84 (d, J=4.0Hz, 1H), 7.35 (m, 2H), 7.20 (m, 1H), 6.25 (s, 1H), 4.20-4.40 (m, 2H), 4.10 (m, 2H), 3.94 (m, 2H), 3.70 (m, 2H), 3.29 (m, 5H), 3.02-3.06 (d, J=16.0Hz, 1H), 2.80-2.84 (d, J=16.0Hz, 1H), 1.46 (s, 6H), 1.11-1.15 (t, $J_1$=8.0Hz, $J_2$=16.0Hz, 3H). MS: calc'd 619 (MH$^+$), measured 619 (MH$^+$).

Example 35

1-[[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]cyclopropanecarboxylic acid

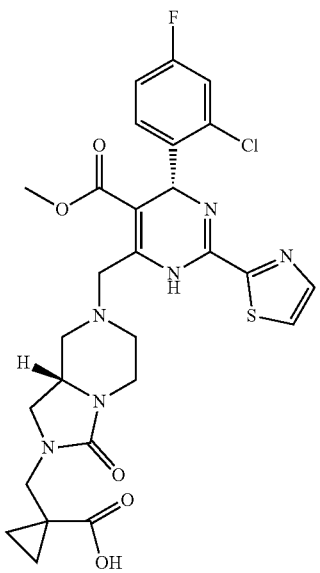 [SMILES: COC(=O)C1=C(CN2CCN3C(=O)N(CC4(C(=O)O)CC4)C[C@@H]3C2)NC(c2nccs2)=N[C@H]1c1ccc(F)cc1Cl]

The title compound was prepared in analogy to Example 19 by using 2-chloro-4-fluorobenzaldehyde, methyl acetoacetate and methyl 1-(aminomethyl)cyclopropanecarboxylate hydrochloride salt (Compound AQ) instead of 2-chloro,3-fluorobenzaldehyde, ethyl acetoacetate and ethyl 3-amino-2,2-dimethyl-propanoate hydrochloride salt. Example 35 was obtained as a light yellow solid (760 mg). $^1$H NMR (400 MHz, METHANOL-$d_4$) d ppm 8.00-8.01 (d, J=4.0Hz, 1H), 7.90-7.91 (d, J=4.0Hz, 1H), 7.55 (m, 1H), 7.29 (m, 1H), 7.13 (m, 1H), 6.20 (s, 1H), 4.77 (d, J=16.0 Hz, 1H), 4.59 (d, J=16.0 Hz, 1H), 4.19 (m, 1H), 4.07-4.10 (m, 1H), 3.73-3.77 (m, 3H), 3.65 (s, 3H), 3.36-3.50 (m, 4H), 3.15-3.24 (m, 2 H), 1.29 (m, 2H), 1.02 (m, 2H). MS: calc'd 603 (MH$^+$), measured 603 (MH$^+$).

Preparation of methyl 1-(aminomethyl)cyclopropanecarboxylate hydrochloride salt (Compound AQ)

The title compound was prepared in analogy to Compound W in Example 20 by using 1-(aminomethyl)cyclopropanecarboxylic acid (CAS number: 139132-50-6, J&K; for its synthesis, please refer to: Mertin A., et al. *Synlett*, 1991, 2, 87-9) instead of DL-3-aminoisobutyric acid.

Example 36

1-[[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]cyclopropanecarboxylic acid

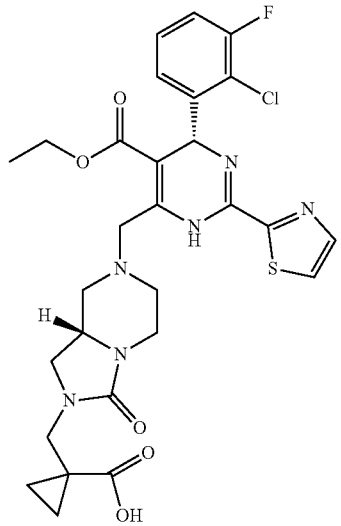 [SMILES: CCOC(=O)C1=C(CN2CCN3C(=O)N(CC4(C(=O)O)CC4)C[C@@H]3C2)NC(c2nccs2)=N[C@H]1c1cccc(F)c1Cl]

The title compound was prepared in analogy to Example 19 by using methyl 1-(aminomethyl)cyclopropanecarboxylate hydrochloride salt (Compound AQ) instead ethyl 3-amino-2,2-dimethyl-propanoate hydrochloride salt. Example 36 was obtained as a light yellow solid (170 mg). $^1$H NMR (400 MHz, METHANOL-$d_4$) d ppm 8.00-8.01 (d, J=4.0Hz, 1H), 7.92-7.91 (d, J=4.0Hz, 1H), 7.38 (m, 2H), 7.26 (m, 1H), 6.27 (s, 1H), 4.77 (d, J=16.0 Hz, 1H), 4.59 (d, J=16.0 Hz, 1H), 4.11 (m, 1H), 4.07-4.10 (m, 3H), 3.72-3.78 (m, 3H), 3.36-3.47 (m, 4H), 3.15-3.24 (m, 2 H), 1.29 (m, 2H), 1.13 (t, J$_1$=8.0Hz, J$_2$=16.0Hz, 3H), 1.02 (m, 2H). MS: calc'd 617 (MH$^+$), measured 617 (MH$^+$).

Example 37

1-[[(8aS)-7-[[(4S)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]cyclopropanecarboxylic acid

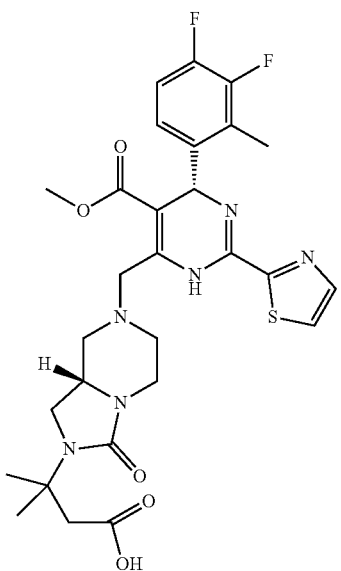 [SMILES: COC(=O)C1=C(CN2CCN3C(=O)N(C(C)(C)CC(=O)O)C[C@@H]3C2)NC(c2nccs2)=N[C@H]1c1ccc(F)c(F)c1C]

The title compound was prepared in analogy to Example 19 by using 2-methyl-3,4-difluorobenzaldehyde, methyl acetoacetate and 3-[(8aS)-3-oxo-1,5,6,7,8,8a-hexahydroimidazo[1,5-a]pyrazin-2-yl]-3-methyl-butanoic acid (Compound AP) instead of 2-chloro-3-fluorobenzaldehyde, ethyl acetoacetate and 3-[(8aS)-3-oxo-1,5,6,7,8,8a-hexahydroimidazo[1,5-a]pyrazin-2-yl]-2,2-dimethyl-propanoic acid (Compound Q). Example 37 was obtained as a light yellow solid (153 mg). $^1$H NMR (400 MHz, METHANOL-d$_4$) d ppm 8.00-8.01 (d, J=4.0Hz, 1H), 7.90-7.91 (d, J=4.0Hz, 1H), 7.26 (m, 1H), 7.10 (m, 1H), 5.95 (s, 1H), 4.74 (d, J=16.0 Hz, 1H), 4.57 (d, J=16.0 Hz, 1H), 4.10 (m, 2H), 3.70-3.80 (m, 3H), 3.66 (s, 3H), 3.36-3.42 (m, 2H), 3.20 (m, 2H), 3.09-3.05 (d, J=16.0Hz, 1H), 2.79-2.83 (d, J=16.0Hz, 1H), 2.53 (s, 3H), 1.47 (s, 6H). MS: calc'd 603 (MH$^+$), measured 603 (MH$^+$).

Example 38

1-[[(8aS)-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]cyclopropanecarboxylic acid

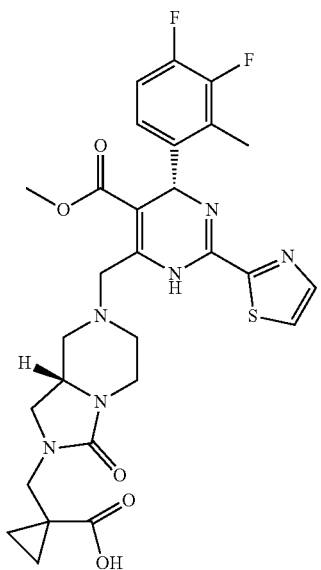 [SMILES: COC(=O)C1=C(CN2CCN3C(=O)N(CC4(C(=O)O)CC4)C[C@@H]3C2)NC(c2nccs2)=N[C@H]1c1ccc(F)c(F)c1C]

The title compound was prepared in analogy to Example 35 by using 2-methyl-3,4-difluorobenzaldehyde instead of 2-chloro-4-fluorobenzaldehyde. Example 38 was obtained as a light yellow solid (54 mg). $^1$H NMR (400 MHz, METHANOL-d$_4$) d ppm 8.00-8.01 (d, J=4.0Hz, 1H), 7.90-7.91 (d, J=4.0Hz, 1H), 7.26 (m, 1H), 7.12 (m, 1H), 5.95 (s, 1H), 4.74 (d, J=16.0 Hz, 1H), 4.56 (d, J=16.0 Hz, 1H), 4.07-4.17 (m, 2H), 3.70-3.77 (m, 3H), 3.66 (s, 3H), 3.35-3.46 (m, 4H), 3.15-3.22 (m, 2H), 2.51 (s, 3H), 1.29 (m, 2H), 1.02 (m, 2H). MS: calc'd 601 (MH$^+$), measured 601 (MH$^+$).

Example 39

3-[(2S,8aR)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclobutanecarboxylic acid

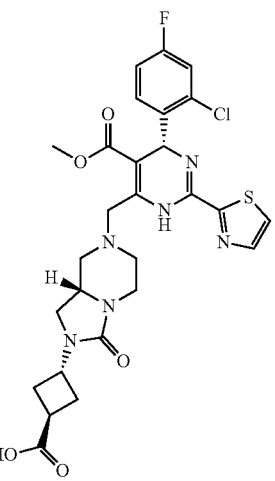

The title compound was prepared in analogy to Example 19 by using 2-chloro-4-fluorobenzaldehyde, methyl acetoacetate and methyl trans-3-amino-cyclobutanecarboxylate hydrochloride (CAS number: 74316-29-3; for its synthesis, please refer to: Grygorenko O. O., et al. *Synthetic Communications*, 2011, 41, 1644-1649) instead of 2-chloro-3-fluorobenzaldehyde, ethyl acetoacetate and ethyl 3-amino-2,2-dimethyl-propanoate hydrochloride. Example 39 was obtained as a light yellow solid (44 mg). $^1$H NMR (400 MHz, METHANOL-$d_4$) d ppm 7.97 (dd, J=4.0, 3.3 Hz, 1H), 7.77 (dd, J=3.1, 1.4 Hz, 1H), 7.43 (ddd, J=8.7, 6.1, 2.5 Hz, 1H), 7.20-7.28 (m, 1H), 6.99-7.13 (m, 1H), 6.18 (s, 1H), 4.58-4.73 (m, 1H), 4.11 (dd, J=16.9, 4.6 Hz, 1H), 3.73-3.97 (m, 3H), 3.61 (s, 3H), 2.82-3.28 (m, 5H), 2.74 (d, J=11.8 Hz, 1H), 2.15-2.65 ppm (m, 6H). MS: calc'd 603 (MH$^+$), measured 603 (MH$^+$).

Example 40

3-[(8aR)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclobutanecarboxylic acid

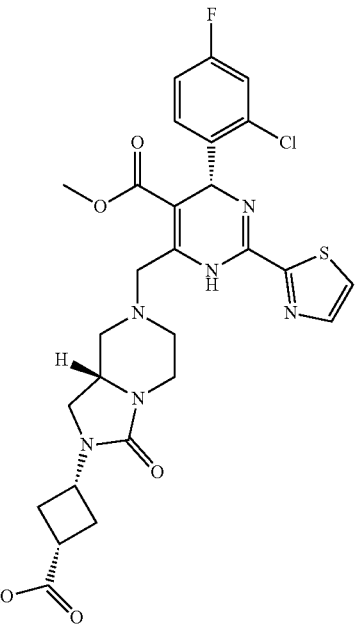

The title compound was prepared in analogy to Example 19 by using 2-chloro-4-fluorobenzaldehyde, methyl acetoacetate and methyl cis-3-amino-cyclobutanecarboxylate hydrochloride (CAS number: 1212304-86-3; for its synthesis, please refer to: Grygorenko O. O., et al. *Synthetic Communications*, 2011, 41, 1644-1649) instead of 2-chloro-3-fluorobenzaldehyde, ethyl acetoacetate and ethyl 3-amino-2,2-dimethyl-propanoate hydrochloride. Example 40 was obtained as a light yellow solid (5 mg). $^1$H NMR (400 MHz, METHANOL-$d_4$) d ppm 7.92-8.02 (m, 1H), 7.77 (dd, J=3.1, 1.4 Hz, 1H), 7.38-7.48 (m, 1H), 7.24 (d, J=6.3 Hz, 1H), 6.98-7.15 (m, 1H), 6.18 (s, 1H), 4.58-4.75 (m, 1H), 4.04-4.19 (m, 1H), 3.72-3.97 (m, 3H), 3.61 (s, 4H), 2.81-3.27 (m, 6H), 2.33-2.63 ppm (m, 5H). MS: calc'd 603 (MH$^+$), measured 603 (MH$^+$).

Example 41

3-[(8aS)-7-[[(4R)-4-(2-chloro-3-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid

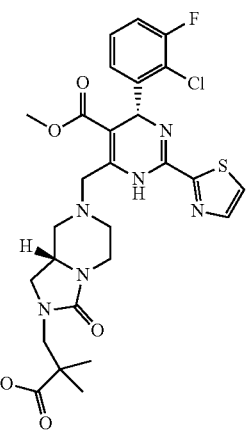

The title compound was prepared in analogy to Example 19 by using methyl acetoacetate instead of ethyl acetoacetate. Example 41 was obtained as a light yellow solid (250 mg). $^1$H NMR (400 MHz, METHANOL-$d_4$) d ppm 7.97 (d, J=3.3 Hz, 1H), 7.76 (d, J=3.0 Hz, 1H), 7.09-7.36 (m, 3H), 6.23 (s, 1H), 4.04-4.15 (m, 1H), 3.78-3.98 (m, 3H), 3.61 (s, 3H), 3.36-3.55 (m, 3H), 3.04-3.28 (m, 2H), 2.76-2.99 (m, 2H), 2.12-2.45 (m, 2H), 1.15-1.25 ppm (m, 6H). MS: calc'd 605 (MH$^+$), measured 605 (MH$^+$).

Example 42

3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid

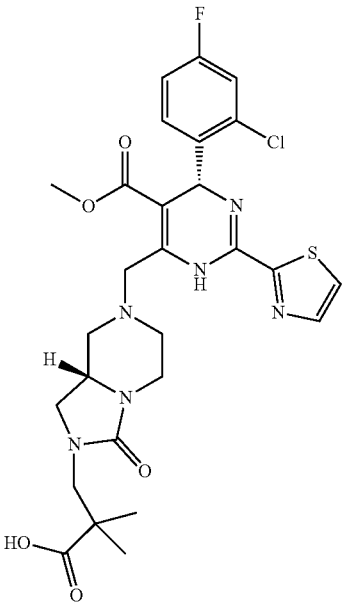 [SMILES: COC(=O)C1=C(CN2CCN3C(=O)N(CC(C)(C)C(=O)O)C[C@@H]3C2)NC(c2nccs2)=N[C@H]1c1ccc(F)cc1Cl]

The title compound was prepared in analogy to Example 19 by using 2-chloro-4-fluorobenzaldehyde and methyl acetoacetate instead of 2-chloro-3-fluorobenzaldehyde and ethyl acetoacetate. Example 42 was obtained as a light yellow solid (260 mg). $^1$H NMR (400 MHz, METHANOL-$d_4$) d ppm 7.97 (d, J=3.0 Hz, 1H), 7.76 (d, J=3.3 Hz, 1H), 7.42 (dd, J=8.5, 6.0 Hz, 1H), 7.24 (dd, J=8.7, 2.6 Hz, 1H), 7.06 (td, J=8.4, 2.8 Hz, 1H), 6.17 (s, 1H), 4.09 (d, J=16.8 Hz, 1H), 3.79-3.98 (m, 3H), 3.61 (s, 3H), 3.51 (t, J=8.9 Hz, 1H), 3.36-3.44 (m, 1H), 3.04-3.26 (m, 3H), 2.75-3.00 (m, 2H), 2.11-2.43 (m, 2H), 1.20 ppm (d, J=3.0 Hz, 6H). MS: calc'd 605 (MH$^+$), measured 605 (MH$^+$).

Example 43

3-[(8aS)-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid

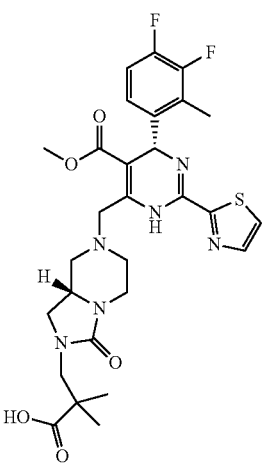 [SMILES: COC(=O)C1=C(CN2CCN3C(=O)N(CC(C)(C)C(=O)O)C[C@@H]3C2)NC(c2nccs2)=N[C@H]1c1ccc(F)c(F)c1C]

The title compound was prepared in analogy to Example 19 by using 2-methyl-3,4-difluorobenzaldehyde and methyl acetoacetate instead of 2-chloro-3-fluorobenzaldehyde and ethyl acetoacetate. Example 43 was obtained as a light yellow solid (110 mg). $^1$H NMR (400 MHz, METHANOL-$d_4$) d ppm 7.95 (d, J=3.3 Hz, 1H), 7.75 (d, J=3.3 Hz, 1H), 6.96-7.09 (m, 2H), 5.93 (s, 1H), 4.04-4.16 (m, 1H), 3.78-3.98 (m, 3H), 3.62 (s, 3H), 3.36-3.56 (m, 3H), 3.05-3.26 (m, 2H), 2.74-2.97 (m, 2H), 2.57 (d, J=2.3 Hz, 3H), 2.36 (td, J=11.7, 3.6 Hz, 1H), 2.18 (t, J=10.9 Hz, 1H), 1.20 ppm (d, J=3.3 Hz, 6H). MS: calc'd 603 (MH$^+$), measured 603 (MH$^+$).

Example 44

3-[(8aS)-7-[[(4S)-4-(3-fluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid

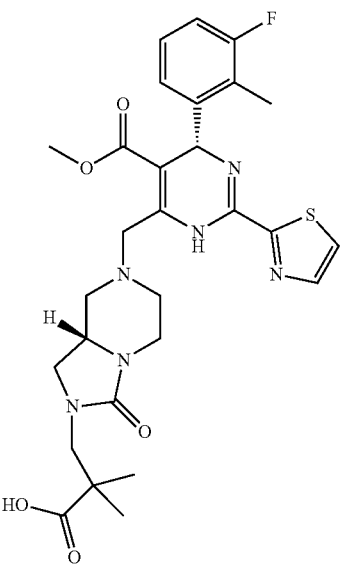 [SMILES: COC(=O)C1=C(CN2CCN3C(=O)N(CC(C)(C)C(=O)O)C[C@@H]3C2)NC(c2nccs2)=N[C@H]1c1cccc(F)c1C]

The title compound was prepared in analogy to Example 19 by using 2-methyl-3-fluorobenzaldehyde and methyl acetoacetate instead of 2-chloro-3-fluorobenzaldehyde and ethyl acetoacetate. Example 44 was obtained as a light yellow solid (74 mg). $^1$H NMR (400 MHz, METHANOL-$d_4$) d ppm 7.95 (d, J=3.0 Hz, 1H), 7.74 (d, J=3.3 Hz, 1H), 7.03-7.21 (m, 2H), 6.88-6.99 (m, 1H), 5.98 (s, 1H), 4.03-4.17 (m, 1H), 3.79-3.99 (m, 4H), 3.62 (s, 3H), 3.41-3.56 (m, 2H), 3.07-3.26 (m, 2H), 2.75-2.98 (m, 2H), 2.53 (d, J=2.0 Hz, 3H), 2.29-2.45 (m, 1H), 2.18 (t, J=11.2 Hz, 1H), 1.20 ppm (d, J=3.3 Hz, 6H). MS: calc'd 585 (MH$^+$), measured 585 (MH$^+$).

Example 45

7-[[(4R)-4-(2-chloro-4-fluoro-phenyl)-5-methoxycarbonyl-2-thiazol-2-yl-1,4-dihydropyrimidin-6-yl]methyl]-2-cyclopropyl-3-oxo-5,6,8,8a-tetrahydro-1H-imidazo[1,5-a]pyrazine-8-carboxylic acid

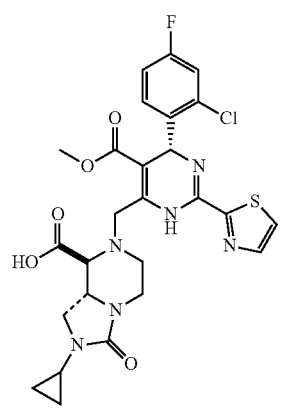 [SMILES: COC(=O)C1=C(CN2CCN3C(=O)N(C4CC4)C[C@@H]3[C@H]2C(=O)O)NC(c2nccs2)=N[C@H]1c1ccc(F)cc1Cl]

Preparation of Example 45

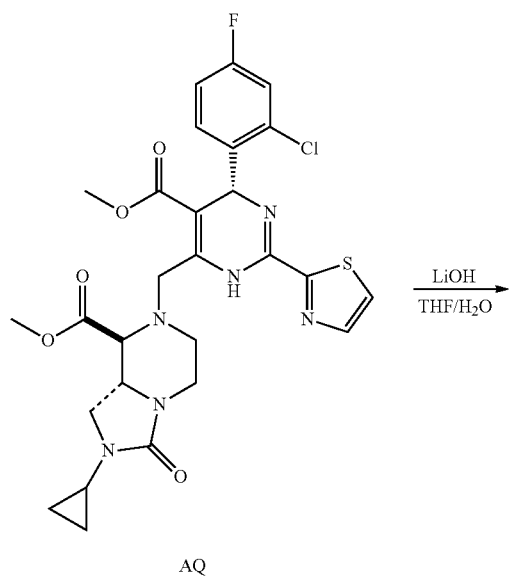

AQ

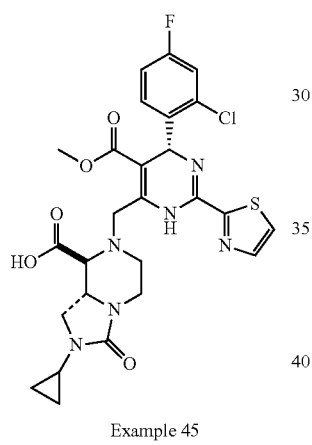

Example 45

The solution of methyl 7-[[(4R)-4-(2-chloro-4-fluoro-phenyl)-5-methoxycarbonyl-2-thiazol-2-yl-1,4-dihydropyrimidin-6-yl]methyl]-2-cyclopropyl-3-oxo-5,6,8,8a-tetrahydro-1H-imidazo[1,5-a]pyrazine-8-carboxylate (Compound AQ, 150 mg, 0.25 mmol) in tetrahydrofuran (1.5 mL) was added lithium hydroxide monohydrate (52 mg, 1.25 mmol) in water (1.5 mL). After the reaction mixture was stirred at room temperature for 2 hours, it was neutralized by 1N hydrochloride solution to pH 3.0. The mixture was extracted with ethyl acetate (30 mL) three times. The combined organic phase was dried over $Na_2SO_4$, filtrated and then concentrated. The residue was purified by Prep-HPLC to give Example 45 as a mixture of two diastereomers (5 mg). $^1$H NMR (400 MHz, METHANOL-$d_4$) d ppm 8.06-7.95 (m, 1H), 7.87 (s, 1H), 7.55-7.44 (m, 1H), 7.32-7.23 (m, 1H), 7.15-7.03 (m, 1H), 6.18 (s, 1H), 4.37-4.21 (m, 1H), 4.09-3.91 (m, 1H), 3.91-3.77 (m, 2H), 3.62 (d, J=2.0 Hz, 4H), 3.52-3.39 (m, 2H), 3.22-2.96 (m, 2H), 2.75-2.58 (m, 1H), 2.50-2.42 (m, 1H), 0.74 (d, J=1.5 Hz, 4H). MS: calc'd 589 (MH$^+$), measured 589 (MH$^+$).

Preparation of 7-[[(4R)-4-(2-chloro-4-fluoro-phenyl)-5-methoxycarbonyl-2-thiazol-2-yl-1,4-dihydro-pyrimidin-6-yl]methyl]-2-cyclopropyl-3-oxo-5,6,8,8a-tetrahydro-1H-imidazo[1,5-a]pyrazine-8-carboxylate (Compound AQ)

The title compound was prepared in analogy to Example 1 by using methyl 2-cyclopropyl-3-oxo-1,5,6,7,8,8a-hexahydroimidazo[1,5-a]pyrazine-8-carboxylate (Compound AR) instead of hexahydro-pyrazino[1,2-c][1,3]oxazin-6-one (Compound D).

Preparation of cis-methyl 2-cyclopropyl-3-oxo-1,5,6,7,8,8a-hexahydroimidazo[1,5-a]pyrazine-8-carboxylate (Compound AR)

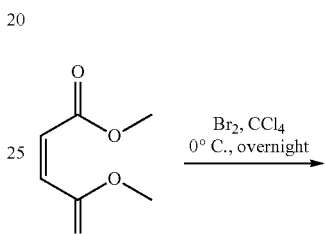

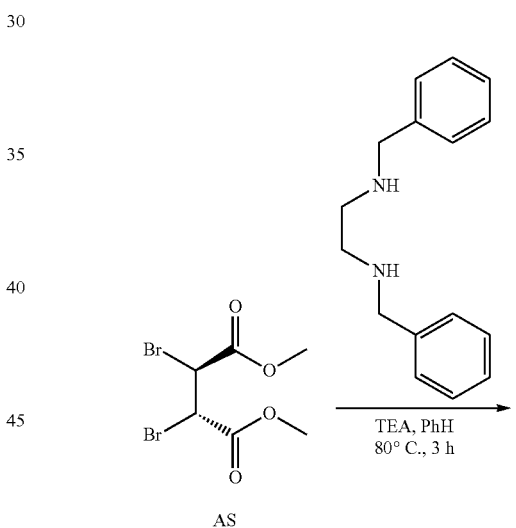

AS

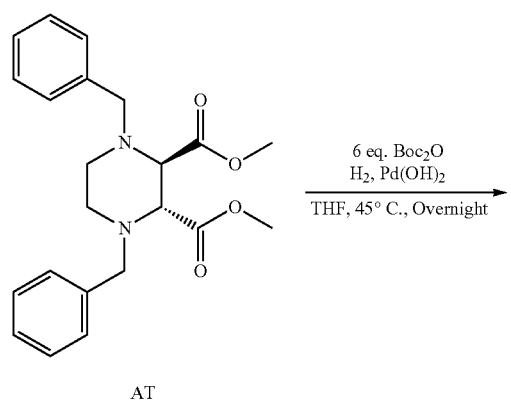

AT

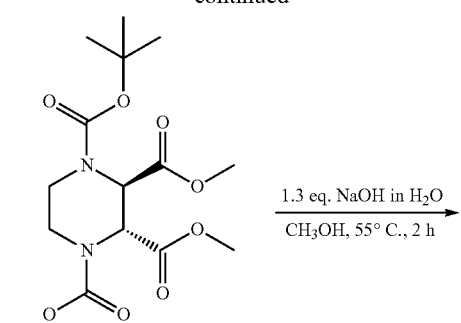

AU

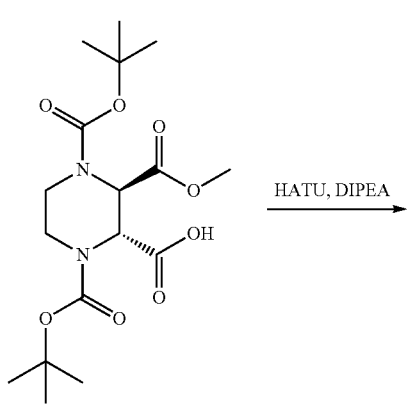

AV

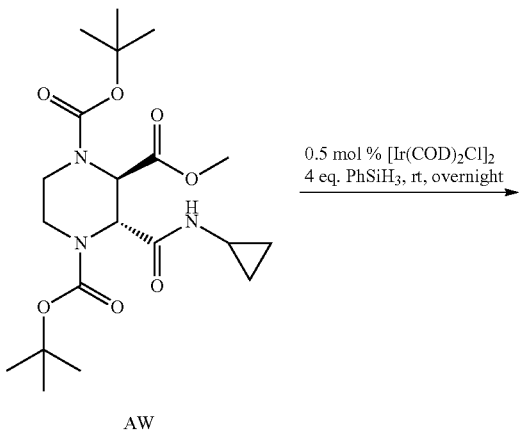

AW

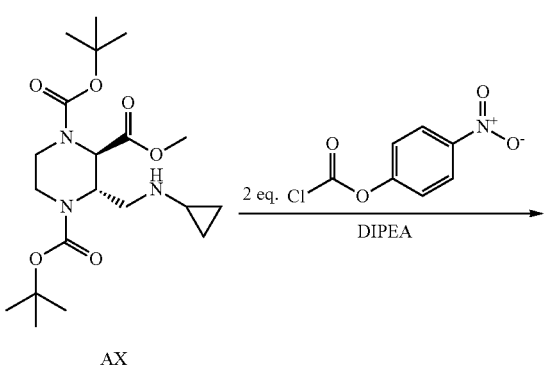

AX

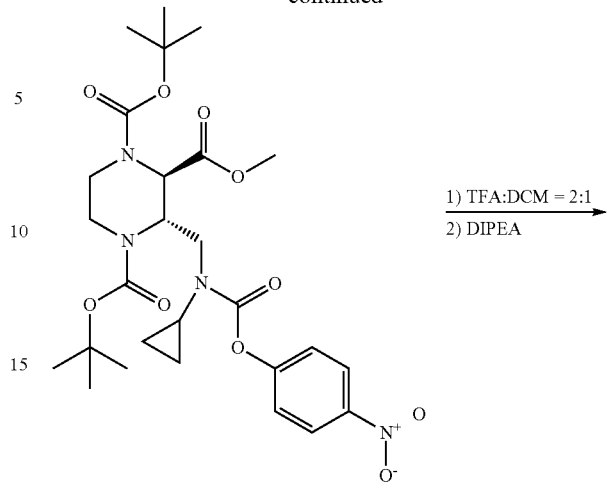

AY

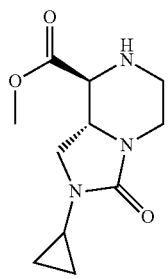

AR

Step 1: To a solution of dimethyl maleate (7.2 g, 50 mmol) in tetrachloromethane (150 mL) was added dropwise bromine (8.8 g, 55 mmol) in tetrachloromethane (10 mL) at 0° C. under nitrogen atmosphere. The reaction mixture was stirred at 0° C. overnight. The reaction mixture was quenched by adding ice-water, and then washed with $Na_2SO_3$ solution. The organic phase was washed with water, separated, dried over $Na_2SO_4$ and then concentrated to give crude Compound AS (15.2 g, crude).

Step 2: To a solution of Compound AS (10.6 g, 35 mmol) in benzene (120 mL) was added dropwise N,N-dibenzylethylenediamine (8.4 g, 35 mmol) and triethyl amine (9.7, 70 mmol) in benzene (20 mL) at 40° C. under nitrogen atmosphere. The reaction mixture was stirred for 10 minutes and heated to reflux overnight. The reaction mixture was cooled down by adding ice-water, and then extracted with petroleum ether/ethyl acetate=10/1 (50 mL) three times, the combined organic phase was dried over $Na_2SO_4$, filtrated and then concentrated. The residue was purified by column chromatography to give Compound AT (3.3 g).

Step 3: To a solution of Compound AT (4.5 g, 11.8 mmol) in THF (60 mL) was added di-tert-butyl dicarbonate and palladium hydroxide on carbon (1.0 g). The reaction mixture was heated to 45° C. overnight under pressure hydrogen atmosphere. The reaction mixture was filtrated and concentrated. The residue was purified by column chromatography to give Compound AU (3.6 g).

Step 4: To a solution of Compound AU (760 mg, 1.89 mmol) in methanol (4.0 mL) at 55° C. was added dropwise sodium hydroxide (98 mg, 2.46 mmol) in water (1 mL). The reaction mixture was stirred at 55° C. for 2 hours. The reaction mixture was cooled down and neutralized to pH 3.0, and then extracted with ethyl acetate (30 mL) three times. The combined organic phase was dried over $Na_2SO_4$, filtrated and then concentrated to give crude Compound AV (660 mg).

Step 5: To a solution of Compound AV (776 mg, 2.0 mmol) in dichloromethane (8.0 mL) was added cyclopropyl amine (120 mg, 2.0 mmol), HATU (950 mg, 2.5 mmol) and diisopropylethylamine (0.5 mL). The reaction mixture was stirred at room temperature overnight. The reaction mixture was quenched by adding ice-water, and then extracted with dichloromethane (30 mL) three times. The combined organic phase was dried over $Na_2SO_4$, and then filtrated and concentrated to give crude Compound AW (578 mg).

Step 6: To a mixture of phenylsilane (1.5 mL) and $[Ir(COD)_2Cl]_2$ (7 mg, 0.01 mmol) in dichloromethane (1.5 mL) was added Compound AW (128 mg, 2.0 mmol). The reaction mixture was stirred at 40° C. overnight. The reaction mixture was concentrated and then diluted with dichloromethane (20 mL), then quenched by adding 3 drops of hydrochloride in dioxane solution (3N). The reaction mixture was washed with water. The organic phase was separated and dried over $Na_2SO_4$, and then filtrated and concentrated. The residue was purified by column chromatography to give crude Compound AX (70 mg).

Step 7: To a solution of Compound AX (72 mg, 0.174 mmol) in dichloromethane (2.0 mL) was added 4-nitrophenyl chloroformate (70 mg, 0.35 mmol) and diisopropylethylamine (5 drops). After the reaction mixture was heated to 40° C. for 2 hours, it was concentrated and the residue was purified by column chromatography to give Compound AY (81 mg).

Step 8: The mixture of Compound AY (578 mg, 1.0 mmol) and TFA/DCM=2/1 (9 mL) was stirred at room temperature for 2 hours. The reaction mixture was concentrated and added toluene for co-evaporation to remove trifluoroacetic acid. The residue was dissolved in dichloromethane (8.0 mL), and then diisopropylethylamine (2 mL) was added. The reaction mixture was heated to 40° C. for 3 hours. The reaction mixture was concentrated to give Compound AR (239 mg, crude).

Example 46

2-[1-[(8aR)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopropyl]acetic acid

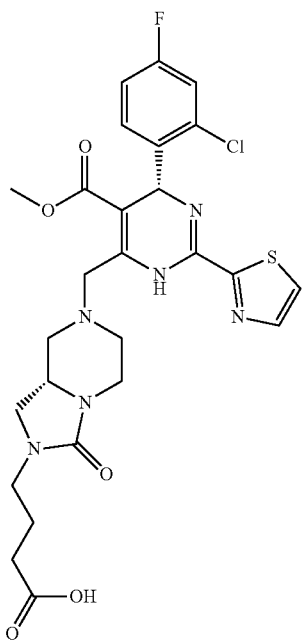 [SMILES: COC(=O)C1=C(CN2CCN3C(=O)N(CCCC(=O)O)C[C@@H]3C2)NC(c2nccs2)=N[C@H]1c1ccc(F)cc1Cl]

Preparation of Example 46

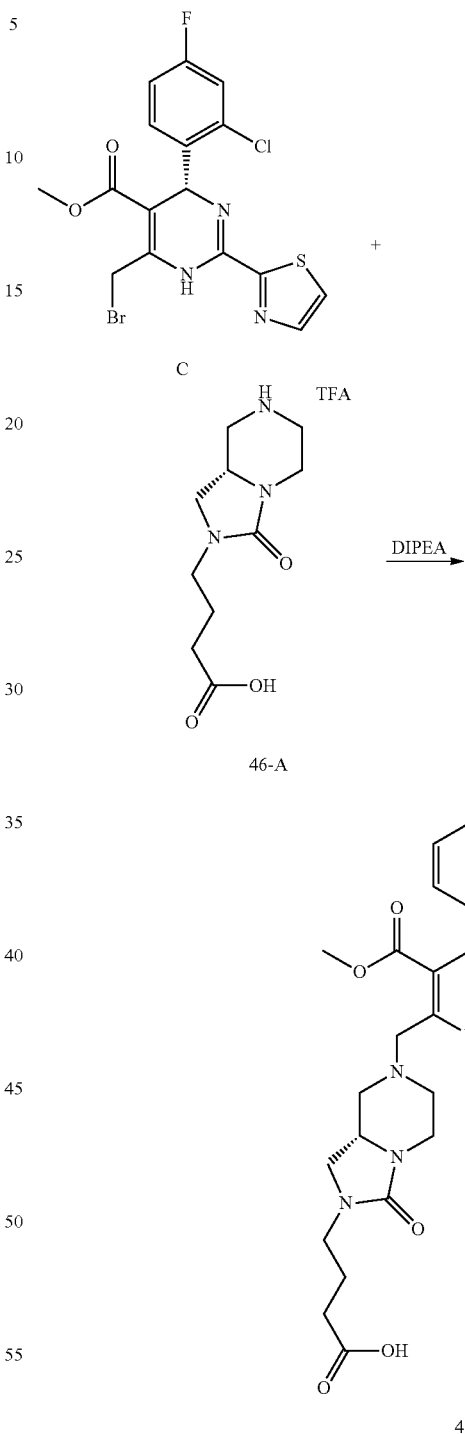

The title compound was prepared in analogy to Example 1 by using 4-[(8aS)-3-oxo-1,5,6,7,8,8a-hexahydroimidazo[1,5-a]pyrazin-2-yl]butanoic acid (Compound 46-A) instead of hexahydro-pyrazino[1,2-c][1,3]oxazin-6-one (Compound D). Example 46 was obtained as a light yellow solid (65 mg). $^1$H NMR (400 MHz, METHANOL-$d_4$) d ppm 7.96 (d, J=3.3 Hz, 1H), 7.76 (d, J=3.0 Hz, 1H), 7.42 (dd, J=6.1, 8.7 Hz, 1H), 7.24 (dd, J=2.8, 8.8 Hz, 1H), 7.05 (dt, J=2.5, 8.4

Hz, 1H), 6.17 (s, 1H), 4.15-4.02 (m, 1H), 3.96-3.71 (m, 3H), 3.66-3.53 (m, 4H), 3.22-3.07 (m, 2H), 2.90 (d, J=11.0 Hz, 1H), 2.80 (d, J=9.0 Hz, 1H), 2.68-2.56 (m, 1H), 2.55-2.46 (m, 1H), 2.37 (dt, J=3.1, 11.6 Hz, 1H), 2.18 (t, J=10.9 Hz, 1H), 1.03-0.81 (m, 4H), MS: calc'd 603 (MH$^+$), measured 603 (MH$^+$).

Preparation of 4-[(8aS)-3-oxo-1,5,6,7,8,8a-hexahydroimidazo[1,5-a]pyrazin-2-yl]butanoic acid (Compound 46-A)

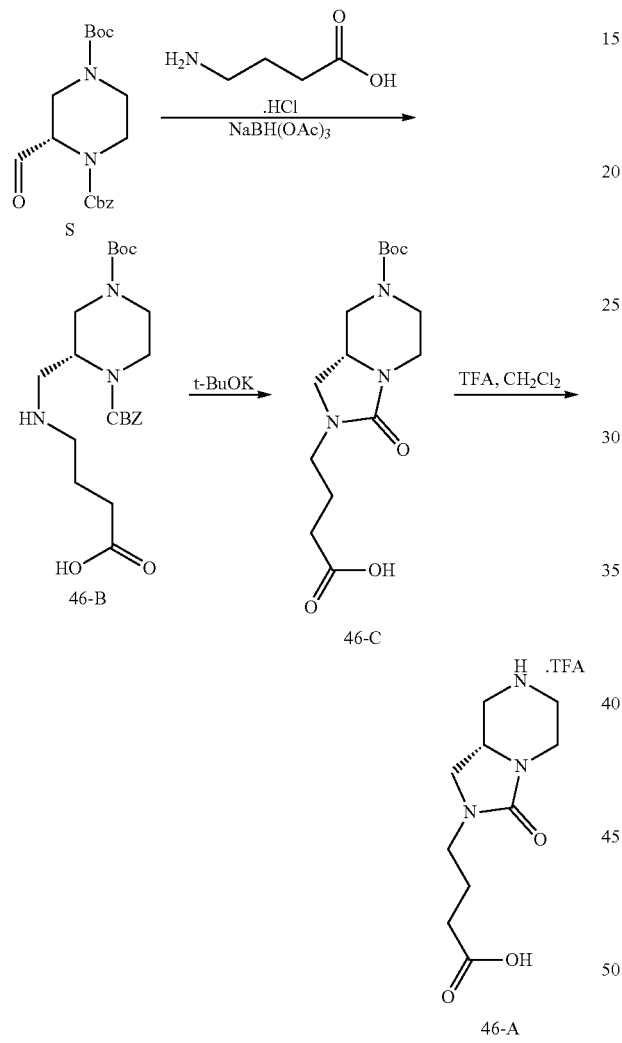

Step 1: tert-Butyl (3S)-3-formyl-4-methyl-piperazine-1-carboxylate (Compound S, 346 mg, 1 mmol) in dichloromethane (3 mL) and Et$_3$N (0.5 mL) was added 4-aminobutanoic acid (103 mg, 1 mmol). The reaction mixture was stirred for 1 hour at room temperature, then concentrated under reduced pressure. Then methanol (5 mL) and sodium cyanoborohydride (248 mg, 4 mmol) was added and the reaction mixture was stirred for another 3 hours at room temperature. The mixture was concentrated under reduced pressure to give crude compound 46-B.

Step 2: Compound 46-B in THF (10 mL) was added potassium tert-butoxide (224 mg, 2 mmol), the reaction mixture was stirred at 80° C. for 4 h. The solution was cooled to room temperature and acidified to pH 5 with aqueous HCl solution. The mixture was then extracted with ethyl acetate 3 times. The combined organic layers were washed with brine, dried over Na$_2$SO$_4$, and concentrated under reduced pressure to give crude compound 46-C (301 mg).

Step 3: To a stirred solution of compound 46-C (301 mg, 0.92 mmol) was dissolved in dichloromethane (4 mL) and treated with trifluoroacetic acid (2 mL) at room temperature. After the reaction mixture was stirred at room temperature for 1 hour, the solvent was removed in vacuo to give 4-[(8aS)-3-oxo-1,5,6,7,8,8a-hexahydroimidazo[1,5-a]pyrazin-2-yl]butanoic acid (Compound 46-A) which was used directly.

Example 47

2-[1-[(8aR)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopropyl]acetic acid

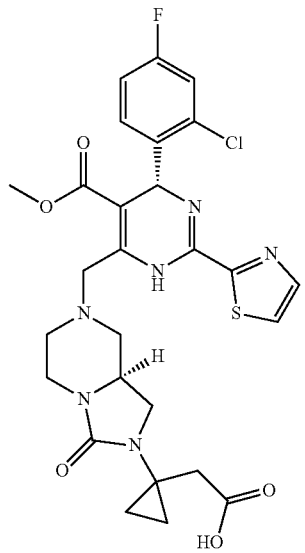 [SMILES: COC(=O)C1=C(CN2CCN3C(=O)N(C4(CC(=O)O)CC4)C[C@@H]3C2)NC(c2nccs2)=N[C@H]1c1ccc(F)cc1Cl]

Preparation of Example 47

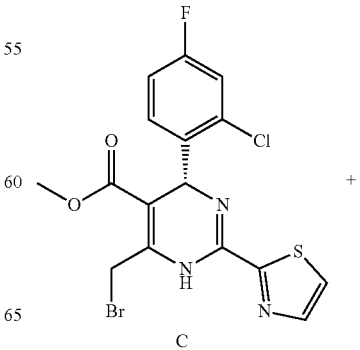

105

-continued

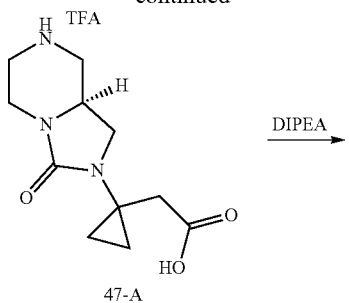
47-A

→ DIPEA

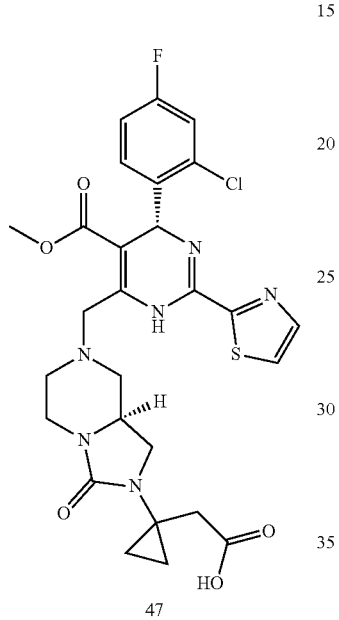
47

The title compound was prepared in analogy to Example 1 by using 2-[1-[(8aR)-3-oxo-1,5,6,7,8,8a-hexahydroimidazo[1,5-a]pyrazin-2yl]cyclopropyl]acetic acid (Compound 47-A) instead of hexahydro-pyrazino[1,2-c][1,3]oxazin-6-one (Compound D). Example 47 was obtained as a light yellow solid (62 mg). $^1$H NMR (400 MHz, METHANOL-$d_4$) d ppm 7.96 (d, J=3.3 Hz, 1H), 7.76 (d, J=3.0 Hz, 1H), 7.42 (dd, J=6.1, 8.7 Hz, 1H), 7.24 (dd, J=2.8, 8.8 Hz, 1H), 7.05 (dt, J=2.5, 8.4 Hz, 1H), 6.17 (s, 1H), 4.15-4.02 (m, 1H), 3.96-3.71 (m, 3H), 3.66-3.53 (m, 4H), 3.22-3.07 (m, 2H), 2.90 (d, J=11.0 Hz, 1H), 2.80 (d, J=9.0 Hz, 1H), 2.68-2.56 (m, 1H), 2.55-2.46 (m, 1H), 2.37 (dt, J=3.1, 11.6 Hz, 1H), 2.18 (t, J=10.9 Hz, 1H), 1.03-0.81 (m, 4H). MS: calc'd 603 (MH$^+$), measured 603 (MH$^+$).

Preparation of 2-[1-[(8aR)-3-oxo-1,5,6,7,8,8a-hexahydroimidazo[1,5-a]pyrazin-2yl]cyclopropyl]acetic acid (Compound 47-A)

Compound 47-A was prepared in analogy to compound Q in Example 19 by using methyl 2-(1-aminocyclopropyl) acetate hydrochloride salt (for its synthesis, refer to: Sandstroem A., et al, *Bioorganic & Medicinal Chemistry*, 16(10), 5590-5605; 2008) instead of ethyl 3-amino-2,2-dimethyl-propanoate hydrochloride salt.

106

Example 48

2-[1-[(8aR)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopropyl]acetic acid

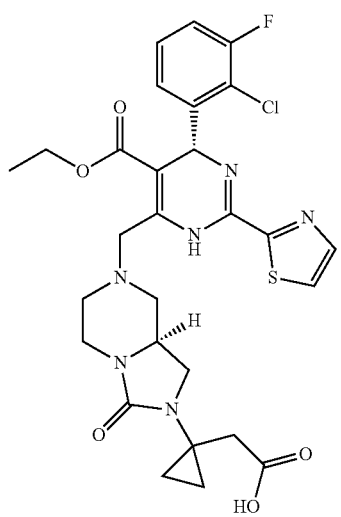 [SMILES: CCOC(=O)C1=C(CN2CCN3C(=O)N(C4(CC(=O)O)CC4)C[C@@H]3C2)NC(c2nccs2)=N[C@H]1c1cccc(F)c1Cl]

Preparation of Example 48

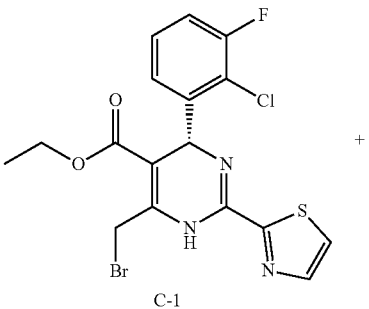
C-1

+

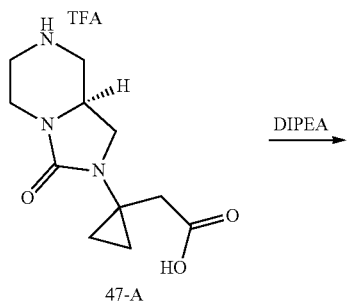
47-A

→ DIPEA

107
-continued

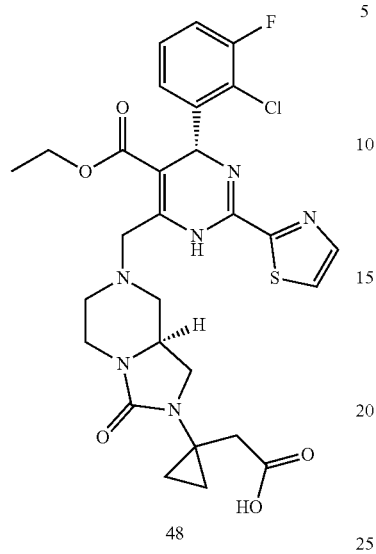

48

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and 2-[1-[(8aR)-3-oxo-1,5,6,7,8,8a-hexahydroimidazo[1,5-a]pyrazin-2yl]cyclopropyl]acetic acid (Compound 47-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 48 was obtained as a light yellow solid (76 mg). $^1$H NMR (400 MHz, METHANOL-$d_4$) d ppm 7.95 (s, 1H), 7.76 (s, 1H), 7.37-7.23 (m, 2H), 7.21-7.10 (m, 1H), 6.24 (s, 1H), 4.04 (d, J=7.0 Hz, 3H), 3.95-3.77 (m, 3H), 3.66-3.54 (m, 1H), 3.20-3.08 (m, 2H), 2.95-2.86 (m, 1H), 2.86-2.74 (m, 1H), 2.67-2.57 (m, 1H), 2.55-2.45 (m, 1H), 2.42-2.30 (m, 1H), 2.23-2.12 (m, 1H), 1.13 (t, J=7.2 Hz, 3H), 1.01-0.81 (m, 4H). MS: calc'd 617 (MH$^+$), measured 617 (MH$^+$).

Preparation of ethyl (4R)-6-(bromomethyl)-4-(2-chloro-3-fluoro-phenyl)-2-thiazol-2-yl-1,4-dihydro-pyrimidine-5-carboxylate (Compound C-1)

Compound C-1 was prepared in analogy to compound C by using ethyl acetoacetate and 2-chloro-3-fluorobenzaldehyde instead of methyl acetoacetate and 2-chloro-4-fluorobenzaldehyde.

108

Example 49

(1S,2R)-2-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopentanecarboxylic acid

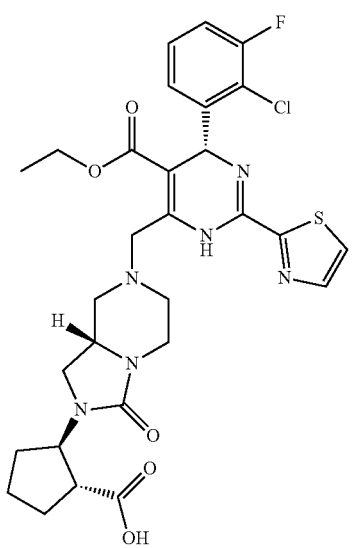 [SMILES: CCOC(=O)C1=C(CN2CCN3C(=O)N([C@@H]4CCC[C@H]4C(=O)O)C[C@@H]3C2)NC(c2nccs2)=N[C@H]1c1cccc(F)c1Cl]

Preparation of Example 49

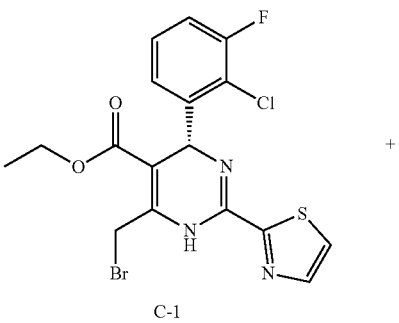

C-1

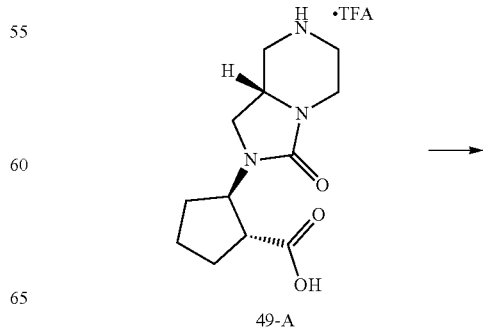

49-A

109
-continued

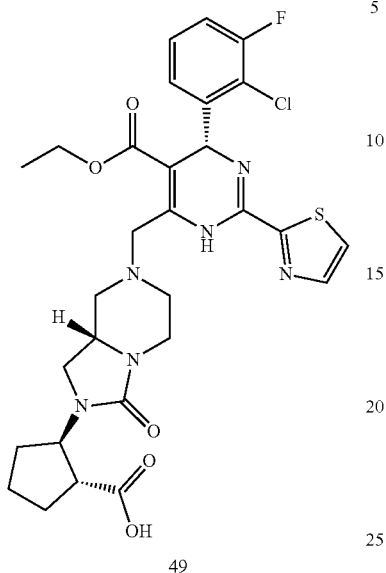

49

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and (1R,2R)-2-[(8aS)-3-oxo-1,5,6,7,8,8a-hexahydroimidazo[1,5-a]pyrazin-2-yl]cyclopentanecarboxylic acid (Compound 49-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 49 was obtained as a light yellow solid (48 mg). $^1$H NMR (400 MHz, METHANOL-$d_4$) d ppm 7.96 (d, J=3.0 Hz, 1H), 7.76 (d, J=3.3 Hz, 1H), 7.27 (s, 2H), 7.21-7.12 (m, 1H), 6.24 (s, 1H), 4.47-4.38 (m, 1H), 4.17-3.98 (m, 3H), 3.97-3.86 (m, 2H), 3.83-3.75 (m, 1H), 3.59 (s, 1H), 3.25-3.11 (m, 2H), 3.03-2.94 (m, 1H), 2.93-2.82 (m, 1H), 2.77-2.68 (m, 1H), 2.45-2.35 (m, 1H), 2.29-2.17 (m, 1H), 2.11-1.84 (m, 3H), 1.82-1.68 (m, 3H), 1.13 (t, J=7.2 Hz, 3H). MS: calc'd 631 (MH$^+$), measured 631 (MH$^+$).

Preparation of (1R,2R)-2-[(8aS)-3-oxo-1,5,6,7,8,8a-hexahydroimidazo[1,5-a]pyrazin-2-yl]cyclopentanecarboxylic acid (Compound 49-A)

Compound 49-A was prepared in analogy to compound Q in Example 19 by using ethyl (1R,2R)-2-aminocyclopentanecarboxylate (Accela Chembio Co., Ltd, SY024586) instead of ethyl 3-amino-2,2-dimethyl-propanoate hydrochloride salt.

110
Example 50

(1R,2R)-2-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclopentanecarboxylic acid

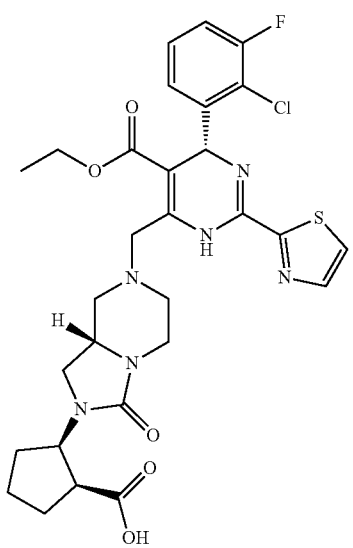 [SMILES: CCOC(=O)C1=C(CN2CCN3C(=O)N([C@@H]4CCC[C@@H]4C(=O)O)C[C@@H]3C2)NC(c2nccs2)=N[C@H]1c1cccc(F)c1Cl]

Preparation of Example 50

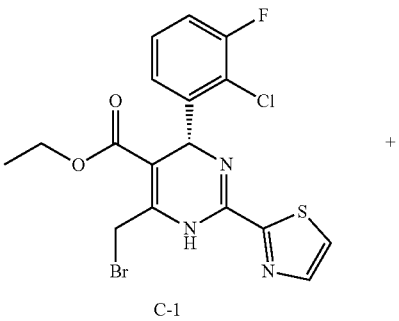
C-1

+

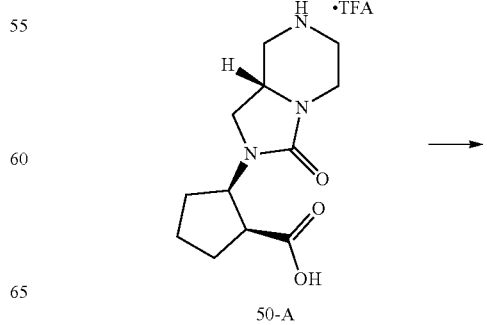
50-A

-continued

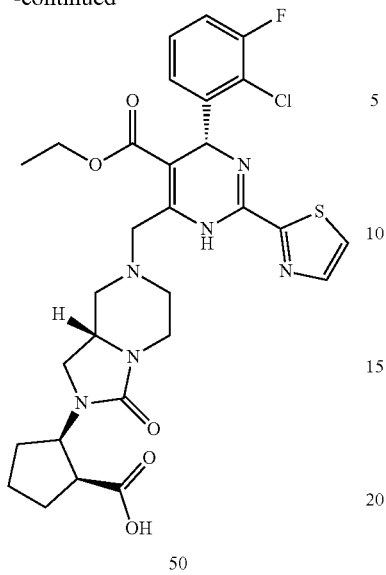

50

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and (1S,2R)-2-[(8aS)-3-oxo-1,5,6,7,8,8a-hexahydroimidazo[1,5-a]pyrazin-2-yl]cyclopentanecarboxylic acid (Compound 50-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 50 was obtained as a light yellow solid (30 mg). $^1$H NMR (400 MHz, METHANOL-$d_4$) d ppm 7.97 (d, J=3.0 Hz, 1H), 7.76 (d, J=3.0 Hz, 1H), 6.97-7.39 (m, 2H), 6.24 (s, 1H), 4.42 (d, J=9.8 Hz, 2H), 3.73-4.19 (m, 5H), 3.52 (m, 4H), 3.12-3.23 (m, 2H), 2.66-2.96 (m, 2H), 2.11-2.47 (m, 3H), 1.60-2.05 (m, 4H), 1.13 ppm (t, J=7.2 Hz, 3H). MS: calc'd 631 (MH$^+$), measured 631 (MH$^+$).

Preparation of (1S,2R)-2-[(8aS)-3-oxo-1,5,6,7,8,8a-hexahydroimidazo[1,5-a]pyrazin-2-yl]cyclopentanecarboxylic acid (Compound 50-A)

Compound 50-A was prepared in analogy to compound Q in Example 19 by using ethyl (1S,2R)-2-aminocyclopentanecarboxylate trifluoroacetic acid salt (compound 50-B) instead of ethyl 3-amino-2,2-dimethyl-propanoate hydrochloride salt.

Preparation of ethyl (1S,2R)-2-aminocyclopentanecarboxylate trifluoroacetic acid salt (Compound 50-B)

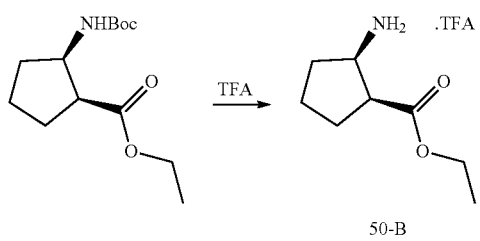 [SMILES: CCOC(=O)[C@H]1CCC[C@H]1NC(=O)OC(C)(C)C ; CCOC(=O)[C@H]1CCC[C@H]1N ; ".TFA"]

50-B (1R,2S)-2-(Boc-amino)cyclopentanecarboxylate (CAS: 1140972-29-7, TCI) (1 mmol) was dissolved in CH$_2$Cl$_2$ (3 mL) followed by the slow addition of TFA (1 mL) at 0° C. The reaction mixture was stirred at rt for 1 hour and then the solvent was removed under vacuum to give the crude product 50-B, which was used directly in the next step.

Example 51

(1R,2S)-2-[(8aS)-7-[[(4R)-4-(2-chloro-4-fluoro-phenyl)-5-methoxycarbonyl-2-thiazol-2-yl-1,4-dihydro-pyrimidin-6-yl]methyl]-3-oxo-5,6,8,8a-tetrahydro-H-imidazazo[1,5-a]pyrazin-2-yl]cyclopentanecarboxyli

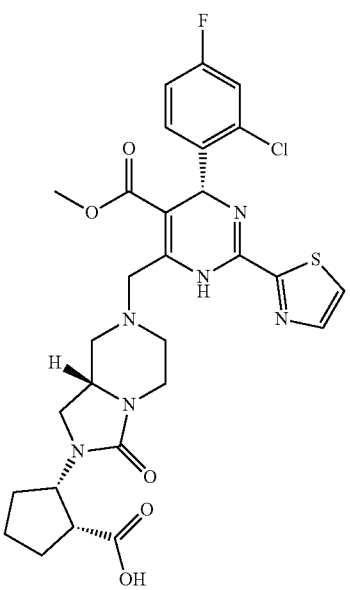 [SMILES: COC(=O)C1=C(CN2CCN3C(=O)N([C@H]4CCC[C@H]4C(=O)O)C[C@@H]3C2)NC(c2nccs2)=N[C@H]1c1ccc(F)cc1Cl]

Preparation of Example 51

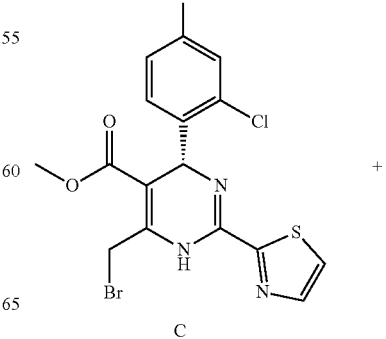

C

-continued

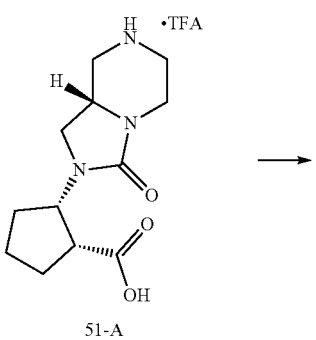

51-A

The title compound was prepared in analogy to Example 1 by using (1R,2S)-2-[(8aS)-3-oxo-1,5,6,7,8,8a-hexahydroimidazo[1,5-a]pyrazin-2-yl]cyclopentanecarboxylic acid TFA salt (Compound 51-A) instead of hexahydro-pyrazino[1,2-c][1,3]oxazin-6-one (Compound D). Example 51 was obtained as a light yellow solid (68 mg). $^1$H NMR (400 MHz, METHANOL-$d_4$) d ppm 8.07-7.89 (m, 1H), 7.78 (d, J=3.0 Hz, 1H), 7.44 (t, J=6.9 Hz, 1H), 7.25 (dd, J=2.5, 8.8 Hz, 1H), 7.06 (dt, J=2.5, 8.4 Hz, 1H), 6.18 (s, 1H), 4.41 (q, J=8.6 Hz, 1H), 4.19 (d, J=16.8 Hz, 1H), 4.05-3.79 (m, 3H), 3.64-3.57 (m, 4H), 3.27-3.14 (m, 1H), 3.10 (dd, J=4.3, 9.0 Hz, 1H), 2.99 (br. s., 1H), 2.94-2.77 (m, 2H), 2.48 (br. s., 1H), 2.29 (br. s., 1H), 2.08-1.84 (m, 3H), 1.84-1.69 (m, 3H). MS: calc'd 617 (MH$^+$), measured 617 (MH$^+$).

Preparation of (1R,2S)-2-[(8aS)-3-oxo-1,5,6,7,8,8a-hexahydroimidazo[1,5-a]pyrazin-2-yl]cyclopentanecarboxylic acid TFA salt (Compound 51-A)

Compound 51-A was prepared in analogy to compound Q in Example 19 by using ethyl (1R,2S)-2-aminocyclopentanecarboxylate (Accela Chembio Co., Ltd, CAS: 197916-36-2) instead of ethyl 3-amino-2,2-dimethyl-propanoate hydrochloride salt.

Example 52

(1S,2S)-2-[(8aS)-7-[[(4R)-4-(2-chloro-4-fluoro-phenyl)-5-methoxycarbonyl-2-thiazol-2-yl-1,4-dihydro-pyrimidin-6-yl]methyl]-3-oxo-5,6,8,8a-tetrahydro-H-imidazo[1,5-a]pyrazin-2-yl]cyclopentanecarboxylic acid

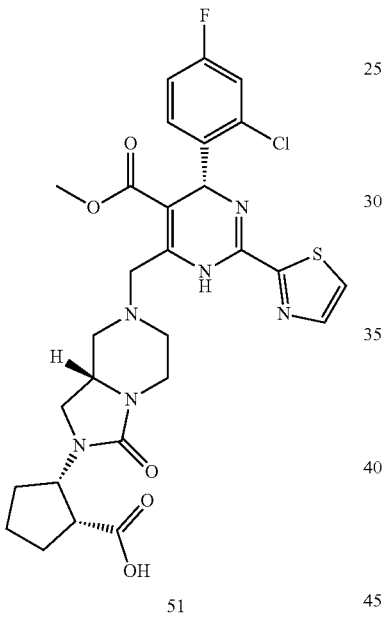

51

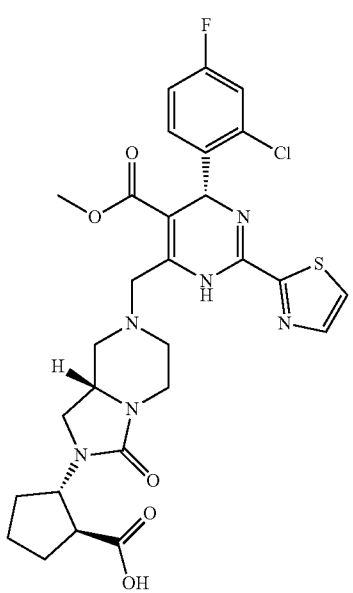 [SMILES: COC(=O)C1=C(CN2CCN3C(=O)N([C@H]4CCC[C@@H]4C(=O)O)C[C@@H]3C2)NC(c2nccs2)=N[C@H]1c1ccc(F)cc1Cl]

Preparation of Example 52

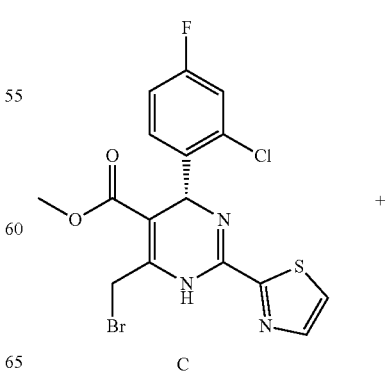

C

-continued

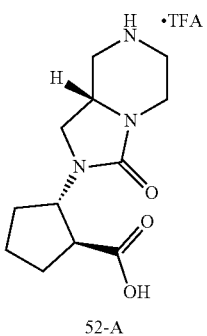 

52-A

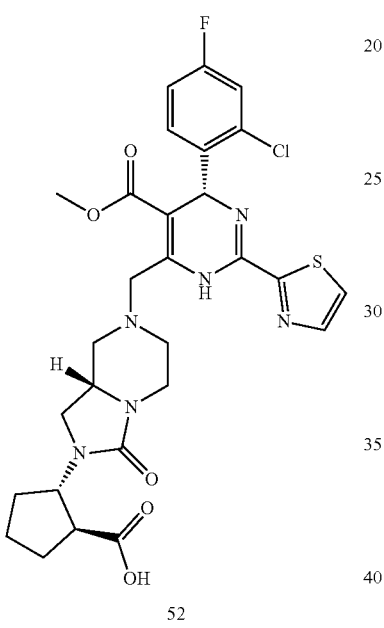

52

The title compound was prepared in analogy to Example 1 by using (1S,2S)-2-[(8aS)-3-oxo-1,5,6,7,8,8a-hexahydroimidazo[1,5-a]pyrazin-2-yl]cyclopentanecarboxylic acid TFA salt (Compound 52-A) instead of hexahydro-pyrazino[1,2-c][1,3]oxazin-6-one (Compound D). Example 52 was obtained as a light yellow solid (1.7 mg). $^1$H NMR (400 MHz, METHANOL-$d_4$) d ppm 1H NMR (MeOD, 400MHz): d=7.97 (d, J=3.0 Hz, 1H), 7.77 (d, J=3.0 Hz, 1H), 7.42 (dd, J=6.0, 8.8 Hz, 1H), 7.24 (dd, J=2.8, 8.8 Hz, 1H), 7.06 (dt, J=2.8, 8.4 Hz, 1H), 6.18 (s, 1H), 4.50-4.25 (m, 1H), 4.09 (d, J=17.1 Hz, 1H), 3.98-3.72 (m, 3H), 3.61 (s, 3H), 3.52 (t, J=8.9 Hz, 1H), 3.26-3.01 (m, 2H), 2.96-2.72 (m, 3H), 2.41-2.17 (m, 2H), 2.05-1.84 (m, 3H), 1.81-1.67 (m, 3H). MS: calc'd 617 (MH$^+$), measured 617 (MH$^+$).

Preparation of (1S,2S)-2-[(8aS)-3-oxo-1,5,6,7,8,8a-hexahydroimidazo[1,5-a]pyrazin-2-yl]cyclopentanecarboxylic acid TFA salt (Compound 52-A)

Compound 52-A was prepared in analogy to compound Q in Example 19 by using ethyl (1S,2S)-2-aminocyclopentanecarboxylate (Accela Chembio Co., Ltd, CAS: 752181-59-2) instead of ethyl 3-amino-2,2-dimethyl-propanoate hydrochloride salt.

Example 53

4-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]butanoic acid

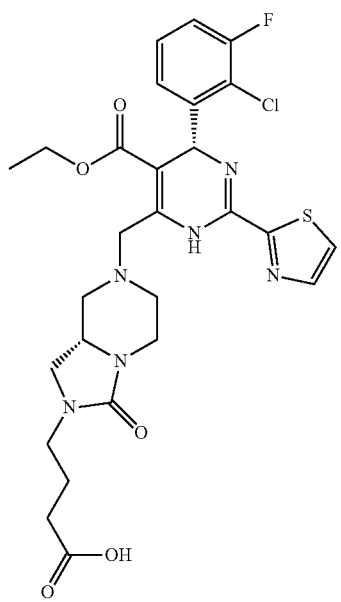 [SMILES: CCOC(=O)C1=C(CN2CCN3C(=O)N(CCCC(=O)O)C[C@@H]3C2)NC(c2nccs2)=N[C@H]1c1cccc(F)c1Cl]

Preparation of Example 53

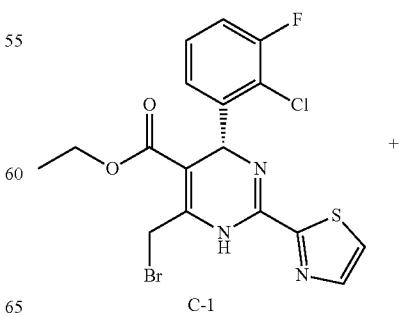

C-1

117
-continued

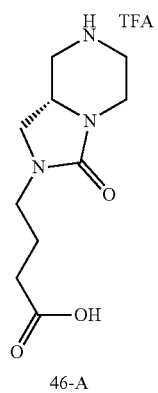
46-A

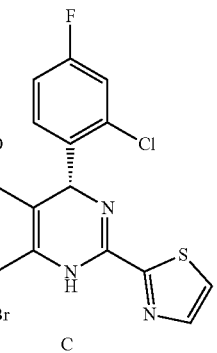
53

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and 4-[(8aS)-3-oxo-1,5,6,7,8,8a-hexahydroimidazo[1,5-a]pyrazin-2-yl]butanoic acid (Compound 46-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 53 was obtained as a light yellow solid (2 mg). $^1$H NMR (400 MHz, METHANOL-$d_4$) d ppm 7.97 (d, J=3.0 Hz, 1H), 7.76 (d, J=3.3 Hz, 1H), 7.27 (s, 2H), 7.16 (s, 1H), 6.24 (s, 1H), 4.18-4.01 (m, 3H), 3.92 (d, J=16.8 Hz, 3H), 3.49 (s, 1H), 3.30-3.25 (m, 1H), 3.25-3.15 (m, 2H), 3.12-3.04 (m, 1H), 2.97-2.81 (m, 2H), 2.33 (s, 3H), 2.26-2.14 (m, 1H), 1.85 (d, J=7.0 Hz, 2H), 1.13 (t, J=7.2 Hz, 3H). MS: calc'd 605 (MH$^+$), measured 605 (MH$^+$).

118

Example 54

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-butanoic acid

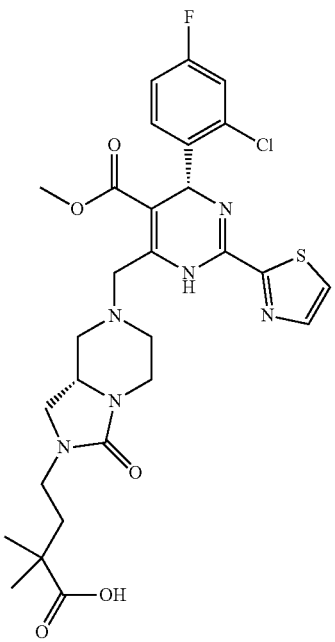 [SMILES: COC(=O)C1=C(CN2CCN3C(=O)N(CCC(C)(C)C(=O)O)C[C@@H]3C2)NC(c2nccs2)=N[C@H]1c1ccc(F)cc1Cl]

Preparation of Example 54

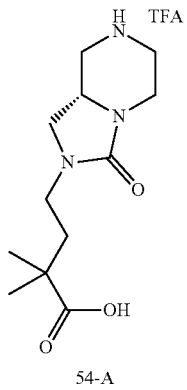
54-A

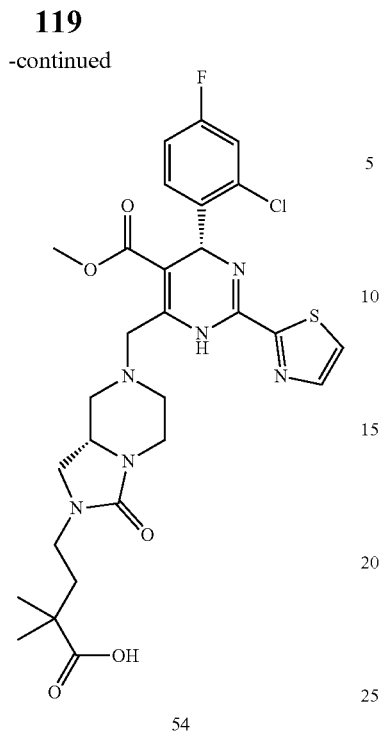

54

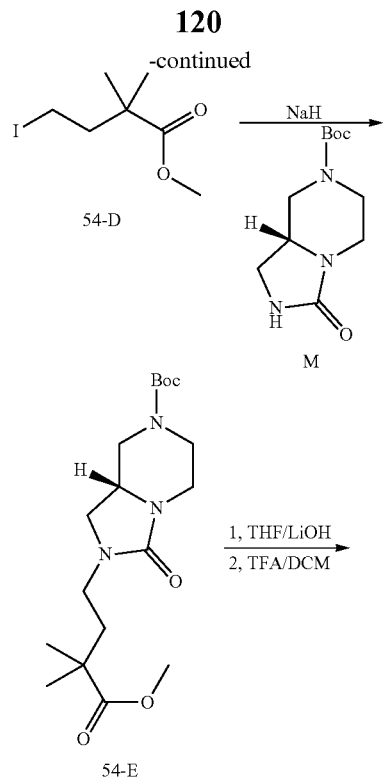

The title compound was prepared in analogy to Example 1 by using 4-[(8aS)-3-oxo-1,5,6,7,8,8a-hexahydroimidazo[1,5-a]pyrazin-2-yl]-2,2-dimethyl-butanoic acid TFA salt (Compound 54-A) instead of hexahydro-pyrazino[1,2-c][1,3]oxazin-6-one (Compound D). Example 54 was obtained as a light yellow solid (23 mg). $^1$H NMR (400 MHz, METHANOL-$d_4$) d ppm 8.01 (d, J=3.0 Hz, 1H), 7.90 (d, J=3.0 Hz, 1H), 7.53 (dd, J=5.9, 8.7 Hz, 1H), 7.29 (dd, J=2.6, 8.7 Hz, 1H), 7.17-7.06 (m, 1H), 6.20 (s, 1H), 4.77-4.64 (m, 1H), 4.57-4.42 (m, 1H), 4.27-4.12 (m, 1H), 4.07 (dd, J=3.3, 14.8 Hz, 1H), 3.75-3.62 (m, 5H), 3.58 (t, J=9.0 Hz, 1H), 3.51-3.37 (m, 2H), 3.27-3.02 (m, 4H), 1.95-1.82 (m, 1H), 1.80-1.66 (m, 1H), 1.31-1.19 (m, 6H). MS: calc'd 619 (MH$^+$), measured 619 (MH$^+$).

Preparation of 4-[(8aS)-3-oxo-1,5,6,7,8,8a-hexahydroimidazo[1,5-a]pyrazin-2-yl]-2,2-dimethyl-butanoic acid TFA salt (Compound 54-A)

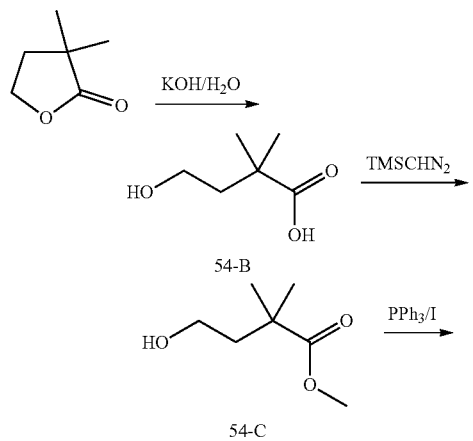

Step 1: A mixture of 2,2-dimethylbutyrolactone (6.84 g, 60 mmol) and KOH (3.36 g) in H$_2$O (60 mL) was heated at reflux for 2 h. The solution was cooled to room temperature and acidified to pH 5 with aqueous HCl solution. The mixture was then extracted with ethyl acetate 3 times. The combined organic layers were washed with brine, dried over Na$_2$SO$_4$, concentrated under reduced pressure to give 4-hydroxy-2,2-dimethyl-butanoic acid compound 54-B (4 g).

Step 2: To the mixture of compound 54-B (2.2 g, 16.6 mmol) in ethyl ether (16 mL) and methanol (24 mL) at 0° C. was added a hexane solution (2.0 M) of trimethylsilyldiazomethane (12.5 mL, 25 mmol). The reaction mixture was stirred at 0° C. for 1 h. The solvent was evaporated and the residue was taken up in ethyl acetate, washed successively with diluted aqueous HCl solution, saturated NaHCO$_3$ solution and brine. The mixture was dried over Na$_2$SO$_4$ and concentrated to give 4-hydroxy-2,2-dimethyl-butyric acid methyl ester compound 54-C (1.5 g).

Step 3: To a solution of the alcohol 54-C (45 mg, 0.34 mmol) in THF (4 mL) at 0° C. were added Ph$_3$P (136 mg, 0.52 mmol), imidazole (71 mg, 1.04 mmol), and I$_2$ (132 mg, 0.52 mmol). After 1 h, the reaction mixture was quenched with saturated Na$_2$S$_2$O$_3$ solution. The aqueous layer was extracted twice with hexanes. The organic layer were dried over Na$_2$SO$_4$ and concentrated under vacuum to give compound 54-D as a crude product.

Step 4: To a stirred solution of compound M (256 mg, 1 mmol) in DMF (2 mL) was added NaH (48 mg, 2 mmol) at room temperature. The reaction mixture was stirred 20 min at room temperature, then compound 54-D (256 mg, 1 mmol) was added. After the reaction mixture was stirred for 4 hours at room temperature, EA was added and the mixture was washed with water and brine. The mixture was dried over Na$_2$SO$_4$, and concentrated under reduced pressure to give the crude product, which was purified by column to give compound 54-E (150 mg).

Step 5: To a stirred solution of compound 54-E (150 mg, 0.4 mmol) in THF (5 mL) and water (2 mL) was added LiOH (96 mg 2.4 mmol). After the reaction mixture was stirred at 80° C. for 18 h, it was concentrated under reduced pressure to give the crude product, which was dissolved in DCM (4 mL) and treated with TFA (4 mL). The mixture was stirred for 2 hours at room temperature, then it was concentrated under reduced pressure to give the crude product 54-A which was used directly.

Example 55

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid Preparation of Example 55

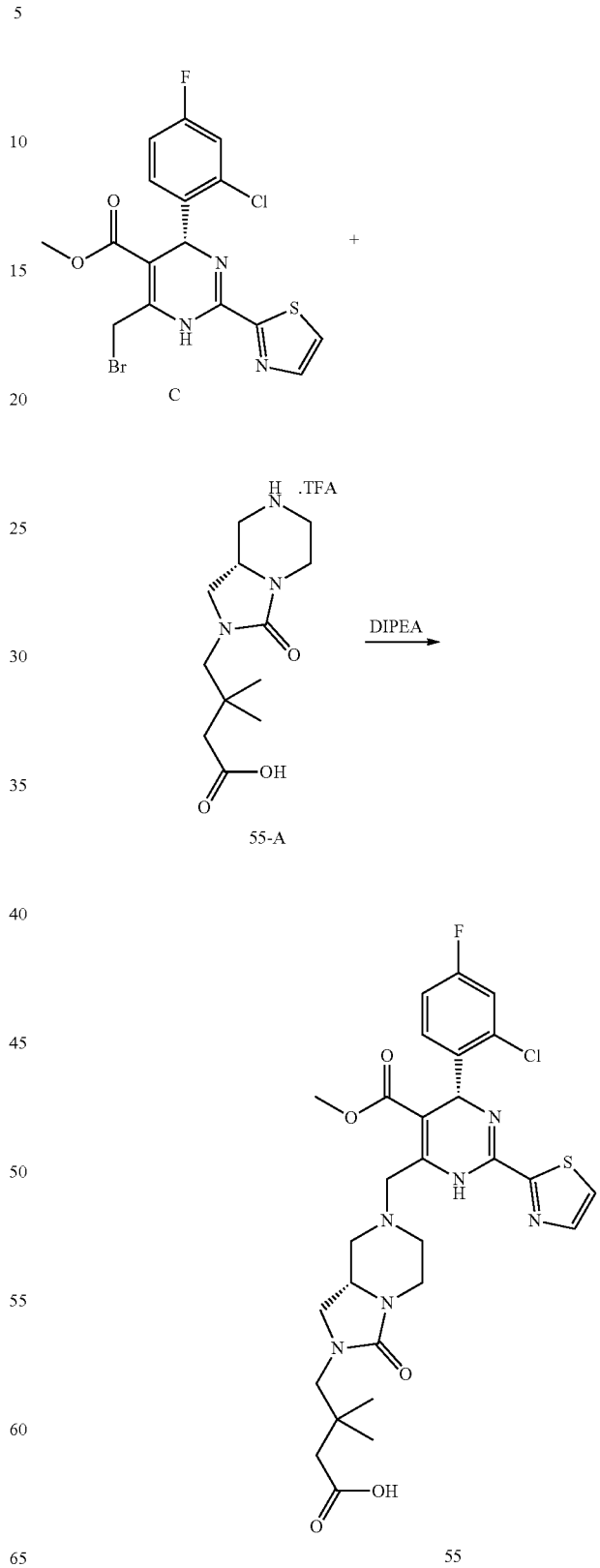

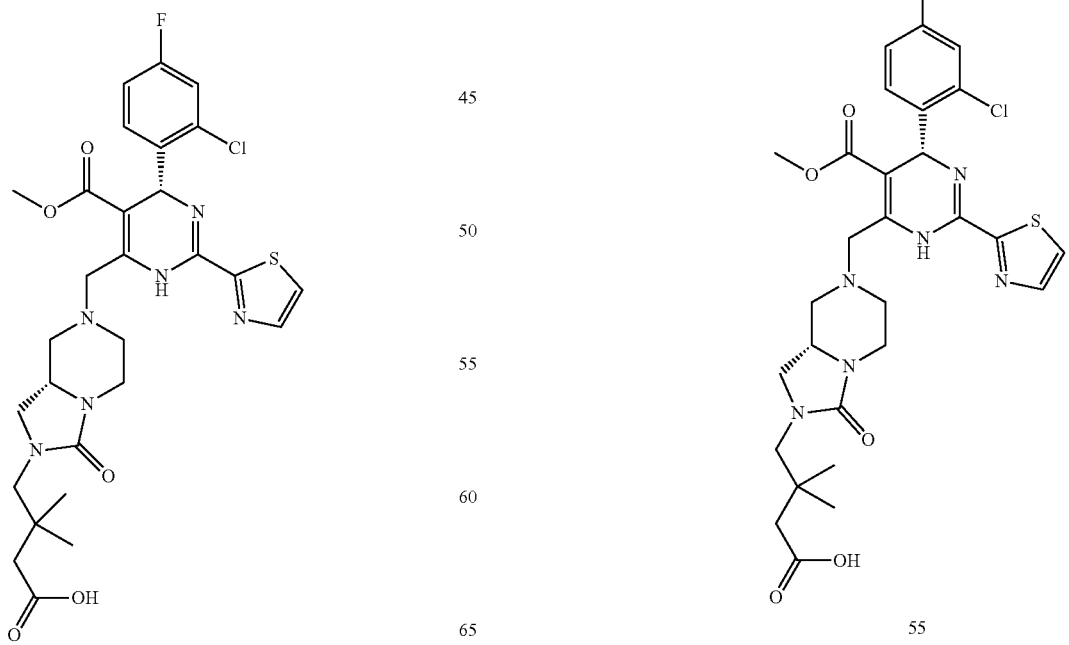

The title compound was prepared in analogy to Example 1 by using 4-[(8aS)-3-oxo-1,5,6,7,8,8a-hexahydroimidazo[1,5-a]pyrazin-2-yl]-3,3-dimethyl-butanoic acid TFA salt (Compound 55-A) instead of hexahydro-pyrazino[1,2-c][1,3]oxazin-6-one (Compound D). Example 55 was obtained as a light yellow solid (22 mg). $^1$H NMR (400 MHz, METHANOL-d$_4$) d ppm 7.96 (d, J=3.3 Hz, 1H), 7.76 (d, J=3.3 Hz, 1H), 7.50-7.35 (m, 1H), 7.29-7.20 (m, 1H), 7.12-7.01 (m, 1H), 6.18 (s, 1H), 4.20-4.06 (m, 1H), 3.94 (s, 3H), 3.61 (s, 4H), 3.19 (d, J=14.6 Hz, 3H), 3.08-2.99 (m, 1H), 2.97-2.82 (m, 2H), 2.47-2.34 (m, 1H), 2.27 (s, 3H), 1.07 (s, 6H). MS: calc'd 619 (MH$^+$), measured 619 (MH$^+$).

Preparation of 4-[(8aS)-3-oxo-1,5,6,7,8,8a-hexahydroimidazo[1,5-a]pyrazin-2-yl]-3,3-dimethyl-butanoic acid TFA salt (Compound 55-A)

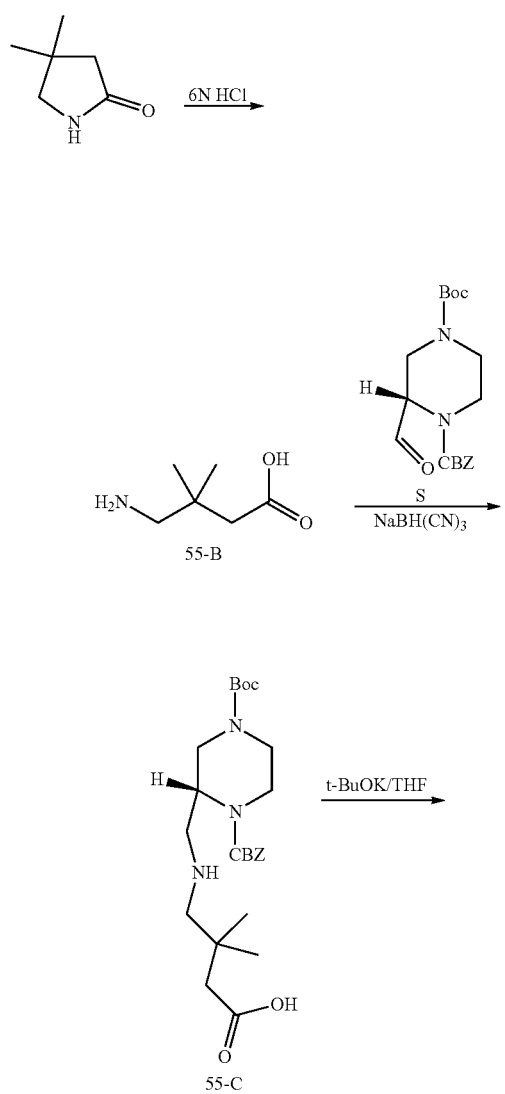

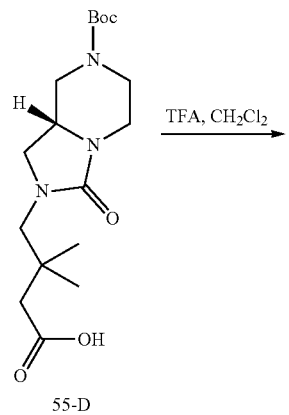

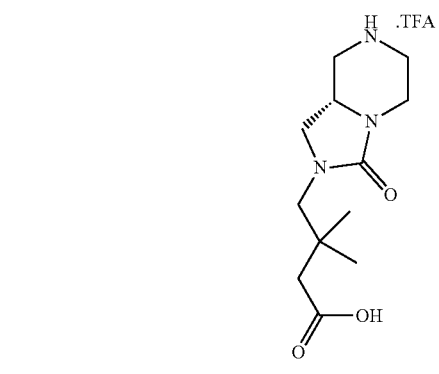

Step 1: 4,4-Dimethyl-2-pyrrolidinone (2.52 g, 22.3 mmol) was added to a mixture of concentrated HCl (50 mL) and water (50 mL) and the resulting mixture was refluxed at 120° C. for 20 hours. After it was cooled to room temperature, the mixture was washed twice with dichloromethane. The aqueous layer was evaporated to give 4-amino-3,3-dimethylbutyric acid hydrochloride compound 55-B (3.4 g) as a white solid.

Step 2: Aldehyde S (346 mg, 1 mmol) in dichloromethane (3 mL) and Et$_3$N (0.5 mL) was added compound 55-B (131 mg, 1 mmol). The reaction mixture was stirred for 1 hour at room temperature, then concentrated under reduced pressure. Methanol (5 mL) was added followed by the addition of sodium cyanoborohydride (248 mg, 4 mmol). After the reaction mixture was stirred at room temperature for 1 h, it was concentrated under reduced pressure to give crude product 55-C.

Step 3: Compound 55-C in THF (10 mL) was added potassium tert-butoxide (224 mg, 2 mmol), then the reaction mixture was stirred at 80° C. for 4 h. The solution was cooled to room temperature and acidified to pH 5 with aqueous HCl solution. The mixture was then extracted with ethyl acetate 3 times. The combined organic layers were washed with brine, dried over Na$_2$SO$_4$, and concentrated under reduced pressure to give crude product 55-D.

Step 4: To a stirred solution of compound 55-D (301 mg, 0.92 mmol) in dichloromethane (4 mL) was added trifluoroacetic acid (2 mL) at room temperature. After the reaction mixture was stirred at room temperature for 1 hour, the solvent was removed under vacuum to give crude product 55-A which was used directly.

Example 56

(R)-6-[(S)-2-(2-Carboxy-ethyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester

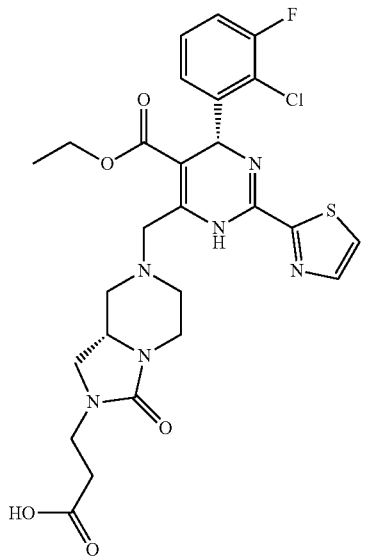 [SMILES: CCOC(=O)C1=C(CN2CCN3C(=O)N(CCC(=O)O)C[C@@H]3C2)NC(c2nccs2)=N[C@H]1c1cccc(F)c1Cl]

Preparation of Example 56

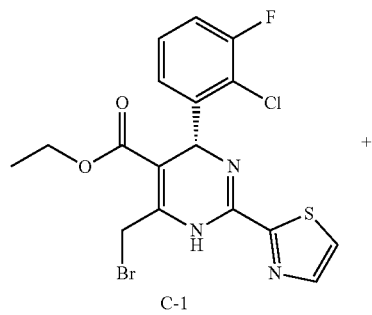

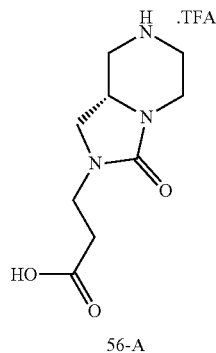

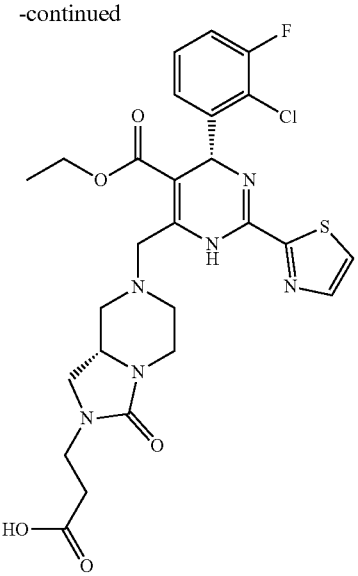

56

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and 3-[(8aS)-3-oxo-1,5,6,7,8,8a-hexahydroimidazo[1,5-a]pyrazin-2-yl]propanoic acid TFA salt (Compound 56-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 56 was obtained as a light yellow solid (60 mg). $^1$H NMR (400 MHz, METHANOL-$d_4$) d ppm 7.95-8.00 (m, 1H), 7.79 (d, 1H), 7.25-7.36 (m, 2H), 7.12-7.22 (m, 1H), 6.25 (s, 1H), 4.24 (d, 1H), 4.06 (m, 3H), 3.86-4.00 (m, 2H), 3.50-3.62 (m, 2H), 3.36-3.50 (m, 1H), 3.24 (m, 1H), 3.15 (m, 1H), 3.04 (d, 2H), 2.56 (m, 3H), 2.40 (br. s., 1H), 1.13 (m, 3H). MS: calc'd 591 (MH$^+$), measured 591 (MH$^+$).

Preparation of 3-[(8aS)-3-oxo-1,5,6,7,8,8a-hexahydroimidazo[1,5-a]pyrazin-2-yl]propanoic acid TFA salt (Compound 56-A)

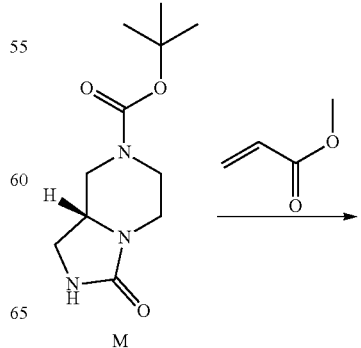

Example 57

(R)-6-[(S)-2-((R)-2-Carboxyl-1-methyl-ethyl)-3-oxo-hexahydro-imidazo[1,5-a]pyrazin-7-ylmethyl]-4-(2-chloro-3-fluoro-phenyl)-2-thiazol-2-yl-1,4-di-hydro-pyrimidine-5-carboxylic acid ethyl ester

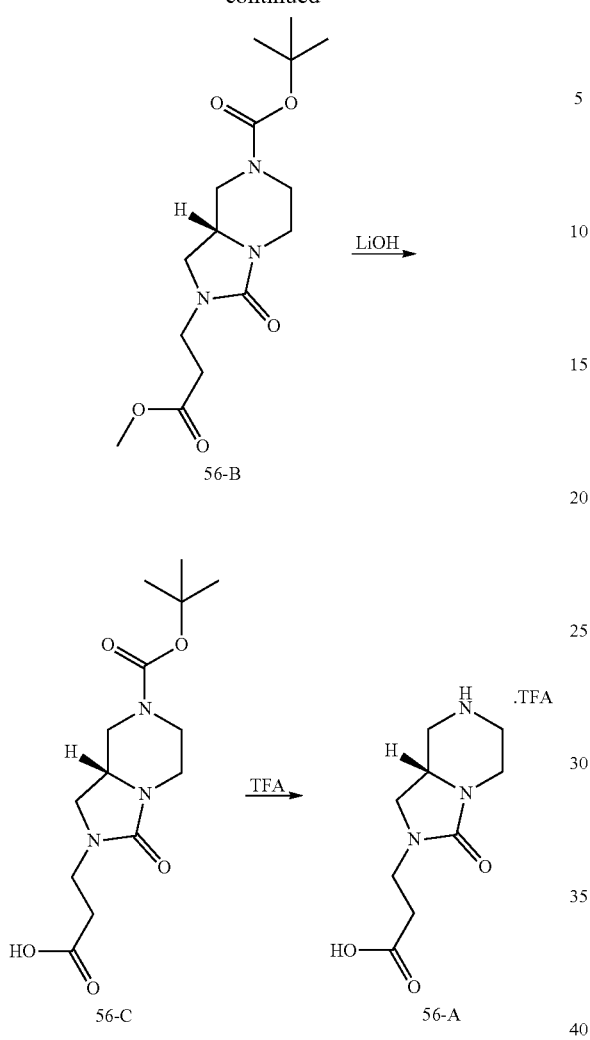

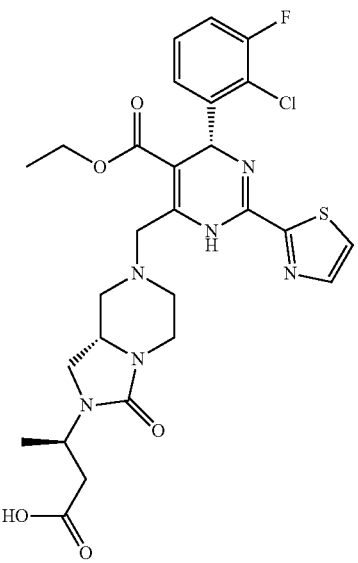 [SMILES: CCOC(=O)C1=C(CN2CCN3C(=O)N([C@H](C)CC(=O)O)C[C@@H]3C2)NC(c2nccs2)=N[C@H]1c1cccc(F)c1Cl]

Preparation of Example 57

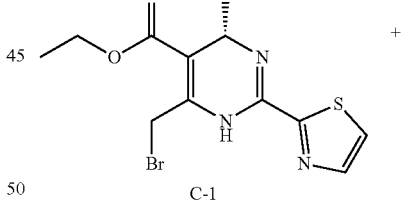

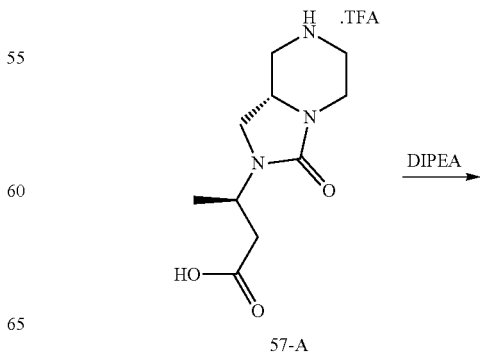

Step 1: To a stirred solution of compound M (150 mg, 0.62 mmol) in THF (3 mL) was added methyl acrylate (534 mg, 6.20 mmol) at room temperature, followed by a small amount of NaOH as a catalyst. LC-MS indicated compound M was consumed completely and the product 56-B was formed already. The resulting mixture was stirred at rt for 6 hours. The reaction mixture was then concentrated and directly used in the next step without further purification. The crude product amount was 180 mg.

Step 2: To a solution of compound 56-B (180 mg, 0.55 mmol) in THF (3 mL) was added a solution of lithium hydroxide monohydrate (116 mg, 2.75 mmol) in H$_2$O (1 mL) at room temperature. The resulting mixture was stirred at room temperature for 3 hours. LC-MS showed starting material 56-B was consumed completely. The mixture was adjusted to pH 4-5 with 1 N HCl, then concentrated. The residue was used directly in the next step and the amount of crude product 56-C was 300 mg.

Step 3: To a solution of 56-C (crude 300 mg, 0.55 mmol) in dichloromethane (3 mL) was added trifluoroacetic acid (3 mL) at room temperature. The resulting mixture was stirred at room temperature for 2 hours. The reaction mixture was concentrated and the residue was directly used in the next step. The amount of crude product 56-A was 350 mg.

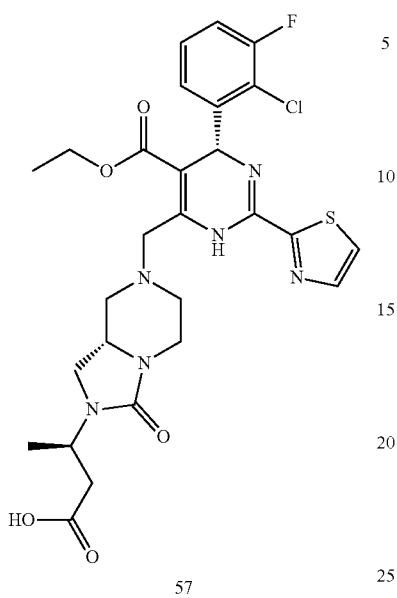

57

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and (3R)-3-[(8aS)-3-oxo-1,5,6,7,8,8a-hexahydroimidazo[1,5-a]pyrazin-2-yl]butanoic acid TFA salt (Compound 57-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 57 was obtained as a light yellow solid (48 mg). $^1$H NMR (400 MHz, METHANOL-$d_4$) d ppm 8.02 (d, 1H), 7.91 (d, 1H), 7.33-7.41 (m, 2H), 7.21-7.29 (m, 1H), 6.27 (s, 1H), 4.72 (d, 1H), 4.54 (d, 1H), 4.27-4.38 (m, 1H), 4.03-4.19 (m, 4H), 3.60-3.74 (m, 3H), 3.38-3.48 (m, 1H), 3.04-3.25 (m, 3H), 2.56-2.66 (m, 1H), 2.47-2.56 (m, 1H), 1.27 (d, 3H), 1.13 (m, 3H). MS: calc'd 605 (MH$^+$), measured 605 (MH$^+$).

Preparation of (3R)-3-[(8aS)-3-oxo-1,5,6,7,8,8a-hexahydroimidazo[1,5-a]pyrazin-2-yl]butanoic acid TFA salt (Compound 57-A)

Compound 57-A was prepared in analogy to compound Q in Example 19 by using methyl (3R)-3-aminobutanoate hydrochloride salt (compound 57-B) instead of ethyl 3-amino-2,2-dimethyl-propanoate hydrochloride salt.

Preparation of methyl (3R)-3-aminobutanoate hydrochloride salt (Compound 57-B)

Compound 57-B was prepared in analogy to compound W in Example 20 by using (R)-3-aminobutanoic acid instead of DL-3-aminoisobutyric acid.

Example 58

(R)-6-[(S)-2-((S)-2-Carboxyl-1-methyl-ethyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester

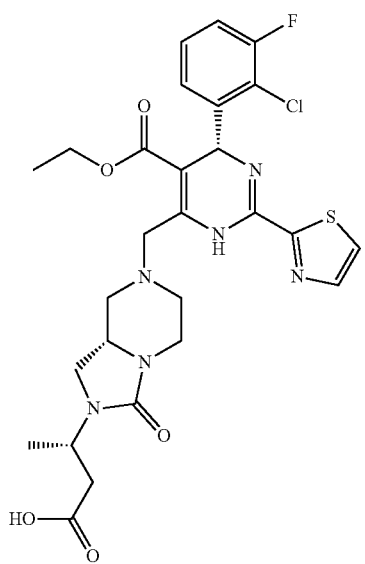 [SMILES: CCOC(=O)C1=C(CN2CCN3C(=O)N([C@@H](C)CC(=O)O)C[C@@H]3C2)NC(c2nccs2)=N[C@H]1c1cccc(F)c1Cl]

Preparation of Example 58

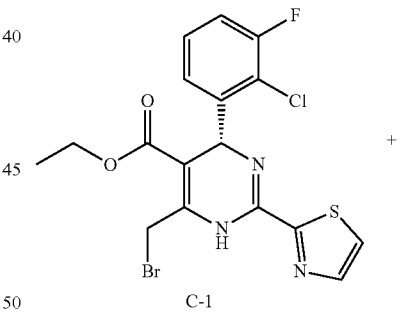

C-1

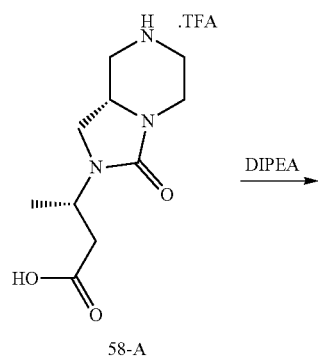

58-A

131
-continued

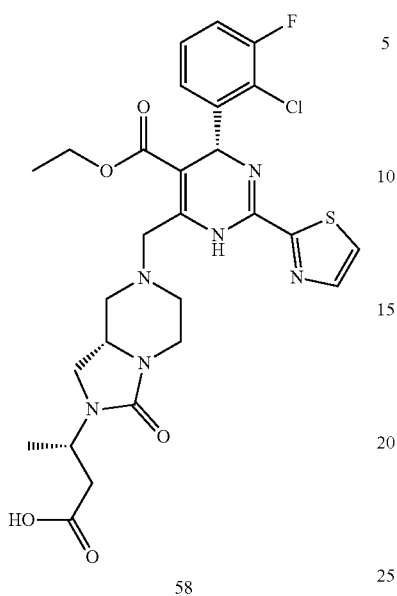

58

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and (3S)-3-[(8aS)-3-oxo-1,5,6,7,8,8a-hexahydroimidazo[1,5-a]pyrazin-2-yl]butanoic acid TFA salt (Compound 58-A) instead of (R)-6-bromomethyl-4-(2-chloro-4-fluoro-phenyl)-2-thiazol-2-yl-1,4-dihydropyrimidine-5-carboxylic acid methyl ester (Compound C) and hexahydro-pyrazino[1,2-c][1,3]oxazin-6-one (Compound D). Example 58 was obtained as a light yellow solid (50 mg). $^1$H NMR (400 MHz, METHANOL-$d_4$) d ppm 8.01 (d, 1H), 7.90 (d, 1H), 7.33-7.40 (m, 2H), 7.21-7.28 (m, 1H), 6.27 (s, 1H), 4.66 (d, 1H), 4.49 (d, 1H), 4.34-4.42 (m, 1H), 4.20-4.20 (m, 1H), 4.04-4.19 (m, 4H), 3.56-3.66 (m, 3H), 3.42-3.50 (m, 1H), 3.22 (m, 1H), 3.01-3.13 (m, 2H), 2.50-2.62 (m, 2H), 1.23 (d, 3H), 1.13 (m, 3H). MS: calc'd 605 (MH$^+$), measured 605 (MH$^+$).

Preparation of (3S)-3-[(8aS)-3-oxo-1,5,6,7,8,8a-hexahydroimidazo[1,5-a]pyrazin-2-yl]butanoic acid TFA salt (Compound 58-A)

Compound 58-A was prepared in analogy to compound Q in Example 19 by using methyl (3S)-3-aminobutanoate hydrochloride salt (compound 58-B) instead of ethyl 3-amino-2,2-dimethyl-propanoate hydrochloride salt.

Preparation of methyl (3R)-3-aminobutanoate hydrochloride salt (Compound 58-B)

Compound 58-B was prepared in analogy to compound W in Example 20 by using (S)-3-aminobutanoic acid instead of DL-3-aminoisobutyric acid.

132
Example 59

(R)-6-[(S)-2-(1-Carboxy-cyclobutylmethyl)-3-oxo-hexahydro-imidazo[1,5-a]pyrazin-7-ylmethyl]-4-(2-chloro-4-fluoro-phenyl)-2-thiazol-2-yl-1,4-dihydropyrimidine-5-carboxylic acid methyl ester

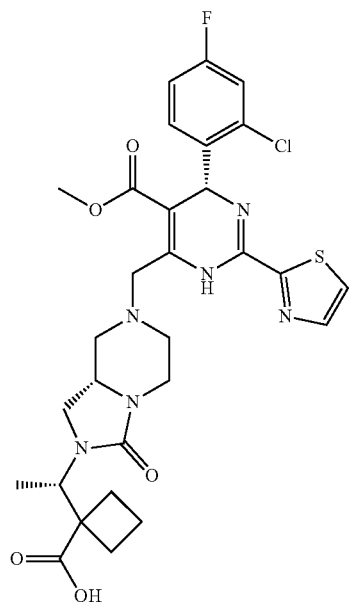 [SMILES: COC(=O)C1=C(CN2CCN3C(=O)N([C@@H](C)C4(C(=O)O)CCC4)C[C@@H]3C2)NC(c2nccs2)=N[C@H]1c1ccc(F)cc1Cl]

Preparation of Example 59

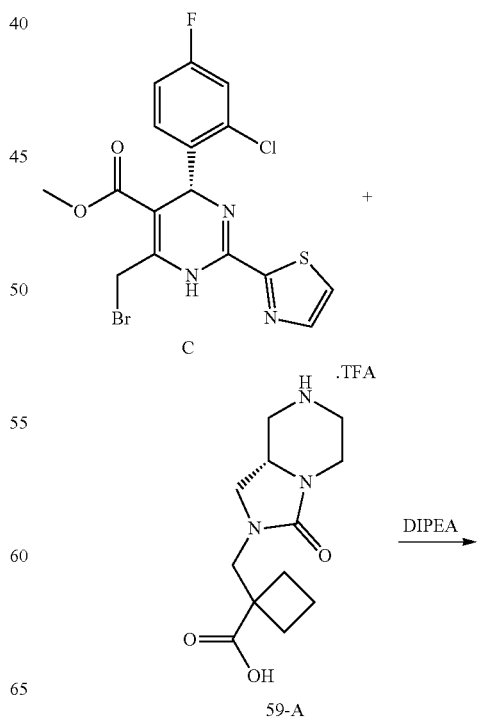

59-A

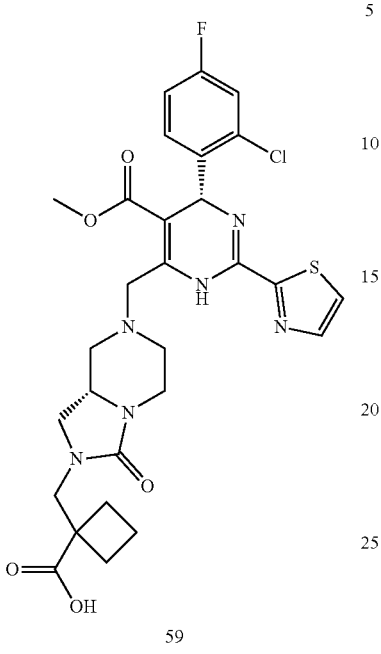

59

The title compound was prepared in analogy to Example 1 by using 1-[[(8aS)-3-oxo-1,5,6,7,8,8a-hexahydroimidazo[1,5-a]pyrazin-2-yl]methyl]cyclobutanecarboxylic acid TFA salt (Compound 59-A) instead of hexahydro-pyrazino[1,2-c][1,3]oxazin-6-one (Compound D). Example 59 was obtained as a light yellow solid (15 mg). $^1$H NMR (400 MHz, METHANOL-$d_4$) d ppm 7.96 (d, 1H), 7.76 (d, 1H), 7.42 (m, 1H), 7.24 (m, 1H), 7.06 (m, 1H), 6.17 (s, 1H), 4.08 (d, 1H), 3.90 (d, 2H), 3.82-3.86 (m, 1H), 3.66-3.72 (m, 1H), 3.61 (s, 3H), 3.54 (d, 1H), 3.47 (m, 1H), 3.14-3.23 (m, 1H), 3.05 (m, 1H), 2.90 (d, 1H), 2.80 (d, 1H), 2.39-2.47 (m, 2H), 2.31-2.39 (m, 1H), 2.16 (m, 1H), 1.99-2.09 (m, 3H), 1.89-1.98 (m, 1H). MS: calc'd 617 (MH$^+$), measured 617 (MH$^+$).

Preparation of 1-[[(8aS)-3-oxo-1,5,6,7,8,8a-hexahydroimidazo[1,5-a]pyrazin-2-yl]methyl]cyclobutanecarboxylic acid TFA salt (Compound 59-A)

Compound 59-A was prepared in analogy to compound Q in Example 19 by using 1-aminomethyl-cyclobutanecarboxylic acid ethyl ester (for its synthesis, please refer to: Cao, Sheldon X. et al PCT Int. Appl. (2009), WO 2009067547) instead of ethyl 3-amino-2,2-dimethyl-propanoate hydrochloride salt.

Example 60

6-[(S)-2-(1-Carboxy-cyclobutylmethyl)-3-oxo-hexahydro-imidazo[1,5-a]pyrazin-7-ylmethyl]-4-((R)-2-chloro-3-fluoro-phenyl)-2-thiazol-2-yl-1,4-dihydropyrimidine-5-carboxylic acid ethyl ester

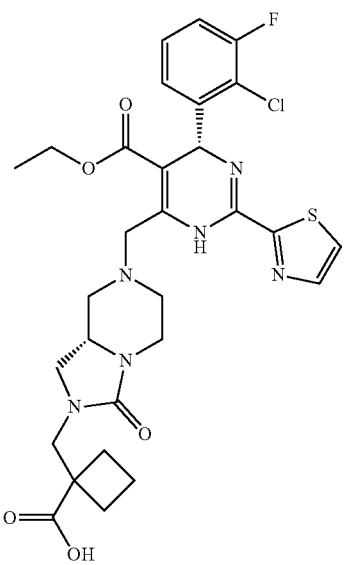 [SMILES: CCOC(=O)C1=C(CN2CCN3C(=O)N(CC4(C(=O)O)CCC4)C[C@@H]3C2)NC(c2nccs2)=N[C@H]1c1cccc(F)c1Cl]

Preparation of Example 60

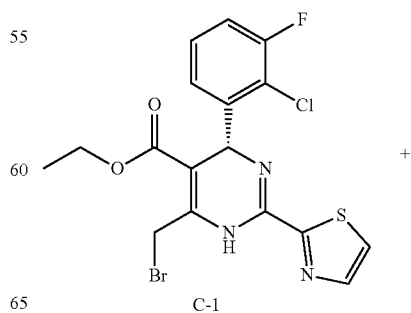

C-1

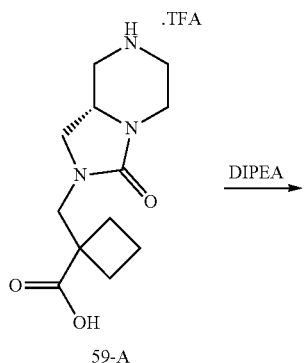

59-A

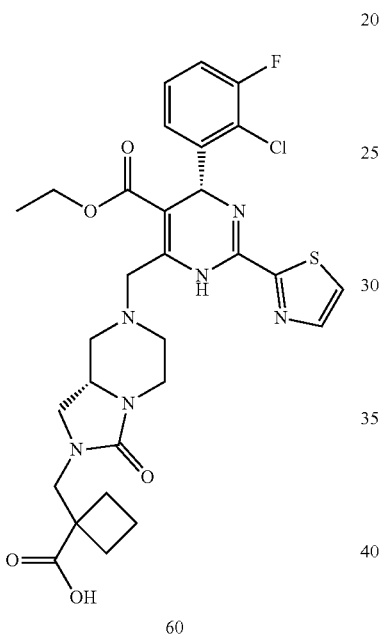

60

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and 1-[[(8aS)-3-oxo-1,5,6,7,8,8a-hexahydroimidazo[1,5-a]pyrazin-2-yl]methyl] cyclobutanecarboxylic acid TFA salt (Compound 59-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino [1,2-c][1,3]oxazin-6-one (Compound D). Example 59 was obtained as a light yellow solid (15 mg). $^1$H NMR (400 MHz, METHANOL-$d_4$) d ppm 7.96 (d, 1H), 7.76 (d, 1H), 7.23-7.35 (m, 2H), 7.16 (m, 1H), 6.24 (s, 1H), 4.02-4.13 (m, 3H), 3.81-3.97 (m, 3H), 3.65-3.74 (m, 1H), 3.43-3.57 (m, 2H), 3.20 (m, 1H), 3.05 (m, 1H), 2.92 (d, 1H), 2.83 (d, 1H), 2.31-2.48 (m, 3H), 2.17 (br. s., 1H), 1.92-2.12 (m, 4H), 1.09-1.17 (m, 3H). MS: calc'd 631 (MH$^+$), measured 631 (MH$^+$).

Example 61 (Mixture of 2 Isomers)

(R)-6-[(S)-2-((1R,3S)-3-Carboxy-cyclopentyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester and (R)-6-[(S)-2-((1S,3R)-3-Carboxy-cyclopentyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester

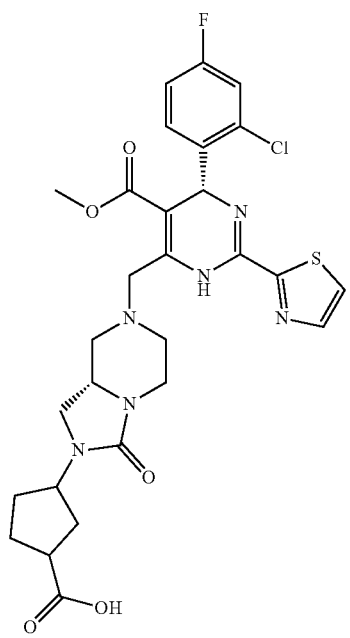 [SMILES: COC(=O)C1=C(CN2CCN3C(=O)N(C4CCC(C(=O)O)C4)C[C@@H]3C2)NC(c2nccs2)=N[C@H]1c1ccc(F)cc1Cl]

Preparation of Example 61

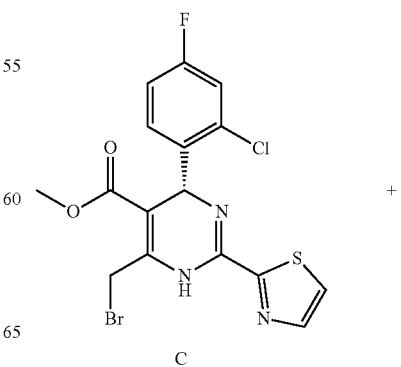

C

+

-continued

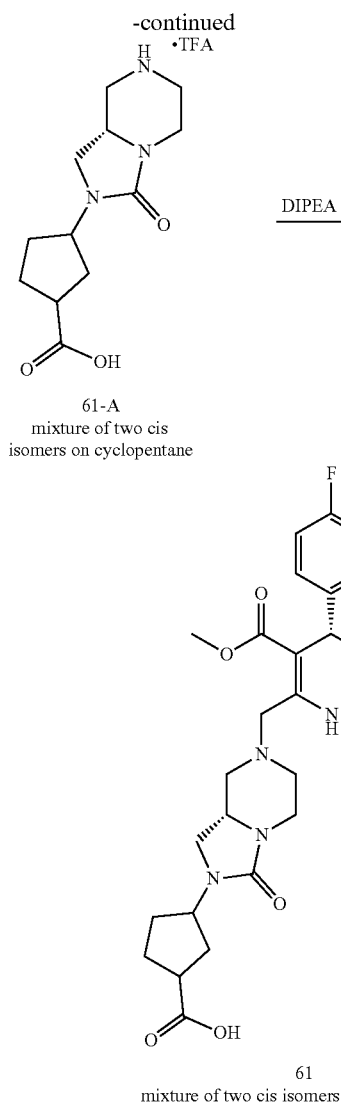

61-A
mixture of two cis
isomers on cyclopentane

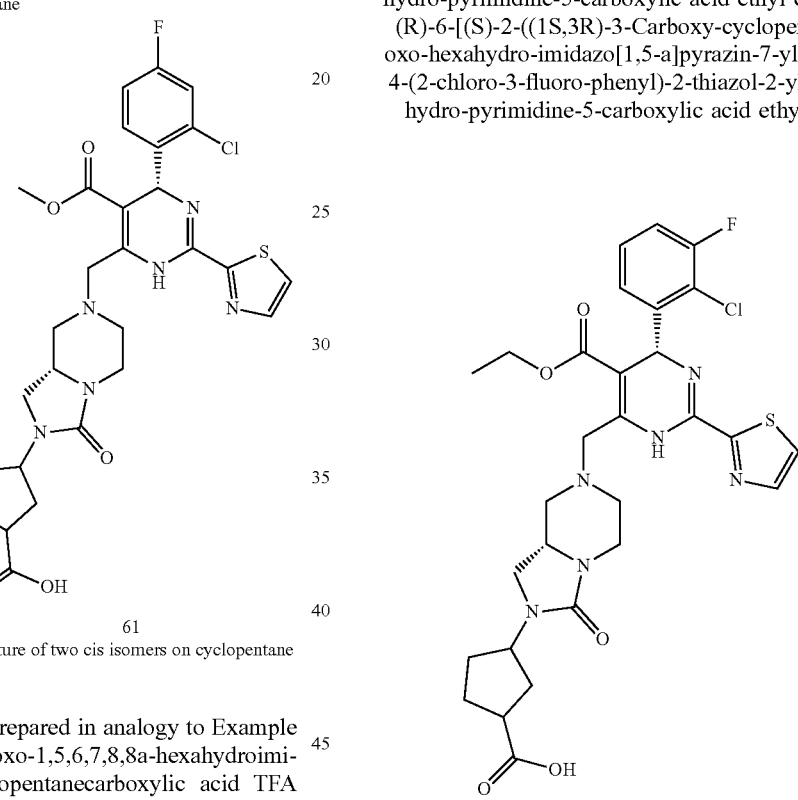

61
mixture of two cis isomers on cyclopentane

The title compound was prepared in analogy to Example 1 by using cis-3-[(8aS)-3-oxo-1,5,6,7,8,8a-hexahydroimidazo[1,5-a]pyrazin-2-yl]cyclopentanecarboxylic acid TFA salt (Compound 61-A) instead of hexahydro-pyrazino[1,2-c][1,3]oxazin-6-one (Compound D). Example 61 was obtained as a light yellow solid (30 mg). $^1$H NMR (400 MHz, METHANOL-d$_4$) d ppm 7.97 (m, 1H), 7.76 (d, 1H), 7.42 (m, 1H), 7.24 (m, 1H), 7.06 (m, 1H), 6.17 (s, 1H), 4.24-4.35 (m, 1H), 4.10 (d, 1H), 3.82-3.94 (m, 3H), 3.61 (s, 3H), 3.53 (m, 1H), 3.03-3.23 (m, 2H), 2.77-2.93 (m, 3H), 2.36 (m, 1H), 2.04-2.23 (m, 2H), 1.67-2.00 (m, 5H). MS: calc'd 617 (MH$^+$), measured 617 (MH$^+$).

Preparation of cis-3-[(8aS)-3-oxo-1,5,6,7,8,8a-hexahydroimidazo[1,5-a]pyrazin-2-yl]cyclopentanecarboxylic acid TFA salt (Compound 61-A)

Compound 61-A was prepared in analogy to compound Q in Example 19 by using cis-methyl 3-aminocyclopentanecarboxylate methyl ester hydrochloride salt (compound 61-B) instead of ethyl 3-amino-2,2-dimethyl-propanoate hydrochloride salt.

Preparation of cis-methyl 3-aminocyclopentanecarboxylate methyl ester hydrochloride salt (Compound 61-B)

Compound 61-B was prepared in analogy to compound W in Example 20 by using cis-3-aminocyclopentanecarboxylic acid (Accela Chembio Co., Ltd, CAS: 49805-32-5) instead of DL-3-aminoisobutyric acid.

Example 62 (Mixture of 2 Isomers)

(R)-6-[(S)-2-((1R,3S)-3-Carboxy-cyclopentyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester and (R)-6-[(S)-2-((1S,3R)-3-Carboxy-cyclopentyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester Preparation of Example 62

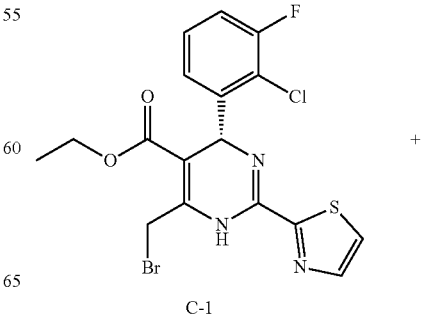

C-1

139

-continued

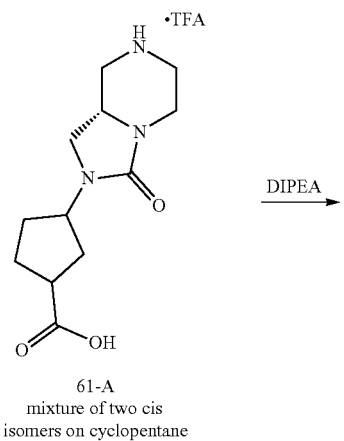

61-A
mixture of two cis
isomers on cyclopentane

140

Example 63 (Mixture of Two Isomers)

(R)-6-[(S)-2-((1R,3R)-3-Carboxy-cyclopentyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester and (R)-6-[(S)-2-((1S,3S)-3-Carboxy-cyclopentyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester

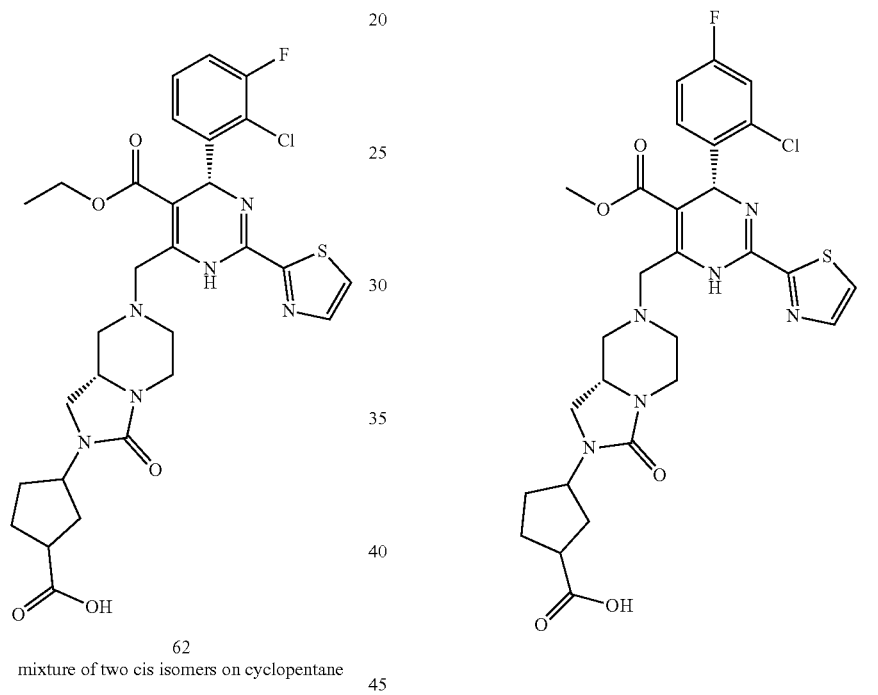

62
mixture of two cis isomers on cyclopentane

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and cis-3-[(8aS)-3-oxo-1,5,6,7,8,8a-hexahydroimidazo[1,5-a]pyrazin-2-yl]cyclopentanecarboxylic acid TFA salt (Compound 61-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 62 was obtained as a light yellow solid (50 mg). $^1$H NMR (400 MHz, METHANOL-d$_4$) d ppm 7.97 (m, 1H), 7.76 (d, 1H), 7.23-7.34 (m, 2H), 7.09-7.19 (m, 1H), 6.24 (s, 1H), 4.23-4.34 (m, 1H), 4.01-4.15 (m, 3H), 3.83-3.95 (m, 3H), 3.53 (m, 1H), 3.04-3.23 (m, 2H), 2.77-2.95 (m, 3H), 2.36 (m, 1H), 2.03-2.22 (m, 2H), 1.90-2.00 (m, 2H), 1.68-1.90 (m, 3H), 1.13 (m, 3H). MS: calc'd 631 (MH$^+$), measured 631 (MH$^+$).

Preparation of Example 63

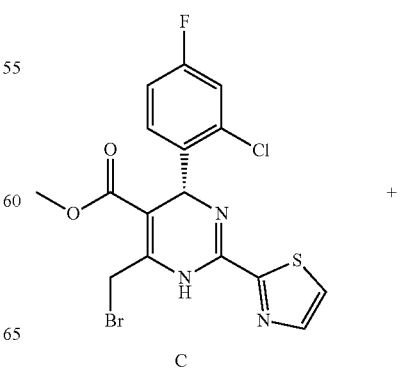

C

+

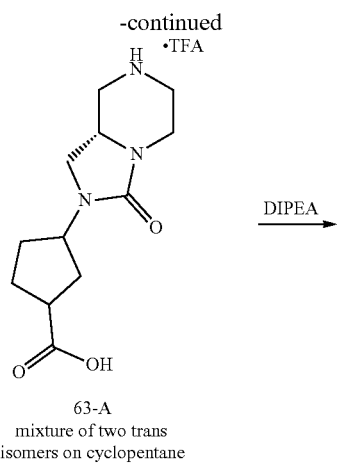

63-A
mixture of two trans
isomers on cyclopentane

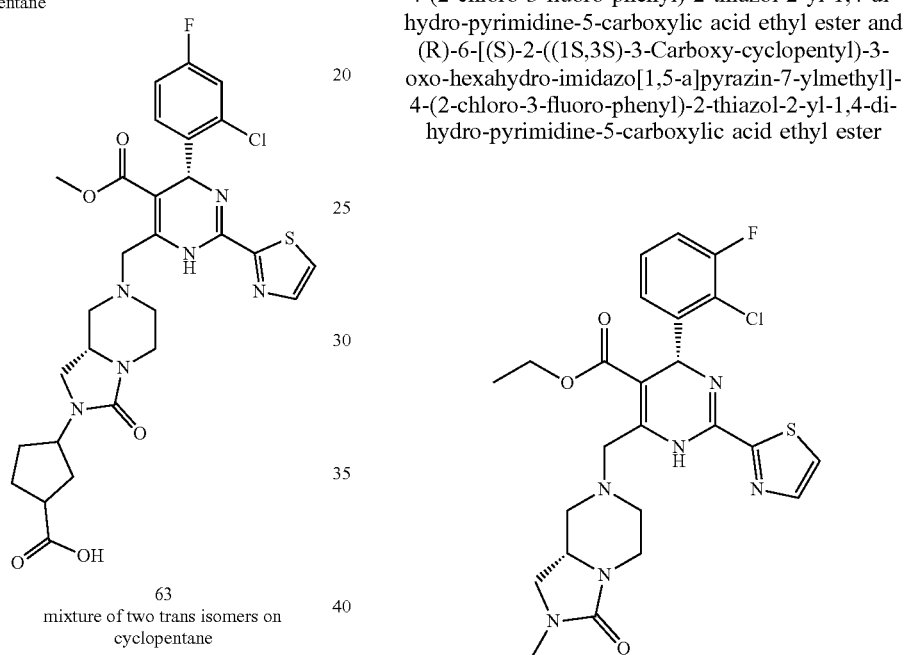

63
mixture of two trans isomers on cyclopentane

The title compound was prepared in analogy to Example 1 by using trans-3-[(8aS)-3-oxo-1,5,6,7,8,8a-hexahydroimidazo[1,5-a]pyrazin-2-yl]cyclopentanecarboxylic acid TFA salt (Compound 63-A) instead of hexahydro-pyrazino[1,2-c][1,3]oxazin-6-one (Compound D). Example 63 was obtained as a light yellow solid (10 mg). $^1$H NMR (400 MHz, METHANOL-$d_4$) d ppm 7.97 (d, 1H), 7.76 (d, 1H), 7.42 (m, 1H), 7.24 (m, 1H), 7.06 (m, 1H), 6.17 (s, 1H), 4.39 (d, 1H), 4.10 (d, 1H), 3.84-3.92 (m, 3H), 3.61 (s, 3H), 3.49-3.53 (m, 1H), 3.18 (d, 1H), 3.06 (d, 1H), 2.89 (br. s., 3H), 2.38 (d, 1H), 2.07-2.19 (m, 3H), 1.86-1.97 (m, 3H), 1.70 (br. s., 1H). MS: calc'd 617 (MH$^+$), measured 617 (MH$^+$).

Preparation of trans-3-[(8aS)-3-oxo-1,5,6,7,8,8a-hexahydroimidazo[1,5-a]pyrazin-2-yl]cyclopentanecarboxylic acid TFA salt (Compound 63-A)

Compound 63-A was prepared in analogy to compound Q in Example 19 by using trans-methyl 3-aminocyclopentanecarboxylate methyl ester hydrochloride salt (compound 63-B) instead of ethyl 3-amino-2,2-dimethyl-propanoate hydrochloride salt.

Preparation of trans-methyl 3-aminocyclopentanecarboxylate methyl ester hydrochloride salt (Compound 63-B)

Compound 63-B was prepared in analogy to compound W in Example 20 by using trans-3-aminocyclopentanecarboxylic acid (for its synthesis, please refer to: Allan, Robin D.; Fong, Joyce *Australian Journal of Chemistry* (1986), 39(6), 855-64.) instead of DL-3-aminoisobutyric acid.

Example 64 (Mixture of Two Isomers)

(R)-6-[(S)-2-((1R,3R)-3-Carboxy-cyclopentyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester and (R)-6-[(S)-2-((1S,3S)-3-Carboxy-cyclopentyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester

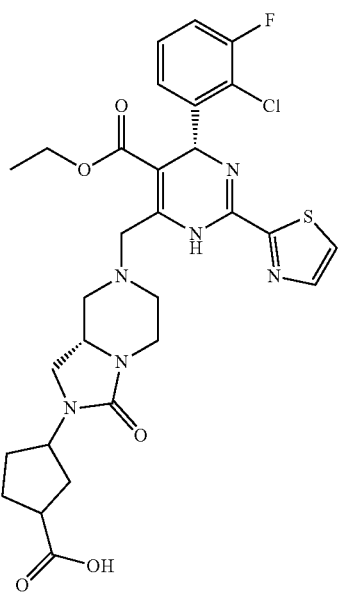 [SMILES: CCOC(=O)C1=C(CN2CCN3C(=O)N(C4CCC(C(=O)O)C4)C[C@@H]3C2)NC(c2nccs2)=N[C@H]1c1cccc(F)c1Cl]

Preparation of Example 64

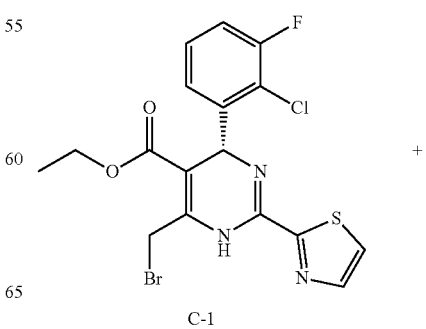

C-1

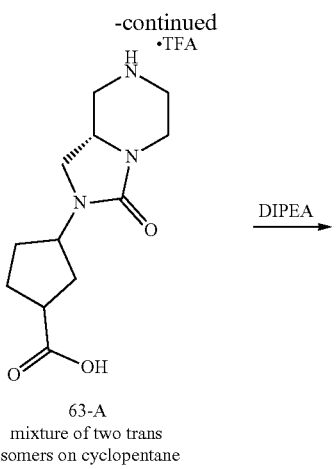

63-A
mixture of two trans
isomers on cyclopentane

DIPEA →

Example 65

(R)-6-[2-(4-Carboxy-benzyl)-3-oxo-hexahydro-imidazo[1,5-a]pyrazin-7-ylmethyl]-4-(2-chloro-4-fluoro-phenyl)-2-thiazol-2-yl-1,4-dihydro-pyrimidine-5-carboxylic acid methyl ester

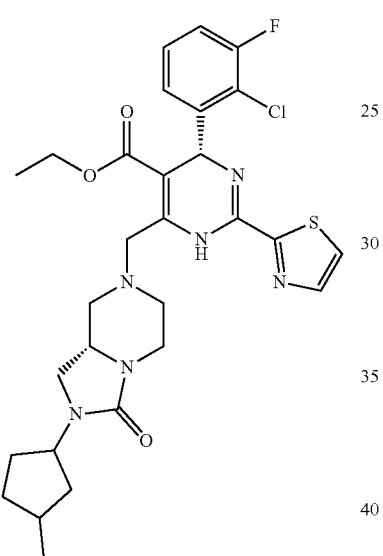

64
mixture of two trans isomers on cyclopentane

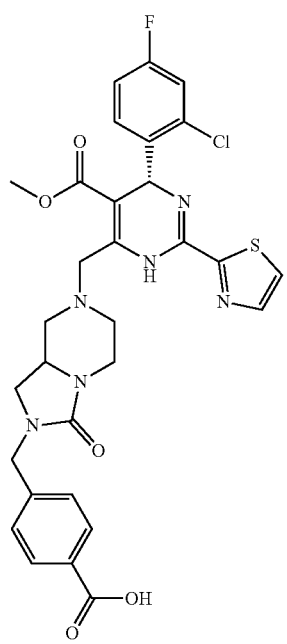 [SMILES: COC(=O)C1=C(CN2CCN3C(=O)N(Cc4ccc(C(=O)O)cc4)CC3C2)NC(c2nccs2)=N[C@H]1c1ccc(F)cc1Cl]

Preparation of Example 65

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and trans-3-[(8aS)-3-oxo-1,5,6,7,8,8a-hexahydroimidazo[1,5-a]pyrazin-2-yl]cyclopentanecarboxylic acid TFA salt (Compound 63-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 64 was obtained as a light yellow solid (10 mg). $^1$H NMR (400 MHz, METHANOL-$d_4$) d ppm 7.97 (m, 1H), 7.76 (d, 1H), 7.24-7.34 (m, 2H), 7.12-7.19 (m, 1H), 6.24 (s, 1H), 4.34-4.42 (m, 1H), 4.02-4.14 (m, 3H), 3.83-3.94 (m, 3H), 3.51 (m, 1H), 3.14-3.22 (m, 1H), 3.04-3.10 (m, 1H), 2.82-2.94 (m, 3H), 2.36 (m, 1H), 2.05-2.20 (m, 3H), 1.81-1.98 (m, 3H), 1.65-1.74 (m, 1H), 1.13 (m, 3H). MS: calc'd 631 (MH$^+$), measured 631 (MH$^+$).

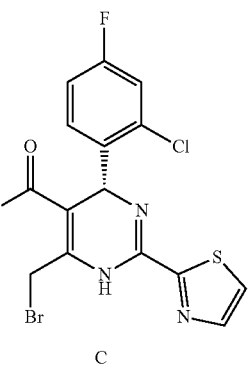
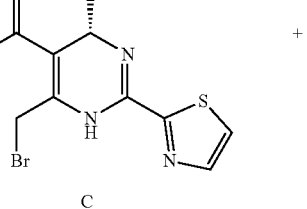

C

-continued

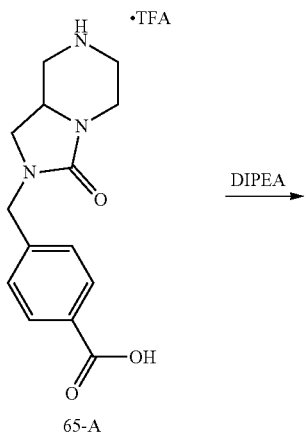

65-A

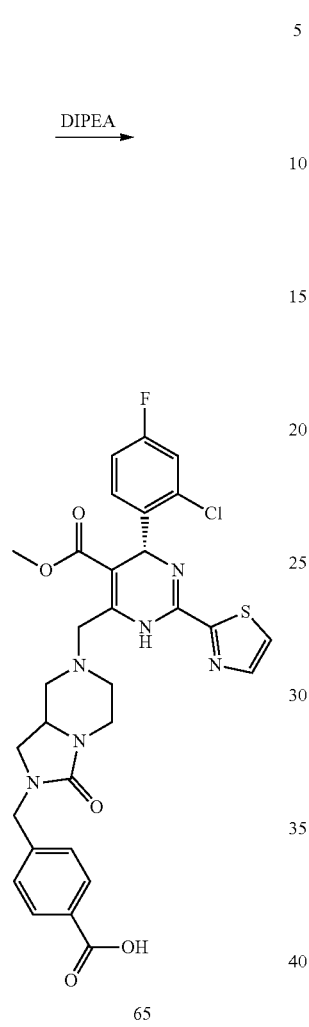

65

The title compound was prepared in analogy to Example 1 by using 4-[(3-oxo-1,5,6,7,8,8a-hexahydroimidazo[1,5-a]pyrazin-2-yl)methyl]benzoic acid TFA salt (Compound 65-A) instead of hexahydro-pyrazino[1,2-c][1,3]oxazin-6-one (Compound D). Example 65 was obtained as a light yellow solid (90 mg). $^1$H NMR (400 MHz, METHANOL-$d_4$) d ppm 8.00-8.06 (m, 3H), 7.91 (m, 1H), 7.53 (m, 1H), 7.40-7.45 (m, 2H), 7.30 (m, 1H), 7.08-7.15 (m, 1H), 6.20 (d, 1H), 4.75 (m, 1H), 4.48-4.62 (m, 3H), 4.12-4.25 (m, 2H), 3.68-3.78 (m, 2H), 3.65 (d, 3H), 3.44-3.58 (m, 2H), 3.16-3.28 (m, 2H), 3.09-3.15 (m, 1H). MS: calc'd 639 (MH$^+$), measured 639 (MH$^+$).

Preparation of 4-[(3-oxo-1,5,6,7,8,8a-hexahydroimidazo[1,5-a]pyrazin-2-yl)methyl]benzoic acid TFA salt (Compound 65-A)

Compound 65-A was prepared in analogy to compound Q in Example 19 by using 4-aminomethyl-benzoic acid methyl ester hydrochloride instead of ethyl 3-amino-2,2-dimethyl-propanoate hydrochloride salt.

Example 66

(R)-6-[2-(4-Carboxy-benzyl)-3-oxo-hexahydro-imidazo[1,5-a]pyrazin-7-ylmethyl]-4-(2-chloro-3-fluoro-phenyl)-2-thiazol-2-yl-1,4-dihydro-pyrimidine-5-carboxylic acid ethyl ester

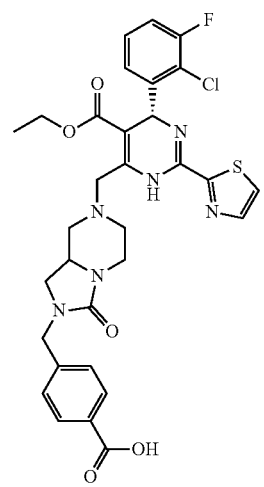 [SMILES: CCOC(=O)C1=C(CN2CCN3C(=O)N(Cc4ccc(C(=O)O)cc4)CC3C2)NC(c2nccs2)=N[C@H]1c1cccc(F)c1Cl]

Preparation of Example 66

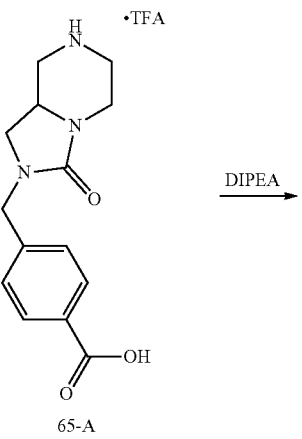

C-1

+

65-A

147
-continued

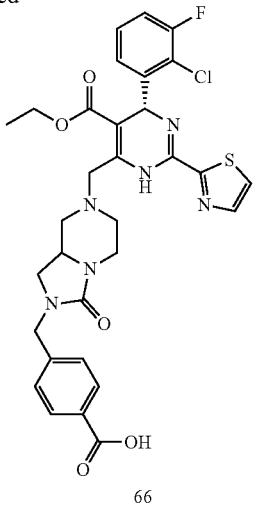

66

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and 4-[(3-oxo-1,5,6,7,8,8a-hexahydroimidazo[1,5-a]pyrazin-2-yl)methyl]benzoic acid TFA salt (Compound 65-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 66 was obtained as a light yellow solid (82 mg). $^1$H NMR (400 MHz, METHANOL-$d_4$) δ ppm 7.99-8.07 (m, 3H), 7.90 (m, 1H), 7.40-7.46 (m, 2H), 7.32-7.39 (m, 2H), 7.21-7.29 (m, 1H), 6.26 (d, 1H), 4.75 (m, 1H), 4.47-4.61 (m, 3H), 4.13-4.25 (m, 2H), 4.06-4.13 (m, 2H), 3.68-3.78 (m, 2H), 3.44-3.58 (m, 2H), 3.18-3.31 (m, 1H), 3.07-3.17 (m, 2H), 1.13 (m, 3H). MS: calc'd 653 (MH$^+$), measured 653 (MH$^+$).

Example 67

2-[2-[7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]ethoxy]acetic acid

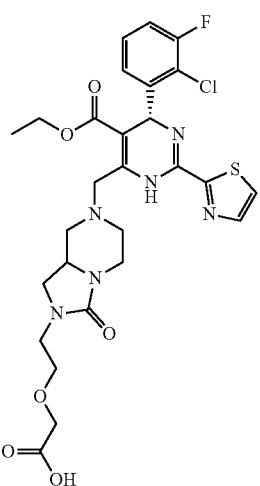 [SMILES: CCOC(=O)C1=C(CN2CCN3C(=O)N(CCOCC(=O)O)CC3C2)NC(c2nccs2)=N[C@H]1c1cccc(F)c1Cl]

148
Preparation of Example 67

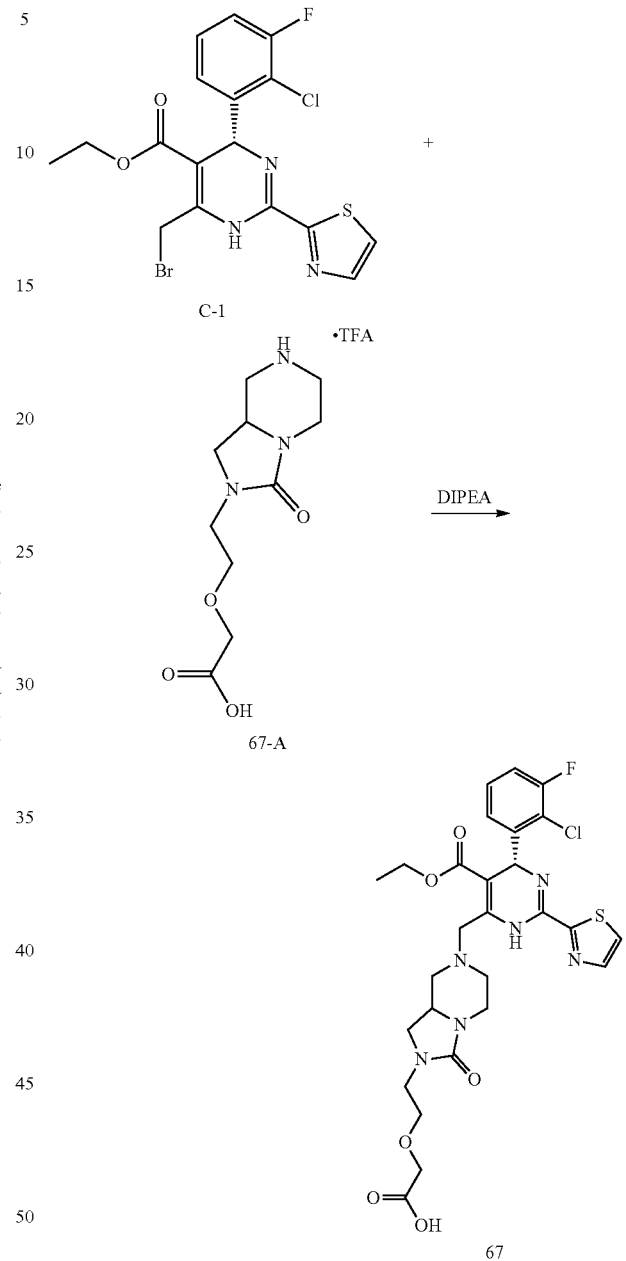

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and 2-[2-(3-oxo-1,5,6,7,8,8a-hexahydroimidazo[1,5-a]pyrazin-2-yl)ethoxy]acetic acid (Compound 67-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 67 was obtained as a light yellow solid (2.5 mg). $^1$H NMR (400 MHz, METHANOL-$d_4$) δ ppm 8.00-8.01 (d, J=4.0 Hz, 1 H), 7.90-7.89 (d, J=4.0Hz, 1 H), 7.35-7.38 (m, 2 H), 7.24 (m, 1 H), 6.26 (s, 1 H), 4.66 (m, 1 H), 4.51 (m, 1 H), 4.05-4.40 (m, 5 H), 3.70-3.83 (m, 3 H), 3.52-3.70 (m, 3H), 3.40 (m, 3H), 3.32 (m, 2 H), 1.13 (m, 3H). MS: calc'd 621 (MH+), measured 621 (MH+).

Preparation of 2-[2-(3-oxo-1,5,6,7,8,8a-hexahydroimidazo[1,5-a]pyrazin-2-yl)ethoxy]acetic acid (Compound 67-A)

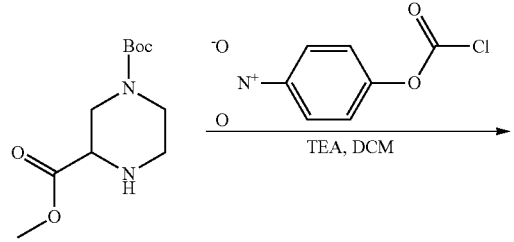

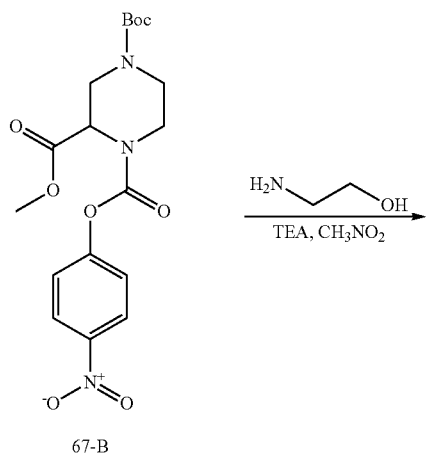

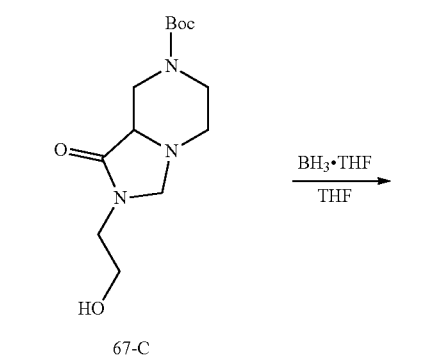

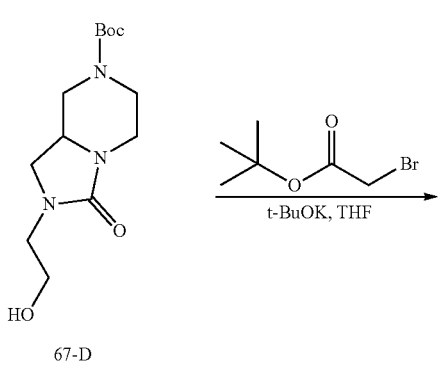

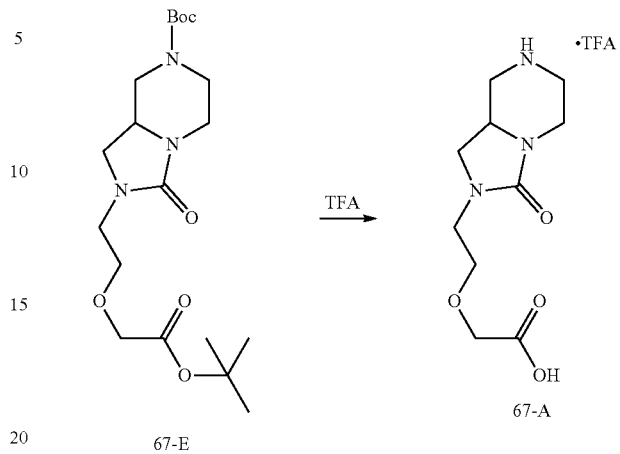

Step 1: The mixture of methyl (±)-4-Boc-piperazine-2-carboxylate (CAS: 129799-08-2, 2.44 g, 0.01 mol), TEA (1.52 g, 0.015 mol) in DCM (10 mL) was added to a solution of (4-nitrophenyl) carbonochloridate (2.42 g, 0.012 mol) in DCM (10 mL). After 1 hour at rt, the organic layer was washed with water and saturated sodium bicarbonate solution, dried over sodium sulfate. After removal of solvent, the crude product 67-B was obtained and used in the next step without purification. MS: calc'd 410 (MH+), measured 410 (MH+).

Step 2: The mixture of compound 67-B (1.0 g, 2.44 mmol), 2-aminoethanol (1.0 g, 16.4 mmol), TEA (0.49 g, 4.88 mmol), nitromethane (2 mL) was heated at 130° C. with microwave for 3 hours. After removal of solvent, the residue was treated with water, extracted with ethyl acetate. Removal of solvent gave the crude product 67-C. MS: calc'd 300 (MH+), measured 300 (MH+).

Step 3: A mixture of compound 67-C (730 mg, 2.44 mmol) and BH$_3$.THF (1M, 4.88 mL). After stirring for 24 hours at rt, the mixture was treated with saturated sodium bicarbonate aqueous solution, extracted with ethyl acetate. After removal of solvent, the product 67-D was obtained. MS: calc'd 286 (MH+), measured 286 (MH+).

Step 4: A mixture of compound 67-D (0.5 g, 1.75 mmol) in THF (15 mL) was added t-BuOK (0.294 g, 2.63 mmol). After stirring for 30 minutes, t-butyl bromoacetate (0.68 g, 3.5 mmol) was added into it. Then the mixture was stirred for another 2 hours at rt, quenched with water, extracted with ethyl acetate. After removal of solvent, the crude product 67-E was obtained and used in the next step. MS: calc'd 400 (MH+), measured 400 (MH+).

Step 5: A mixture of compound 67-E (0.70 g, 1.75 mmol) in DCM (5 mL) was treated with TFA (2 mL). After stirring for 1 hour at rt, the solvent and residue TFA was removed under reduced pressure to afford the product 67-A. MS: calc'd 244 (MH+), measured 244 (MH+).

Example 68

2-[3-[7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]propoxy]acetic acid

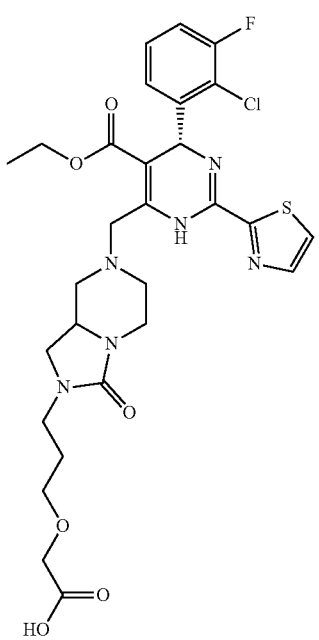 [SMILES: CCOC(=O)C1=C(CN2CCN3C(=O)N(CCCOCC(=O)O)CC3C2)NC(c2nccs2)=N[C@H]1c1cccc(F)c1Cl]

Preparation of Example 68

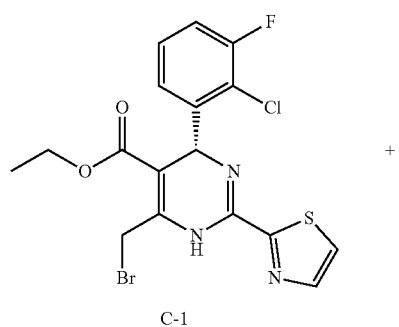

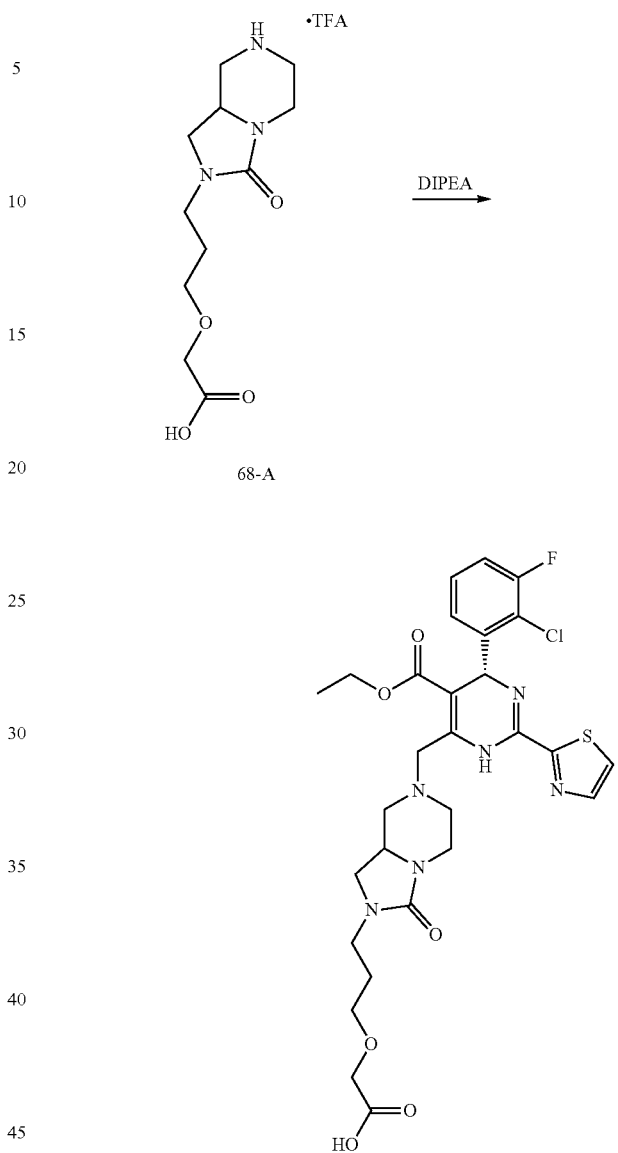

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and 2-[3-(3-oxo-1,5,6,7,8,8a-hexahydroimidazo[1,5-a]pyrazin-2-yl)propoxy]acetic acid (Compound 68-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 68 was obtained as a light yellow solid (6.5 mg). $^1$H NMR (400 MHz, METHANOL-$d_4$) d ppm 7.99-7.98 (d, J=4.0Hz, 1 H), 7.81-7.82 (d, J=4.0Hz, 1 H), 7.32 (m, 2 H), 7.21 (m, 1 H), 6.25 (s, 1 H), 3.90-4.35 (m, 6 H), 3.56 (m, 3 H), 3.10-3.40 (m, 4H), 2.60 (m, 2H), 1.85 (m, 2H), 1.15 (m, 3H). MS: calc'd 635 (MH$^+$), measured 635 (MH$^+$).

Preparation of 2-[3-(3-oxo-1,5,6,7,8,8a-hexahydroimidazo[1,5-a]pyrazin-2-yl)propoxy]acetic acid (Compound 68-A)

Compound 68-A was prepared in analogy to Compound 67-A by using 3-aminopropan-1-ol instead of 2-aminoethanol.

Example 69

Methyl (4R)-4-(2-chloro-4-fluoro-phenyl)-6-[[2-(5-hydroxy-4,4-dimethyl-pentyl)-3-oxo-5,6,8,8a-tetrahydro-1H-imidazo[1,5-a]pyrazin-7-yl]methyl]-2-thiazol-2-yl-1,4-dihydropyrimidine-5-carboxylate

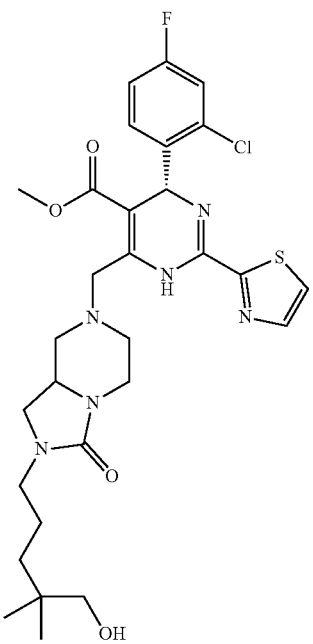 [SMILES: COC(=O)C1=C(CN2CCN3C(=O)N(CCCC(C)(C)CO)CC3C2)NC(c2nccs2)=N[C@H]1c1ccc(F)cc1Cl]

Preparation of Example 69

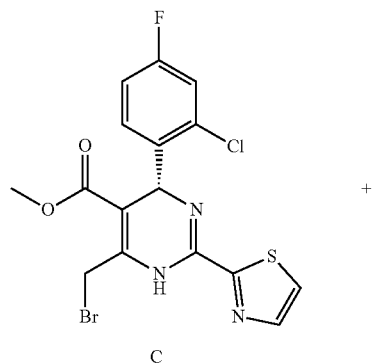

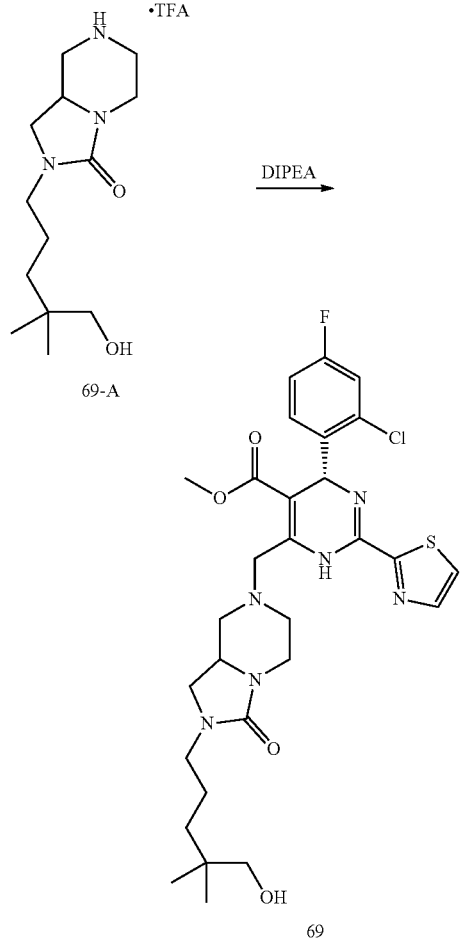

The title compound was prepared in analogy to Example 1 by using 2-(5-hydroxy-4,4-dimethyl-pentyl)-1,5,6,7,8,8a-hexahydroimidazo[1,5-a]pyrazin-3-one (Compound 69-A) instead of hexahydro-pyrazino[1,2-c][1,3]oxazin-6-one (Compound D). Example 69 was obtained as a light yellow solid (55 mg). $^1$H NMR (400 MHz, METHANOL-$d_4$) d ppm 7.97-7.98 (d, J=4.0Hz, 1 H), 7.80-7.81 (d, J=4.0Hz, 1 H), 7.45-7.48 (m, 1 H), 7.27 (m, 1 H), 7.08 (m, 1H), 6.18 (s, 1 H), 3.80-4.40 (m, 4 H), 3.65 (s, 3 H), 3.55 (m, 1H), 3.10-3.30 (m, 6 H), 2.50 (m, 2H), 1.50 (m, 2H), 1.25 (m, 2H), 0.89 (s, 6H). MS: calc'd 619 (MH$^+$), measured 619 (MH$^+$).

Preparation of 2-(5-hydroxy-4,4-dimethyl-pentyl)-1,5,6,7,8,8a-hexahydroimidazo[1,5-a]pyrazin-3-one (Compound 69-A)

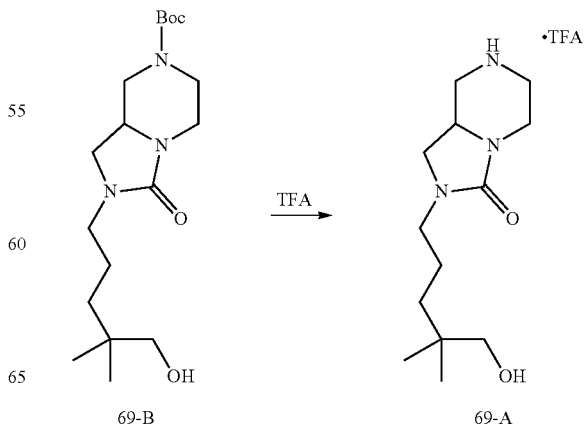

tert-Butyl 2-(5-hydroxy-4,4-dimethyl-pentyl)-3-oxo-5,6,8,8a-tetrahydro-1H-imidazo[1,5-a]pyrazine-7-carboxylate (Compound 69-B) (1 mmol) was dissolved in CH₂Cl₂ (3 mL) followed by the slow addition of TFA (1 mL) at 0° C. The reaction mixture was stirred at rt for 1 hour and then the solvent was removed under vacuum to give the crude product 69-A, which was used directly in the next step.

Preparation of tert-butyl 2-(5-hydroxy-4,4-dimethyl-pentyl)-3-oxo-5,6,8,8a-tetrahydro-1H-imidazo[1,5-a]pyrazine-7-carboxylate (Compound 69-B)

Compound 69-B was prepared in analogy to Compound 67-D by using 5-amino-2,2-dimethyl-pentan-1-ol instead of 2-aminoethanol.

Example 70

Ethyl (4R)-4-(2-chloro-3-fluoro-phenyl)-6-[[2-(2-hydroxyethyl)-3-oxo-5,6,8,8a-tetrahydro-1H-imidazo[1,5-a]pyrazin-7-yl]methyl]-2-thiazol-2-yl-1,4-dihydropyrimidine-5-carboxylate

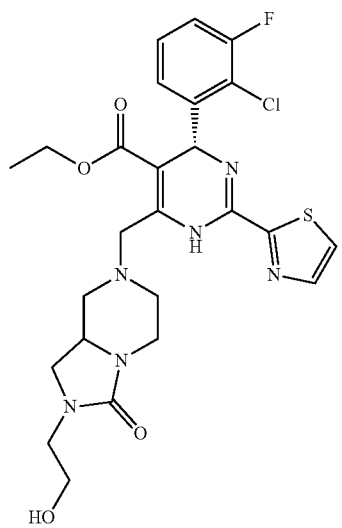 [SMILES: CCOC(=O)C1=C(CN2CCN3C(=O)N(CCO)CC3C2)NC(c2nccs2)=N[C@H]1c1cccc(F)c1Cl]

Preparation of Example 70

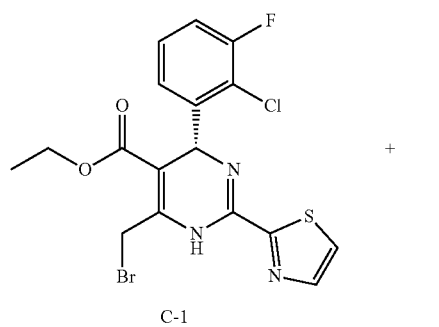

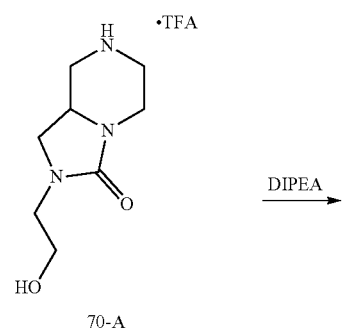

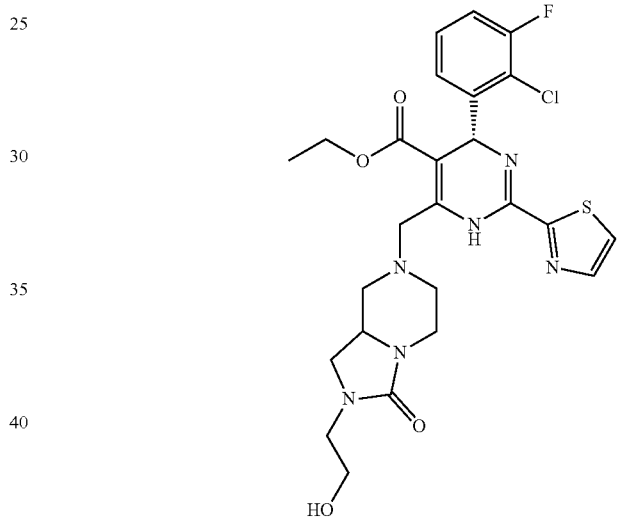

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and 2-(2-hydroxyethyl)-1,5,6,7,8,8a-hexahydroimidazo[1,5-a]pyrazin-3-one (Compound 70-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 70 was obtained as a light yellow solid (45 mg). ¹H NMR (400 MHz, METHANOL-d₄) d ppm 8.01-8.02 (d, J=4.0Hz, 1 H), 7.91-7.92 (d, J=4.0Hz, 1 H), 7.38 (m, 2 H), 7.27 (m, 1 H), 6.27 (s, 1 H), 4.55-4.78 (m, 2 H), 4.10-4.25 (m, 4 H), 3.72 (m, 5 H), 3.45 (m, 2H), 3.10-3.35 (m, 7 H). MS: calc'd 563 (MH⁺), measured 563 (MH⁺).

Preparation of 2-(2-hydroxyethyl)-1,5,6,7,8,8a-hexahydroimidazo[1,5-a]pyrazin-3-one (Compound 70-A)

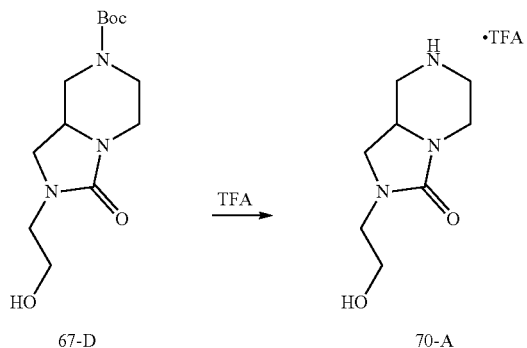 [SMILES: CC(C)(C)OC(=O)N1CCN2C(=O)N(CCO)CC2C1 ; O=C1N(CCO)CC2CNCCN12]

tert-Butyl 2-(2-hydroxyethyl)-3-oxo-5,6,8,8a-tetrahydro-1H-imidazo[1,5-a]pyrazine-7-carboxylate (Compound 67-D) (1 mmol) was dissolved in CH$_2$Cl$_2$ (3 mL) followed by the slow addition of TFA (1 mL) at 0° C. The reaction mixture was stirred at rt for 1 hour and then the solvent was removed in vacuum to give the crude product 70-A, which was used directly in the next step.

Example 71

Ethyl (4R)-4-(2-chloro-3-fluoro-phenyl)-6-[[2-(2-hydroxyethyl)-3-oxo-5,6,8,8a-tetrahydro-1H-imidazo[1,5-a]pyrazin-7-yl]methyl]-2-thiazol-2-yl-1,4-dihydropyrimidine-5-carboxylate

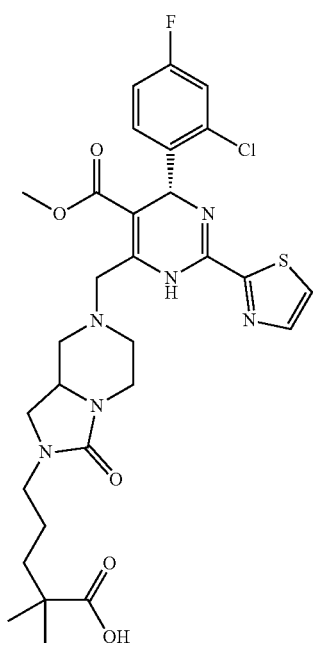 [SMILES: COC(=O)C1=C(CN2CCN3C(=O)N(CCCC(C)(C)C(=O)O)CC3C2)NC(c2nccs2)=N[C@H]1c1ccc(F)cc1Cl]

Preparation of Example 71

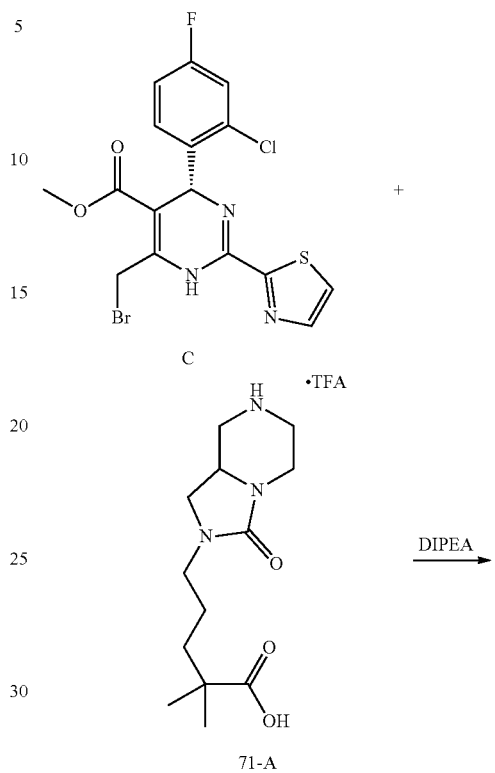

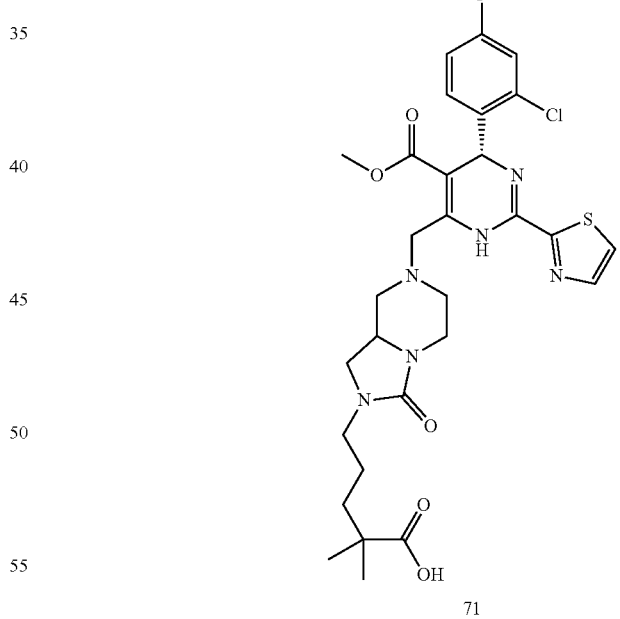

The title compound was prepared in analogy to Example 1 by using 2,2-dimethyl-5-(3-oxo-1,5,6,7,8,8a-hexahydroimidazo[1,5-a]pyrazin-2-yl)pentanoic acid (Compound 71-A) instead of hexahydro-pyrazino[1,2-c][1,3]oxazin-6-one (Compound D). Example 71 was obtained as a light yellow solid (45 mg). $^1$H NMR (400 MHz, METHANOL-d$_4$) d ppm 8.01-8.02 (d, J=4.0Hz, 1 H), 7.91-7.92 (d, J=4.0Hz, 1 H), 7.53 (m, 1 H), 7.40 (m, 1 H), 7.10 (m, 1H), 6.20 (s, 1 H), 4.52-4.75 (m, 2 H), 4.10-4.25 (m, 2 H), 3.65

(m, 5 H), 3.45 (m, 1H), 3.10-3.35 (m, 4 H), 1.55 (m, 4H), 1.20 (s, 6H). MS: calc'd 563 (MH+), measured 563 (MH+).

Preparation of 2,2-dimethyl-5-(3-oxo-1,5,6,7,8,8a-hexahydroimidazo[1,5-a]pyrazin-2-yl)pentanoic acid (Compound 71-A)

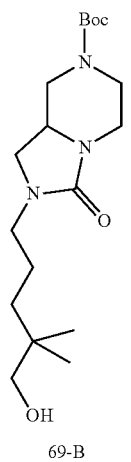

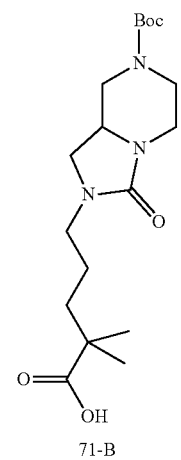

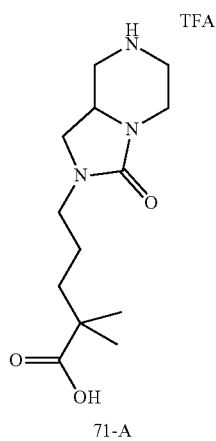

Step 1: A mixture of tert-butyl 2-(5-hydroxy-4,4-dimethyl-pentyl)-3-oxo-5,6,8,8a-tetrahydro-1H-imidazo[1,5-a]pyrazine-7-carboxylate (compound 69-B) (0.4 g, 1.1 mmol) and pyridinium dichromate (1.7 g, 4.4 mmol) in DMF (10 mL) was stirred for 12 hours, then treated with water, adjusted pH<7 with acetic acid, extracted with ethyl acetate. After removal of solvent, the crude product 71-B was obtained. MS: calc'd 370 (MH+), measured 370 (MH+).

Step 2: A mixture of compound 71-B (0.41 g, 1.1 mmol), TFA (2 mL) in DCM (2 mL) was stirred for 1.2 hours at rt. After removal of solvent and TFA, the crude product 71-A was obtained and used in the next step. MS: calc'd 270 (MH+), measured 270 (MH+).

Example 72

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclohexanecarboxylic acid

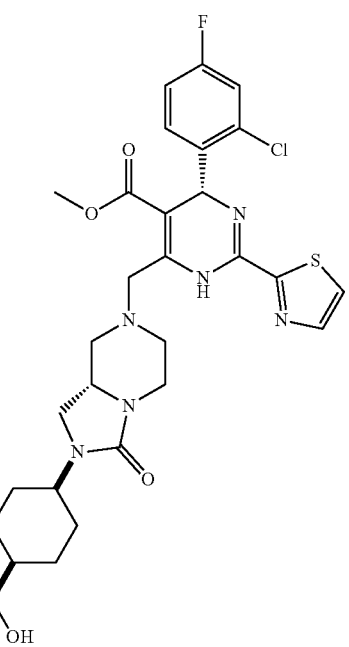

Preparation of Example 72

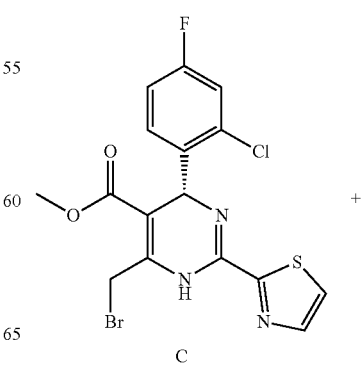

C

161
-continued

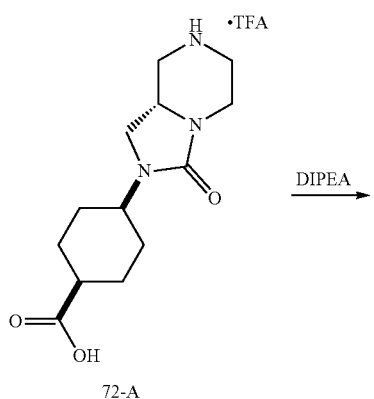

72-A

→ DIPEA

162

Preparation of cis-4-[(2R)-3-oxo-1,5,6,7,8,8a-hexa-hydroimidazo[1,5-a]pyrazin-2-yl]cyclohexanecarboxylic acid TFA salt (Compound 72-A)

Compound 72-A was prepared in analogy to compound Q in Example 19 by using methyl cis-4-aminocyclohexanecarboxylate hydrochloride (CAS: 61367-16-6, TCI) instead of ethyl 3-amino-2,2-dimethyl-propanoate hydrochloride salt.

Example 73

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]cyclohexanecarboxylic acid

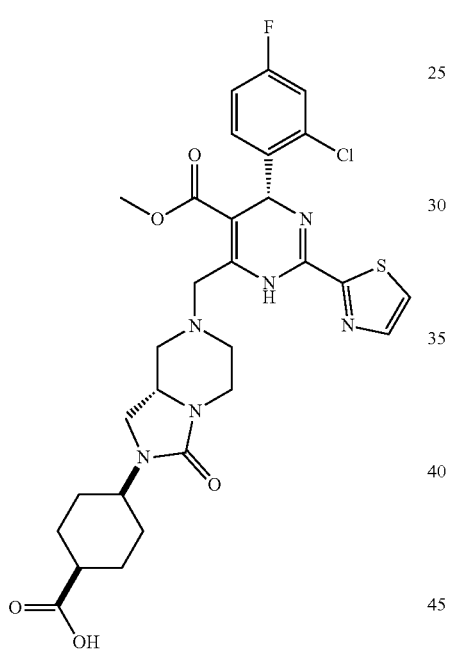

72

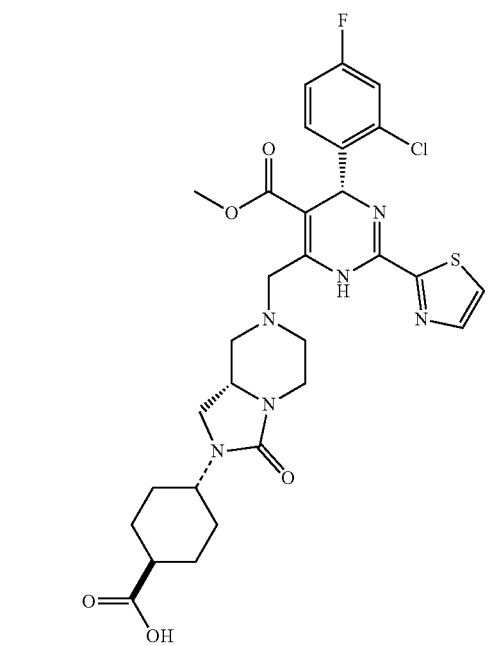

Preparation of Example 73

The title compound was prepared in analogy to Example 1 by using cis-4-[(2R)-3-oxo-1,5,6,7,8,8a-hexahydroimidazo[1,5-a]pyrazin-2-yl]cyclohexanecarboxylic acid TFA salt (Compound 72-A) instead of hexahydro-pyrazino[1,2-c][1,3]oxazin-6-one (Compound D). Example 72 was obtained as a light yellow solid (30 mg). $^1$H NMR (400 MHz, METHANOL-d$_4$) d ppm 7.97 (d, J=3.3 Hz, 1H), 7.77 (d, J=3.0 Hz, 1H), 7.42 (dd, J=8.8, 6.3 Hz, 1H), 7.24 (dd, J=8.8, 2.5 Hz, 1H), 7.06 (td, J=8.5, 2.6 Hz, 1H), 6.17 (s, 1H), 4.10 (d, J=16.8 Hz, 1H), 3.79-3.97 (m, 3H), 3.55-3.70 (m, 4H), 3.48 (t, J=8.9 Hz, 1H), 3.11-3.26 (m, 1H), 3.03 (dd, J=9.3, 4.0 Hz, 1H), 2.71-2.96 (m, 3H), 2.04-2.42 (m, 5H), 1.77 (br. s., 2H), 1.46-1.62 ppm (m, 3H). MS: calc'd 631 (MH$^+$), measured 631 (MH$^+$).

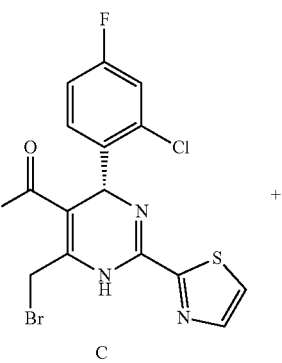

C

+

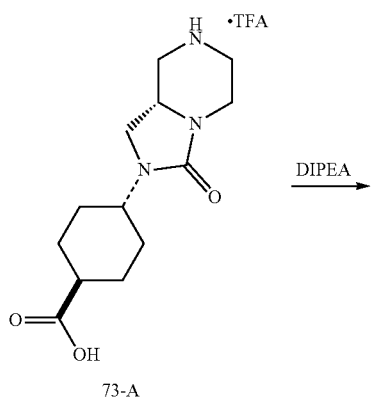

73-A

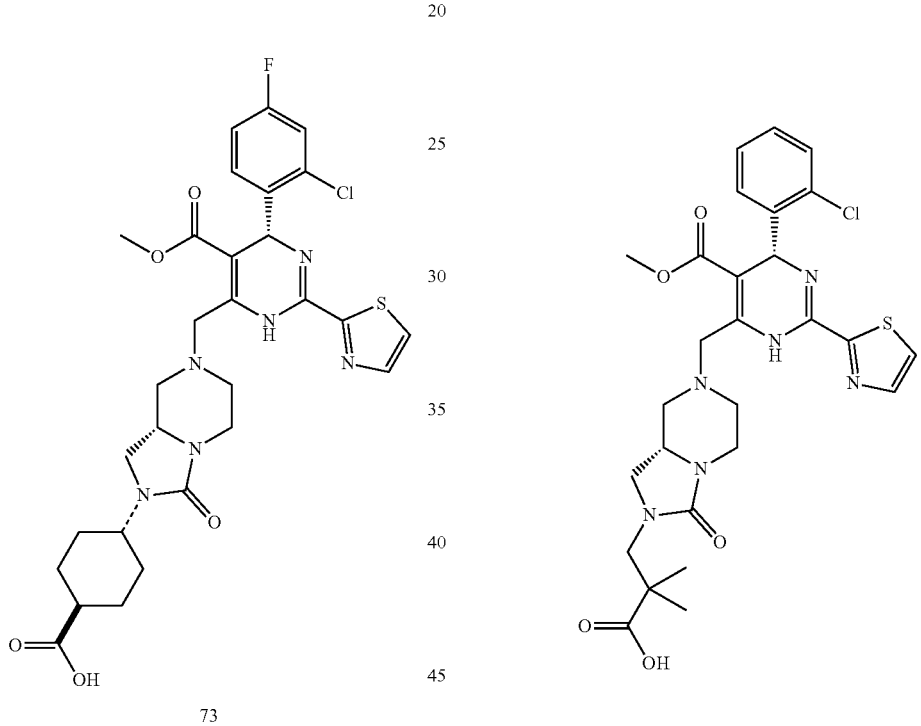

73

The title compound was prepared in analogy to Example 1 by using trans-4-[(2R)-3-oxo-1,5,6,7,8,8a-hexahydroimidazo[1,5-a]pyrazin-2-yl]cyclohexanecarboxylic acid TFA salt (Compound 73-A) instead of hexahydro-pyrazino[1,2-c][1,3]oxazin-6-one (Compound D). Example 73 was obtained as a light yellow solid (46 mg). $^1$H NMR (400 MHz, METHANOL-$d_4$) d ppm 7.97 (d, J=3.0 Hz, 1H), 7.77 (d, J=3.0 Hz, 1H), 7.42 (dd, J=8.8, 6.3 Hz, 1H), 7.24 (dd, J=8.5, 2.8 Hz, 1H), 7.06 (td, J=8.5, 2.5 Hz, 1H), 6.17 (s, 1H), 4.10 (d, J=17.1 Hz, 1H), 3.78-3.97 (m, 3H), 3.61 (s, 3H), 3.41-3.52 (m, 1H), 3.19 (d, J=11.0 Hz, 1H), 3.03 (dd, J=9.5, 4.0 Hz, 1H), 2.75-2.94 (m, 2H), 2.36 (dd, J=11.7, 7.9 Hz, 2H), 1.93-2.24 (m, 5H), 1.77 (br. s., 2H), 1.53 ppm (d, J=10.0 Hz, 3H). MS: calc'd 631 (MH$^+$), measured 631 (MH$^+$).

Preparation of trans-4-[(2R)-3-oxo-1,5,6,7,8,8a-hexahydroimidazo[1,5-a]pyrazin-2-yl]cyclohexanecarboxylic acid TFA salt (Compound 73-A)

Compound 73-A was prepared in analogy to compound Q in Example 19 by using methyl-trans-4-amino-cyclohexanecarboxylic acid methyl ester (CAS: 61367-07-5, TCI) instead of ethyl 3-amino-2,2-dimethyl-propanoate hydrochloride salt.

Example 74

3-[(8aS)-7-[[(4R)-4-(2-chlorophenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid Preparation of Example 74

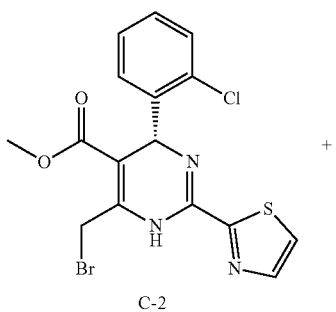

C-2

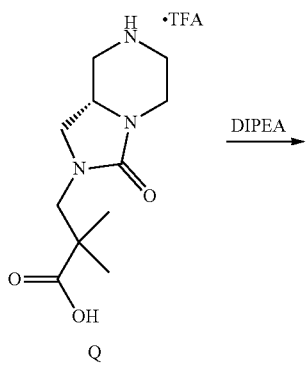

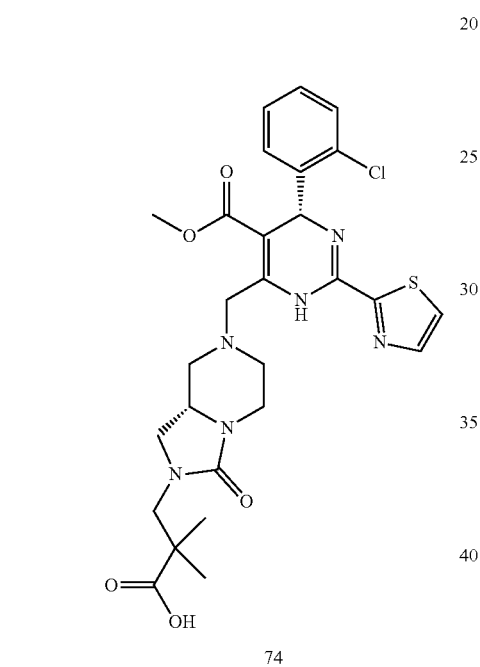

74

The title compound was prepared in analogy to Example 1 by using methyl (4R)-6-(bromomethyl)-4-(2-chlorophenyl)-2-thiazol-2-yl-1,4-dihydropyrimidine-5-carboxylate (Compound C-2) and 3-[(8aS)-3-oxo-1,5,6,7,8,8a-hexahydroimidazo[1,5-a]pyrazin-2-yl]-2,2-dimethyl-propanoic acid (Compound Q) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 74 was obtained as a light yellow solid (6 mg). $^{1}$H NMR (400 MHz, METHANOL-$d_4$) δ ppm 7.97 (d, J=3.3 Hz, 1H), 7.76 (d, J=3.3 Hz, 1H), 7.41 (td, J=7.4, 1.8 Hz, 2H), 7.19-7.33 (m, 2H), 6.21 (s, 1H), 4.08 (d, J=17.1 Hz, 1H), 3.79-3.96 (m, 3H), 3.60 (s, 2H), 3.51 (t, J=9.2 Hz, 1H), 3.37-3.42 (m, 1H), 3.07-3.28 (m, 3H), 2.74-2.94 (m, 2H), 2.12-2.41 (m, 4H), 1.39 (d, J=6.3 Hz, 2H), 1.18 ppm (d, J=4.0 Hz, 3H). MS: calc'd 587 (MH$^+$), measured 587 (MH$^+$).

Preparation of methyl (4R)-6-(bromomethyl)-4-(2-chlorophenyl)-2-thiazol-2-yl-1,4-dihydropyrimidine-5-carboxylate (Compound C-2)

Compound C-2 was prepared in analogy to compound C by using 2-chlorobenzaldehyde instead of 2-chloro-4-fluorobenzaldehyde.

Example 75

2-[[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl]butanoic acid

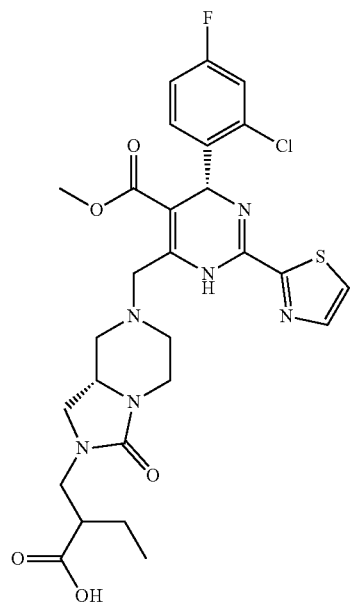 [SMILES: CCC(CN1C[C@@H]2CN(CC3=C(C(=O)OC)[C@H](c4ccc(F)cc4Cl)N=C(c4nccs4)N3)CCN2C1=O)C(=O)O]

Preparation of Example 75

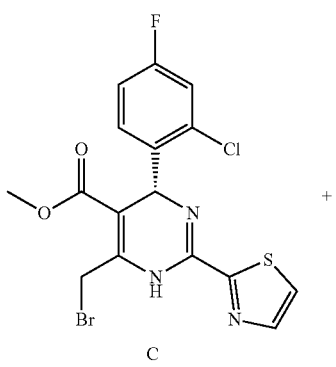

C

167

-continued

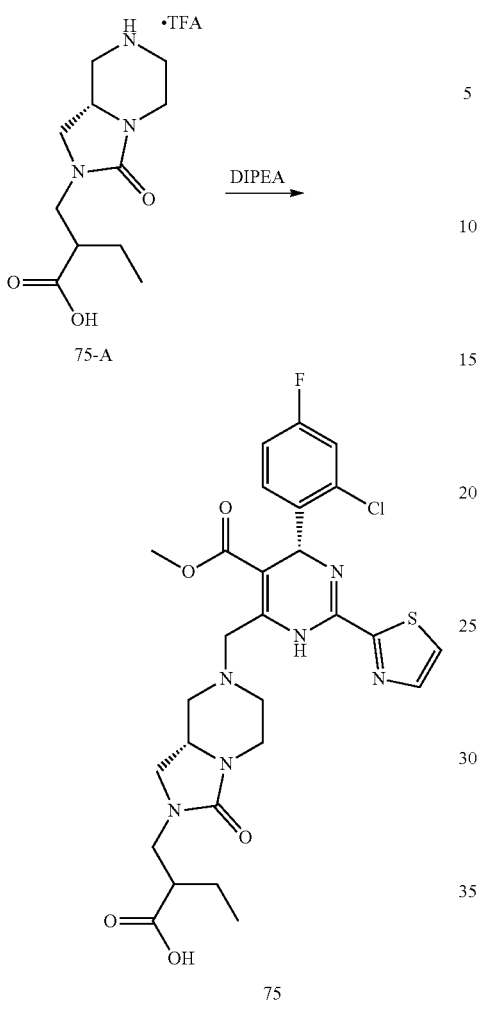

75-A

75

The title compound was prepared in analogy to Example 1 by using 2-[[(8aS)-3-oxo-1,5,6,7,8,8a-hexahydroimidazo[1,5-a]pyrazin-2-yl]methyl]butanoic acid TFA salt (Compound 75-A) instead of hexahydro-pyrazino[1,2-c][1,3]oxazin-6-one (Compound D). Example 75 was obtained as a light yellow solid (50 mg). $^1$H NMR (400 MHz, METHANOL-$d_4$) d ppm 7.96-7.97 (m, 1H), 7.92 (d, J=3.3 Hz, 1H), 7.54 (dd, J=8.8, 6.0 Hz, 1H), 7.30 (dd, J=8.7, 2.6 Hz, 1H), 7.12 (td, J=8.3, 2.6 Hz, 1H), 6.20 (s, 1H), 4.64-4.81 (m, 2H), 4.46-4.60 (m, 1H), 4.01-4.26 (m, 2H), 3.60-3.78 (m, 5H), 3.35-3.57 (m, 3H), 3.03-3.29 (m, 3H), 2.62 (dtd, J=14.1, 8.4, 5.5 Hz, 1H), 1.50-1.74 (m, 2H), 0.99 ppm (t, J=7.4 Hz, 3H). MS: calc'd 605 (MH$^+$), measured 605 (MH$^+$).

Preparation of 2-[[(8aS)-3-oxo-1,5,6,7,8,8a-hexahydroimidazo[1,5-a]pyrazin-2-yl]methyl]butanoic acid TFA salt (Compound 75-A)

Compound 75-A was prepared in analogy to compound Q by using methyl 2-(aminomethyl)butanoate (for its synthesis, please refer to: Kaptein, Bernardus; et al PCT Int. Appl. 2005, WO 2005085462) instead of ethyl 3-amino-2,2-dimethyl-propanoate hydrochloride salt.

168

Example 76

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid

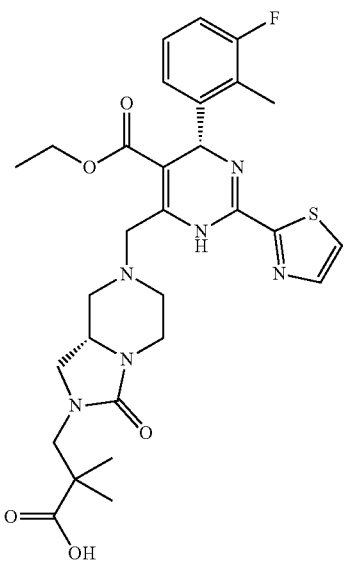 [SMILES: CCOC(=O)C1=C(CN2CCN3C(=O)N(CC(C)(C)C(=O)O)C[C@@H]3C2)NC(c2nccs2)=N[C@H]1c1cccc(F)c1C]

Preparation of Example 76

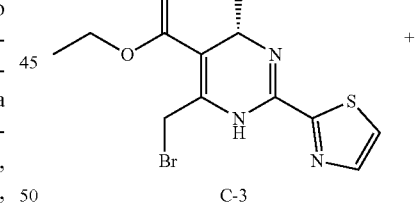

C-3

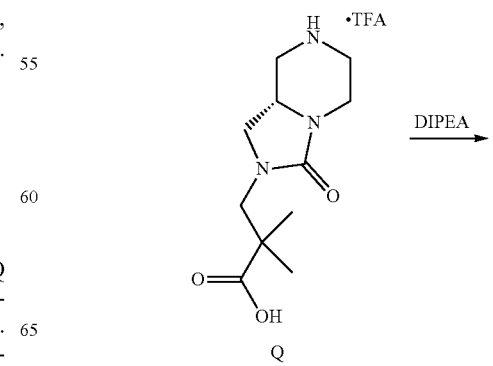

Q

Example 77

3-[(8aS)-7-[[4-(4-chlorophenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid

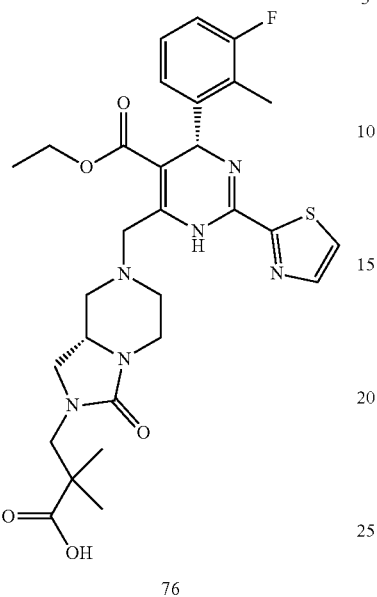

76

The title compound was prepared in analogy to Example 1 by using ethyl (4S)-6-(bromomethyl)-4-(3-fluoro-2-methyl-phenyl)-2-thiazol-2-yl-1,4-dihydropyrimidine-5-carboxylate (Compound C-3) and 3-[(8aS)-3-oxo-1,5,6,7,8,8a-hexahydroimidazo[1,5-a]pyrazin-2-yl]-2,2-dimethyl-propanoic acid (Compound Q) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 76 was obtained as a light yellow solid (132 mg). $^1$H NMR (400 MHz, METHANOL-$d_4$) d ppm 7.95 (d, J=3.3 Hz, 1H), 7.75 (d, J=3.3 Hz, 1H), 7.08-7.23 (m, 2H), 6.95 (t, J=8.8 Hz, 1H), 5.99 (s, 1H), 4.02-4.17 (m, 3H), 3.79-4.00 (m, 3H), 3.36-3.57 (m, 2H), 3.26-3.33 (m, 1H), 3.17-3.25 (m, 1H), 3.11 (dd, J=9.3, 4.0 Hz, 1H), 2.78-2.99 (m, 2H), 2.53 (d, J=2.0 Hz, 3H), 2.39 (dd, J=11.2, 8.2 Hz, 1H), 2.14-2.26 (m, 1H), 1.21 (d, J=2.8 Hz, 6H), 1.15 ppm (t, J=7.2 Hz, 3H). MS: calc'd 599 (MH$^+$), measured 599 (MH$^+$).

Preparation of ethyl (4S)-6-(bromomethyl)-4-(3-fluoro-2-methyl-phenyl)-2-thiazol-2-yl-1,4-dihydro-pyrimidine-5-carboxylate (Compound C-3)

Compound C-3 was prepared in analogy to compound C by using 2-methyl-3-fluorobenzaldehyde instead of 2-chloro-4-fluorobenzaldehyde and ethyl acetoacetate instead of methyl acetoacetate.

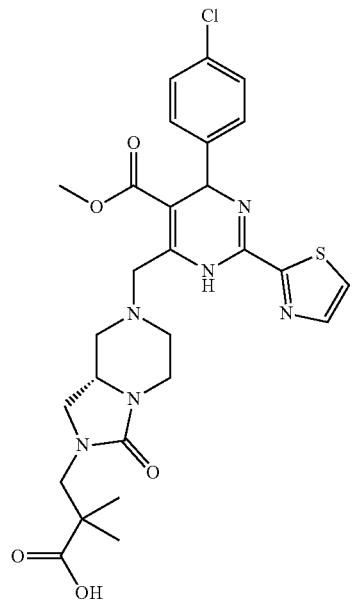 [SMILES: COC(=O)C1=C(CN2CCN3C(=O)N(CC(C)(C)C(=O)O)C[C@@H]3C2)NC(c2nccs2)=NC1c1ccc(Cl)cc1]

Preparation of Example 77

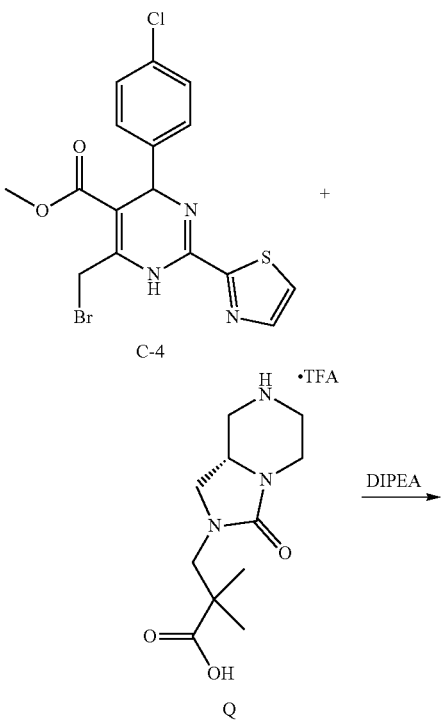

Example 78

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2-methoxy-propanoic acid

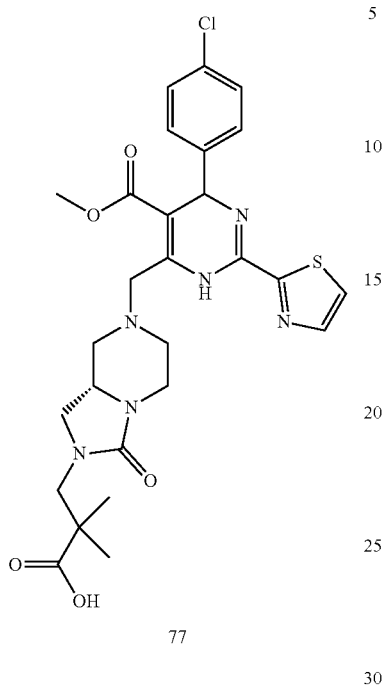

77

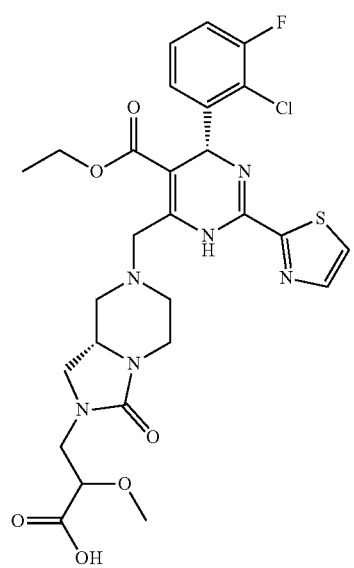 [SMILES: CCOC(=O)C1=C(CN2CCN3C(=O)N(CC(OC)C(=O)O)C[C@@H]3C2)NC(c2nccs2)=N[C@H]1c1cccc(F)c1Cl]

The title compound was prepared in analogy to Example 1 by using methyl 6-(bromomethyl)-4-(4-chlorophenyl)-2-thiazol-2-yl-1,4-dihydropyrimidine-5-carboxylate (Compound C-4) and 3-[(8aS)-3-oxo-1,5,6,7,8,8a-hexahydroimidazo[1,5-a]pyrazin-2-yl]-2,2-dimethyl-propanoic acid (Compound Q) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydropyrazino[1,2-c][1,3]oxazin-6-one (Compound D). Example 77 was obtained as a light yellow solid (60 mg). $^1$H NMR (400 MHz, METHANOL-$d_4$) d ppm 7.99 (dd, J=3.1, 1.4 Hz, 1H), 7.80 (d, J=3.3 Hz, 1H), 7.26-7.42 (m, 4H), 5.64-5.82 (m, 1H), 4.06 (dd, J=16.8, 4.3 Hz, 1H), 3.72-3.90 (m, 3H), 3.69 (s, 3H), 3.37-3.61 (m, 2H), 3.00-3.24 (m, 2H), 2.55-2.97 (m, 3H), 2.11-2.39 (m, 2H), 1.19 ppm (dd, J=4.4, 2.9 Hz, 6H). MS: calc'd 587 (MH$^+$), measured 587 (MH$^+$).

Preparation of methyl 6-(bromomethyl)-4-(4-chlorophenyl)-2-thiazol-2-yl-1,4-dihydropyrimidine-5-carboxylate (Compound C-4)

Compound C-4 was prepared in analogy to compound C by using 4-chlorobenzaldehyde instead of 2-chloro-4-fluorobenzaldehyde without chiral SFC separation of dihydropyrimidine intermediate in Scheme 1-1.

Preparation of Example 78

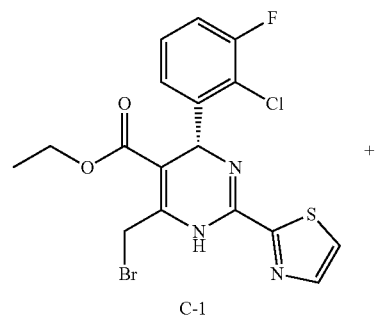

C-1

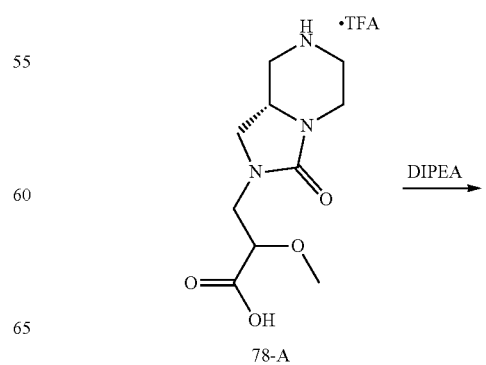

78-A

173
-continued

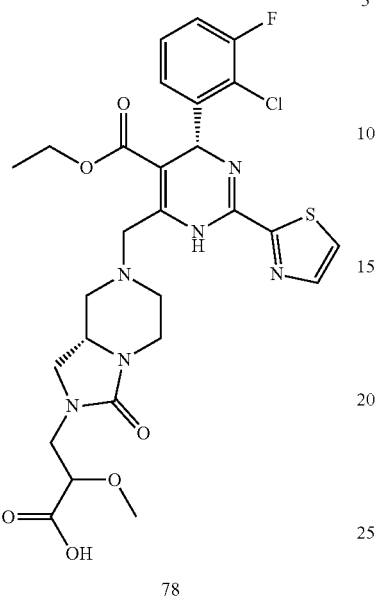

78

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and 2-methoxy-3-(3-oxo-1,5,6,7,8,8a-hexahydroimidazo[1,5-a]pyrazin-2-yl)propanoic acid TFA salt (Compound 78-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 78 was obtained as a light yellow solid (25 mg). $^1$H NMR (400 MHz, METHANOL-d$_4$) d ppm 8.01 (d, J=3.3 Hz, 1H), 7.92 (d, J=3.0 Hz, 1H), 7.33-7.43 (m, 2H), 7.19-7.30 (m, 1H), 6.27 (s, 1H), 4.76 (d, J=16.1 Hz, 1H), 4.58 (d, J=16.1 Hz, 1H), 3.96-4.21 (m, 6H), 3.41-3.83 (m, 10H), 3.10-3.31 (m, 5H), 1.13 ppm (t, J=7.2 Hz, 3H). MS: calc'd 621 (MH$^+$), measured 621 (MH$^+$).

Preparation of 2-methoxy-3-(3-oxo-1,5,6,7,8,8a-hexahydroimidazo[1,5-a]pyrazin-2-yl)propanoic acid TFA salt (Compound 78-A)

Compound 78-A was prepared in analogy to compound Q in Example 19 by using methyl 2-(aminomethyl)butanoate (for its synthesis, please refer to: Liang, Congxin; Feng, Yangbo U.S. Pat. Appl. Publ. 2007, US 20070072934) instead of ethyl 3-amino-2,2-dimethyl-propanoate hydrochloride salt.

174
Example 79

2-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]spiro[3.3]heptane-6-carboxylic acid

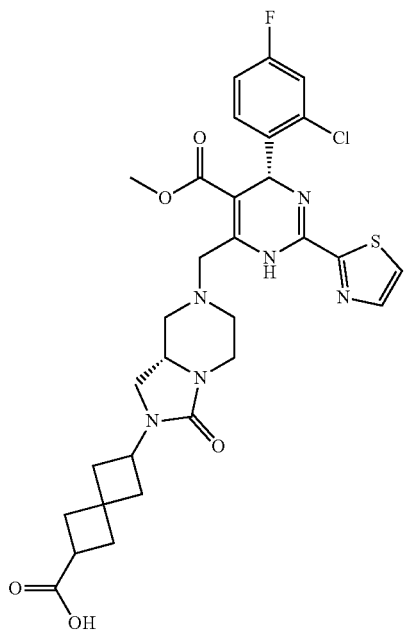 [SMILES: COC(=O)C1=C(CN2CCN3C(=O)N(C4CC5(CC(C(=O)O)C5)C4)C[C@@H]3C2)NC(c2nccs2)=N[C@H]1c1ccc(F)cc1Cl]

Preparation of Example 79

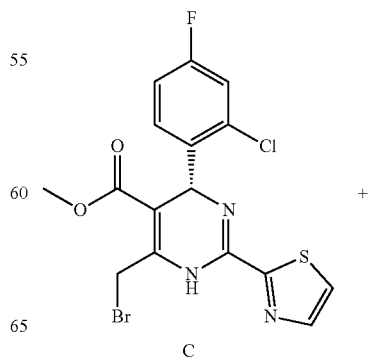

C

175
-continued

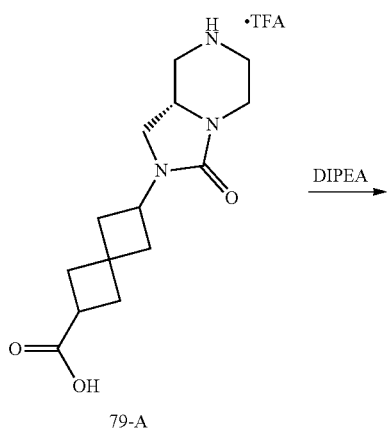

79-A

The title compound was prepared in analogy to Example 1 by using 2-[(8aS)-3-oxo-1,5,6,7,8,8a-hexahydroimidazo [1,5-a]pyrazin-2-yl]spiro[3.3]heptane-6-carboxylic acid TFA salt (Compound 79-A) instead of hexahydro-pyrazino [1,2-c][1,3]oxazin-6-one (Compound D). Example 79 was obtained as a light yellow solid (7 mg). $^1$H NMR (400 MHz, METHANOL-$d_4$) d ppm 8.00-7.92 (m, 1H), 7.77 (d, J=3.3 Hz, 1H), 7.42 (dd, J=6.3, 8.5 Hz, 1H), 7.24 (dd, J=2.5, 8.8 Hz, 1H), 7.06 (dt, J=2.5, 8.4 Hz, 1H), 6.18 (s, 1H), 4.33-4.20 (m, 1H), 4.10 (dd, J=4.4, 16.9 Hz, 1H), 3.96-3.73 (m, 4H), 3.66-3.58 (m, 3H), 3.57-3.46 (m, 1H), 3.21-2.97 (m, 3H), 2.95-2.80 (m, 2H), 2.73 (d, J=10.3 Hz, 1H), 2.44-2.05 (m, 8H). MS: calc'd 626 (MH$^+$), measured 626 (MH$^+$).

176

Preparation of 2-[(8aS)-3-oxo-1,5,6,7,8,8a-hexahydroimidazo[1,5-a]pyrazin-2-yl]spiro[3.3]heptane-6-carboxylic acid TFA salt (Compound 79-A)

Compound 79-A was prepared in analogy to compound Q in Example 19 by using methyl 2-aminospiro[3.3]heptane-6-carboxylate hydrochloride salt (PharmaBlock (Nanjing) R&D Co. Ltd, PBLG1036) instead of ethyl 3-amino-2,2-dimethyl-propanoate hydrochloride salt.

Example 80

5-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]pentanoic acid

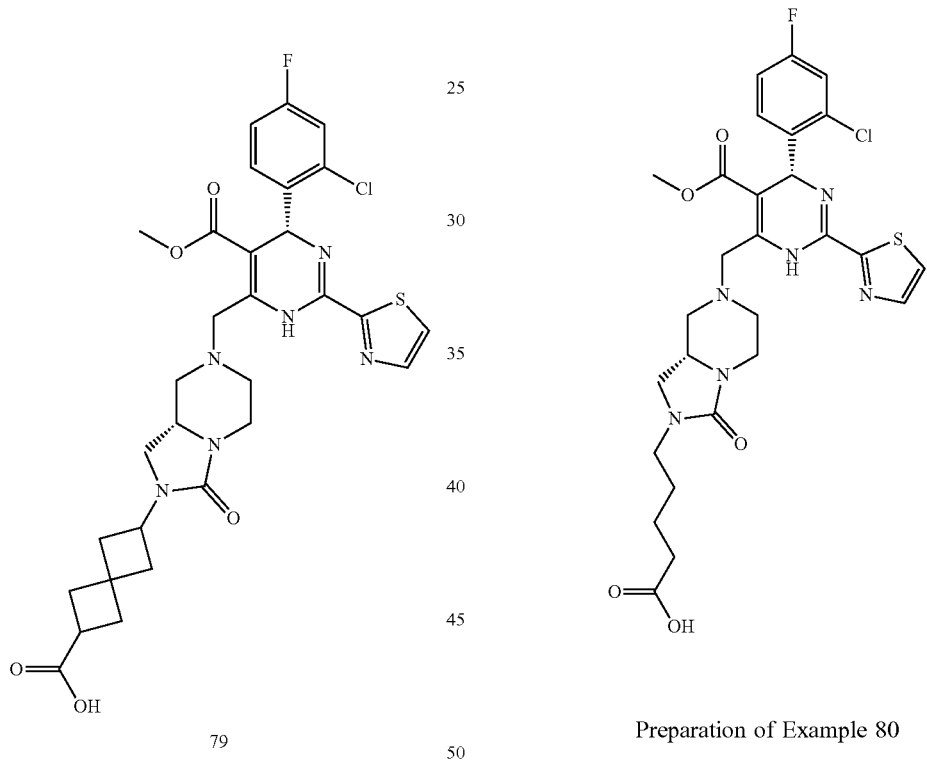

Preparation of Example 80

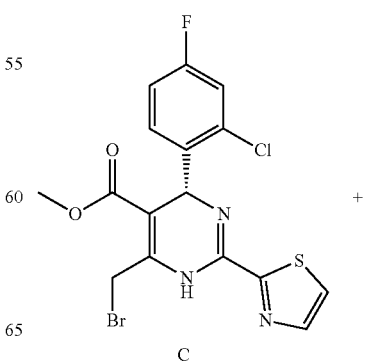

C

177
-continued

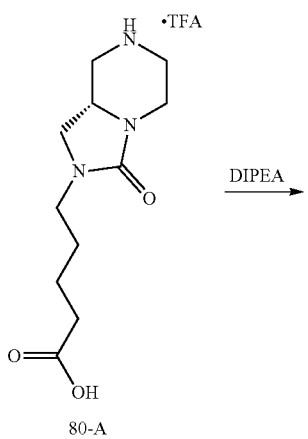

80-A

The title compound was prepared in analogy to Example 1 by using 5-[(8aS)-3-oxo-1,5,6,7,8,8a-hexahydroimidazo[1,5-a]pyrazin-2-yl]pentanoic acid TFA salt (Compound 80-A) instead of hexahydro-pyrazino[1,2-c][1,3]oxazin-6-one (Compound D). Example 80 was obtained as a light yellow solid (18 mg). $^1$H NMR (400 MHz, METHANOL-$d_4$) d ppm 8.02 (d, J=3.0 Hz, 1H), 7.92 (d, J=3.0 Hz, 1H), 7.54 (ddd, J=1.5, 6.0, 8.8 Hz, 1H), 7.30 (dd, J=2.5, 8.5 Hz, 1H), 7.22-7.09 (m, 1H), 6.20 (s, 1H), 4.76 (d, J=16.1 Hz, 1H), 4.66-4.39 (m, 1H), 4.20 (td, J=3.4, 11.7 Hz, 1H), 4.10 (td, J=4.1, 14.8 Hz, 1H), 3.83-3.56 (m, 6H), 3.54-3.38 (m, 1H), 3.30-3.10 (m, 5H), 2.43-2.28 (m, 2H), 1.62 (dd, J=3.1, 5.9 Hz, 4H). MS: calc'd 605 (MH$^+$), measured 605 (MH$^+$).

178

Preparation of 5-[(8aS)-3-oxo-1,5,6,7,8,8a-hexahydroimidazo[1,5-a]pyrazin-2-yl]pentanoic acid TFA salt (Compound 80-A)

Compound 80-A was prepared in analogy to compound Q in Example 19 by using methyl 5-aminopentanoate hydrochloride salt instead of ethyl 3-amino-2,2-dimethyl-propanoate hydrochloride salt.

Example 81

3-[[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]methyl] cyclobutanecarboxylic acid

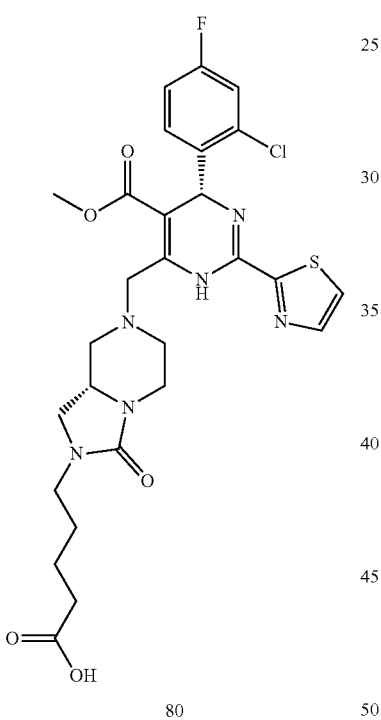

80

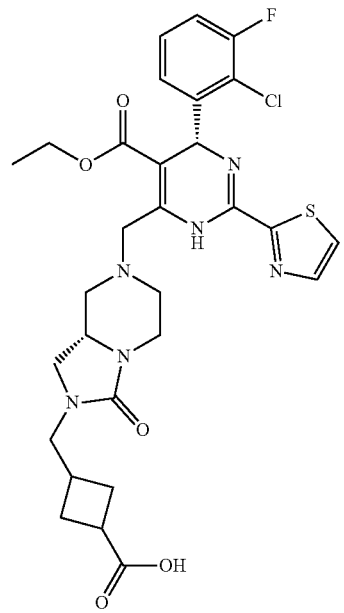 [SMILES: CCOC(=O)C1=C(CN2CCN3C(=O)N(CC4CC(C(=O)O)C4)C[C@@H]3C2)NC(c2nccs2)=N[C@H]1c1cccc(F)c1Cl]

Preparation of Example 81

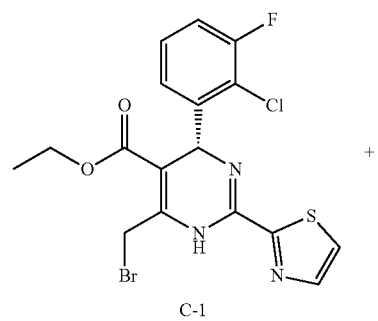

C-1

-continued

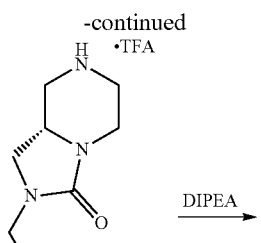

81-A

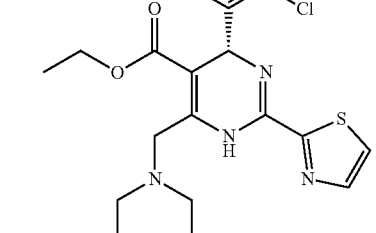

81

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and 3-[(3-oxo-1,5,6,7,8,8a-hexahydroimidazo[1,5-a]pyrazin-2-yl)methyl] cyclobutanecarboxylic acid TFA salt (Compound 81-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 81 was obtained as a light yellow solid (7 mg). $^1$H NMR (400 MHz, METHANOL-$d_4$) d ppm 7.99 (d, J=3.0 Hz, 1H), 7.84 (d, J=2.3 Hz, 1H), 7.43-7.28 (m, 2H), 7.27-7.13 (m, 1H), 6.25 (s, 1H), 4.52-4.33 (m, 1H), 4.32-4.18 (m, 1H), 4.07 (q, J=7.0 Hz, 3H), 3.68-3.47 (m, 2H), 3.32-2.98 (m, 7H), 2.65 (d, J=7.5 Hz, 3H), 2.44-2.27 (m, 2H), 2.10-1.98 (m, 2H), 1.13 (t, J=7.2 Hz, 3H). MS: calc'd 631 (MH$^+$), measured 631 (MH$^+$).

Preparation of 3-[(3-oxo-1,5,6,7,8,8a-hexahydroimidazo[1,5-a]pyrazin-2-yl)methyl]cyclobutanecarboxylic acid TFA salt (Compound 81-A)

Compound 81-A was prepared in analogy to compound Q in Example 19 by using methyl 3-(aminomethyl)cyclobutanecarboxylate hydrochloride salt (compound 81-B) instead of ethyl 3-amino-2,2-dimethyl-propanoate hydrochloride salt.

Preparation of methyl 3-(aminomethyl)cyclobutanecarboxylate hydrochloride salt (Compound 81-B)

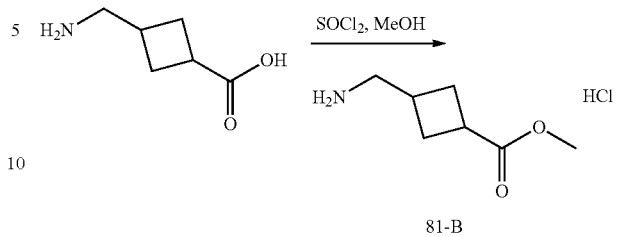

81-B

Compound 81-B was prepared in analogy to compound W in Example 20 by using 3-(aminomethyl)cyclobutanecarboxylic acid (PharmaBlock (Nanjing) R&D Co. Ltd, CAS: 1310729-95-3) instead of DL-3-aminoisobutyric acid.

Example 82A and 82B (Separated Two Single Isomers)

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-cyclopropyl-3-oxo-5,6,8,8a-tetrahydro-1H-imidazo[1,5-a]pyrazine-8-carboxylic acid; and (8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-cyclopropyl-3-oxo-5,6,8,8a-tetrahydro-1H-imidazo[1,5-a]pyrazine-8-carboxylic acid

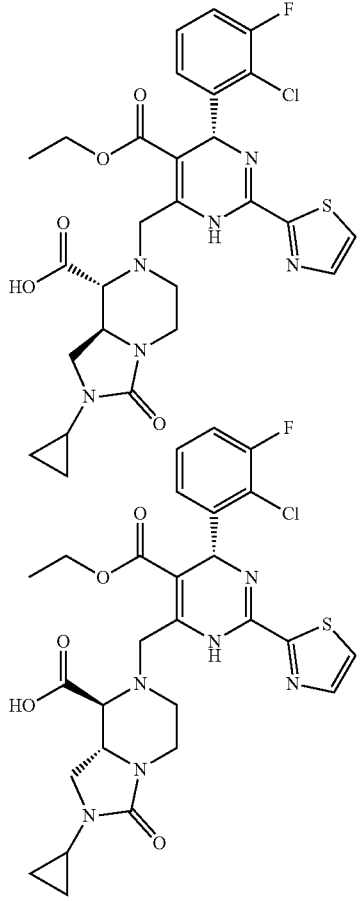

Preparation of Example 82A and 82B

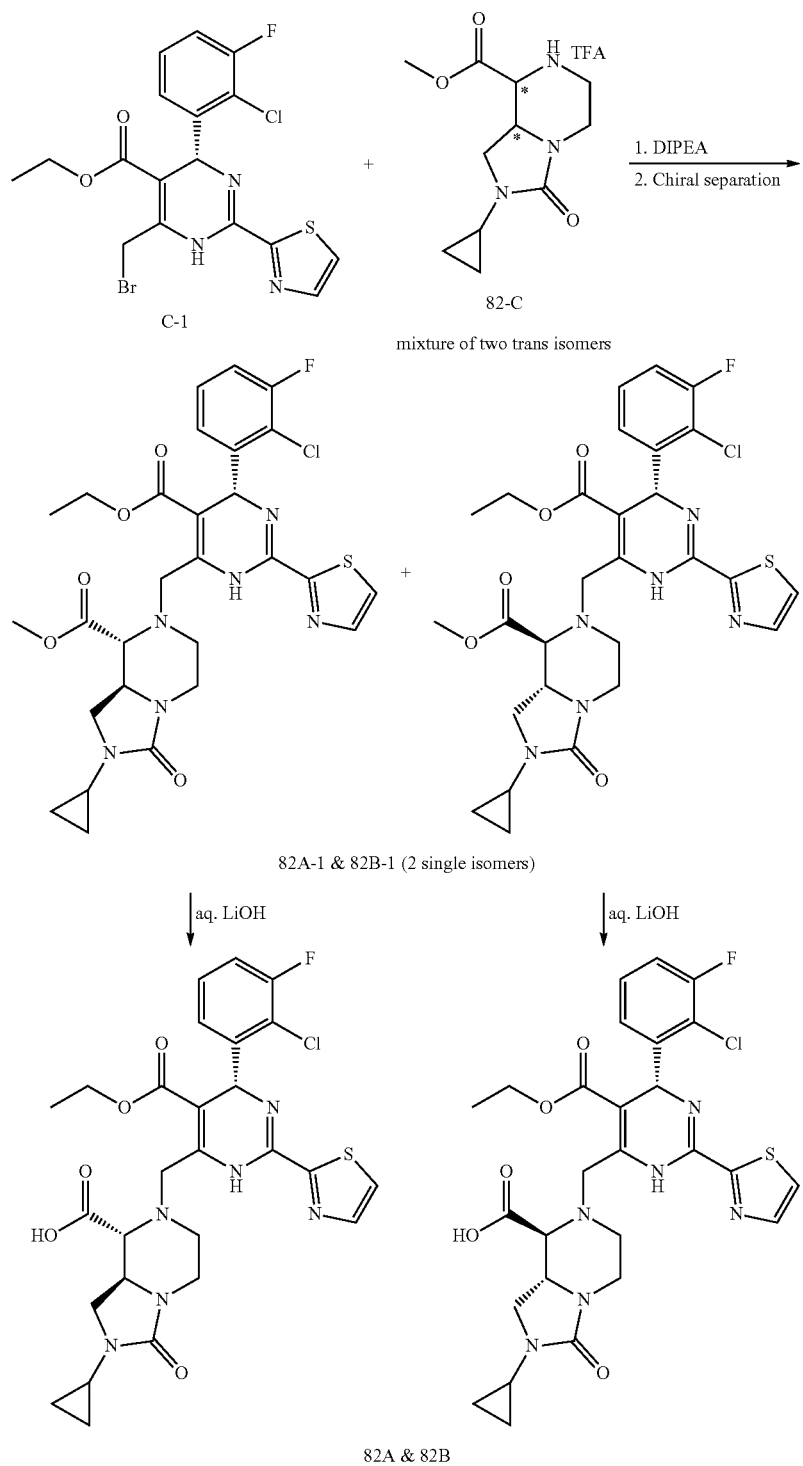

To a stirred solution of trans-methyl 2-cyclopropyl-3-oxo-1,5,6,7,8,8a-hexahydroimidazo[1,5-a]pyrazine-8-carboxylate (compound 82-C, 176 mg, 0.5 mmol) in dry dimethylformamide (3.0 mL) was added diisopropylethylamine (1.0 mL), potassium iodide (125 mg, 0.75 mmol) and compound C-1 (250 mg, 0.55 mmol). The reaction mixture was flushed with nitrogen and heated to 55° C. for 2 hours. The reaction mixture was quenched by adding ice-water, extracted with ethyl acetate (30 mL) three times. The organic phase was separated, dried over Na$_2$SO$_4$, filtrated and concentrated. The residue was purified by HPLC to give a mixture of two isomers which were further resolved by SFC to give two single isomers: 82A-1 (faster eluting, 77.3 mg, yield: 25%) and 82B-1 (slower eluting, 93 mg, yield: 30%) with 30% isopropanol (0.05% DEA)/CO₂ on ChiralPak AD-3 column. MS: calc'd 617 (MH⁺), measured 617 (MH⁺).

The solution of compound 82A-1 (77.3 mg, 0.125 mmol) in tetrahydrofuran (0.62 mL) was added lithium hydroxide monohydrate (52.7 mg, 1.25 mmol) in water (0.62 mL). After the reaction mixture was stirred at 35° C. for 2 hours, it was neutralized with 1N hydrochloride solution to pH 3.0. The mixture was extracted with ethyl acetate (30 mL) three times. The combined organic phase was dried over Na₂SO₄, filtrated and then concentrated. The residue was purified by Prep-HPLC to give Example 82A (56.2 mg). ¹H NMR (400 MHz, METHANOL-d₄) d ppm 7.97 (d, J=3.0 Hz, 1H), 7.78 (d, J=3.0 Hz, 1H), 7.34-7.27 (m, 2H), 7.16 (s, 1H), 6.25 (s, 1H), 4.31 (d, J=17.3 Hz, 1H), 4.10-4.00 (m, 2H), 3.91 (d, J=16.8 Hz, 1H), 3.86-3.75 (m, 2H), 3.62-3.54 (m, 1H), 3.46 (dd, J=5.4, 9.7 Hz, 1H), 3.32-3.28 (m, 1H), 3.21-3.08 (m, 1H), 2.90 (br. s., 1H), 2.55 (br. s., 1H), 2.46 (t, J=4.9 Hz, 1H), 1.13 (t, J=7.2 Hz, 3H), 0.77-0.66 (m, 4H). MS: calc'd 603 (MH⁺), measured 603 (MH⁺).

Example 82B (68.3 mg) was prepared in analogy to Example 82A. ¹H NMR (400 MHz, METHANOL-d₄) d ppm 7.96 (d, J=3.3 Hz, 1H), 7.77 (d, J=3.0 Hz, 1H), 7.29 (s, 2H), 7.21-7.13 (m, 1H), 6.22 (s, 1H), 4.24 (d, J=17.1 Hz, 1H), 4.08-3.95 (m, 3H), 3.89-3.77 (m, 2H), 3.60-3.52 (m, 1H), 3.43 (dd, J=5.3, 9.5 Hz, 1H), 3.32-3.28 (m, 1H), 3.22-3.12 (m, 1H), 3.06 (br. s., 1H), 2.66 (br. s., 1H), 2.50-2.42 (m, 1H), 1.12 (t, J=7.0 Hz, 3H), 0.73 (s, 4H). MS: calc'd 603 (MH⁺), measured 603 (MH⁺).

Preparation of trans-methyl 2-cyclopropyl-3-oxo-1,5,6,7,8,8a-hexahydroimidazo[1,5-a]pyrazine-8-carboxylate trifluoroacetic acid salt (Compound 82-C)

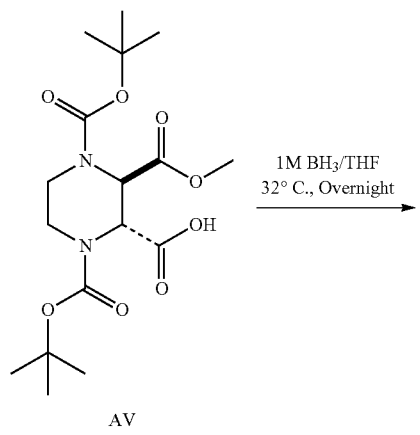

AV
mixture of two trans isomers

1M BH₃/THF
32° C., Overnight

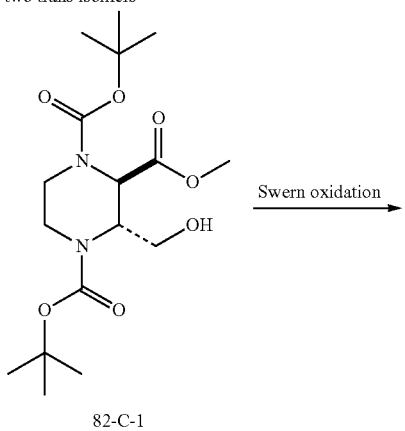

82-C-1

Swern oxidation

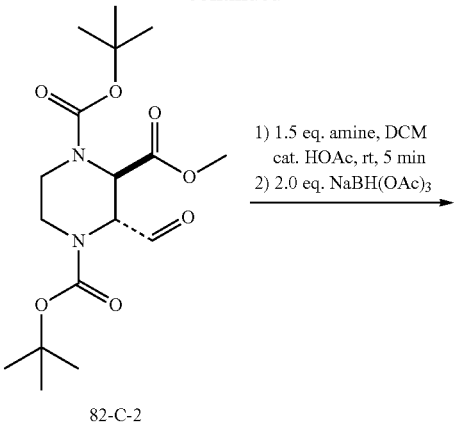

82-C-2

1) 1.5 eq. amine, DCM
   cat. HOAc, rt, 5 min
2) 2.0 eq. NaBH(OAc)₃

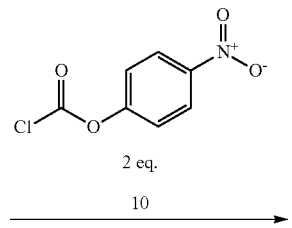

2 eq.

DIPEA

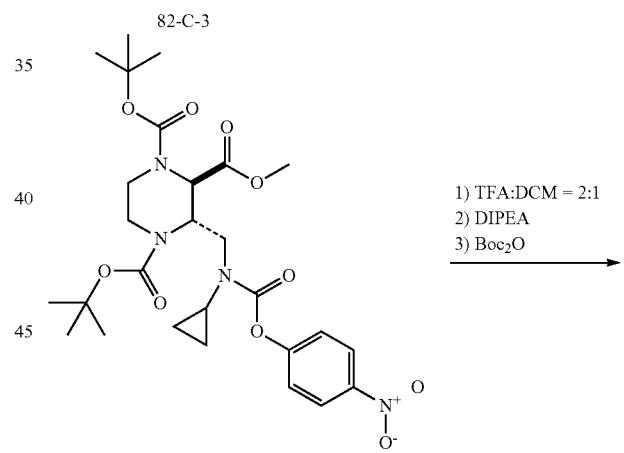

82-C-3

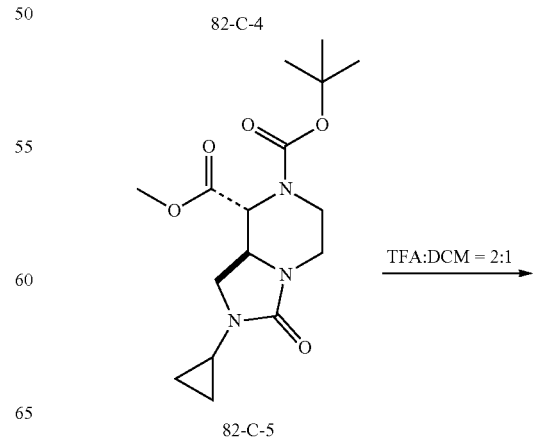

82-C-4

1) TFA:DCM = 2:1
2) DIPEA
3) Boc₂O

82-C-5

TFA:DCM = 2:1

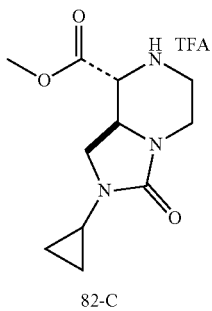

82-C mixture of two trans isomers

Step 1: The mixture of compound AV (6.5 g, 16.7 mmol) and borane-THF complex solution 1.0 M in THF (40 mL, 40 mmol) was stirred at 32° C. overnight. The reaction mixture was concentrated. The residue was dissolved in ethyl acetate (60 mL) and added 2.0 mL of hydrogen chloride solution (4.0 M in dioxane). The mixture was extracted with ethyl acetate (50 mL) three times. The combined organic phase was dried over $Na_2SO_4$, filtrated and concentrated. The residue was purified by column to give compound 82-C-1 (4.0 g).

Step 2: To a solution of oxalyl chloride (2.0 mL) in dry dichloromethane (60 mL) under nitrogen at −78° C. was added dropwise of dimethyl sulfoxide (3.3 mL, 47 mmol) in dry dichloromethane (2.0 mL). After addition, the reaction mixture was stirred for 1 hour at −78° C. Then to the reaction mixture was added compound 82-C-1 (4.0 g, 10.7 mmol) in dry dichloromethane (6.0 mL) dropwise and stirred for another hour at −78° C. The reaction was quenched by adding triethylamine (12 mL, 86 mmol) dropwise over 30 minutes. The resulting mixture was warmed up to room temperature, and the organic phase was washed by ice-water, separated and dried over $Na_2SO_4$, then filtrated and concentrated to give crude compound 82-C-2 (3.72 g, crude), which was used directly.

Step 3: To a solution of compound 82-C-2 (930 mg, 2.5 mmol) in dichloromethane (10 mL) was added cyclopropylamine (260 μL, 3.75 mmol), catalytic amount of acetic acid (2 drops) and sodium triacetoxyborohydride (1.06 g, 5 mmol). The reaction mixture was stirred at room temperature overnight. The reaction was quenched by adding ice-water, extracted with dichloromethane (30 mL) two times and the organic phase was washed with sodium bicarbonate solution and dried over $Na_2SO_4$, then filtrated and concentrated to give crude compound 82-C-3 (1.03 g, crude).

Step 4: The mixture of compound 82-C-3 (1.03 g, 2.5 mmol) in dichloromethane (15 mL) was added diisopropylethylamine (1.0 mL) and 4-nitrophenyl chloroformate (1.0 g, 5.0 mmol). The reaction mixture was stirred at 40° C. for 2 hours. The reaction was quenched by adding ice-water and extracted with dichloromethane (30 mL) two times. The organic phase was washed with sodium bicarbonate solution and dried over $Na_2SO_4$, then filtrated and concentrated. The residue was purified by column to give compound 82-C-4 (1.4 g).

Step 5: The mixture of compound 82-C-4 (1.4 g, 2.42 mmol) and TFA/DCM=2/1 (6 mL) was stirred at room temperature for 30 minutes. The reaction mixture was concentrated and added toluene for co-evaporation to remove trifluoroacetic acid. The residue was dissolved in dichloromethane (15 mL), and then diisopropylethylamine (2 mL) was added. The reaction mixture was heated to 40° C. overnight. To the reaction mixture was added di-tert-butyl dicarbonate (1.1 g, 5.0 mmol) and stirred for another 5 hours. The reaction mixture was quenched by adding ice-water, extracted with ethyl acetate (30 mL) two times. The organic phase was separated, dried over $Na_2SO_4$, filtrated and concentrated. The residue was purified by column to give compound 82-C-5 (680 mg).

Step 6: The mixture of compound 82-C-5 (170 mg, 0.5 mmol) and TFA/DCM=2/1 (3 mL) was stirred at room temperature for 30 minutes. The reaction mixture was concentrated and added toluene for co-evaporation to remove trifluoroacetic acid to give crude compound 82-C which was used directly.

Example 83A and 83B (Separated Two Single Isomers)

(8R,8aS)-2-cyclopropyl-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; and (8S,8aR)-2-cyclopropyl-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid

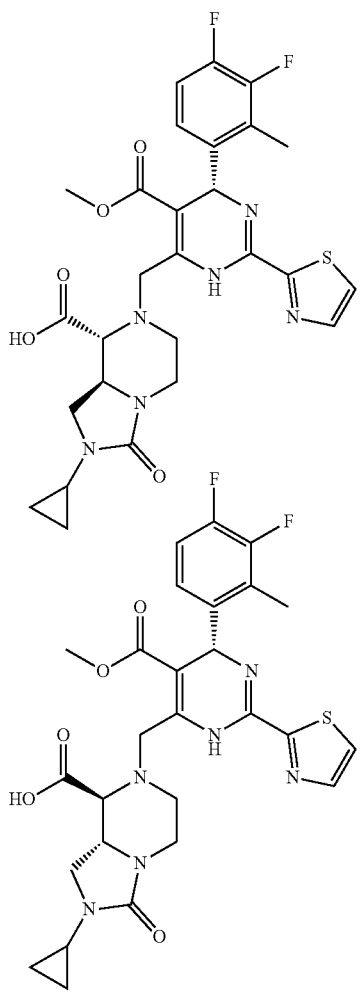

Preparation of Example 83A and 83B
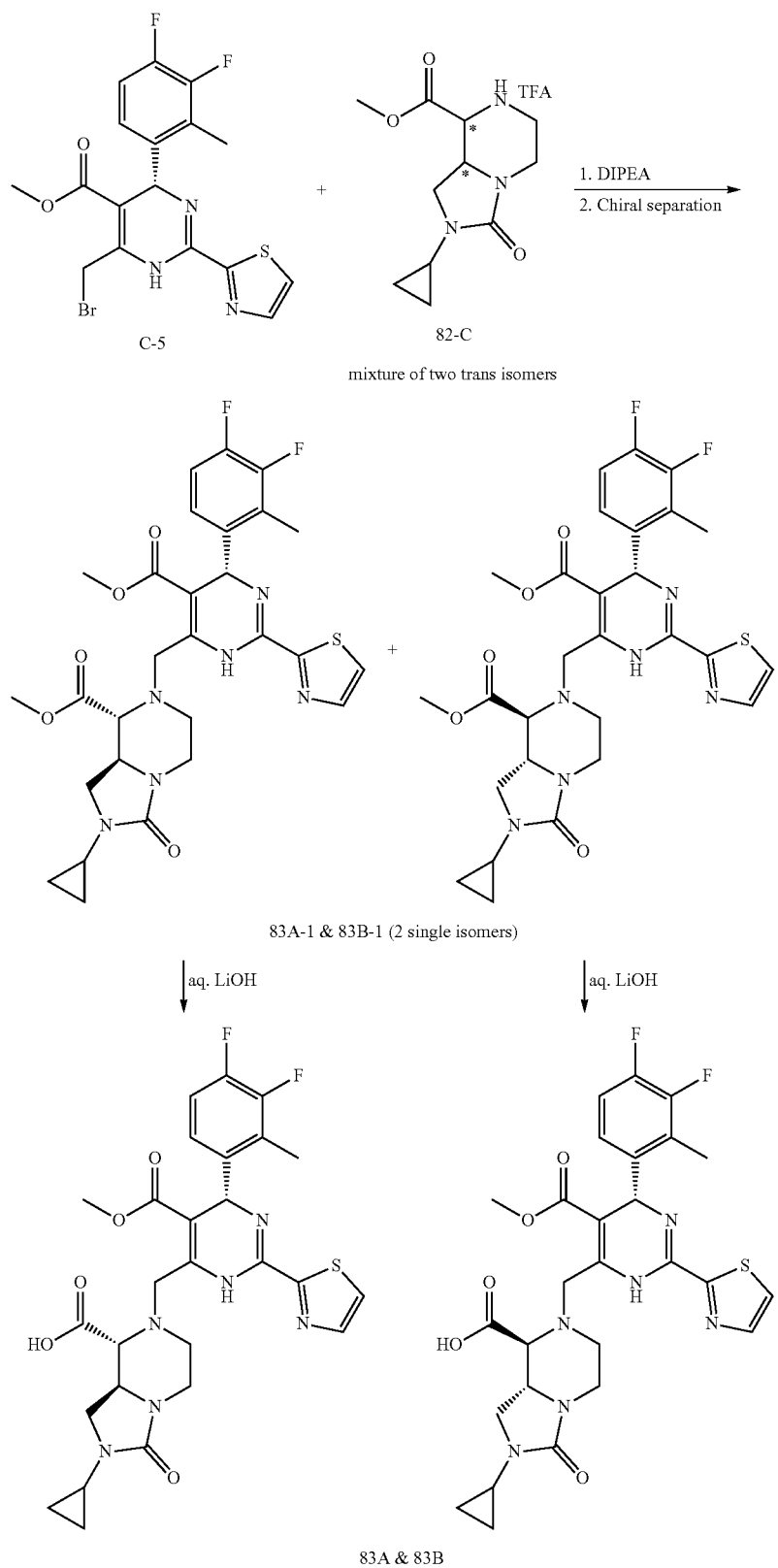

The title two compounds were prepared in analogy to Example 82A and 82B by using methyl (4S)-6-(bromomethyl)-4-(3,4-difluoro-2-methyl-phenyl)-2-thiazol-2-yl-1,4-dihydropyrimidine-5-carboxylate (compound C-5) instead of ethyl (4R)-6-(bromomethyl)-4-(2-chloro-3-fluoro-phenyl)-2-thiazol-2-yl-1,4-dihydropyrimidine-5-carboxylate (compound C-1).

Example 83A was obtained as a light yellow solid (99 mg). $^1$H NMR (400 MHz, METHANOL-$d_4$) d ppm 7.95 (d, J=3.3 Hz, 1H), 7.76 (d, J=3.0 Hz, 1H), 7.14-7.07 (m, 1H), 7.06-6.98 (m, 1H), 5.93 (s, 1H), 4.29 (d, J=17.1 Hz, 1H), 3.88 (d, J=17.3 Hz, 1H), 3.79 (br. s., 2H), 3.62 (s, 3H), 3.55 (s, 1H), 3.46 (d, J=5.5 Hz, 1H), 3.26 (d, J=9.8 Hz, 1H), 3.20-3.09 (m, 1H), 2.85 (d, J=10.8 Hz, 1H), 2.56 (d, J=2.3 Hz, 3H), 2.54-2.42 (m, 2H), 0.78-0.68 (m, 4H). MS: calc'd 587 (MH$^+$), measured 587 (MH$^+$).

Example 83B was obtained as a light yellow solid (72.9 mg). $^1$H NMR (400 MHz, METHANOL-$d_4$) d ppm 7.94 (d, J=3.3 Hz, 1H), 7.75 (d, J=3.3 Hz, 1H), 7.09 (d, J=4.8 Hz, 2H), 5.90 (s, 1H), 4.21 (d, J=17.1 Hz, 1H), 3.97 (d, J=17.1 Hz, 1H), 3.88-3.76 (m, 2H), 3.61 (s, 3H), 3.58-3.50 (m, 1H), 3.46-3.40 (m, 1H), 3.28 (s, 1H), 3.21-3.12 (m, 1H), 3.08-2.99 (m, 1H), 2.63 (d, J=3.3 Hz, 1H), 2.56 (d, J=2.3 Hz, 3H), 2.50-2.42 (m, 1H), 0.79-0.66 (m, 4H). MS: calc'd 587 (MH$^+$), measured 587 (MH$^+$).

Example 83A was synthesized from compound 83A-1 (faster eluting) and Example 83B was synthesized from compound 83B-1 (slower eluting) on ChiralCel OJ-H column eluting with 25% methanol (0.05% DEA)/$CO_2$.

Preparation of methyl (4S)-6-(bromomethyl)-4-(3,4-difluoro-2-methyl-phenyl)-2-thiazol-2-yl-1,4-dihydropyrimidine-5-carboxylate (Compound C-5)

Compound C-5 was prepared in analogy to compound C by using 3,4-difluoro-2-methylbenzaldehyde instead of 2-chloro-4-fluorobenzaldehyde.

Example 84A and 84B (Separated Two Single Isomers)

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-isopropyl-3-oxo-5,6,8,8a-tetrahydro-1H-imidazo[1,5-a]pyrazine-8-carboxylic acid; and (8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-isopropyl-3-oxo-5,6,8,8a-tetrahydro-1H-imidazo[1,5-a]pyrazine-8-carboxylic acid

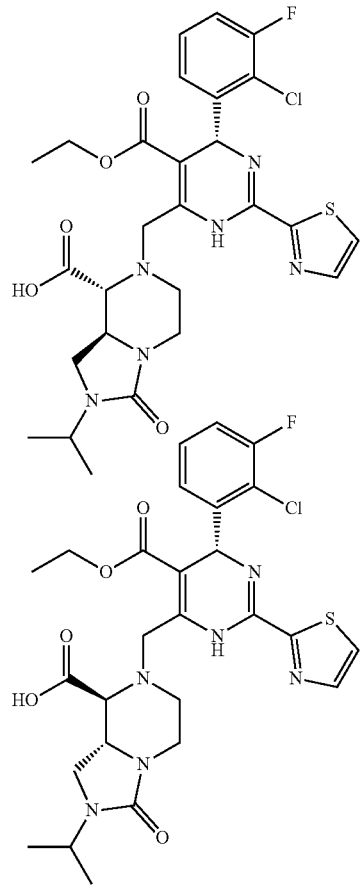

Preparation of Example 84A and 84B

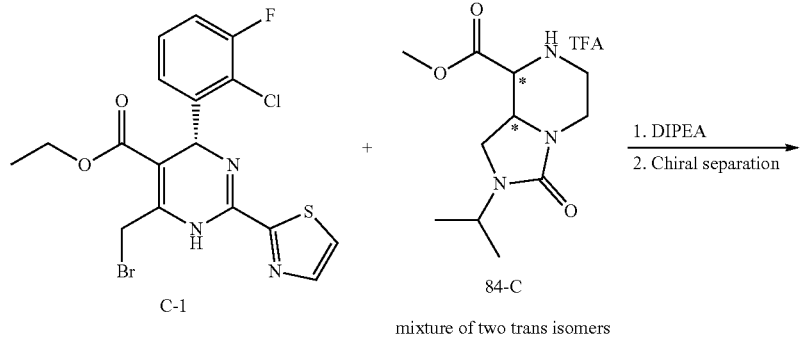

mixture of two trans isomers

-continued

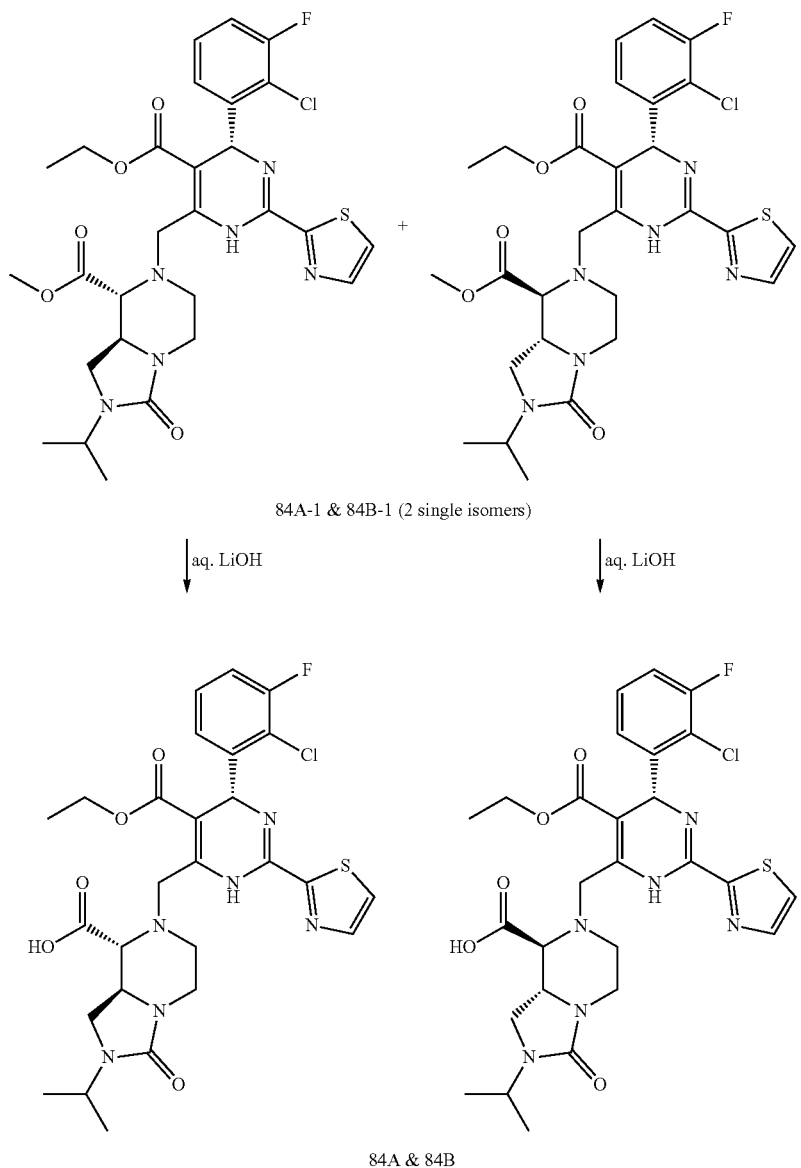

84A-1 & 84B-1 (2 single isomers)

| aq. LiOH

| aq. LiOH

84A & 84B

The title two compounds were prepared in analogy to Example 82A and 82B by using methyl 2-isopropyl-3-oxo-1,5,6,7,8,8a-hexahydroimidazo[1,5-a]pyrazine-8-carboxylate (compound 84-C) instead of trans-methyl 2-cyclopropyl-3N-oxo-1,5,6,7,8,8a-hexahydroimidazo[1,5-a]pyrazine-8-carboxylate (compound 82-C).

Example 84A was obtained as a light yellow solid (20.3 mg). $^1$H NMR (400 MHz, METHANOL-d$_4$) d ppm 8.11 (d, J=3.0 Hz, 1H), 8.01 (d, J=3.0 Hz, 1H), 7.39 (d, J=2.0 Hz, 2H), 7.28-7.21 (m, 1H), 6.32 (s, 1H), 4.38 (d, J=17.3 Hz, 1H), 4.08 (d, J=6.5 Hz, 4H), 3.93-3.82 (m, 2H), 3.62-3.47 (m, 3H), 3.24-3.14 (m, 1H), 3.10-3.04 (m, 1H), 2.69 (d, J=3.5 Hz, 1H), 1.25-1.11 (m, 9H). MS: calc'd 605 (MH$^+$), measured 605 (MH$^+$).

Example 84B was obtained as a light yellow solid (32.5 mg). $^1$H NMR (400 MHz, METHANOL-d$_4$) d ppm 8.10 (s, 1H), 8.02 (s, 1H), 7.38 (d, J=4.3 Hz, 2H), 7.29-7.23 (m, 1H), 6.30 (s, 1H), 4.36 (d, J=16.6 Hz, 1H), 4.14-4.03 (m, 4H), 3.87 (d, J=3.3 Hz, 2H), 3.56 (d, J==9.8 Hz, 2H), 3.50-3.44 (m, 1H), 3.20 (s, 2H), 2.77 (d, J=3.5 Hz, 1H), 1.24-1.10 (m, 9H). MS: calc'd 605 (MH$^+$), measured 605 (MH$^+$).

Example 84A was synthesized from compound 84A-1 (faster eluting) and Example 84B was synthesized from compound 84B-1 (slower eluting) on ChiralPak AD-3 column eluting with 30% isopropanol (0.05% DEA)/CO$_2$.

Preparation of methyl 2-isopropyl-3-oxo-1,5,6,7,8, 8a-hexahydroimidazo[1,5-a]pyrazine-8-carboxylate (Compound 84-C)

Compound 84-C was prepared in analogy to compound 82-C by using isopropylamine instead of cyclopropylamine.

193

Example 85A and 85B (Separated Two Single Isomers)

(8R,8aS)-7-[[(4S)-4-(3,4-difluoro-2-methyl-phenyl)-5-methoxycarbonyl-2-thiazol-2-yl-1,4-dihydropyrimidin-6-yl]methyl]-2-isopropyl-3-oxo-5,6,8,8a-tetrahydro-1H-imidazo[1,5-a]pyrazine-8-carboxylic acid; and (8S,8aR)-7-[[(4S)-4-(3,4-difluoro-2-methyl-phenyl)-5-methoxycarbonyl-2-thiazol-2-yl-1,4-dihydropyrimidin-6-yl]methyl]-2-isopropyl-3-oxo-5,6,8,8a-tetrahydro-1H-imidazo[1,5-a]pyrazine-8-carboxylic acid

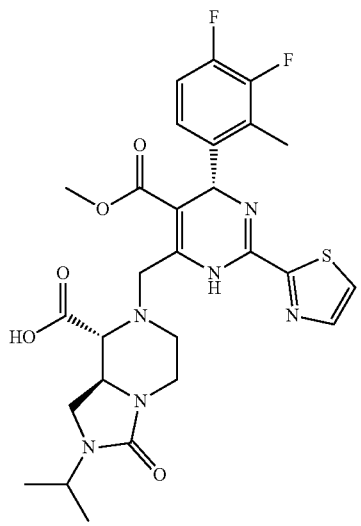

194

-continued

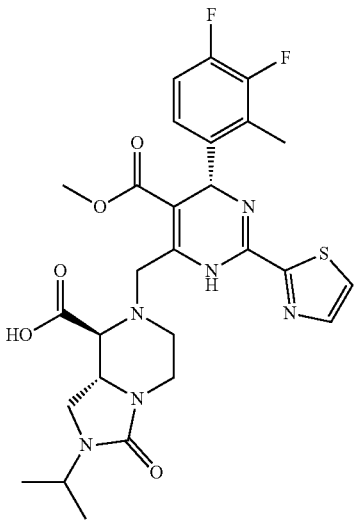

Preparation of Example 85A and 85B

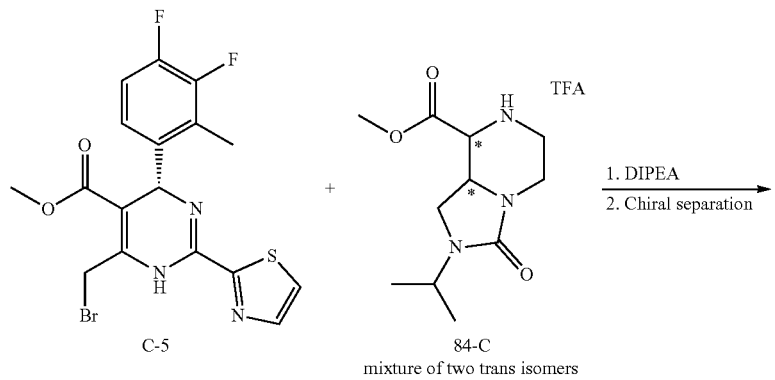

-continued

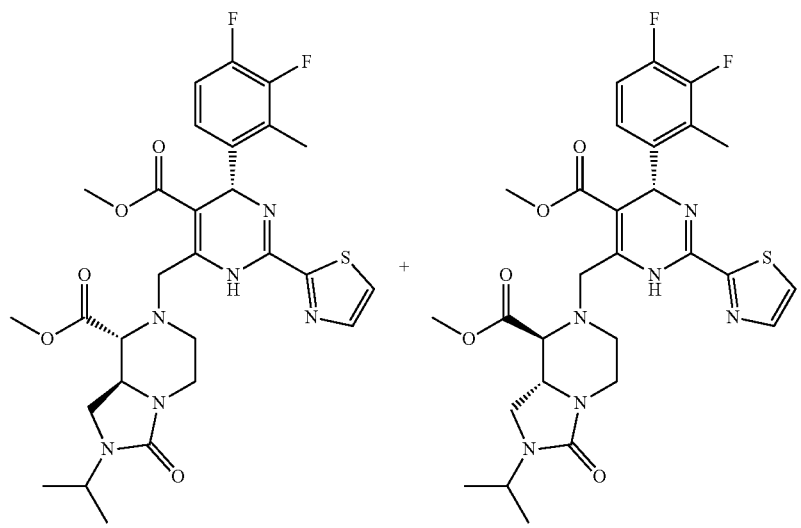

85A-1 & 85B-1 (2 single isomers)

| aq. LiOH          | aq. LiOH          |

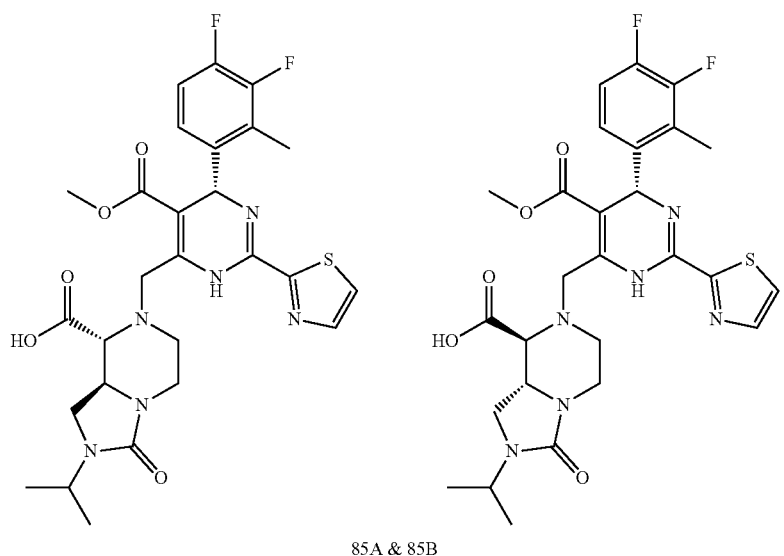

85A & 85B

The title two compounds were prepared in analogy to Example 82A and 82B by using methyl (4S)-6-(bromomethyl)-4-(3,4-difluoro-2-methyl-phenyl)-2-thiazol-2-yl-1,4-dihydropyrimidine-5-carboxylate (compound C-5) instead of ethyl (4R)-6-(bromomethyl)-4-(2-chloro-3-fluoro-phenyl)-2-thiazol-2-yl-1,4-dihydropyrimidine-5-carboxylate (compound C-1) and methyl 2-isopropyl-3-oxo-1,5,6,7,8,8a-hexahydroimidazo[1,5-a]pyrazine-8-carboxylate (compound 84-C) instead of trans-methyl 2-cyclopropyl-3-oxo-1,5,6,7,8,8a-hexahydroimidazo[1,5-a]pyrazine-8-carboxylate (compound 82-C).

Example 85A was obtained as a light yellow solid (3.6 mg). $^1$H NMR (400 MHz, METHANOL-$d_4$) d ppm 8.10 (d, J=3.3 Hz, 1H), 7.99 (d, J=3.0 Hz, 1H), 7.26-7.19 (m, 1H), 7.14-7.04 (m, 1H), 6.01 (s, 1H), 4.34 (d, J=17.1 Hz, 1H), 4.11 (s, 1H), 3.98 (d, J=17.3 Hz, 1H), 3.85 (d, J=4.8 Hz, 2H), 3.65 (s, 3H), 3.61-3.54 (m, 1H), 3.50 (s, 2H), 3.22-3.13 (m, 1H), 3.03-2.96 (m, 1H), 2.70-2.60 (m, 1H), 2.56 (d, J=2.3 Hz, 3H), 1.20 (dd, J=6.8, 14.3 Hz, 6H). MS: calc'd 589 (MH$^+$), measured 589 (MH$^+$).

Example 85B was obtained as a light yellow solid (2.3 mg). $^1$H NMR (400 MHz, METHANOL-$d_4$) d ppm 8.07 (d, J=3.0 Hz, 1H), 7.96 (d, J=3.3 Hz, 1H), 7.25-7.17 (m, 1H), 7.16-7.07 (m, 1H), 5.99 (s, 1H), 4.30 (d, J=16.8 Hz, 1H), 4.16-3.99 (m, 2H), 3.92-3.82 (m, 2H), 3.65 (s, 3H), 3.59-3.53 (m, 1H), 3.51-3.43 (m, 2H), 3.24-3.09 (m, 2H), 2.78-2.68 (m, 1H), 2.55 (d, J=2.3 Hz, 3H), 1.19 (dd, J=6.8, 14.1 Hz, 6H). MS: calc'd 589 (MH$^+$), measured 589 (MH$^+$).

Example 85A was synthesized from compound 85A-1 (faster eluting) and Example 85B was synthesized from compound 85B-1 (slower eluting) on ChiralPak AD-3 column eluting with 20% isopropanol (0.05% DEA)/CO$_2$.

Example 86A and 86B (Separated Two Single Isomers)

(8R,8aS)-2-tert-butyl-7-[[(4R)-4-(2-chloro-4-fluorophenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; and (8S,8aR)-2-tert-butyl-7-[[(4R)-4-(2-chloro-4-fluorophenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid

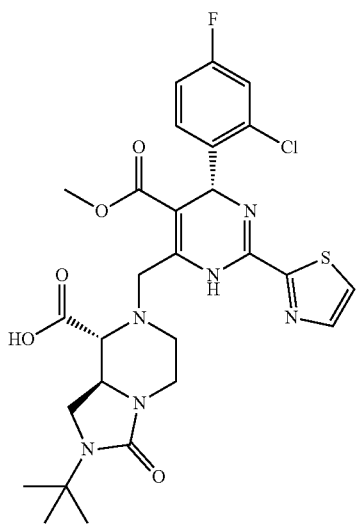

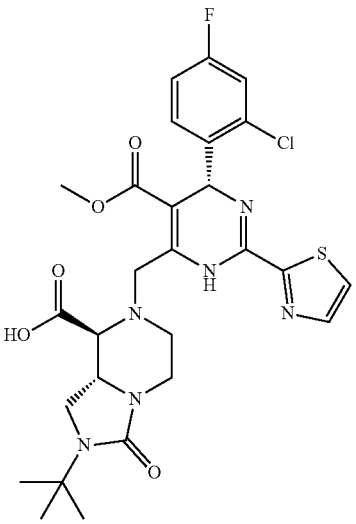

Preparation of Example 86A and 86B

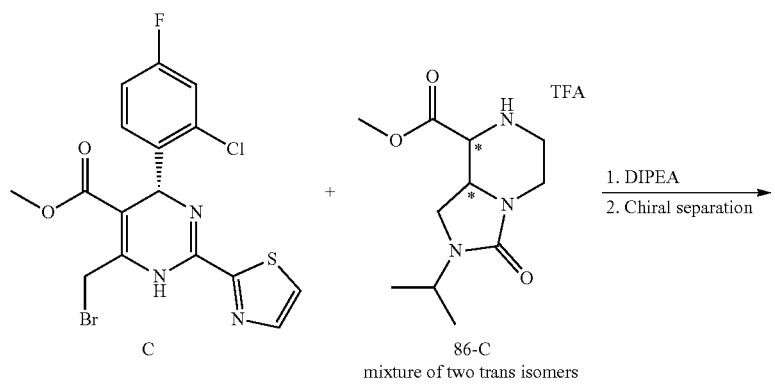

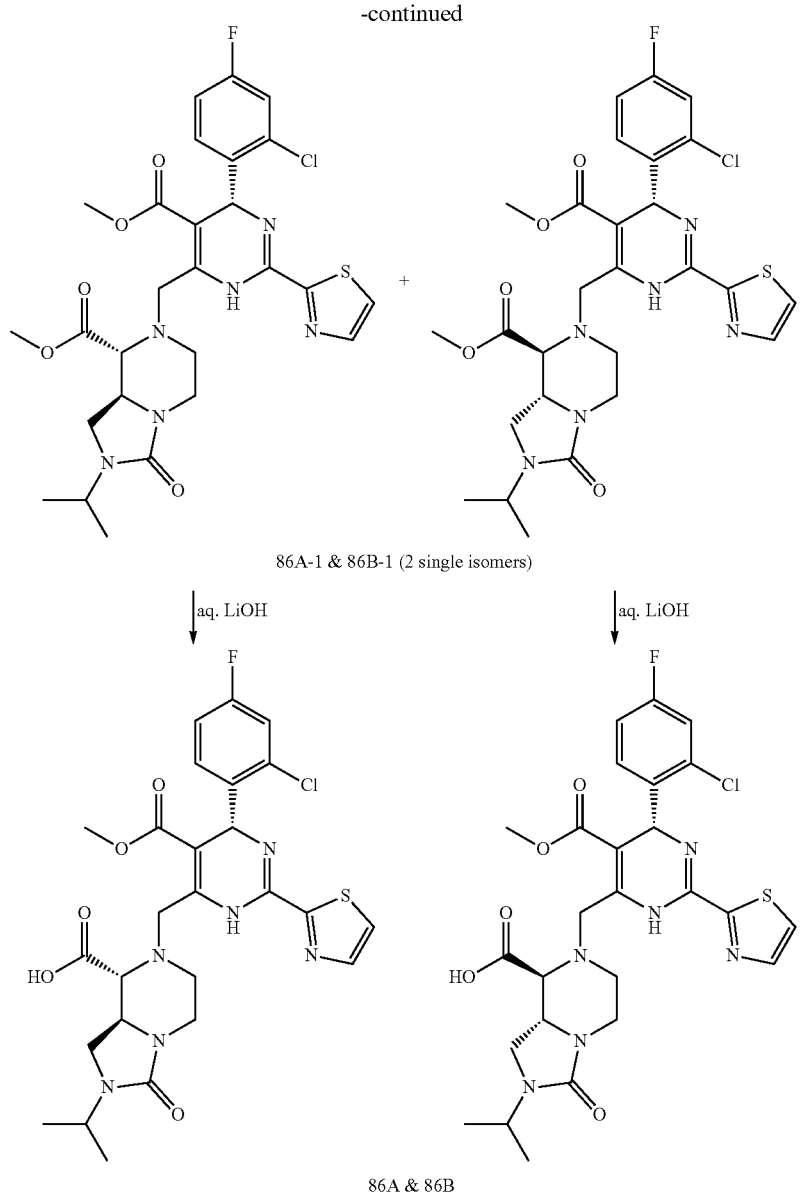

86A & 86B

The title two compounds were prepared in analogy to Example 82A and 82B by using (R)-6-bromomethyl-4-(2-chloro-4-fluoro-phenyl)-2-thiazol-2-yl-1,4-dihydro-pyrimidine-5-carboxylic acid methyl ester (Compound C) instead of ethyl (4R)-6-(bromomethyl)-4-(2-chloro-3-fluoro-phenyl)-2-thiazol-2-yl-1,4-dihydropyrimidine-5-carboxylate (compound C-1) and methyl 2-tert-butyl-3-oxo-1,5,6,7,8,8a-hexahydroimidazo[1,5-a]pyrazine-8-carboxylate (compound 86-C) instead of trans-methyl 2-cyclopropyl-3-oxo-1,5,6,7,8,8a-hexahydroimidazo[1,5-a]pyrazine-8-carboxylate (compound 82-C).

Example 86A was obtained as a light yellow solid (64.8 mg). ¹H NMR (400 MHz, METHANOL-d₄) d ppm 7.98 (d, J=3.0 Hz, 1H), 7.80 (d, J=3.3 Hz, 1H), 7.52-7.45 (i, 1H), 7.24 (dd, J=2.6, 8.7 Hz, 1H), 7.06 (d, J=2.8 Hz, 1H), 6.19 (s, 1H), 4.32 (d, J=17.3 Hz, 1H), 3.97 (br. s., 1H), 3.82-3.72 (m, 2H), 3.65-3.58 (m, 4H), 3.57-3.51 (m, 1H), 3.42-3.36 (m, 1H), 3.19-3.09 (m, 1H), 2.99-2.89 (m, 1H), 2.65-2.53 (m, 1H), 1.41 (s, 9H). MS: calc'd 605 (MH⁺), measured 605 (MH⁺).

Example 86B was obtained as a light yellow solid (71.1 mg). ¹H NMR (400 MHz, METHANOL-d₄) d ppm 7.97 (d, J=3.0 Hz, 1H), 7.78 (d, J=3.0 Hz, 1H), 7.46 (dd, J=6.1, 8.7 Hz, 1H), 7.25 (dd, J=2.6, 8.7 Hz, 1H), 7.13-7.05 (i, 1H), 6.15 (s, 1H), 4.25 (d, J=17.3 Hz, 1H), 4.03 (br. s., 1H), 3.86-3.72 (m, 2H), 3.65-3.57 (m, 4H), 3.55-3.48 (m, 1H), 3.41-3.36 (m, 1H), 3.19-3.05 (m, 2H), 2.75-2.62 (m, 1H), 1.40 (s, 9H). MS: calc'd 605 (MH⁺), measured 605 (MH⁺).

Example 86A was synthesized from compound 86A-1 (faster eluting) and Example 86B was synthesized from compound 86B-1 (slower eluting) on ChiralPak AD-3 column eluting with 25% isopropanol (0.05% DEA)/CO₂.

Preparation of methyl 2-tert-butyl-3-oxo-1,5,6,7,8,8a-hexahydroimidazo[1,5-a]pyrazine-8-carboxylate (Compound 86-C)

Compound 86-C was prepared in analogy to compound 82-C by using tert-butylamine instead of cyclopropylamine.

Example 87A and 87B (Separated Two Single Isomers)

(8R,8aS)-2-tert-butyl-7-[[(4R)-4-(2-chloro-3-fluorophenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; and (8S,8aR)-2-tert-butyl-7-[[(4R)-4-(2-chloro-3-fluorophenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid

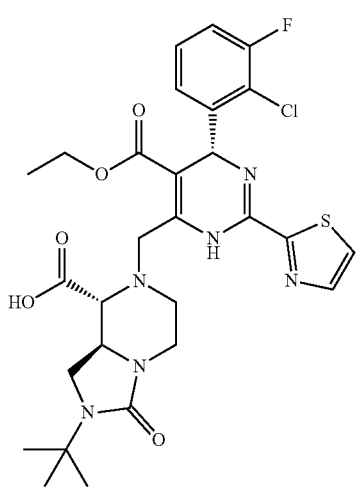

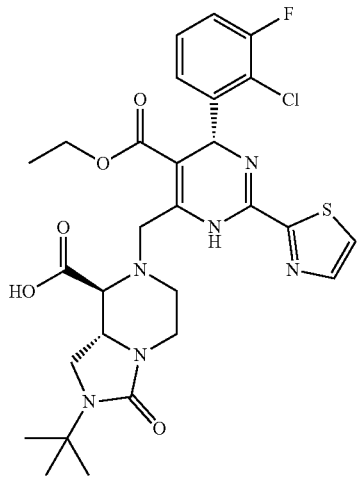

Preparation of Example 87A and 87B

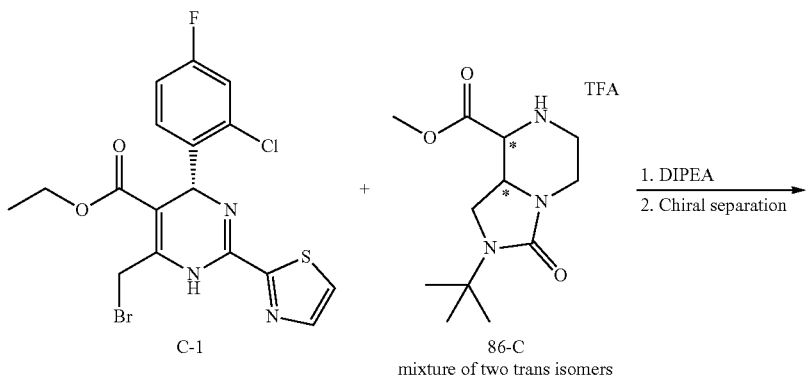

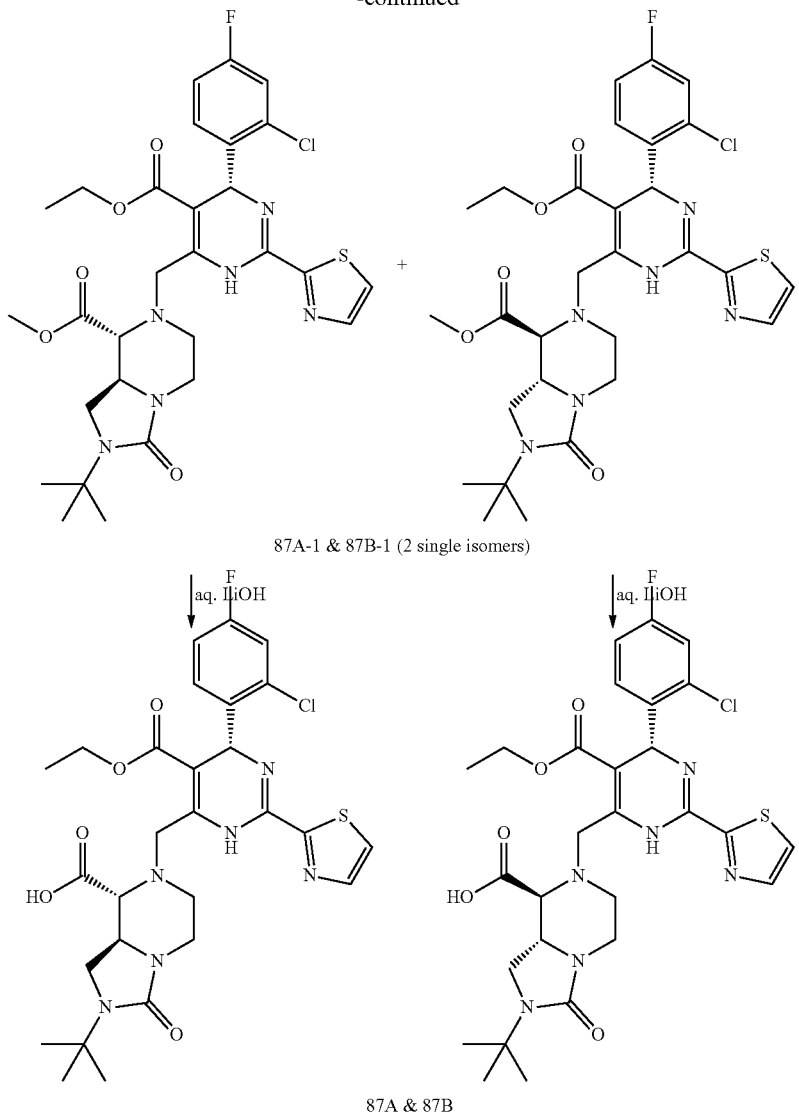

87A-1 & 87B-1 (2 single isomers)

aq. LiOH

87A & 87B

The title two compounds were prepared in analogy to Example 82A and 82B by using methyl 2-tert-butyl-3-oxo-1,5,6,7,8,8a-hexahydroimidazo[1,5-a]pyrazine-8-carboxylate (compound 86-C) instead of trans-methyl 2-cyclopropyl-3-oxo-1,5,6,7,8,8a-hexahydroimidazo[1,5-a]pyrazine-8-carboxylate (compound 82-C).

Compound 87B-1 (Single isomer. Structure is either one of the two structures showing above): Methyl (8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylate; or Methyl (8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylate (compound 82-C).

Compound 87B-1 was obtained as a light yellow solid (316 mg). $^1$H NMR (400 MHz, METHANOL-$d_4$) d ppm 7.97 (d, J=3.0 Hz, 1H), 7.76 (d, J=3.0 Hz, 1H), 7.34-7.23 (m, 2H), 7.16 (t, J=8.5 Hz, 1H), 6.22 (s, 1H), 5.51 (s, 2H), 4.14 (d, J=17.1 Hz, 1H), 4.08-4.00 (m, 2H), 3.89 (s, 1H), 3.81-3.69 (m, 5H), 3.58-3.52 (m, 1H), 3.35 (br. s., 1H), 3.27 (d, J=9.5 Hz, 1H), 3.16-3.04 (m, 1H), 2.95 (d, J=12.3 Hz, 1H), 2.52 (dt, J=3.4, 12.0 Hz, 1H), 1.39 (s, 9H), 1.13 (t, J=7.2 Hz, 3H). MS: calc'd 633 (MH$^+$), measured 633 (MH$^+$)

Example 87A was obtained as a light yellow solid (52.7 mg). $^1$H NMR (400 MHz, METHANOL-$d_4$) d ppm 7.98 (d, J=3.0 Hz, 1H), 7.79 (d, J=3.0 Hz, 1H), 7.35-7.27 (m, 2H), 7.17 (s, 1H), 6.25 (s, 1H), 4.39-4.28 (m, 1H), 4.09-4.01 (m, 2H), 3.99-3.86 (m, 1H), 3.76 (d, J=9.8 Hz, 2H), 3.64-3.58 (m, 1H), 3.57-3.51 (m, 1H), 3.40-3.36 (m, 1H), 3.13 (br. s., 1H), 3.00-2.84 (m, 1H), 2.63-2.47 (m, 1H), 1.41 (s, 9H), 1.13 (t, J=7.2 Hz, 3H). MS: calc'd 619 (MH$^+$), measured 619 (MH$^+$).

Example 87B was obtained as a light yellow solid (61.3 mg). $^1$H NMR (400 MHz, METHANOL-$d_4$) d ppm 7.96 (d, J=3.3 Hz, 1H), 7.77 (d, J=3.0 Hz, 1H), 7.36-7.26 (m, 2H), 7.21-7.14 (m, 1H), 6.22 (s, 1H), 4.27 (d, J=16.8 Hz, 1H), 4.09-3.97 (m, 3H), 3.86-3.71 (m, 2H), 3.65-3.55 (m, 1H), 3.55-3.46 (m, 1H), 3.39-3.34 (m, 1H), 3.20-3.02 (m, 2H), 2.66 (br. s., 1H), 1.40 (s, 9H), 1.13 (t, J=7.2 Hz, 3H). MS: calc'd 619 (MH$^+$), measured 619 (MH$^+$)

Example 87A was synthesized from compound 87A-1 (faster eluting) and Example 87B was synthesized from compound 87B-1 (slower eluting) on ChiralPak AD-3 column eluting with 30% isopropanol (0.05% DEA)/CO$_2$.

Example 88A and 88B (Separated Two Single Isomers)

(8R,8aS)-2-tert-butyl-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; and (8S,8aR)-2-tert-butyl-7-[[(4S)-4-(3,4-difluoro-2-methyl-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid

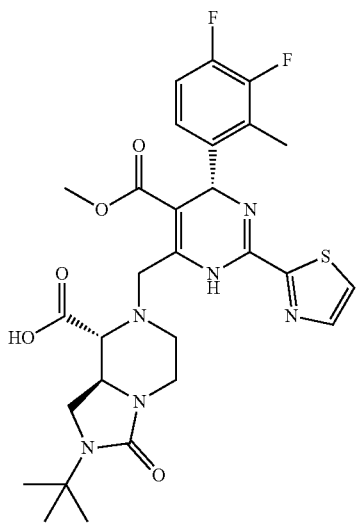

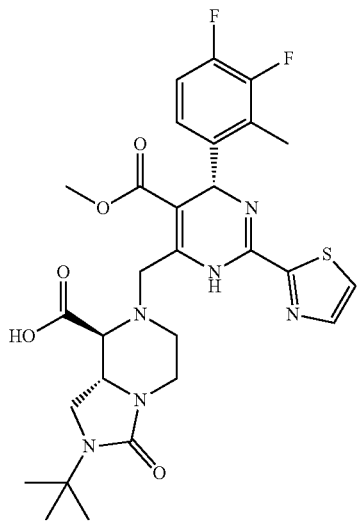

Preparation of Example 88A and 88B

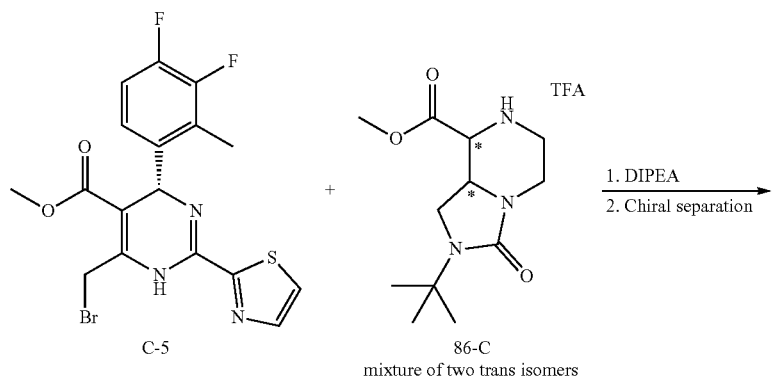

-continued

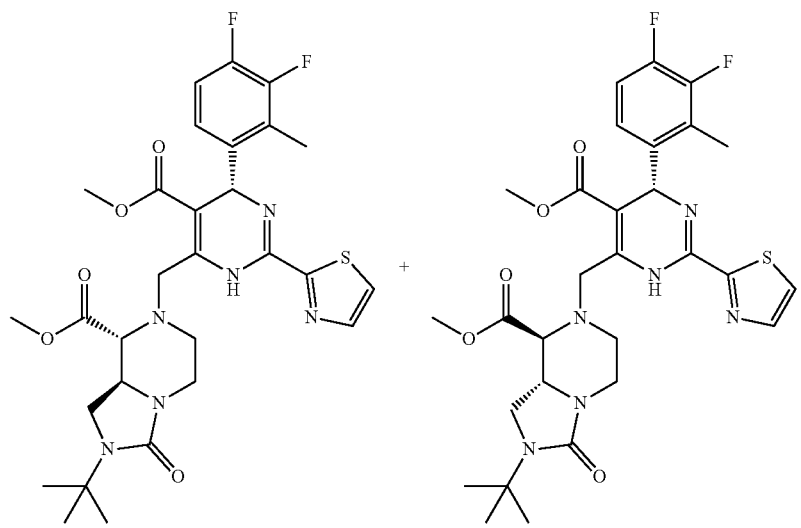

88A-1 & 88B-1 (2 single isomers)

| aq. LiOH      | aq. LiOH

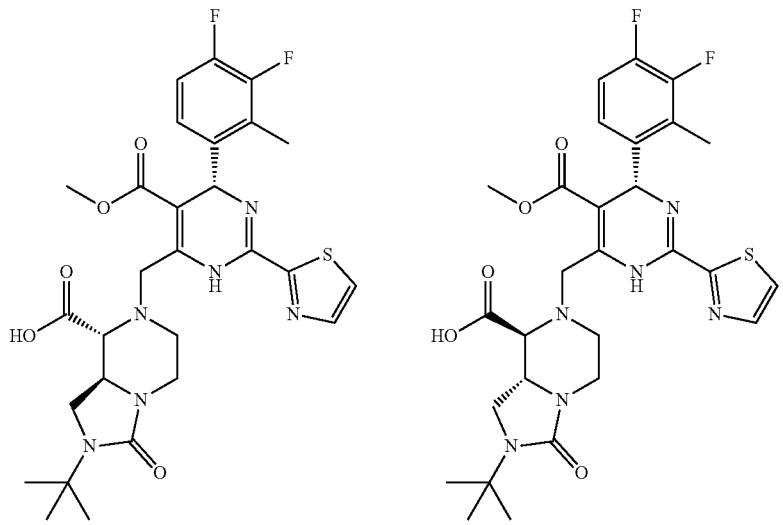

88A & 88B

The title two compounds were prepared in analogy to Example 82A and 82B by using methyl (4S)-6-(bromomethyl)-4-(3,4-difluoro-2-methyl-phenyl)-2-thiazol-2-yl-1,4-dihydropyrimidine-5-carboxylate (compound C-5) instead of ethyl (4R)-6-(bromomethyl)-4-(2-chloro-3-fluoro-phenyl)-2-thiazol-2-yl-1,4-dihydropyrimidine-5-carboxylate (compound C-1) and methyl 2-tert-butyl-3-oxo-1,5,6,7,8,8a-hexahydroimidazo[1,5-a]pyrazine-8-carboxylate (compound 86-C) instead of trans-methyl 2-cyclopropyl-3-oxo-1,5,6,7,8,8a-hexahydroimidazo[1,5-a]pyrazine-8-carboxylate (compound 82-C).

Example 88A was obtained as a light yellow solid (37.2 mg). $^1$H NMR (400 MHz, METHANOL-$d_4$) d ppm 7.97 (d, J=3.3 Hz, 1H), 7.78 (d, J=3.0 Hz, 1H), 7.14-7.09 (m, 1H), 7.08-6.99 (m, 1H), 5.94 (s, 1H), 4.32 (d, J=17.1 Hz, 1H), 3.91 (d, J=17.1 Hz, 1H), 3.79-3.71 (m, 2H), 3.66-3.58 (m, 4H), 3.56-3.50 (m, 1H), 3.36 (d, J=9.8 Hz, 1H), 3.17-3.06 (m, 1H), 2.89 (d, J=11.3 Hz, 1H), 2.56 (d, J=2.3 Hz, 4H), 1.40 (s, 9H). MS: calc'd 603 (MH$^+$), measured 603 (MH$^+$).

Example 88B was obtained as a light yellow solid (61.2 mg). $^1$H NMR (400 MHz, METHANOL-$d_4$) d ppm 7.95 (d, J=3.3 Hz, 1H), 7.77 (d, J=3.3 Hz, 1H), 7.14-7.02 (m, 2H), 5.91 (s, 1H), 4.25 (d, J=17.1 Hz, 1H), 4.01 (d, J=17.1 Hz, 1H), 3.85-3.72 (m, 2H), 3.66-3.56 (m, 4H), 3.54-3.46 (m, 1H), 3.37 (br. s., 1H), 3.20-3.02 (m, 2H), 2.69 (d, J=10.3 Hz, 1H), 2.56 (d, J=2.5 Hz, 3H), 1.40 (s, 9H). MS: calc'd 603 (MH$^+$), measured 603 (MH$^+$).

Example 88A was synthesized from compound 88A-1 (faster eluting) and Example 88B was synthesized from compound 88B-1 (slower eluting) on ChiralPak AD-3 column eluting with 30% isopropanol (0.05% DEA)/CO$_2$.

Example 89

Methyl 7-[[(4R)-4-(2-chloro-4-fluoro-phenyl)-5-methoxycarbonyl-2-thiazol-2-yl-1,4-dihydropyrimidin-6-yl]methyl]-3-oxo-2,5,6,8-tetrahydro-1H-imidazo[1,5-a]pyrazine-8a-carboxylate

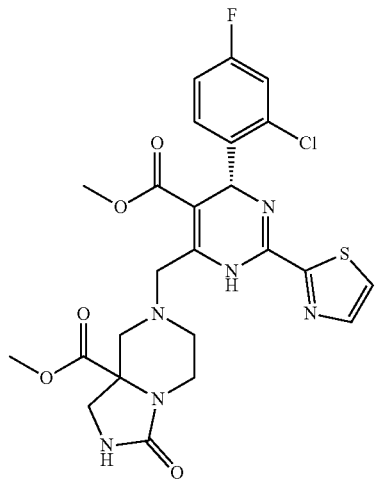 [SMILES: COC(=O)C1=C(CN2CCN3C(=O)NCC3(C(=O)OC)C2)NC(c2nccs2)=N[C@H]1c1ccc(F)cc1Cl]

Preparation of Example 89

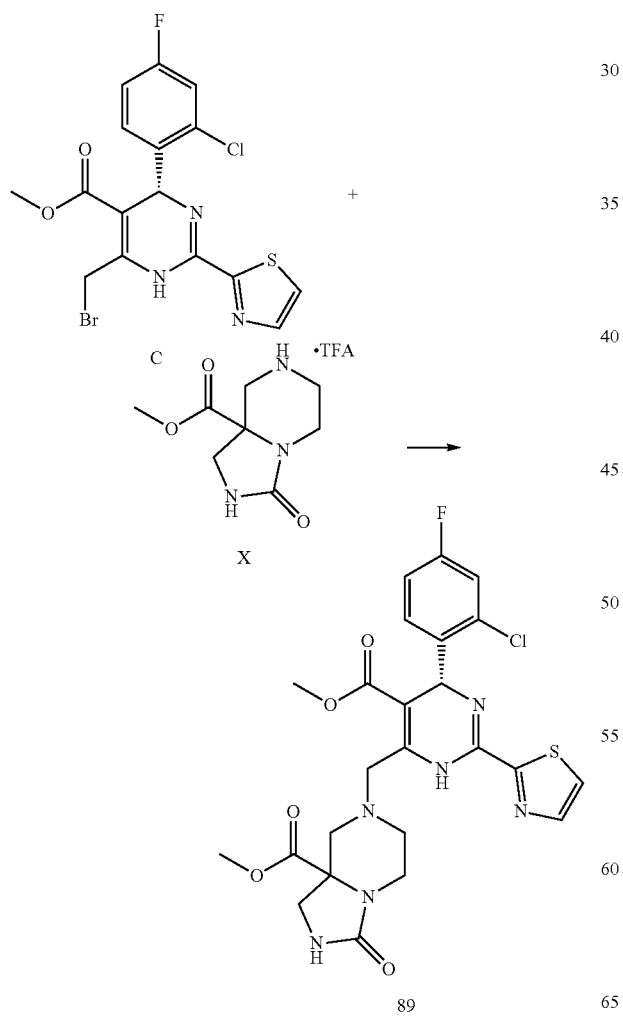

The title compound was prepared in analogy to Example 1 by using methyl 3-oxo-1,2,5,6,7,8-hexahydroimidazo[1,5-a]pyrazine-8a-carboxylate TFA salt (Compound X) instead of hexahydro-pyrazino[1,2-c][1,3]oxazin-6-one (Compound D).

Example 90A and 90B (Separated Two Single Isomers)

2-[(8aS)-7-[[(4R)-4-(2-chloro-4-fluoro-phenyl)-5-methoxycarbonyl-2-thiazol-2-yl-1,4-dihydropyrimidin-6-yl]methyl]-1,1-dimethyl-3-oxo-6,8-dihydro-5H-oxazolo[3,4-a]pyrazin-8a-yl]acetic acid; and

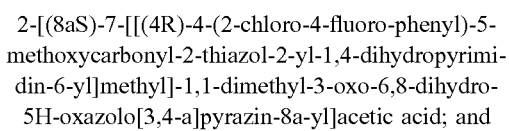

2-[(8aR)-7-[[(4R)-4-(2-chloro-4-fluoro-phenyl)-5-methoxycarbonyl-2-thiazol-2-yl-1,4-dihydropyrimidin-6-yl]methyl]-1,1-dimethyl-3-oxo-6,8-dihydro-5H-oxazolo[3,4-a]pyrazin-8a-yl]acetic acid

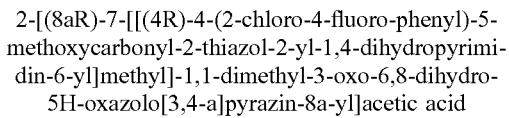

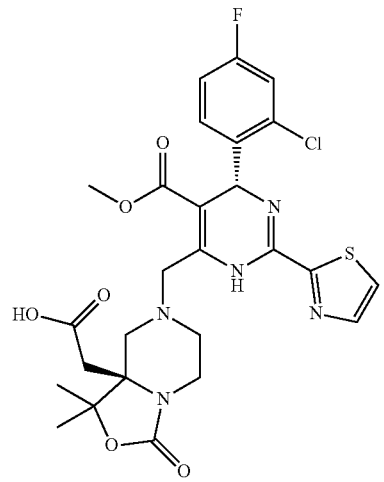

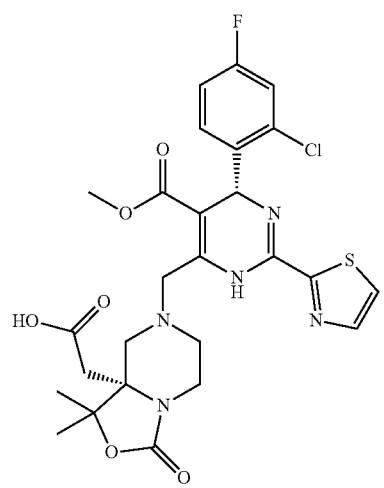

Preparation of Example 90A and 90B
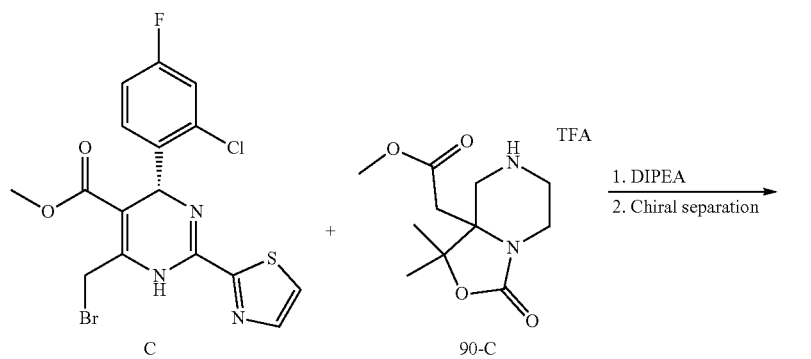
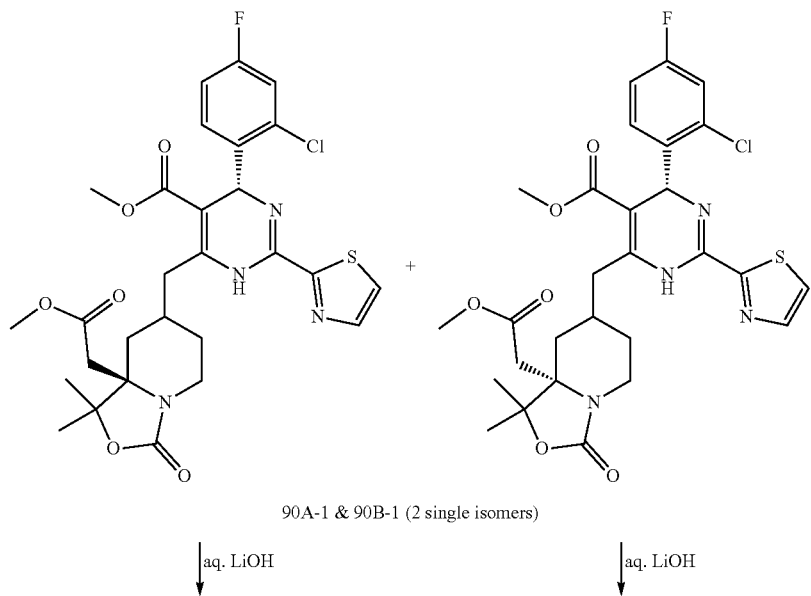
90A-1 & 90B-1 (2 single isomers)
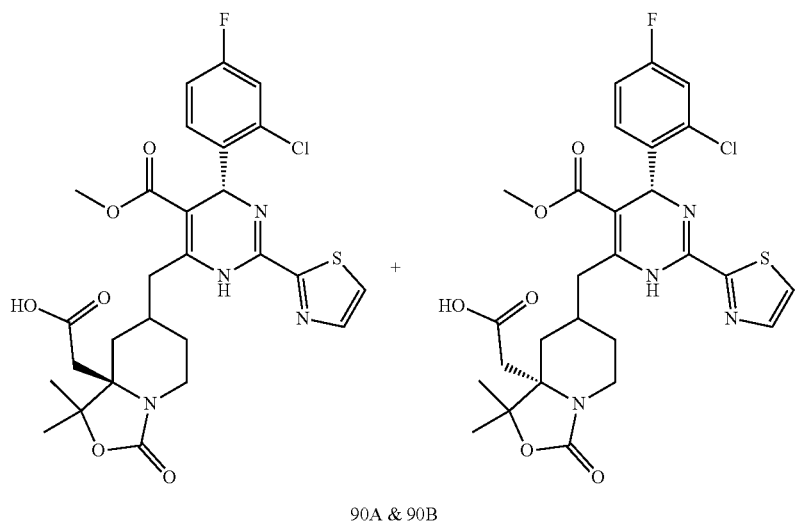
90A & 90B The title two compounds were prepared in analogy to Example 82A and 82B by using (R)-6-bromomethyl-4-(2-chloro-4-fluoro-phenyl)-2-thiazol-2-yl-1,4-dihydro-pyrimidine-5-carboxylic acid methyl ester (Compound C) instead of ethyl (4R)-6-(bromomethyl)-4-(2-chloro-3-fluoro-phenyl)-2-thiazol-2-yl-1,4-dihydropyrimidine-5-carboxylate (compound C-1) and methyl 2-(1,1-dimethyl-3-oxo-5,6,7,8-tetrahydrooxazolo[3,4-a]pyrazin-8a-yl)acetate (compound 90-C) instead of trans-methyl 2-cyclopropyl-3-oxo-1,5,6,7,8,8a-hexahydroimidazo[1,5-a]pyrazine-8-carboxylate (compound 82-C).

Example 90A was obtained as a light yellow solid (13 mg). $^1$H NMR (400 MHz, MeOD) δ ppm 7.92 (d, J=3.3 Hz, 1H), 7.71 (d, J=3.0 Hz, 1H), 7.43 (dd, J=6.0, 8.8 Hz, 1H), 7.23 (dd, J=2.5, 8.8 Hz, 1H), 7.06 (dt, J=2.5, 8.4 Hz, 1H), 6.16 (s, 1H), 4.21 (d, J=16.3 Hz, 1H), 3.87-3.71 (m, 3H), 3.61 (s, 3H), 3.52 (d, J=11.5 Hz, 1H), 3.37 (br, 1H), 2.94 (d, J=11.3 Hz, 1H), 2.63 (d, J=16.1 Hz, 1H), 2.46-2.30 (m, 2H), 1.47 (s, 3H), 1.42 (s, 3H). LC/MS: calc'd 592 (MH+), exp 592 (MH+).

Example 90B was obtained as a light yellow solid (25 mg). $^1$H NMR (400 MHz, MeOD) δ ppm 7.96 (d, J=3.0 Hz, 1H), 7.75 (d, J=3.0 Hz, 1H), 7.54 (dd, J=6.3, 8.8 Hz, 1H), 7.21 (dd, J=2.8, 8.8 Hz, 1H), 7.06 (dt, J=2.5, 8.4 Hz, 1H), 6.16 (s, 1H), 4.09-3.90 (m, 2H), 3.89-3.71 (m, 2H), 3.66-3.55 (m, 4H), 3.36 (br, 1H), 2.82 (d, J=8.3 Hz, 1H), 2.72 (d, J=16.8 Hz, 1H), 2.43 (d, J=11.3 Hz, 1H), 2.31 (dt, J=4.0, 11.9 Hz, 1H), 1.57 (s, 3H), 1.47 (s, 3H); LC/MS: calc'd 592 (MH+), exp 592 (MH+).

Example 90A was synthesized from compound 90A-1 (faster eluting) and Example 90B was synthesized from compound 90B-1 (slower eluting) on ChiralPak AD-3 column eluting with 30% isopropanol (0.05% DEA)/CO$_2$.

Preparation of methyl 2-(1,1-dimethyl-3-oxo-5,6,7,8-tetrahydrooxazolo[3,4-a]pyrazin-8a-yl)acetate (Compound 90-C)

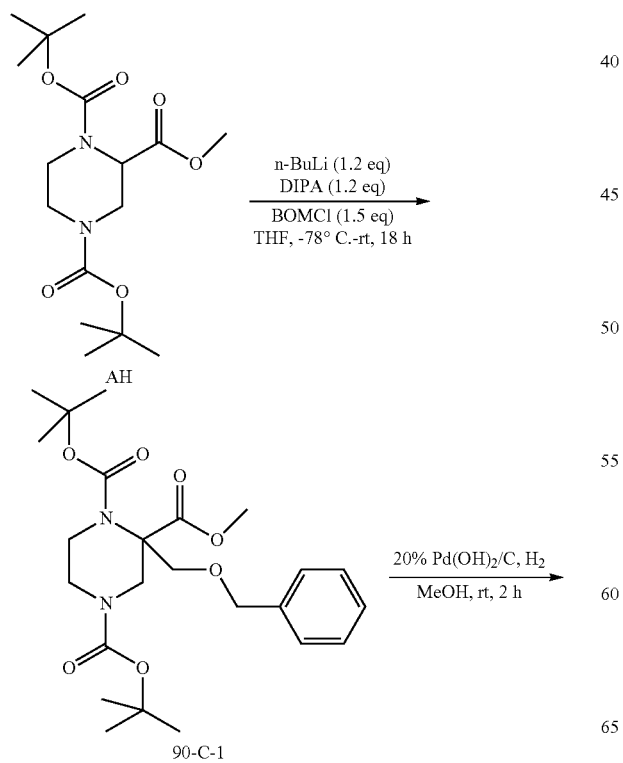

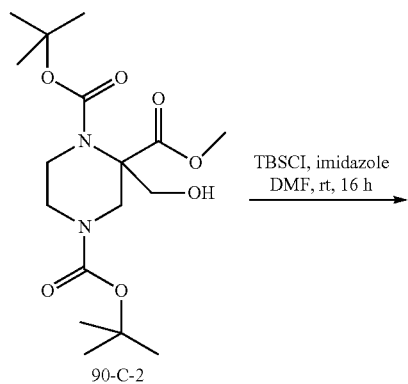

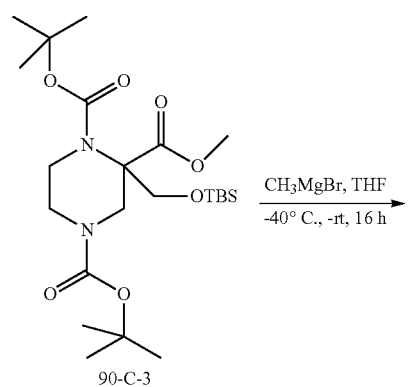

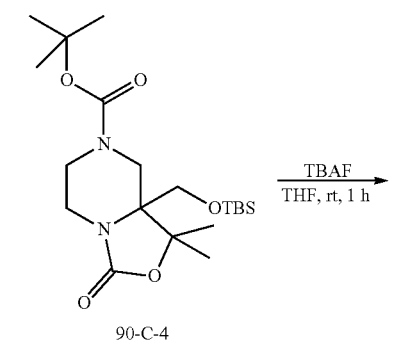

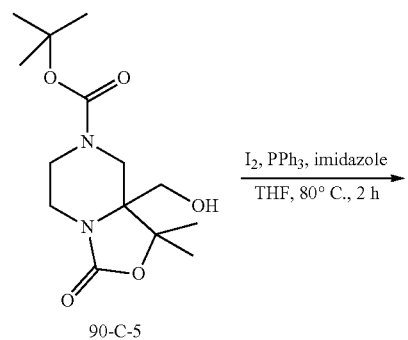

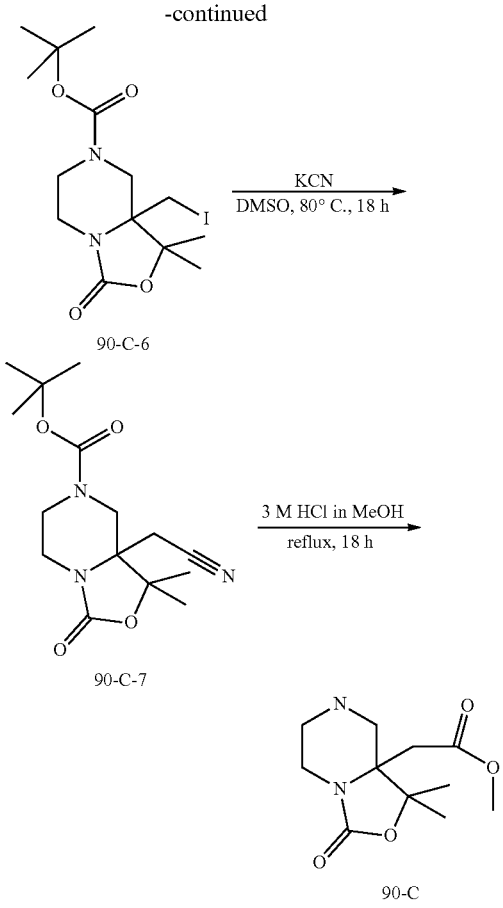

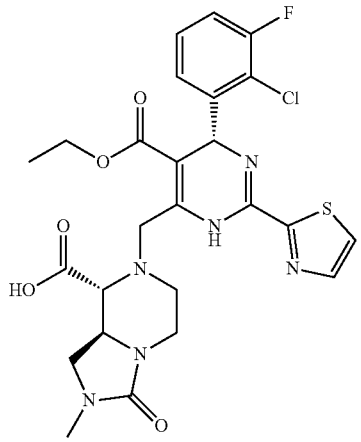

Step 1: To a solution of DIPA (3.67 g, 36 mmol, 1.2 eq) in THF (18 mL) was added n-BuLi (2M, 18 mL, 1.2 eq) dropwise at −78° C. over 15 min and the mixture was stirred for another 15 min at −78° C. Then compound AH (10.3 g, 30 mmol, 1.0 eq) in THF (30 mL) was added dropwise to the reaction at −78° C., after the addition was completed, the mixture was stirred for another 30 min at −78° C. BOMCl (7 g, 45 mmol) in THF (20 mL) was added dropwise over 20 min at −78° C., the reaction mixture was stirred for 16 h and the temperature was warmed to rt during this period. The reaction was quenched with 1M HCl (50 mL), extracted with EA (100 mL) two times, the organic layer was dried and concentrated, the residue was purified on silica gel (EA/PE: 0%-20%) to give compound 90-C-1 as colorless oil (8.2 g).

Step 2: A mixture of compound 90-C-1 (8.2 g, 17.6 mmol) and Pd(OH)$_2$/C (500 mg, 20%) in MeOH (100 mL) was stirred at rt for 2 h under hydrogen, then the solid was filtered off, the filtrate was concentrated and the residue was purified on silica gel (EA/PE: 0%-40%) to give compound 90-C-2 as a colorless oil (6.1 g).

Step 3: To a solution of 90-C-2 (3.74 g, 0.01 mol, 1.0 eq) and imidazole (0.81 g, 0.012 mol, 1.2 eq) in DMF (20 mL) was added TBSCl (1.65 g, 0.11 mol, 1.1 eq) slowly at rt, then the mixture was stirred at rt for 16 h, diluted with EA (50 mL) washed with water (50 mL) and brine (50 mL), the organic layer was dried over Na$_2$SO$_4$ and concentrated to give compound 90-C-3 as a colorless oil (4.4 g). MS: calc'd 489 (MH$^+$), measured 489 (MH$^+$).

Step 4: To a solution of 90-C-3 (4.4 g, 9 mmol, 1.0 eq) in THF (50 mL) was added CH$_3$MgBr (3.2M, 15 mL, 5.0 eq) dropwise at −40° C. over 15 min, then the reaction mixture was stirred for 16 h and the temperature was warmed to rt during this period. The reaction was quenched with 1M HCl (50 mL), extracted with EA (100 mL), the organic layer was dried and concentrated, and residue was purified on silica gel (EA/PE: 20%-40%) to give compound 90-C-4 as colorless oil (1.9 g). MS: calc'd 415 (MH$^+$), measured 415 (MH$^+$).

Step 5: A solution of 90-C-4 (1.86 g, 4.5 mmol, 1.0 eq) and TBAF (1 M, 9 mL, 2.0 eq) in THF (20 mL) was stirred at rt for 2 h, diluted with EA (50 mL), washed with water (50 mL) and brine (50 mL), the organic layer was dried over Na$_2$SO$_4$ and concentrated, the residue was purified on silica gel (EA/PE: 30%-70%) to give compound 90-C-5 as colorless oil (1.2 g). MS: calc'd 301 (MH$^+$), measured 301 (MH$^+$).

Step 6: A solution of 90-C-5 (0.9 g, 3 mmol, 1.0 eq), PPh$_3$ (1.57 g, 6 mmol, 2.0 eq) and imidazole (0.41 g, 6 mmol, 2.0 eq) in THF (20 mL) was refluxed for 1 h, then Iodine (1.3 g, 4.5 mmol, 1.5 eq) was added and refluxed for 2 h. Then reaction diluted with EA (50 mL), washed with water (50 mL) and brine (50 mL), the organic layer was dried (Na$_2$SO$_4$) and concentrated, the residue was purified on silica gel (EA/PE: 0%-25%) to give compound 90-C$_{1-6}$ as colorless oil (0.61 g). MS: calc'd 411 (MH$^+$), measured 411 (MH$^+$).

Step 7: A mixture of 90-C$_{1-6}$ (0.61 g, 1.5 mmol, 1.0 eq) and KCN (0.195 g, 3 mmol, 2.0 eq) in DMSO (10 mL) was stirred at 80° C. for 16 h. Then reaction diluted with EA (50 mL), washed with water (50 mL) and brine (50 mL), the organic layer was dried over Na$_2$SO$_4$ and concentrated, the residue was purified on silica gel (EA/PE: 0%-25%) to give compound 90-C-7 as colorless oil (0.41 g). MS: calc'd 310 (MH$^+$), measured 310 (MH$^+$).

Step 8: A mixture of 90-C-7 (0.41 g, 1.3 mmol, 1.0 eq) in HCl/MeOH (3M, 10 mL) was stirred at 80° C. for 16 h. Then reaction was concentrated to give compound 90-C as white solid (0.36 g). MS: calc'd 243 (MH$^+$), measured 243 (MH$^+$).

Example 91A and 91B (Separated Two Single Isomers)

(8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; and (8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid -continued
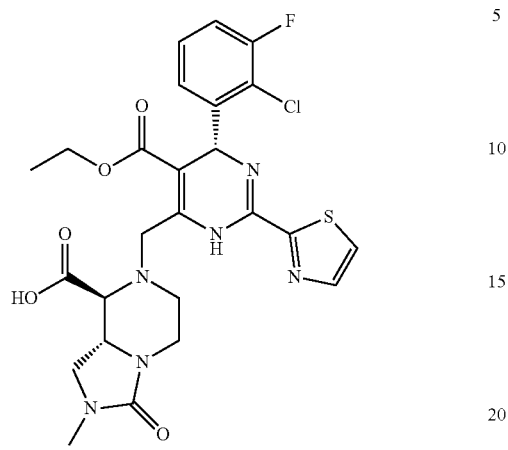
Preparation of Example 91A and 91B
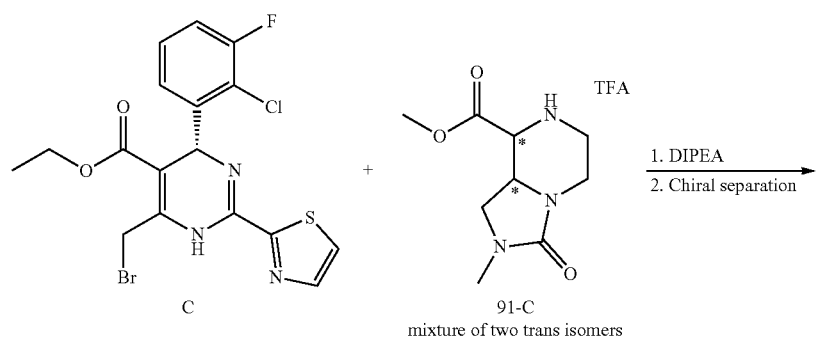
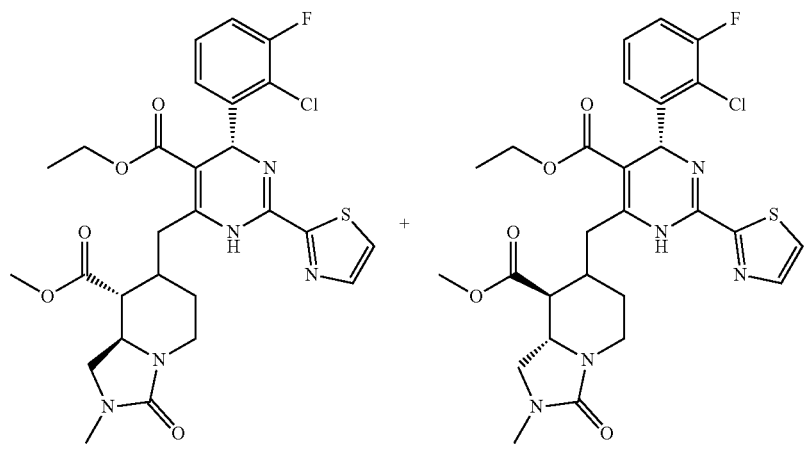

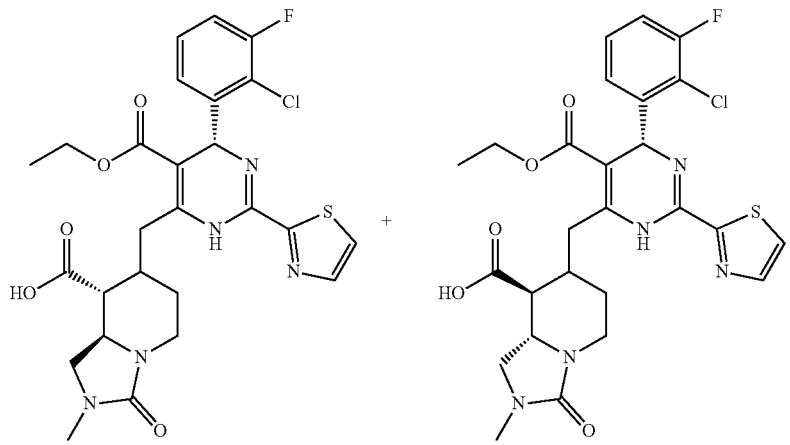

91A & 91B

The title two compounds were prepared in analogy to Example 82A and 82B by using methyl 2-methyl-3-oxo-1,5,6,7,8,8a-hexahydroimidazo[1,5-a]pyrazine-8-carboxylate (compound 91-C) instead of trans-methyl 2-cyclopropyl-3-oxo-1,5,6,7,8,8a-hexahydroimidazo[1,5-a]pyrazine-8-carboxylate (compound 82-C).

Example 91A was obtained as a light yellow solid (26 mg). $^1$H NMR (400MHz, MeOD) 7.97 (d, J=3.3 Hz, 1H), 7.77 (d, J=3.0 Hz, 1H), 7.36-7.26 (m, 2H), 7.22-7.11 (m, 1H), 6.25 (s, 1H), 4.30 (d, J=17.3 Hz, 1H), 4.04 (q, J=7.2 Hz, 2H), 3.95-3.82 (m, 3H), 3.61-3.45 (m, 2H), 3.31-3.11 (m, 2H), 2.93-2.81 (m, 4H), 2.49 (br, 1H), 1.13 (t, J=7.0 Hz, 3H). LC/MS: calc'd 577 (MH+), exp 577 (MH+).

Example 91B was obtained as a light yellow solid (38 mg). $^1$H NMR (400MHz, MeOD) 7.96 (d, J=3.0 Hz, 1H), 7.76 (d, J=3.0 Hz, 1H), 7.39-7.25 (m, 2H), 7.17 (td, J=2.0, 7.5, 9.1 Hz, 1H), 6.21 (s, 1H), 4.24 (d, J=16.8 Hz, 1H), 4.04 (q, J=7.1 Hz, 2H), 3.98-3.78 (m, 3H), 3.60-3.42 (m, 2H), 3.31-3.16 (m, 2H), 3.04 (d, J=10.3 Hz, 1H), 2.83 (s, 3H), 2.61 (br, 1H), 1.12 (t, J=7.0 Hz, 3H). LC/MS: calc'd 577 (MH+), exp 577 (MH+).

Example 91A was synthesized from compound 91A-1 (faster eluting) and Example 91B was synthesized from compound 91B-1 (slower eluting) on ChiralPak AD-3 column eluting with 30% isopropanol (0.05% DEA)/CO$_2$.

Preparation of methyl 2-methyl-3-oxo-1,5,6,7,8,8a-hexahydroimidazo[1,5-a]pyrazine-8-carboxylate (Compound 91-C)

Compound 91-C was prepared in analogy to compound 82-C by using methyl amine instead of cyclopropylamine.

Example 92A and 92B (Separated Two Single Isomers)

Methyl (4R)-6-[[(8R,8aS)-2-tert-butyl-8-carbamoyl-3-oxo-5,6,8,8a-tetrahydro-1H-imidazo[1,5-a]pyrazin-7-yl]methyl]-4-(2-chloro-4-fluoro-phenyl)-2-thiazol-2-yl-1,4-dihydropyrimidine-5-carboxylate; and Methyl (4R)-6-[[(8S,8aR)-2-tert-butyl-8-carbamoyl-3-oxo-5,6,8,8a-tetrahydro-1H-imidazo[1,5-a]pyrazin-7-yl]methyl]-4-(2-chloro-4-fluoro-phenyl)-2-thiazol-2-yl-1,4-dihydropyrimidine-5-carboxylate

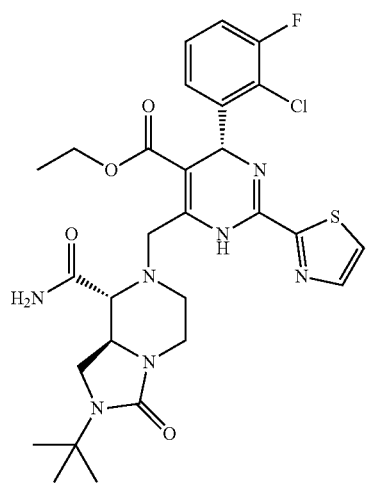

-continued

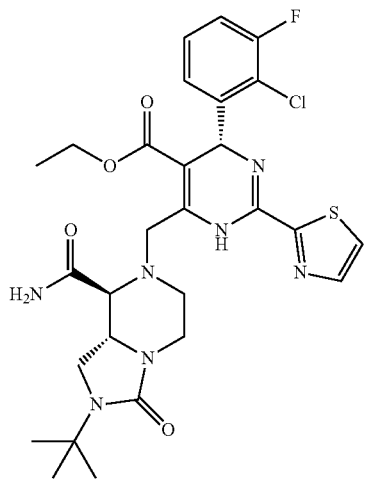

Preparation of Example 92A and 92B

The title two compounds were prepared in analogy to Example 82A and 82B by using trans-2-tert-butyl-3-oxo-1,5,6,7,8,8a-hexahydroimidazo[1,5-a]pyrazine-8-carboxamide (compound 92-C) instead of trans-methyl 2-cyclopropyl-3-oxo-1,5,6,7,8,8a-hexahydroimidazo[1,5-a]pyrazine-8-carboxylate (compound 82-C). The crude product was purified by HPLC to give a mixture of two isomers which were further resolved by SFC to give two single isomers: 92A (faster eluting) and 92B (slower eluting) with 30% isopropanol (0.05% DEA)/$CO_2$ on ChiralPak AD-3 column.

Example 92A was obtained as a light yellow solid (30 mg). $^1$H NMR (400MHz, MeOD) δ=7.97 (d, J=3.0 Hz, 1H), 7.74 (d, J=3.3 Hz, 1H), 7.37-7.21 (m, 2H), 7.20-7.08 (m, 1H), 6.20 (s, 1H), 4.18 (d, J=17.1 Hz, 1H), 4.02 (q, J=7.0 Hz, 2H), 3.84-3.72 (m, 3H), 3.55 (t, J=8.8 Hz, 2H), 3.14 (dt, J=3.5, 12.7 Hz, 1H), 3.05 (d, J=9.3 Hz, 1H), 3.00-2.89 (m, 1H), 2.45 (dt, J=3.5, 11.9 Hz, 1H), 1.40 (s, 9H), 1.12 (t, J=7.2 Hz, 3H). MS: calc'd 618 ($MH^+$), exp 618 ($MH^+$).

Example 92B was obtained as a light yellow solid (30 mg). $^1$H NMR (400MHz, MeOD) δ=7.98 (d, J=3.0 Hz, 1H), 7.76 (d, J=3.0 Hz, 1H), 7.36-7.23 (m, 2H), 7.20-7.09 (m, 1H), 6.25 (s, 1H), 4.24 (d, J=17.3 Hz, 1H), 4.04 (q, J=7.1 Hz, 2H), 3.85-3.68 (m, 3H), 3.57 (t, J=8.8 Hz, 1H), 3.37-2.35 (m, 1H), 3.20-2.99 (m, 2H), 2.85-2.69 (m, 1H), 2.32 (dt, J=3.4, 12.0 Hz, 1H), 1.49-1.34 (s, 9H), 1.13 (t, J=7.0 Hz, 3H). MS: calc'd 618 ($MH^+$), exp 618 ($MH^+$).

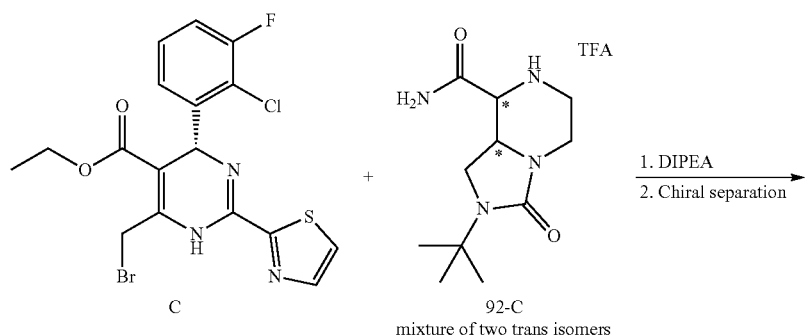

C     92-C
mixture of two trans isomers

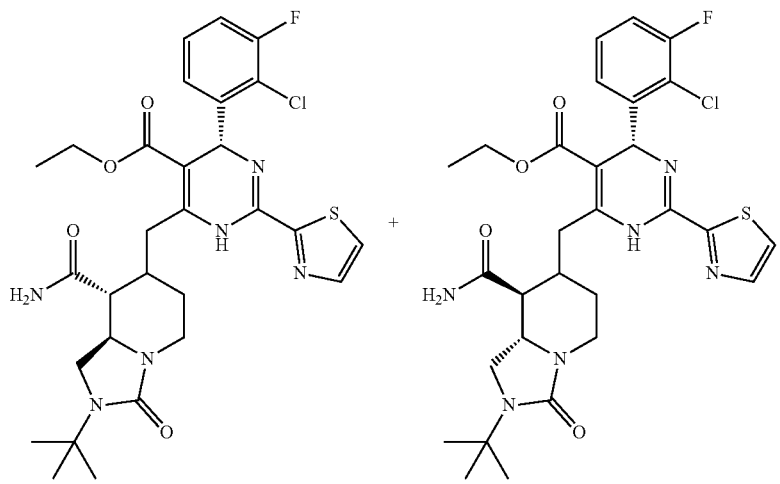

92A & 92B

Preparation of trans-2-tert-butyl-3-oxo-1,5,6,7,8,8a-hexahydroimidazo[1,5-a]pyrazine-8-carboxamide (Compound 92-C)

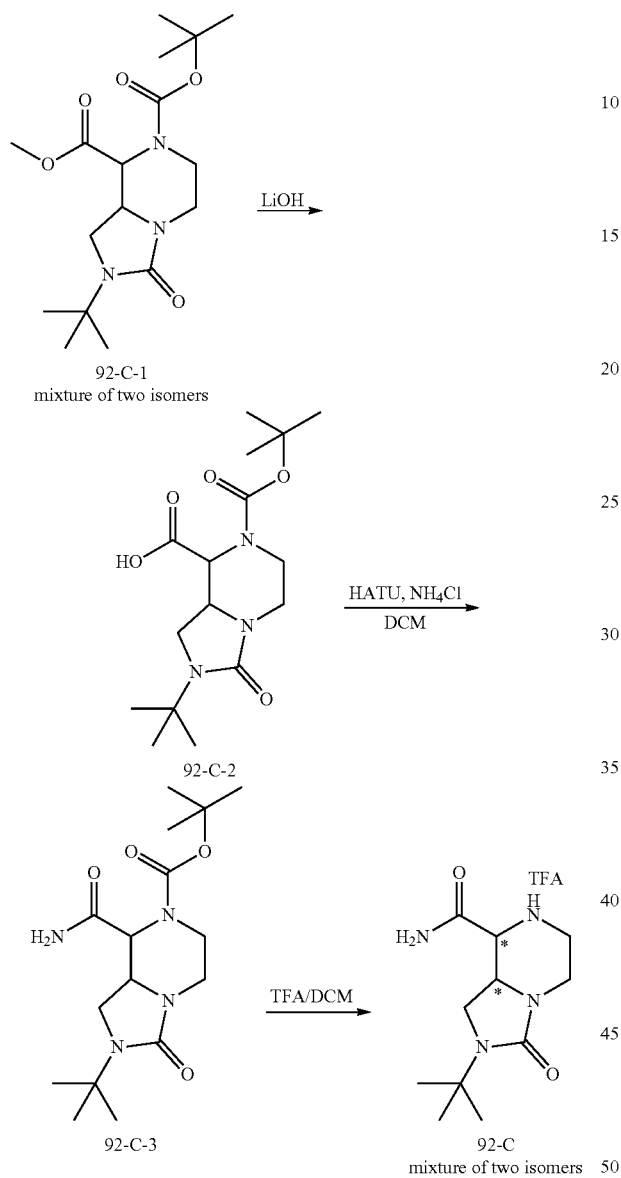

Step 1: To a solution of compound 92-C-1 (355 mg, 1 mmol) in THF (5 mL) was added lithium hydroxide monohydrate (124 mg, 3 mmol) in water (1 mL). After the reaction mixture was stirred at 35° C. for 2 hours, it was neutralized with 1N hydrochloride solution to pH 3.0. The mixture was extracted with ethyl acetate (30 mL) three times. The combined organic phase was dried over $Na_2SO_4$, filtrated and then concentrated to give compound 92-C-2 as a white solid (340 mg). MS: calc'd 356 ($MH^+$), exp 356 ($MH^+$).

Step 2: A mixture of compound 92-C-2 (340 mg, 1 mmol), HATU (380 mg, 1 mmol), $NH_4Cl$ (275 mg, 5 mmol) and DIPEA (775 mg, 6 mmol) in THF (10 mL) was stirred 50° C. for 2 hours. Then the undissolved material was filtered off and the filtrate was concentrated. The residue was purified on silica gel (EA/PE: 0%-40%) to give compound 92-C-3 as a white solid (200 mg). MS: calc'd 355 ($MH^+$), exp 355 ($MH^+$).

Step 3: A mixture of compound 92-C-3 (200 mg, 0.6 mmol) in DCM/TFA (5 mL, 2:1) was stirred at room temperature for 2 hours, then the mixture was concentrated under reduced pressure to give compound 92-C as a slight yellow oil (200 mg), which was used directly in the next step. MS: calc'd 255 ($MH^+$), exp 255 ($MH^+$).

Preparation of trans-7-tert-butyl-8-methyl 2-tert-butyl-3-oxo-5,6,8,8a-tetrahydro-1H-imidazo[1,5-a]pyrazine-7,8-dicarboxylate (Compound 92-C-1)

Compound 92-C-1 was prepared in analogy to compound 82-C-5 by using tert-butylamine instead of cyclopropylamine.

Example 93

3-[(8aS)-7-[[(4R)-4-(2-chloro-3-fluoro-phenyl)-5-propoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid

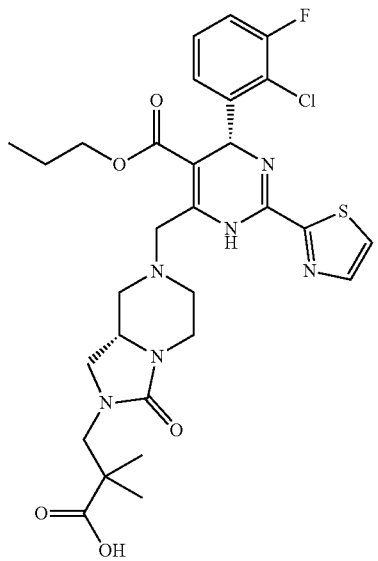 [SMILES: CCCOC(=O)C1=C(CN2CCN3C(=O)N(CC(C)(C)C(=O)O)C[C@@H]3C2)NC(c2nccs2)=N[C@H]1c1cccc(F)c1Cl]

Preparation of Example 93

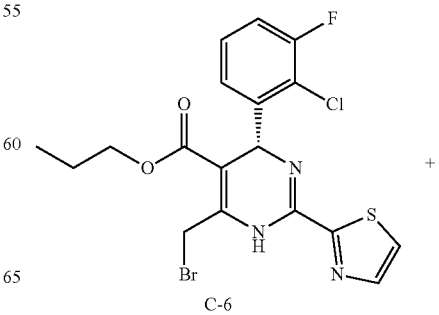

225

-continued

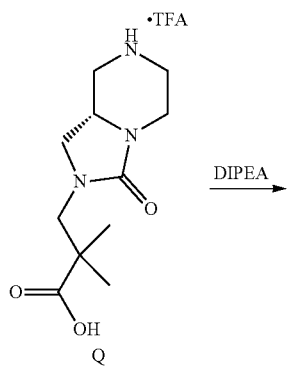

Q

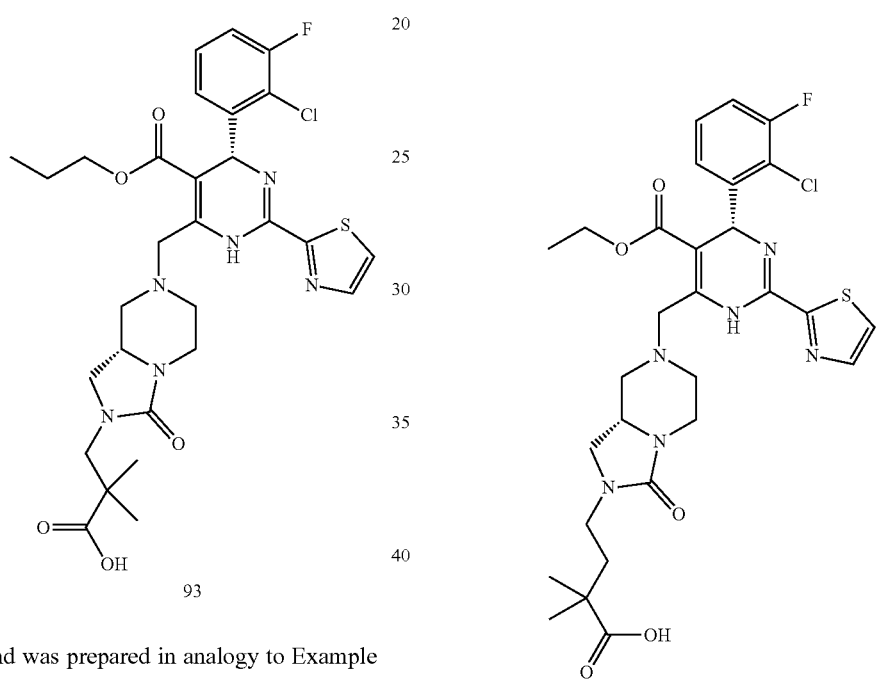

93

The title compound was prepared in analogy to Example 1 by using 3-[(8aS)-7-[[(4R)-4-(2-chloro-3-fluoro-phenyl)-5-propoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid (compound $C_{1-6}$) and 3-[(8aS)-3-oxo-1,5,6,7,8,8a-hexahydroimidazo[1,5-a]pyrazin-2-yl]-2,2-dimethyl-propanoic acid (Compound Q) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 93 was obtained as a light yellow solid (6 mg). $^1$H NMR (400MHz, MeOD) δ=7.96 (d, J=3.0 Hz, 1H), 7.75 (d, J=3.0 Hz, 1H), 7.34-7.21 (m, 2H), 7.15 (dt, J=1.6, 8.5 Hz, 1H), 6.24 (s, 1H), 4.19-4.06 (m, 1H), 4.03-3.81 (m, 5H), 3.51 (t, J=8.9 Hz, 1H), 3.45-3.37 (m, 1H), 3.33-3.29 (m, 1H), 3.25-3.15 (m, 1H), 3.11 (dd, J=4.0, 9.5 Hz, 1H), 2.97-2.78 (m, 2H), 2.41-2.29 (m, 1H), 2.19 (t, J=10.9 Hz, 1H), 1.59-1.47 (m, 2H), 1.21 (d, J=2.8 Hz, 6H), 0.76 (t, J=7.4 Hz, 3H). MS: calc'd 633 (MH$^+$), measured 633 (MH$^+$).

226

Preparation of propyl (4R)-6-(bromomethyl)-4-(2-chloro-3-fluoro-phenyl)-2-thiazol-2-yl-1,4-dihydro-pyrimidine-5-carboxylate (Compound $C_{1-6}$)

Compound C6 was prepared in analogy to compound C by using n-propyl acetoacetate instead of methyl acetoacetate.

Example 94

4-[(8aS)-7-[[(4R)-4-(2-chloro-4-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-butanoic acid Preparation of Example 94

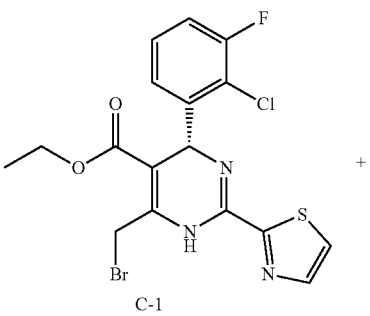

C-1

227
-continued

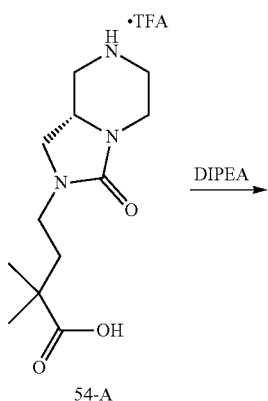

54-A

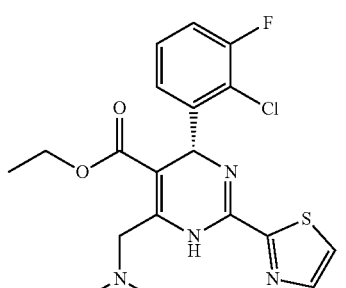

94

The title compound was prepared in analogy to Example 1 by using ethyl (4R)-6-(bromomethyl)-4-(2-chloro-3-fluoro-phenyl)-2-thiazol-2-yl-1,4-dihydropyrimidine-5-carboxylate (compound C-1) and (3R)-3-[(8aS)-3-oxo-1,5,6,7,8,8a-hexahydroimidazo[1,5-a]pyrazin-2-yl]butanoic acid TFA salt (Compound 54-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 57 was obtained as a light yellow solid (48 mg). $^1$H NMR (MeOD, 400MHz): δ=7.97 (d, J=3.3 Hz, 1H), 7.76 (d, J=3.0 Hz, 1H), 7.02-7.39 (m, 3H), 6.24 (s, 1H), 3.99-4.16 (m, 2H), 3.73-3.95 (m, 3H), 3.47 (t, J=9.0 Hz, 2H), 3.02-3.25 (m, 3H), 2.68-2.97 (m, 2H), 2.10-2.48 (m, 3H), 1.76 (br. s., 2H), 1.23 (s, 6H), 1.13 ppm (t, J=7.2 Hz, 3H). MS: calc'd 633 (MH$^+$), measured 633 (MH$^+$).

228

Example 95

5-[7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]pyridine-2-carboxylic acid

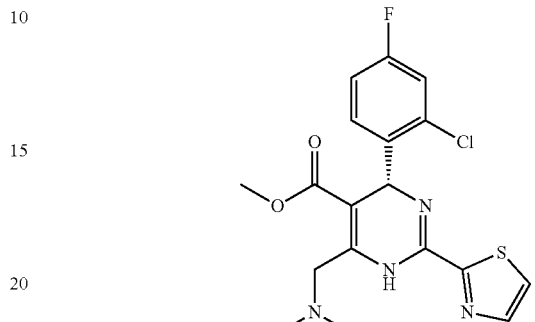

Preparation of Example 95

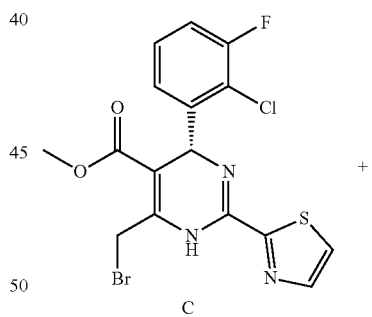

C

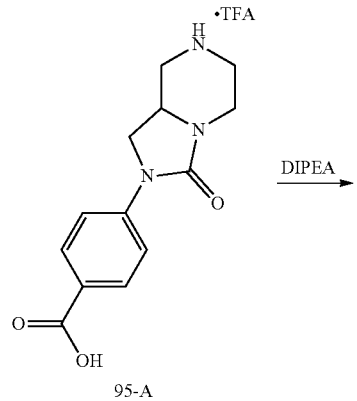

95-A

-continued

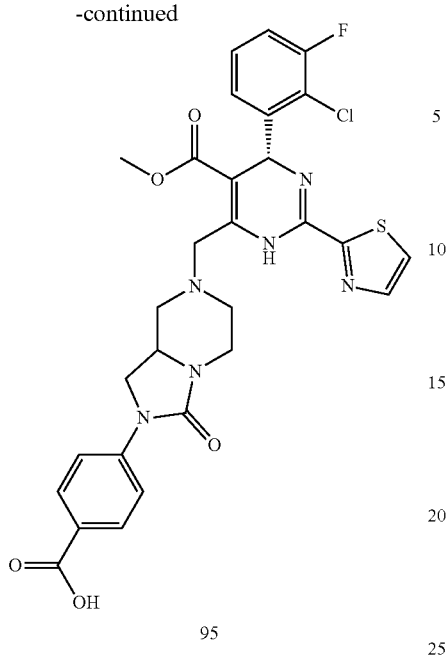

95

The title compound was prepared in analogy to Example 1 by using 5-(3-oxo-1,5,6,7,8,8a-hexahydroimidazo[1,5-a]pyrazin-2-yl)pyridine-2-carboxylic acid TFA salt (Compound 95-A) instead of hexahydro-pyrazino[1,2-c][1,3]oxazin-6-one (Compound D). Example 95 was obtained as a light yellow solid (48 mg). ¹H NMR (400 MHz, METHANOL-d₄) d ppm 9.02 (s, 1H), 8.17 (s, 2H), 8.01 (s, 1H), 7.88 (s, 1H), 7.51-7.54 (m, 1 H), 7.30-7.28 (m, 1 H), 7.10-7.13 (m, 1 H), 6.20 (s, 1H), 4.41-4.63 (m, 2H), 4.17-4.35 (m, 3H), 3.51-3.75 (m, 7 H), 3.01-3.12 (m, 2H). MS: calc'd 626 (MH⁺), measured 626 (MH⁺).

Preparation of 5-(3-oxo-1,5,6,7,8,8a-hexahydroimidazo[1,5-a]pyrazin-2-yl)pyridine-2-carboxylic acid (Compound 95-A)

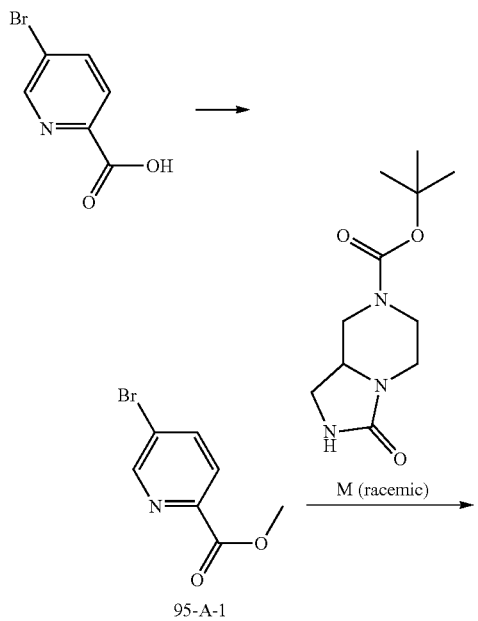

-continued

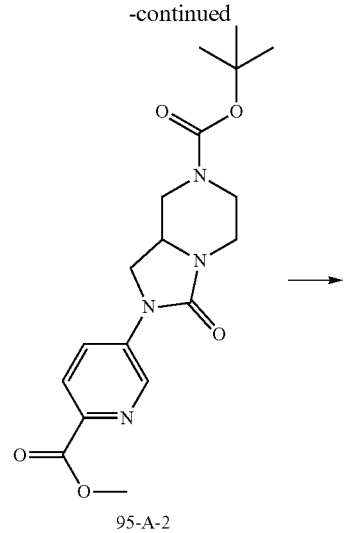

95-A-2

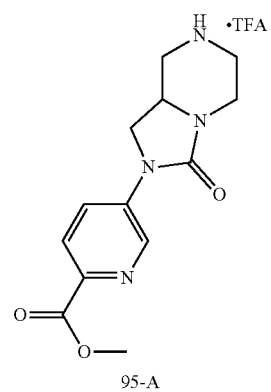

95-A

Step 1: A solution of 5-bromopyridine-2-carboxylic acid (5.0 g, 24.75 mmol) in MeOH (30 mL) was added thionyl chloride (10 mL) dropwise at 0° C. Then the mixture was stirred for 12 hours at 60° C. After removal of solvent and the residual thionyl chloride, the crude product methyl 5-bromopyridine-2-carboxylate was obtained and used in the next step without further purification.

Step 2: A mixture of methyl 5-bromopyridine-2-carboxylate (compound 95-A-1, 0.72 g, 3.28 mmol), tert-butyl 3-oxo-1,2,5,6,8,8a-hexahydroimidazo[1,5-a]pyrazine-7-carboxylate (racemic compound M, 0.40 g, 1.64 mmol), bis(dibenzylideneacetone) palladium (94.4 mg, 0.164 mmol), (+)-2,2'-bis(diphenylphosphino)-1,1'-binaphthyl (196.8 mg, 0.33 mmol), cesium carbonate (160.4 mg, 4.92 mmol) in dioxane (3 mL) was stirred for 3 hours at 130° C. in microwave. After removal of solvent, the residue was purified by column to afford product 95-A-2 as white solid. MS: calc'd 377 (MH⁺), measured 377 (MH⁺).

Step 3: A mixture of compound 95-A-2 (0.24 g, 0.64 mmol), lithium hydroxide (0.13 g, 3.2 mmol) in water (2 mL) and MeOH (5 mL) was stirred for 12 hours at room temperature. The reaction mixture was then neutralized with 1 N HCl to pH 6, extracted with ethyl acetate. The organic layer was dried over sodium sulfate. After removal of solvent, the residue was treated with TFA (2 mL) in DCM (10 mL). After the reaction mixture was stirred for 30 minutes, the solvent was removed to give the crude product, which was used in the next step directly. MS: calc'd 263 (MH⁺), measured 263 (MH⁺).

Example 96

(S)-6-[(S)-2-(2-Carboxy-2,2-difluoro-ethyl)-3-oxo-hexahydro-imidazo[1,5-a]pyrazin-7-ylmethyl]-4-(3,4-difluoro-2-methyl-phenyl)-2-thiazol-2-yl-1,4-dihydro-pyrimidine-5-carboxylic acid ethyl ester

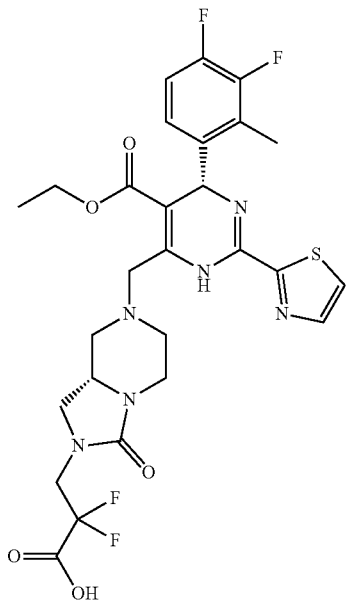 [SMILES: CCOC(=O)C1=C(CN2CCN3C(=O)N(CC(F)(F)C(=O)O)C[C@@H]3C2)NC(c2nccs2)=N[C@H]1c1ccc(F)c(F)c1C]

Preparation of Example 96

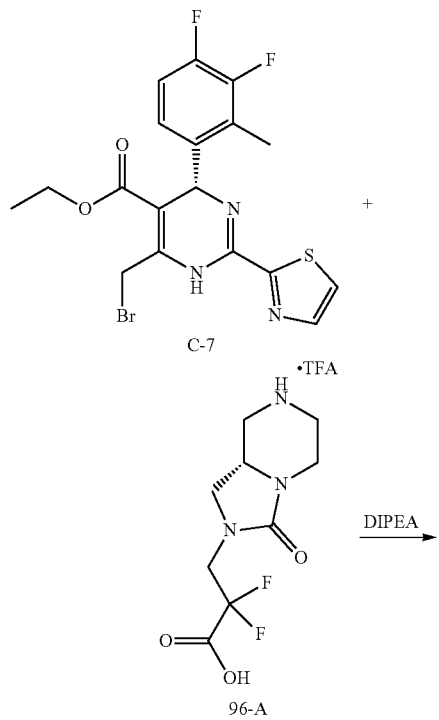

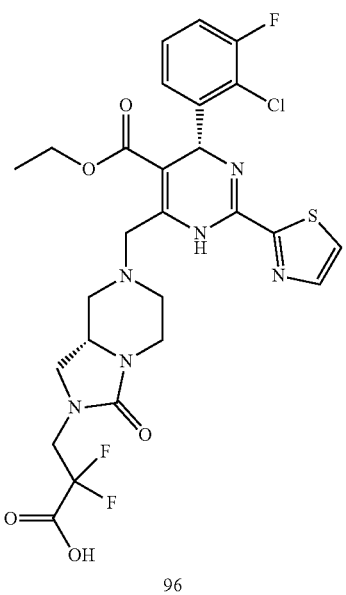

The title compound was prepared in analogy to Example 1 by using ethyl (4S)-6-(bromomethyl)-4-(3,4-difluoro-2-methyl-phenyl)-2-thiazol-2-yl-1,4-dihydropyrimidine-5-carboxylate (compound C-7) and 2,2-difluoro-3-((S)-3-oxo-hexahydro-imidazo[1,5-a]pyrazin-2-yl)-propionic acid trifluoroacetate salt (Compound 96-A) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 96 was obtained as a light yellow solid (15 mg). ¹H NMR (400 MHz, METHANOL-$d_4$) d ppm 8.01 (d, 1H), 7.90 (d, 1H), 7.26 (m, 1H), 7.07-7.15 (m, 1H), 5.94-5.98 (m, 1H), 4.69 (d, 1H), 4.51 (d, 1H), 4.05-4.20 (m, 4H), 3.86-3.98 (m, 2H), 3.62-3.80 (m, 4H), 3.41-3.52 (m, 1H), 3.07-3.22 (m, 3H), 2.52 (d, 3H), 1.15 (m, 3H). MS: calc'd 625 (MH⁺), measured 625 (MH⁺).

Preparation of 2,2-difluoro-3-((S)-3-oxo-hexahydro-imidazo[1,5-a]pyrazin-2-yl)-propionic acid trifluoroacetate salt (Compound 96-A)

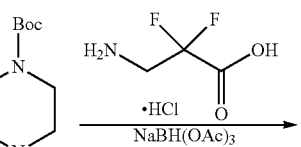

-continued

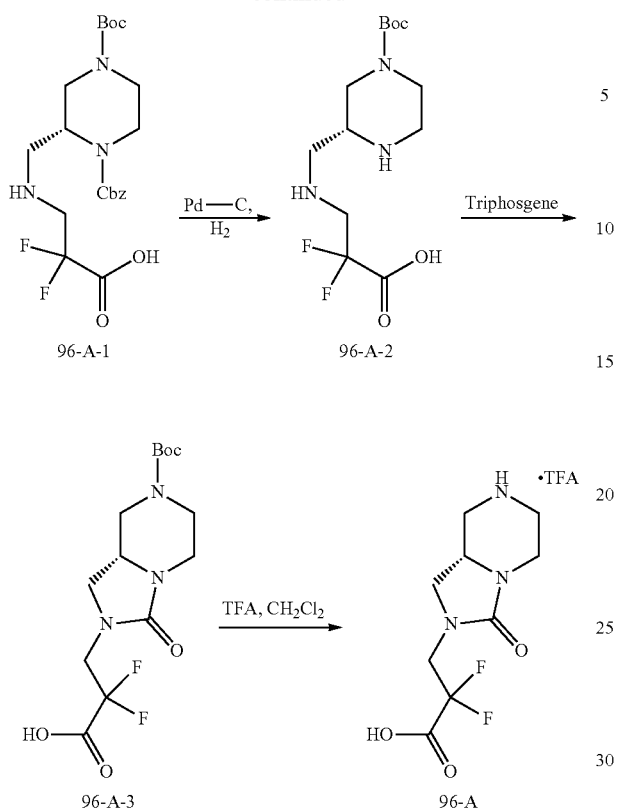

Preparation of ethyl (4S)-6-(bromomethyl)-4-(3,4-difluoro-2-methyl-phenyl)-2-thiazol-2-yl-1,4-dihydropyrimidine-5-carboxylate (compound C-7)

Compound C-7 was prepared in analogy to compound C by using 3,4-difluoro-2-methylbenzaldehyde and ethyl acetoacetate instead of 2-chloro-4-fluorobenzaldehyde and methyl acetoacetate.

Example 97A and 97B (Separated Two Single Isomers)

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-(cyclopropylmethyl)-3-oxo-5,6,8,8a-tetrahydro-1H-imidazo[1,5-a]pyrazine-8-carboxylic acid; and (8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-(cyclopropylmethyl)-3-oxo-5,6,8,8a-tetrahydro-1H-imidazo[1,5-a]pyrazine-8-carboxylic acid

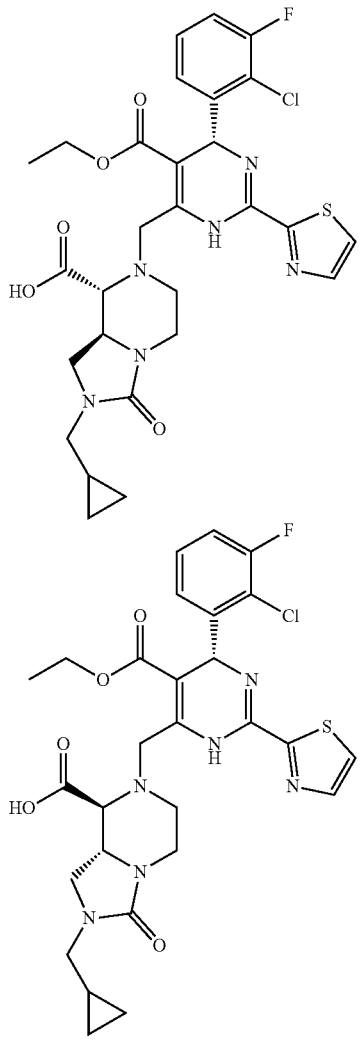

Step 1: To a stirred solution of 3-amino-2,2-difluoropropionic acid hydrochloride salt (400 mg, 1.10 mmol) in DCM (5 mL) was added DIPEA (142 mg, 1.10 mmol) at 0° C., sequentially followed by a solution of compound S (350 mg, 1 mmol) in DCM (5 mL). The reaction mixture was stirred at 0° C. for five minutes. Then NaBH(OAc)$_3$ was added to the mixture. The resulting mixture was stirred at rt overnight. The reaction mixture was partitioned between DCM and water. The organic layer was separated, dried over Na$_2$SO$_4$, concentrated in vacuum and isolated to give compound 96-A-1 (320 mg).

Step 2: A mixture of compound 96-A-1 (320 mg, 0.70 mmol) and Pd/C (30 mg) in MeOH (5 mL) was stirred with a hydrogen balloon at room temperature overnight. The reaction mixture was filtered and the filtrate was concentrated. The crude product 96-A-2 was obtained (226 mg) and used in the next step without further purification.

Step 3: To a solution of compound 96-A-2 (crude 226 mg, 0.70 mmol) in dichloromethane (3 ml) was added DIPEA (0.6 mL, 3.50 mmol) at 0° C., then triphosgene (103 mg, 0.35 mmol) was added to the reaction mixture. The resulting mixture was warmed to rt and stirred overnight. The reaction mixture was concentrated and the residue was directly used in the next step. The amount of crude product 96-A-3 was 340 mg.

Step 4: To a solution of compound 96-A-3 (crude 340 mg, 0.70 mmol) in dichloromethane (2 mL) was added trifluoroacetic acid (5 mL) at room temperature. After the reaction mixture was stirred for 1.5 hours, the solvent was removed to give the crude product 96-A (260 mg) which was used directly in the next step.

Preparation of Example 97A and 97B
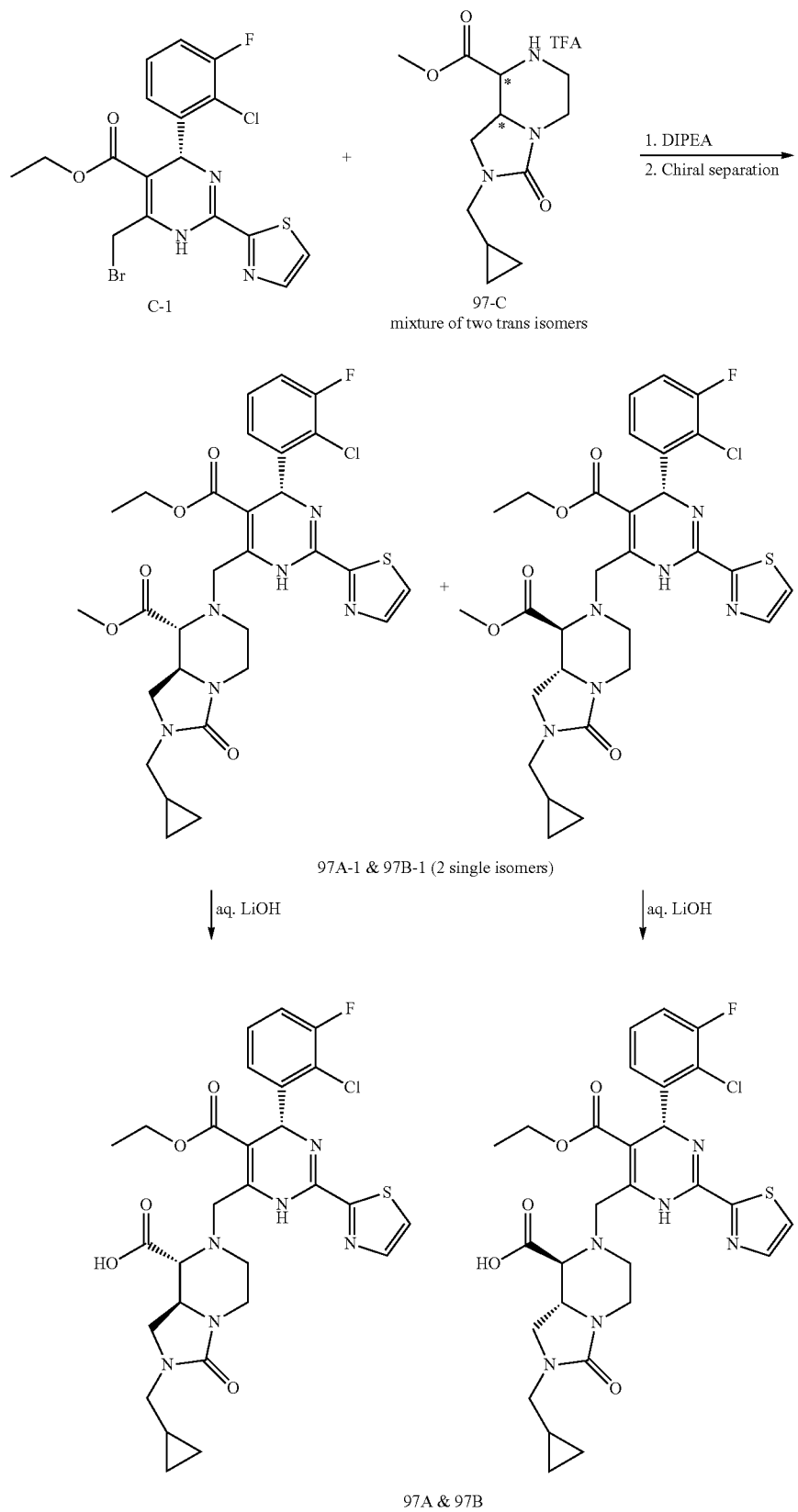
97A & 97B

The title two compounds were prepared in analogy to Example 82A and 82B by using trans-methyl 2-(cyclopropylmethyl)-3-oxo-1,5,6,7,8,8a-hexahydroimidazo[1,5-a]pyrazine-8-carboxylate (compound 97-C) instead of trans-methyl 2-cyclopropyl-3-oxo-1,5,6,7,8,8a-hexahydroimidazo[1,5-a]pyrazine-8-carboxylate (compound 82-C).

Example 97A was obtained as a light yellow solid (25 mg). ¹H NMR (400 MHz, METHANOL-d₄) d ppm 7.98 (d, J=3.0 Hz, 1H), 7.78 (d, J=3.0 Hz, 1H), 7.35-7.26 (m, 2H), 7.20-7.11 (m, 1H), 6.25 (s, 1H), 4.30 (s, 1H), 4.10-3.99 (m, 2H), 3.95-3.86 (m, 2H), 3.81 (d, J=11.5 Hz, 1H), 3.68 (d, J=8.0 Hz, 1H), 3.65-3.58 (m, 1H), 3.37-3.34 (m, 2H), 3.25-3.16 (m, 1H), 3.25-3.16 (m, 1H), 3.15-3.07 (m, 2H), 2.91 (d, J=11.5 Hz, 1H), 2.60-2.49 (m, 1H), 1.13 (t, J=7.2 Hz, 3H), 1.03-0.93 (m, 1H), 0.61-0.53 (m, 2H), 0.28-0.23 (m, 2H). MS: calc'd 617 (MH⁺), measured 617 (MH⁺).

Example 97B was obtained as a light yellow solid (19 mg). ¹H NMR (400 MHz, METHANOL-d₄) d ppm 7.33-7.23 (m, 3H), 7.15 (t, J=8.3 Hz, 1H), 6.22 (s, 1H), 4.12-4.02 (m, 3H), 3.95-3.84 (m, 3H), 3.52 (t, J=8.9 Hz, 1H), 3.44-3.38 (m, 1H), 3.29 (s, 1H), 3.24-3.09 (m, 2H), 2.93 (d, J=11.0 Hz, 1H), 2.84 (d, J=8.5 Hz, 1H), 2.48 (d, J=0.8 Hz, 3H), 2.37 (dt, J=3.4, 11.6 Hz, 1H), 2.18 (t, J=10.9 Hz, 1H), 1.21 (d, J=3.0 Hz, 6H), 1.13 (t, J=7.2 Hz, 3H). MS: calc'd 617 (MH⁺), measured 617 (MH⁺).

Example 97A was synthesized from compound 97A-1 (faster eluting) and Example 97B was synthesized from compound 97B-1 (slower eluting) on ChiralPak AD-3 column eluting with 30% isopropanol (0.05% DEA)/CO₂.

Preparation of trans-methyl 2-(cyclopropylmethyl)-3-oxo-1,5,6,7,8,8a-hexahydroimidazo[1,5-a]pyrazine-8-carboxylate (compound 97-C)

Compound 97-C was prepared in analogy to compound 82-C by using cyclopropylmethanamine instead of cyclopropylamine.

Example 98

3-[(8aS)-7-[[(4R)-4-(2-chloro-3-fluoro-phenyl)-5-ethoxycarbonyl-2-(4-methylthiazol-2-yl)-1,4-dihydropyrimidin-6-yl]methyl]-3-oxo-5,6,8,8a-tetrahydro-1H-imidazo[1,5-a]pyrazin-2-yl]-2,2-dimethyl-propanoic acid

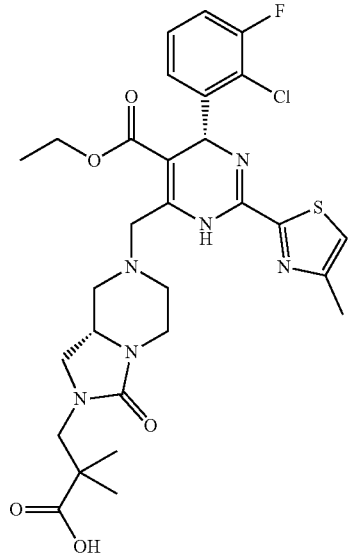 [SMILES: CCOC(=O)C1=C(CN2CCN3C(=O)N(CC(C)(C)C(=O)O)C[C@@H]3C2)NC(c2nc(C)cs2)=N[C@H]1c1cccc(F)c1Cl]

Preparation of Example 93

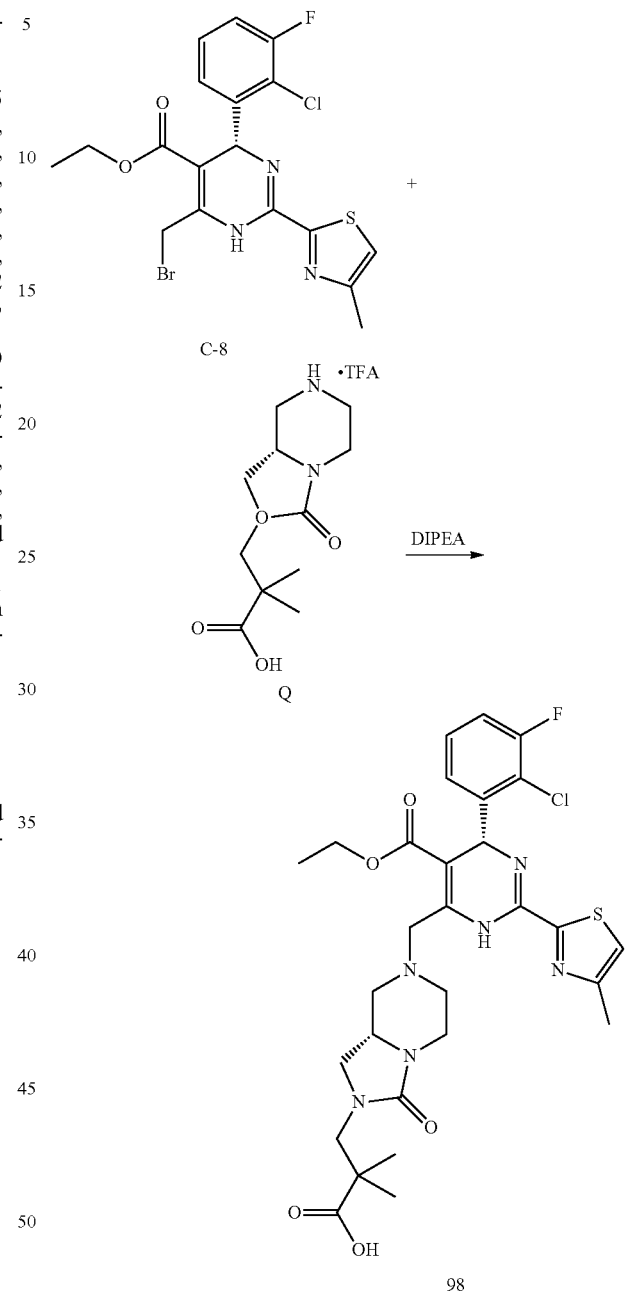

The title compound was prepared in analogy to Example 1 by using ethyl (4R)-6-(bromomethyl)-4-(2-chloro-3-fluoro-phenyl)-2-(4-methylthiazol-2-yl)-1,4-dihydropyrimidine-5-carboxylate (compound C-8) and 3-[(8aS)-3-oxo-1,5,6,7,8,8a-hexahydroimidazo[1,5-a]pyrazin-2-yl]-2,2-dimethyl-propanoic acid (Compound Q) instead of (R)-6-bromomethyl-4-(2-chloro-4-fluoro-phenyl)-2-thiazol-2-yl-1,4-dihydro-pyrimidine-5-carboxylic acid methyl ester (Compound C) and hexahydro-pyrazino[1,2-c][1,3]oxazin-6-one (Compound D). Example 93 was obtained as a light yellow solid (60 mg). ¹H NMR (400MHz, MeOD) δ=7.33-7.23 (m, 3H), 7.15 (t, J=8.3 Hz, 1H), 6.22 (s, 1H), 4.12-4.02 (m, 3H), 3.95-3.84 (m, 3H), 3.52 (t, J=8.9 Hz, 1H), 3.44-

3.38 (m, 1H), 3.29 (s, 1H), 3.24-3.09 (m, 2H), 2.93 (d, J=11.0 Hz, 1H), 2.84 (d, J=8.5 Hz, 1H), 2.48 (d, J=0.8 Hz, 3H), 2.37 (dt, J=3.4, 11.6 Hz, 1H), 2.18 (t, J=10.9 Hz, 1H), 1.21 (d, J=3.0 Hz, 6H), 1.13 (t, J=7.2 Hz, 3H). MS: calc'd 633 (MH⁺), measured 633 (MH⁺).

Preparation of ethyl (4R)-6-(bromomethyl)-4-(2-chloro-3-fluoro-phenyl)-2-(4-methylthiazol-2-yl)-1,4-dihydropyrimidine-5-carboxylate (compound C-8)

Compound C-8 was prepared in analogy to compound C by using 4-methylthiazole-2-carbonitrile and ethyl acetoacetate instead of thiazole-2-carbonitrile and methyl acetoacetate.

Example 99

2-[[(4R)-4-(2-chloro-3-fluoro-phenyl)-5-ethoxycarbonyl-2-thiazol-2-yl-1,4-dihydropyrimidin-6-yl]methyl]-6-oxo-1,3,4,7,8,8a-hexahydropyrrolo[1,2-a]pyrazine-1-carboxylic acid (Mixture of Two Isomers)

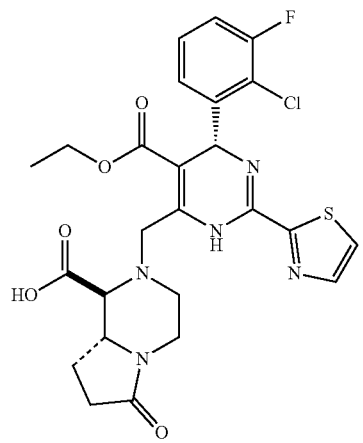 [SMILES: CCOC(=O)C1=C(CN2CCN3C(=O)CC[C@@H]3[C@H]2C(=O)O)NC(c2nccs2)=N[C@H]1c1cccc(F)c1Cl]

Preparation of Example 99

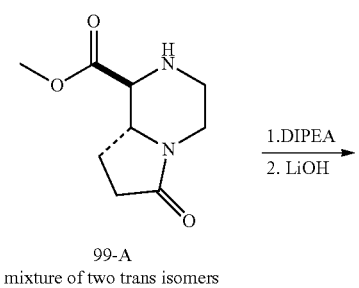

99-A
mixture of two trans isomers

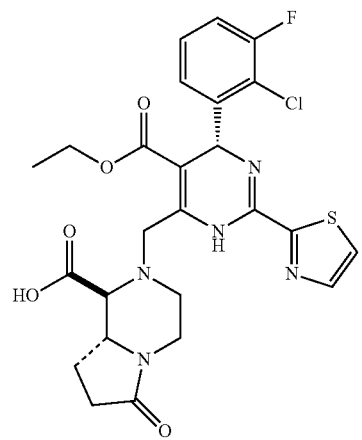

99
mixture of two trans isomers

The title two compounds were prepared in analogy to Example 82A and 82B by using trans-6-oxo-2,3,4,7,8,8a-hexahydro-1H-pyrrolo[1,2-a]pyrazine-1-carboxylic acid (Compound 99-A) instead of trans-methyl 2-cyclopropyl-3-oxo-1,5,6,7,8,8a-hexahydroimidazo[1,5-a]pyrazine-8-carboxylate (compound 82-C) without chiral separation of two trans isomers. Example 99 was obtained as a mixture of two isomers (light yellow solid, 79 mg). ¹H NMR (400MHz, MeOD) δ=7.95 (d, J=3.0 Hz, 1H), 7.75 (d, J=3.3 Hz, 1H), 7.35-7.26 (m, 2H), 7.17 (t, J=8.2 Hz, 1H), 6.22 (s, 1H), 4.25 (d, J=17.1 Hz, 1H), 4.08-4.01 (m, 3H), 3.98 (s, 2H), 3.20-3.09 (m, 3H), 2.61 (t, J=12.7 Hz, 1H), 2.52-2.42 (m, 2H), 2.34-2.23 (m, 1H), 2.08-1.97 (m, 1H), 1.12 (t, J=7.2 Hz, 3H). MS: calc'd 562 (MH⁺), measured 562 (MH⁺).

Preparation of trans-6-oxo-2,3,4,7,8,8a-hexahydro-1H-pyrrolo[1,2-a]pyrazine-1-carboxylic acid (Compound 99-A)

82-C-2
mixture of two trans isomer

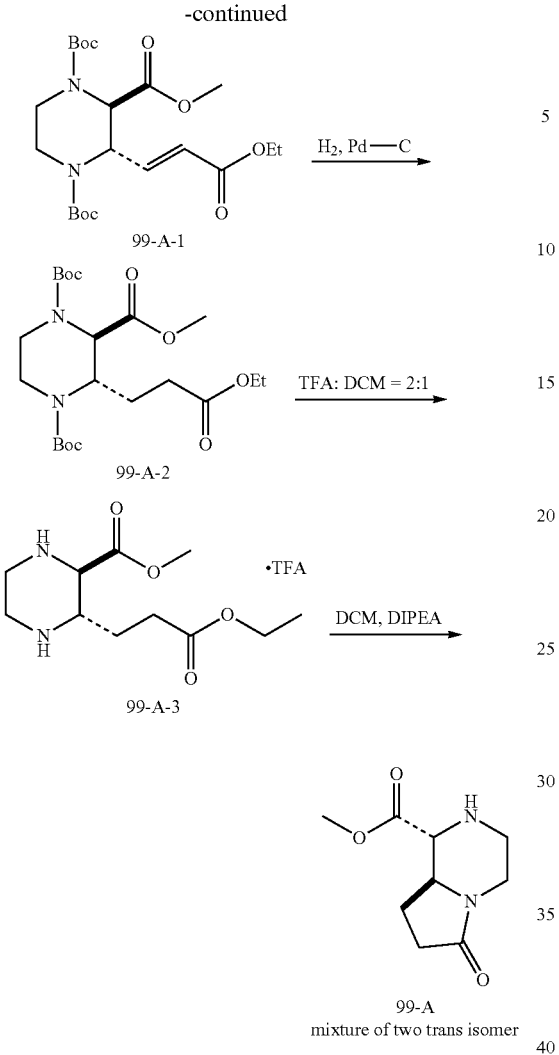

Step 1: To a stirred solution of compound 82-C-2 (12 g, 32.3 mmol) in DCM (100 mL) was added TEA (6.6 g, 64.5 mmol) and ethyl (triphenylphosphoranylidene)acetate (12.3 g, 35.5 mmol). The mixture was stirred at 25° C. for 15 h. Water (100 mL) was added, and the mixture was extracted with DCM (100 mL). The organic layer was separated and dried over $Na_2SO_4$. The solvent was removed and the residue was purified by column to give compound 99-A-1 (10 g). $^1$H NMR (400MHz, $CDCl_3$) δ=4.90-4.76 (m, 1H), 4.71-4.48 (m, 1H), 4.24-4.08 (m, 2H), 4.03-3.90 (m, 1H), 3.85-3.71 (m, 5H), 3.21-2.87 (m, 2H), 2.31 (dq, J=8.5, 16.5 Hz, 2H), 2.22-2.05 (m, 1H), 1.98-1.80 (m, 1H), 1.57-1.40 (m, 21H), 1.33-1.23 (m, 3H).

Step 2: To a stirred solution of compound 99-A-1 (20 g, 45.2 mmol) in MeOH (600 mL) was added Pd/C (10 g). The mixture was stirred at 30° C. (50 Psi) for 15 h. The mixture was filtered and the solvent was removed in vacuum to give crude product, which was purified by column to give compound 99-A-2 (17 g, crude).

Step 3: To a stirred solution of compound 99-A-2 (17 g, 38.2 mmol) in anhydrous DCM (90 mL) was added TFA (180 mL). After the reaction mixture was stirred for 3 hours, the solvent was removed in vacuum to give crude product 99-A-3 (19 g, crude).

Step 4: To a stirred solution of compound 99-A-3 (11 g, 25.1 mmol) in anhydrous DCM (250 mL) was added DIPEA (16 g, 125.6 mmol). After the mixture was refluxed for 4 hours, the solvent was removed to give the crude product 99-A (7 g), which was used directly in the next step.

Example 101A and 101B (Separated Two Single Isomers)

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-isobutyl-3-oxo-5,6,8,8a-tetrahydro-H-imidazo[1,5-a]pyrazine-8-carboxylic acid; and (8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-isobutyl-3-oxo-5,6,8,8a-tetrahydro-H-imidazo[1,5-a]pyrazine-8-carboxylic acid

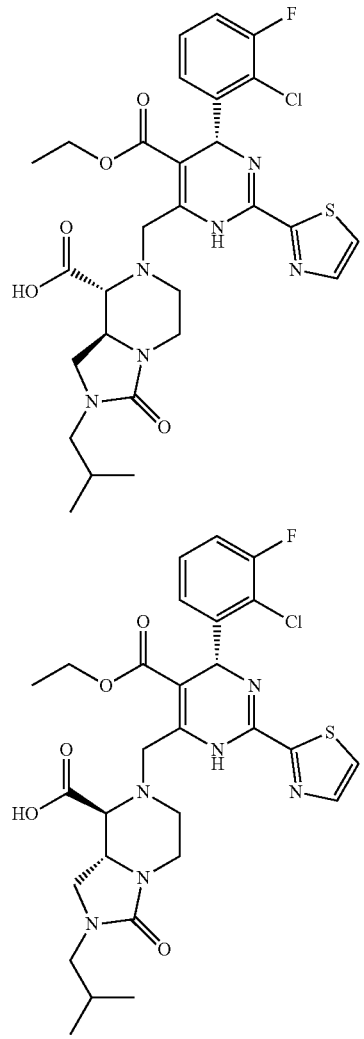

Preparation of Example 101A and 101B
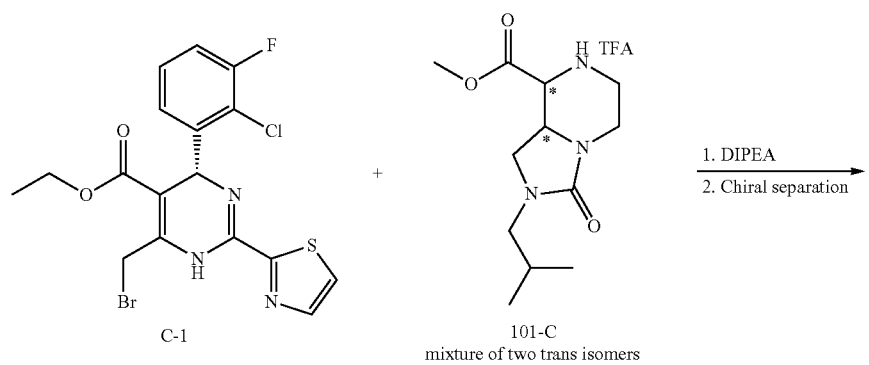
C-1
101-C
mixture of two trans isomers
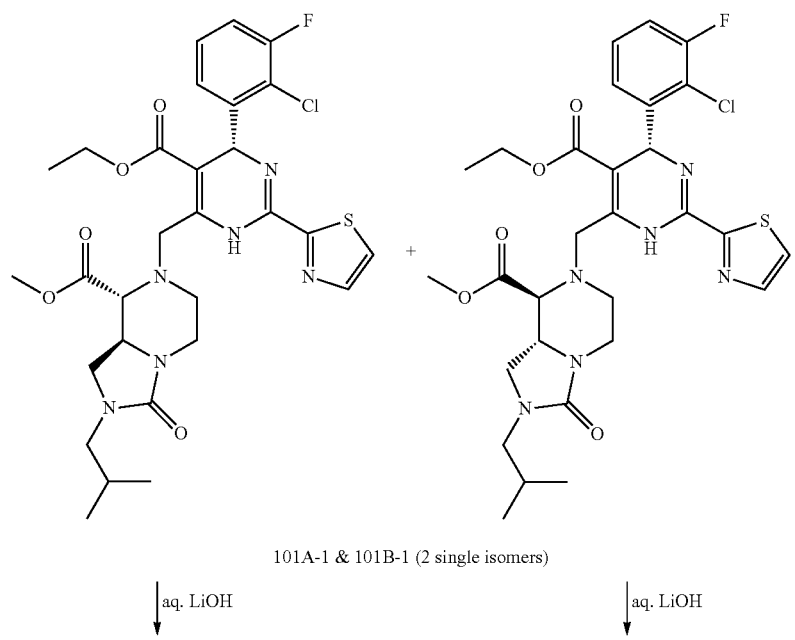
101A-1 & 101B-1 (2 single isomers)
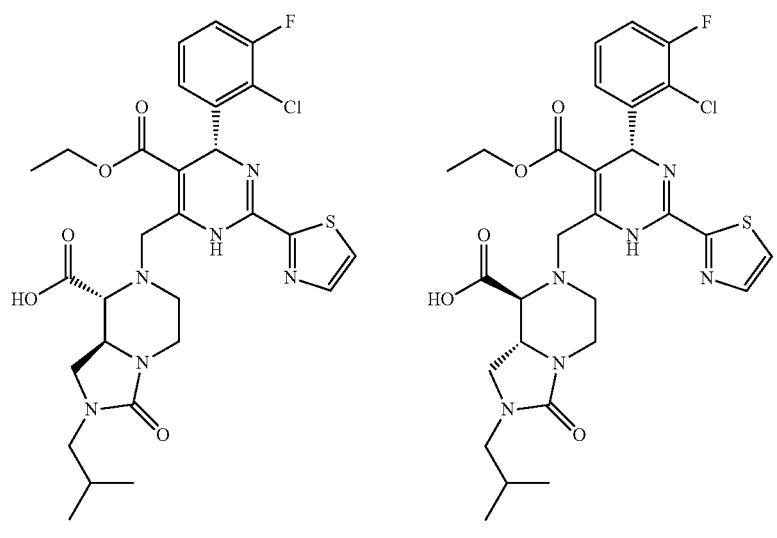
101A & 101B The title two compounds were prepared in analogy to Examples 82A and 82B by using trans-methyl 2-isobutyl-3-oxo-1,5,6,7,8,8a-hexahydroimidazo[1,5-a]pyrazine-8-carboxylate (compound 101-C) instead of trans-methyl 2-cyclopropyl-3-oxo-1,5,6,7,8,8a-hexahydroimidazo[1,5-a]pyrazine-8-carboxylate (compound 82-C).

Example 101A was obtained as a light yellow solid (10 mg). $^1$H NMR (400 MHz, METHANOL-$d_4$) d ppm 7.98 (d, J=3.3 Hz, 1H), 7.78 (d, J=3.3 Hz, 1H), 7.34-7.27 (m, 2H), 7.19-7.13 (m, 1H), 6.25 (s, 1H), 4.31 (d, J=17.1 Hz, 1H), 4.09-4.01 (m, 2H), 3.94-3.86 (m, 2H), 3.83-3.76 (m, 1H), 3.60-3.48 (m, 2H), 3.29 (d, J=9.5 Hz, 1H), 3.25-3.16 (m, 1H), 3.10-2.98 (m, 2H), 2.90 (d, J=11.0 Hz, 1H), 2.57-2.45 (m, 1H), 1.99-1.88 (m, 1H), 1.13 (t, J=7.0 Hz, 3H), 0.95 (dd, J=4.9, 6.7 Hz, 6H). MS: calc'd 619 (MH$^+$), measured 619 (MH$^+$).

Example 101B was obtained as a light yellow solid (14 mg). $^1$H NMR (400 MHz, METHANOL-$d_4$) d ppm 7.96 (d, J=3.3 Hz, 1H), 7.76 (d, J=3.0 Hz, 1H), 7.36-7.27 (m, 2H), 7.19-7.14 (m, 1H), 6.21 (s, 1H), 4.24 (d, J=16.8 Hz, 1H), 4.07-3.93 (m, 3H), 3.92-3.82 (m, 2H), 3.59-3.45 (m, 2H), 3.29-3.18 (m, 2H), 3.03 (dd, J=7.5, 11.0 Hz, 3H), 2.66-2.56 (m, 1H), 1.98-1.88 (m, 1H), 1.12 (t, J=7.0 Hz, 3H), 0.94 (d, J=6.8 Hz, 6H). MS: calc'd 619 (MH$^+$), measured 619 (MH$^+$).

Example 101A was synthesized from compound 101A-1 (faster eluting) and Example 101B was synthesized from compound 101B-1 (slower eluting) on ChiralPak AD-3 column eluting with 30% isopropanol (0.05% DEA)/CO$_2$.

Preparation of trans-methyl 2-isobutyl-3-oxo-1,5,6,7,8,8a-hexahydroimidazo[1,5-a]pyrazine-8-carboxylate (Compound 101-C)

Compound 101-C was prepared in analogy to compound 82-C by using 2-methylpropan-1-amine instead of cyclopropylamine.

Example 102A and 102B (Separated Two Single Isomers)

(8R,8aR)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-oxazolo[3,4-a]pyrazine-8-carboxylic acid; and (8S,8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-oxazolo[3,4-a]pyrazine-8-carboxylic acid

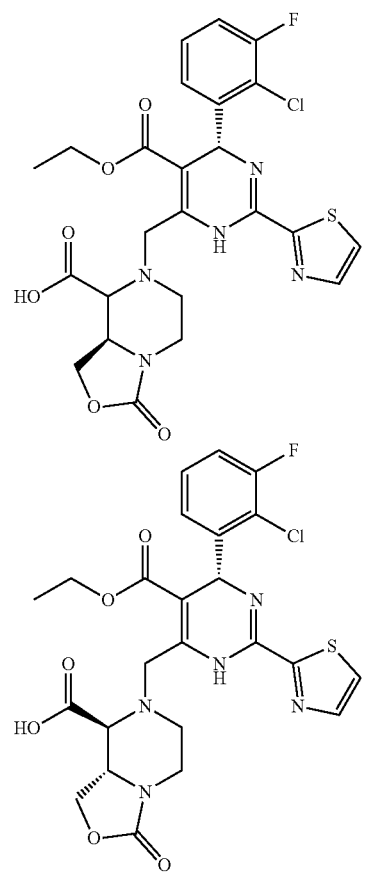

Preparation of Example 102A and 102B

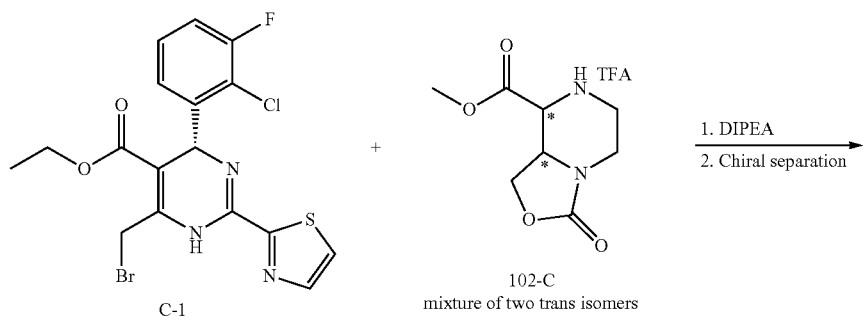

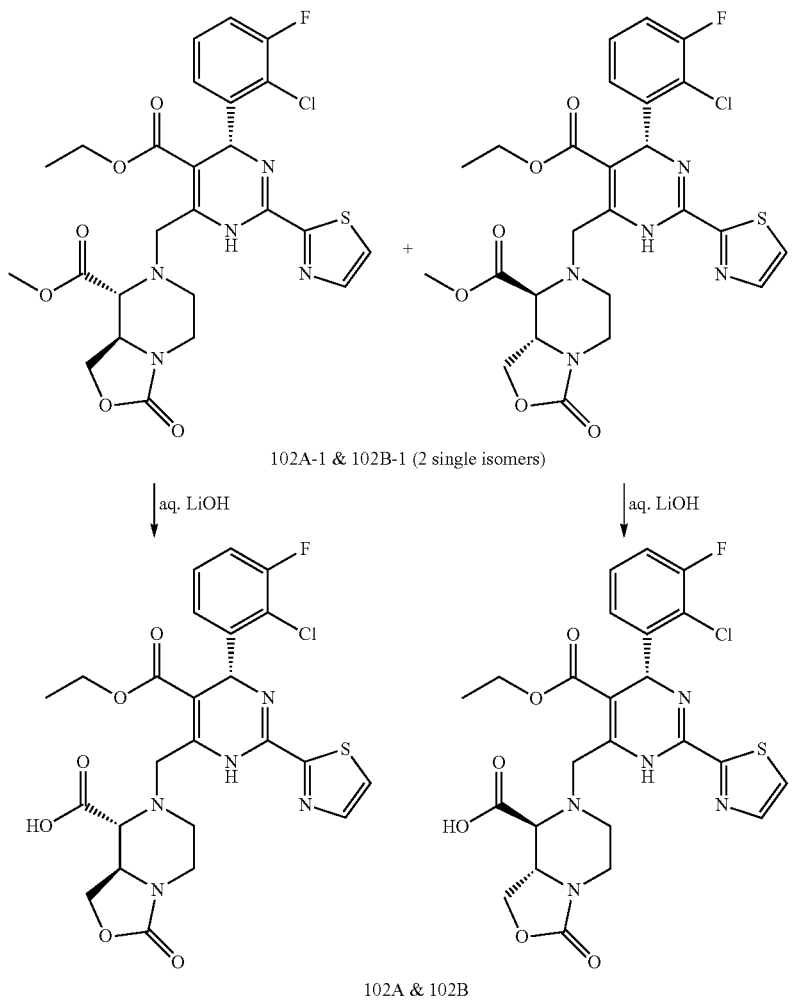

102A-1 & 102B-1 (2 single isomers)

102A & 102B

The title two compounds were prepared in analogy to Example 82A and 82B by using trans-methyl 3-oxo-1,5,6,7,8,8a-hexahydrooxazolo[3,4-a]pyrazine-8-carboxylate (compound 102-C) instead of trans-methyl 2-cyclopropyl-3-oxo-1,5,6,7,8,8a-hexahydroimidazo[1,5-a]pyrazine-8-carboxylate (compound 82-C).

Example 102A was obtained as a light yellow solid (29 mg). $^1$H NMR (400 MHz, METHANOL-$d_4$) d ppm 7.97 (d, J=3.3 Hz, 1H), 7.78 (d, J=3.0 Hz, 1H), 7.35-7.27 (m, 2H), 7.20-7.13 (m, 1H), 6.26 (s, 1H), 4.63-4.53 (m, 1H), 4.44 (dd, J=6.0, 9.3 Hz, 1H), 4.28 (d, J=17.1 Hz, 1H), 4.15-3.97 (m, 4H), 3.77 (dd, J=2.3, 13.3 Hz, 1H), 3.47 (d, J=9.8 Hz, 1H), 3.30 (d, J=3.5 Hz, 1H), 2.96 (dd, J=2.1, 12.2 Hz, 1H), 2.68-2.58 (m, 1H), 1.13 (t, J=7.2 Hz, 3H). MS: calc'd 564 (MH$^+$), measured 564 (MH$^+$).

Example 102B was obtained as a light yellow solid (27 mg). $^1$H NMR (400 MHz, METHANOL-$d_4$) d ppm 7.95 (d, J=3.3 Hz, 1H), 7.77 (d, J=3.0 Hz, 1H), 7.35-7.28 (m, 2H), 7.20-7.14 (m, 1H), 6.23 (s, 1H), 4.61-4.53 (m, 1H), 4.40 (dd, J=6.3, 9.3 Hz, 1H), 4.23-4.17 (m, 1H), 4.13-4.02 (m, 4H), 3.80 (dd, J=2.5, 13.6 Hz, 1H), 3.46 (d, J=9.8 Hz, 1H), 3.39-3.27 (m, 1H), 3.08 (dd, J=2.3, 12.3 Hz, 1H), 2.73 (dt, J=3.6, 12.2 Hz, 1H), 1.13 (t, J=7.2 Hz, 3H). MS: calc'd 564 (MH$^+$), measured 564 (MH$^+$).

Example 102A was synthesized from compound 102A-1 (faster eluting) and Example 102B was synthesized from compound 102B-1 (slower eluting) on ChiralPak AD-3 column eluting with 30% isopropanol (0.05% DEA)/CO$_2$.

Preparation of trans-methyl 3-oxo-1,5,6,7,8,8a-hexahydrooxazolo[3,4-a]pyrazine-8-carboxylate (compound 102-C)

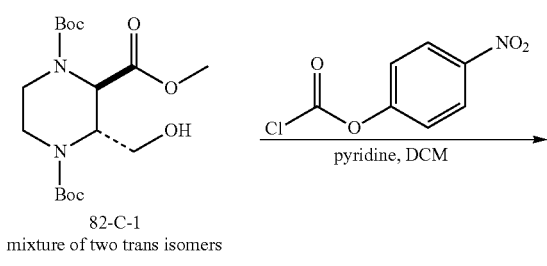

82-C-1
mixture of two trans isomers

249

-continued

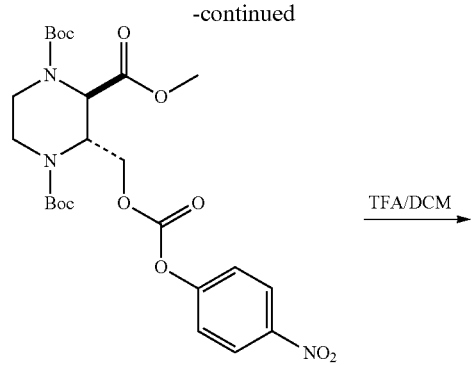

102-C-1

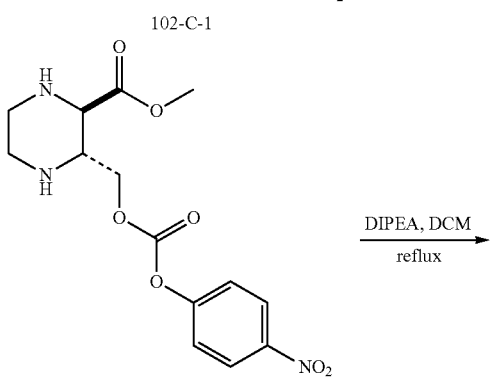

102-C-2

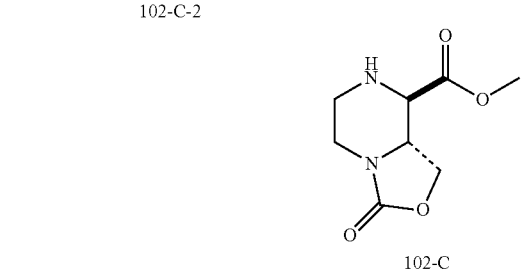

102-C
mixture of two trans isomers

Step I: To a stirred solution of compound 82-C-1 (8.6 g, 23 mmol) and pyridine (3.64 g, 46 mmol) in DCM (80 mL) was added a solution of (4-nitrophenyl) carbonochloridate (6.95 g, 34.5 mmol) in DCM (20 mL) at 0° C. Then the mixture was warmed to rt and stirred for about 2~3 hrs. The solvent was diluted with DCM (100 mL) and the mixture was washed successively with 0.6N HCl (50 mL), aq. NaHCO$_3$ (50 mL) and brine. The organic layer was dried over Na$_2$SO$_4$, filtered and concentrated in vacuum. The obtained crude product was purified by column chromatography on silica to get the title product 102-C-1 (9.5 g). $^1$H NMR (400 MHz, CDCl$_3$) d ppm 8.30 (d, J=8.8 Hz, 2H), 7.43 (t, J=8.5 Hz, 2H), 5.30-5.09 (m, 1H), 4.88-4.71 (m, 1H), 4.54-4.23 (m, 2H), 4.08-3.93 (m, 1H), 3.91-3.77 (m, 5H), 3.33-2.97 (m, 1H), 3.33-2.97 (m, 1H), 1.51-1.47 (t, 18H)

Step II: To a solution of compound 102-C-1 (9.5 g, 17.6 mmol) in DCM (70 mL) was added TFA (70 mL) at room temperature. Then the mixture was stirred for about 3 h. The solvent was removed under reduced pressure to give the crude product 102-C-2 (10 g crude) as TFA salt which was used in the next step without further purification.

250

Step III: To a stirred solution of compound 102-C-2 (crude, 10 g, 17.6 mmol) in DCM (160 mL) was added DIPEA (28 mL) at room temperature. Then the mixture was heated to reflux and stirred for about 4 h. The crude product was purified by column chromatography on silica to give the title compound 102-C (2 g). MS: calc'd 201 (MH$^+$), measured 201 (MH$^+$).

Example 103A and 103B (Separated Two Single Isomers)

Ethyl (4R)-6-[[(8R,8aS)-2-tert-butyl-8-(hydroxymethyl)-3-oxo-5,6,8,8a-tetrahydro-1H-imidazo[1,5-a]pyrazin-7-yl]methyl]-4-(2-chloro-3-fluoro-phenyl)-2-thiazol-2-yl-1,4-dihydropyrimidine-5-carboxylate; and Ethyl (4R)-6-[[(8S,8aR)-2-tert-butyl-8-(hydroxymethyl)-3-oxo-5,6,8,8a-tetrahydro-1H-imidazo[1,5-a]pyrazin-7-yl]methyl]-4-(2-chloro-3-fluoro-phenyl)-2-thiazol-2-yl-1,4-dihydropyrimidine-5-carboxylate

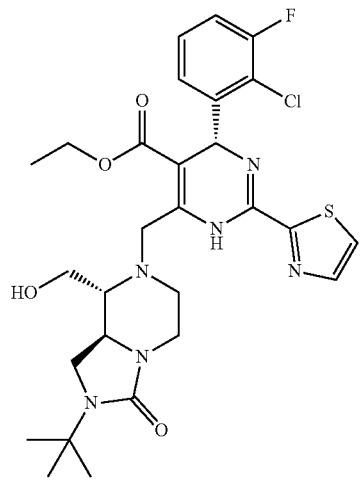

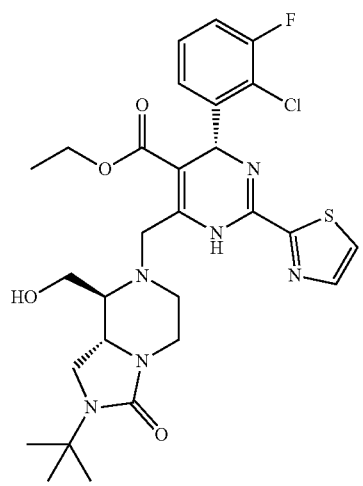

Preparation of Example 103A and 103B

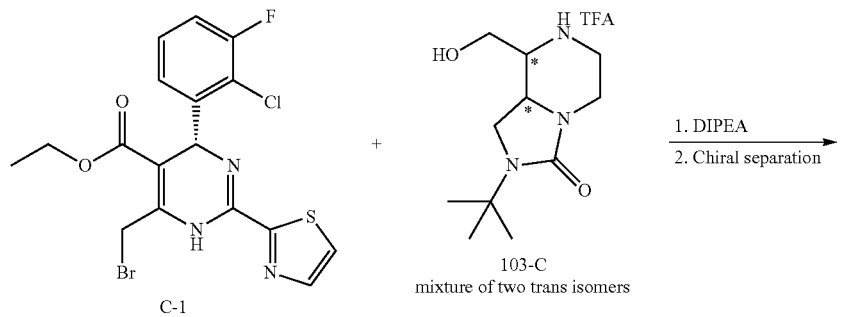

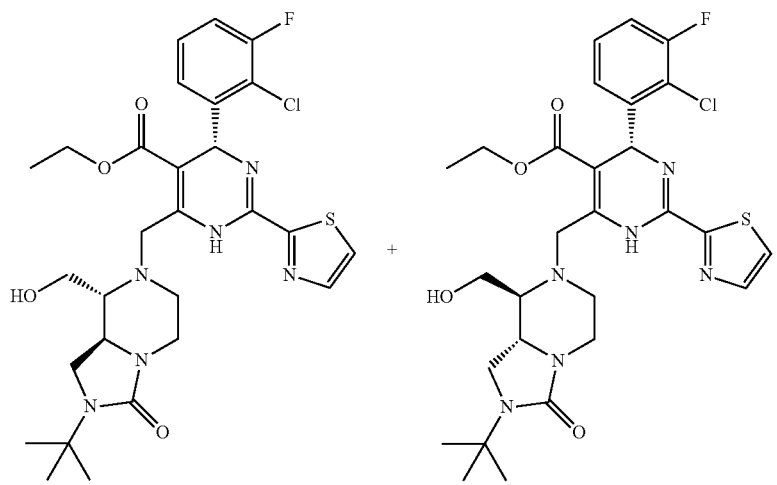

103A & 103B (2 single isomers)

The title two compounds were prepared in analogy to Example 82A-1 and 82B-1 by using trans-2-tert-butyl-8-(hydroxymethyl)-1,5,6,7,8,8a-hexahydroimidazo[1,5-a]pyrazin-3-one (compound 103-C) instead of trans-methyl 2-cyclopropyl-3-oxo-1,5,6,7,8,8a-hexahydroimidazo[1,5-a]pyrazine-8-carboxylate (compound 82-C).

Example 103A (faster eluting on ChiralPak AD-3 column with 30% isopropanol (0.05% DEA)/$CO_2$) was obtained as a light yellow solid (43 mg). $^1$H NMR (400 MHz, METHANOL-$d_4$) d ppm 7.95 (d, J=3.0 Hz, 1H), 7.74 (d, J=3.0 Hz, 1H), 7.35-7.26 (m, 2H), 7.19-7.11 (m, 1H), 6.25 (s, 1H), 4.43 (d, J=17.6 Hz, 1H), 4.13-4.01 (m, 3H), 3.97-3.84 (m, 1H), 3.75 (dd, J=4.0, 12.5 Hz, 1H), 3.69-3.60 (m, 2H), 3.58-3.51 (m, 1H), 3.28 (dd, J=7.2, 8.7 Hz, 1H), 3.01 (dt, J=3.1, 12.4 Hz, 1H), 2.81-2.71 (m, 1H), 2.53-2.41 (m, 2H), 1.39 (s, 9H), 1.13 (t, J=7.2 Hz, 3H). MS: calc'd 605 (MH$^+$), measured 605 (MH$^+$).

Example 103B (slower eluting on ChiralPak AD-3 column eluting with 30% isopropanol (0.05% DEA)/$CO_2$) was obtained as a light yellow solid (25 mg). $^1$H NMR (400 MHz, METHANOL-$d_4$) d ppm 7.98-7.92 (m, 1H), 7.77-7.70 (m, 1H), 7.33-7.23 (m, 2H), 7.19-7.11 (m, 1H), 6.24 (s, 1H), 4.53 (d, J=17.8 Hz, 1H), 4.08-3.95 (m, 3H), 3.74-3.62 (m, 4H), 3.57-3.47 (m, 1H), 3.26 (dd, J=7.4, 8.7 Hz, 1H), 3.07-2.99 (m, 1H), 2.94 (d, J=11.8 Hz, 1H), 2.61 (dt, J=3.5, 11.8 Hz, 1H), 2.50-2.40 (m, 1H), 1.39 (s, 9H), 1.16-1.10 (m, 3H). MS: calc'd 605 (MH$^+$), measured 605 (MH$^+$).

Preparation of trans-methyl 3-oxo-1,5,6,7,8,8a-hexahydrooxazolo[3,4-a]pyrazine-8-carboxylate (Compound 102-C)

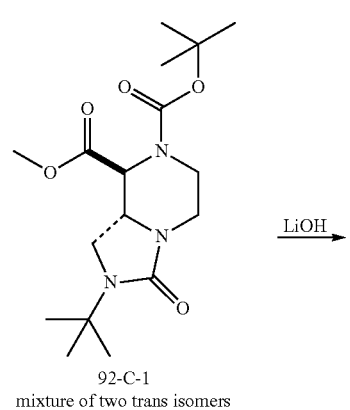

92-C-1
mixture of two trans isomers

253
-continued

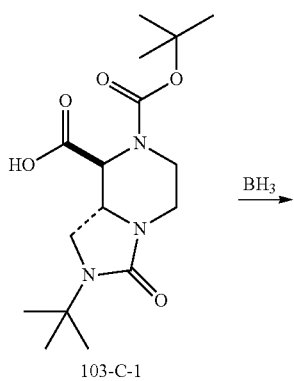

103-C-1

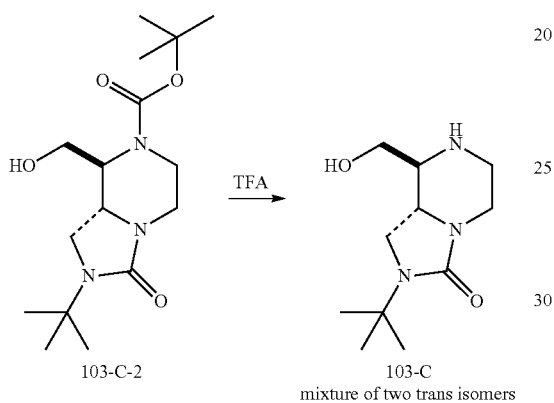

103-C-2     103-C
mixture of two trans isomers

Step I: LiOH.H$_2$O (1.26 g, 30 mmol) in H$_2$O (10 mL) was added to a solution of compound 92-C-1 (3.55 g, 10 mmol) in methanol (40 mL) at rt. After the mixture was stirred at rt for 5 h, methanol was removed under reduced pressure and the mixture was adjusted to pH=5 with 2N HCl solution. The mixture was extracted with ethyl acetate (50 mL, 3 times). The combined organic phase was dried and concentrated to afford crude product 103-C-1 (3.14 g) which was used in the next step without further purification. MS: calc'd 342 (MH$^+$), measured 342 (MH$^+$).

Step II: BH$_3$.THF (1M in THF, 30 mL) was added to a solution of compound 103-C-1 (3 g, 8.8 mmol) in THF (20 mL) at rt. After the reaction mixture was refluxed for 3 hours, it was cooled to 0° C. Methanol was added slowly to previous reaction mixture to quench the reaction. The solvent was removed and the residue was purified by column chromatography to afford product 103-C-2 (2.47 g). MS: calc'd 328 (MH$^+$), measured 328 (MH$^+$).

Step III: TFA (2 mL) was added to a stirring solution of compound 103-C-2 (2 g, 6.1 mmol) in CH$_2$Cl$_2$ (20 mL) at rt. After 3 hours, LC-MS indicated that the start materials were consumed. The solvent was removed to give the crude product 103-C which was used in the next step without further purification. MS: calc'd 228 (MH$^+$), measured 228 (MH$^+$).

254

Example 104A and 104B (Separated Two Single Isomers)

Ethyl (4R)-6-[[(8aR)-2-isopropyl-3-oxo-5,6,8,8a-tetrahydro-H-imidazo[1,5-a]pyrazin-7-yl]methyl]-4-(2-chloro-3-fluoro-phenyl)-2-thiazol-2-yl-1,4-dihydropyrimidine-5-carboxylate; and Ethyl (4R)-6-[[(8aS)-2-isopropyl-3-oxo-5,6,8,8a-tetrahydro-1H-imidazo[1,5-a]pyrazin-7-yl]methyl]-4-(2-chloro-3-fluoro-phenyl)-2-thiazol-2-yl-1,4-dihydropyrimidine-5-carboxylate

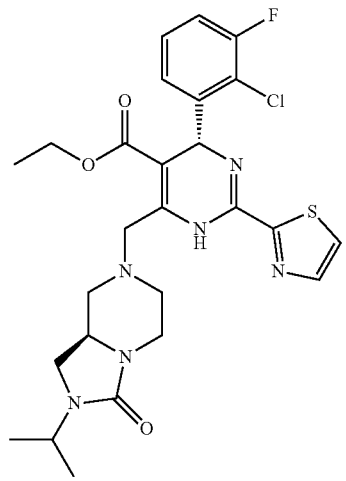

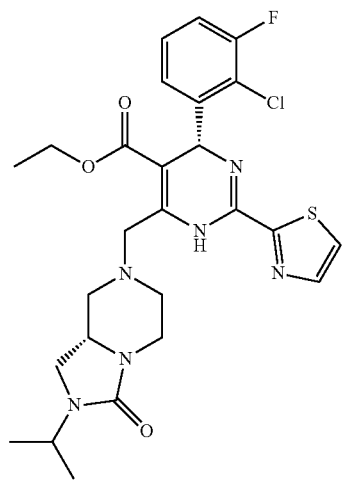

Preparation of Example 104A and 104B

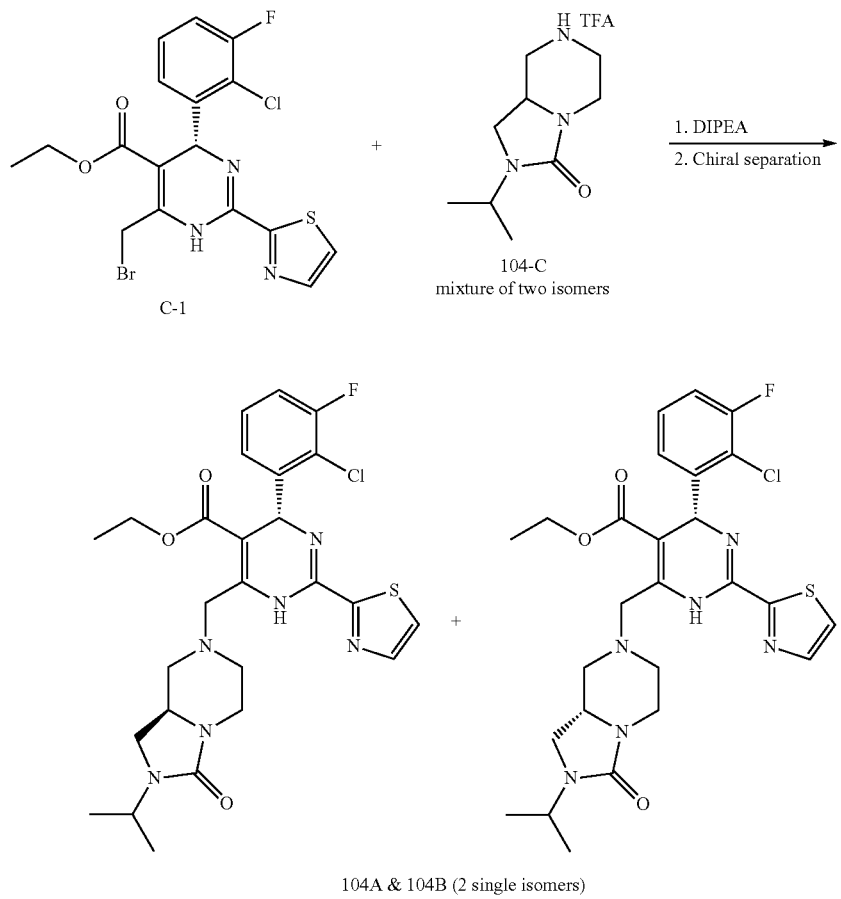

104A & 104B (2 single isomers)

The title two compounds were prepared in analogy to Example 82A-1 and 82B-1 by using 2-isopropyl-1,5,6,7,8,8a-hexahydroimidazo[1,5-a]pyrazin-3-one (compound 104-C) instead of trans-methyl 2-cyclopropyl-3-oxo-1,5,6,7,8,8a-hexahydroimidazo[1,5-a]pyrazine-8-carboxylate (compound 82-C).

Example 104A (faster eluting on ChiralPak AD-3 column with 30% isopropanol (0.05% DEA)/CO$_2$) was obtained as a light yellow solid (71 mg). $^1$H NMR (400 MHz, METHANOL-d$_4$) d ppm 7.96 (d, J=3.3 Hz, 1H), 7.75 (d, J=3.0 Hz, 1H), 7.32-7.24 (m, 2H), 7.15 (t, J=8.3 Hz, 1H), 6.24 (s, 1H), 4.12-4.01 (m, 4H), 3.94-3.85 (m, 2H), 3.80 (dd, J=2.0, 13.3 Hz, 1H), 3.51 (t, J=8.9 Hz, 1H), 3.18-3.04 (m, 2H), 2.99 (dd, J=2.8, 10.8 Hz, 1H), 2.79-2.67 (m, 1H), 2.29 (t, J=10.9 Hz, 1H), 2.25-2.17 (m, 1H), 1.20-1.10 (m, 9H). MS: calc'd 561 (MH$^+$), measured 561 (MH$^+$).

Example 103B (slower eluting on ChiralPak AD-3 column eluting with 30% isopropanol (0.05% DEA)/CO$_2$) was obtained as a light yellow solid (77 mg). $^1$H NMR (400 MHz, METHANOL-d$_4$) d ppm 7.96 (d, J=3.1 Hz, 1H), 7.75 (d, J=3.3 Hz, 1H), 7.33-7.23 (m, 2H), 7.15 (t, J=8.5 Hz, 1H), 6.24 (s, 1H), 4.13-4.00 (m, 4H), 3.94-3.83 (m, 3H), 3.45 (t, J=8.9 Hz, 1H), 3.22-3.12 (m, 1H), 3.00 (dd, J=4.0, 9.3 Hz, 1H), 2.93-2.80 (m, 2H), 2.34 (dt, J=3.4, 11.6 Hz, 1H), 2.15 (t, J=10.9 Hz, 1H), 1.18-1.09 (m, 9H). MS: calc'd 561 (MH$^+$), measured 561 (MH$^+$).

Preparation of 2-isopropyl-1,5,6,7,8,8a-hexahydroimidazo[1,5-a]pyrazin-3-one (Compound 104-C)

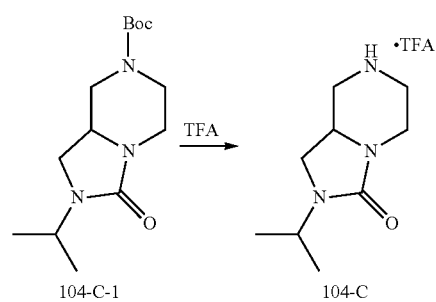 [SMILES: CC(C)N1CC2CN(C(=O)OC(C)(C)C)CCN2C1=O ; CC(C)N1CC2CNCCN2C1=O]

tert-Butyl 2-isopropyl-3-oxo-5,6,8,8a-tetrahydro-1H-imidazo[1,5-a]pyrazine-7-carboxylate (compound 104-C-1) (1 mmol) was dissolved in CH$_2$Cl$_2$ (3 mL) followed by the slow addition of TFA (1 mL) at 0° C. After the reaction mixture was stirred at rt for 1 hour, the solvent was removed in vacuum to give the crude product 104-C, which was used directly in the next step.

le;.3qPreparation of tert-Butyl 2-isopropyl-3-oxo-5,6,8,8a-tetrahydro-1H-imidazo[1,5-a]pyrazine-7-carboxylate (Compound 104-C-1)

Compound 104-C-1 was prepared in analogy to Compound 67-D by using iso-propyl amine instead of 2-aminoethanol.

Example 105A and 105B (Separated Two Single Isomers)

(8R,8aS)-7-[[(4R)-4-(2-chloro-3-fluoro-phenyl)-5-ethoxycarbonyl-2-thiazol-2-yl-1,4-dihydropyrimidin-6-yl]methyl]-2-(2,2-difluoroethyl)-3-oxo-5,6,8,8a-tetrahydro-1H-imidazo[1,5-a]pyrazine-8-carboxylic acid; and (8S,8aR)-7-[[(4R)-4-(2-chloro-3-fluoro-phenyl)-5-ethoxycarbonyl-2-thiazol-2-yl-1,4-dihydropyrimidin-6-yl]methyl]-2-(2,2-difluoroethyl)-3-oxo-5,6,8,8a-tetrahydro-1H-imidazo[1,5-a]pyrazine-8-carboxylic acid

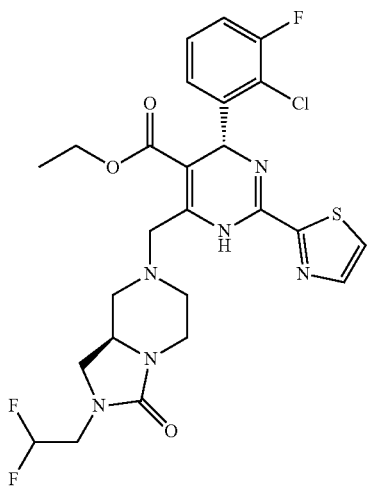

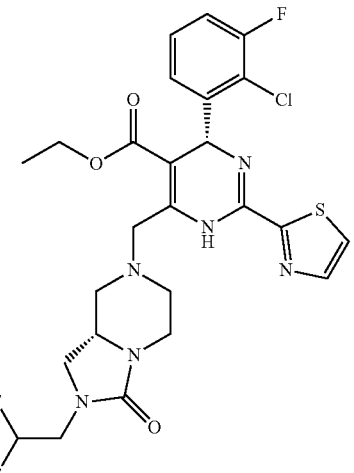

Preparation of Example 105A and 105B

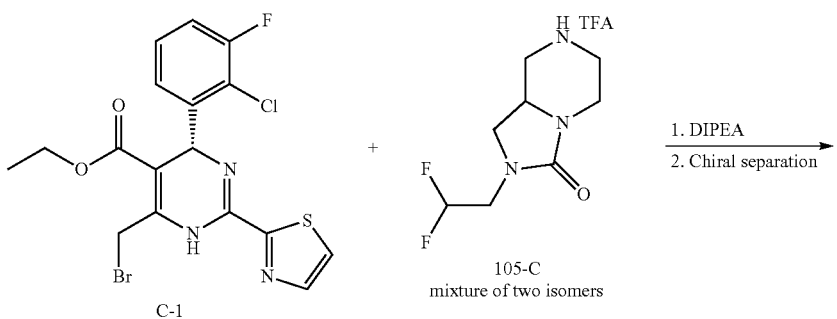

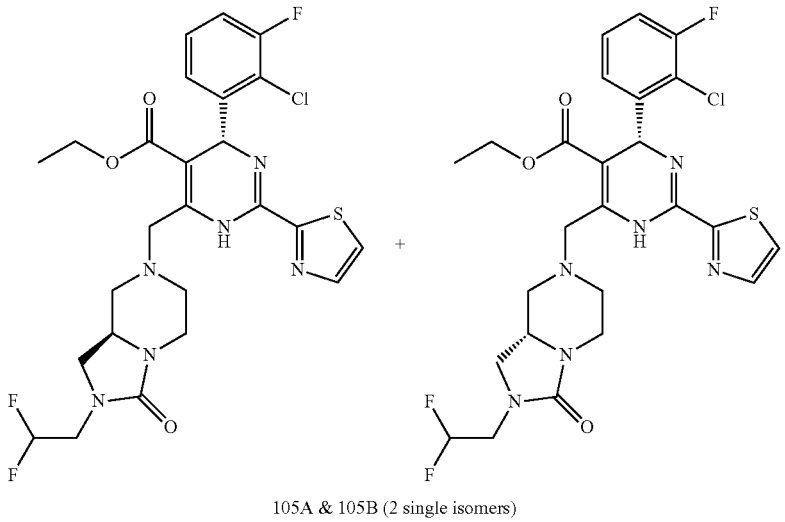

105A & 105B (2 single isomers)

The title two compounds were prepared in analogy to Example 82A-1 and 82B-1 by using 2-(2,2-difluoroethyl)-1,5,6,7,8,8a-hexahydroimidazo[1,5-a]pyrazin-3-one (compound 105-C) instead of trans-methyl 2-cyclopropyl-3-oxo-1,5,6,7,8,8a-hexahydroimidazo[1,5-a]pyrazine-8-carboxylate (compound 82-C).

Example 105A (faster eluting on ChiralPak AD-3 column with 30% isopropanol (0.05% DEA)/CO$_2$) was obtained as a light yellow solid (22 mg). $^1$H NMR (400 MHz, METHANOL-d$_4$) d ppm 7.97 (d, J=3.3 Hz, 1H), 7.77 (d, J=3.0 Hz, 1H), 7.34-7.26 (m, 2H), 7.19-7.12 (m, 1H), 6.25 (s, 1H), 6.17-5.83 (m, 1H), 4.31 (d, J=17.1 Hz, 1H), 4.08-4.00 (m, 2H), 3.96-3.86 (m, 2H), 3.80 (dd, J=2.0, 13.6 Hz, 1H), 3.74-3.68 (m, 1H), 3.66-3.56 (m, 3H), 3.28-3.16 (m, 1H), 2.95-2.87 (m, 2H), 2.53 (dt, J=3.4, 12.0 Hz, 1H), 1.13 (t, J=7.2 Hz, 3H). MS: calc'd 627 (MH$^+$), measured 627 (MH$^+$).

Example 105B (slower eluting on ChiralPak AD-3 column eluting with 30% isopropanol (0.05% DEA)/CO$_2$) was obtained as a light yellow solid (22 mg). $^1$H NMR (400 MHz, METHANOL-d$_4$) d ppm 7.96 (d, J=3.0 Hz, 1H), 7.76 (d, J=3.0 Hz, 1H), 7.35-7.27 (m, 2H), 7.17 (t, J=8.1 Hz, 1H), 6.21 (s, 1H), 6.16-5.83 (m, 1H), 4.23 (d, J=16.6 Hz, 1H), 4.06-4.00 (m, 2H), 3.98-3.81 (m, 3H), 3.72-3.66 (m, 1H), 3.65-3.55 (m, 3H), 3.29-3.17 (m, 2H), 3.04 (d, J=10.3 Hz, 1H), 2.66-2.54 (m, 1H), 1.12 (t, J=7.2 Hz, 3H). MS: calc'd 627 (MH$^+$), measured 627 (MH$^+$).

Preparation of 2-(2,2-difluoroethyl)-1,5,6,7,8,8a-hexahydroimidazo[1,5-a]pyrazin-3-one (Compound 105-C)

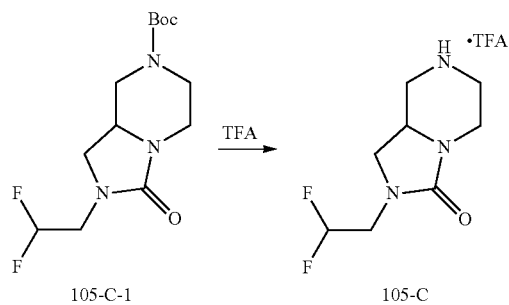 [SMILES: CC(C)(C)OC(=O)N1CCN2C(=O)N(CC(F)F)CC2C1 ; O=C1N(CC(F)F)CC2CNCCN12]

105-C-1                    105-C tert-Butyl 2-(2,2-difluoroethyl)-3-oxo-5,6,8,8a-tetrahydro-1H-imidazo[1,5-a]pyrazine-7-carboxylate (compound 105-C-1) (1 mmol) was dissolved in CH$_2$Cl$_2$ (3 mL) followed by the slow addition of TFA (1 mL) at 0° C. After the reaction mixture was stirred at rt for 1 hour, the solvent was removed in vacuum to give the crude product 105-C, which was used directly in the next step.

Preparation of tert-butyl 2-(2,2-difluoroethyl)-3-oxo-5,6,8,8a-tetrahydro-1H-imidazo[1,5-a]pyrazine-7-carboxylate (Compound 105-C-1)

Compound 105-C-1 was prepared in analogy to Compound 67-D by using 2,2-difluoroethanamine instead of 2-aminoethanol.

261

Example 106A and 106B (Separated Two Single Isomers)

Ethyl (4R)-6-[[(8aR)-2-(2-hydroxy-2-methyl-propyl)-3-oxo-5,6,8,8a-tetrahydro-1H-imidazo[1,5-a]pyrazin-7-yl]methyl]-4-(2-chloro-3-fluoro-phenyl)-2-thiazol-2-yl-1,4-dihydropyrimidine-5-carboxylate; and Ethyl (4R)-6-[[(8aS)-2-(2-hydroxy-2-methyl-propyl)-3-oxo-5,6,8,8a-tetrahydro-1H-imidazo[1,5-a]pyrazin-7-yl]methyl]-4-(2-chloro-3-fluoro-phenyl)-2-thiazol-2-yl-1,4-dihydropyrimidine-5-carboxylate

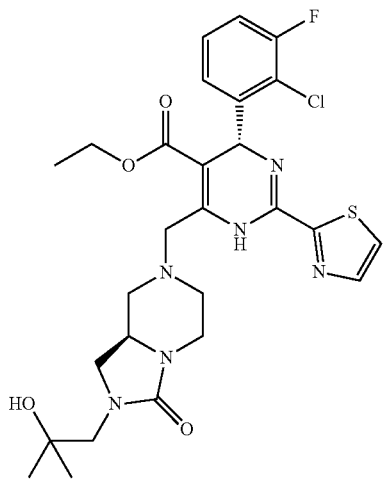

262

-continued

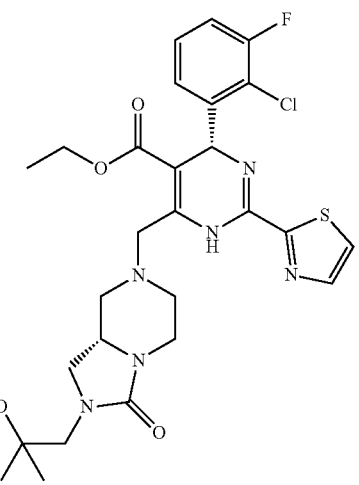

Preparation of Example 106A and 106B

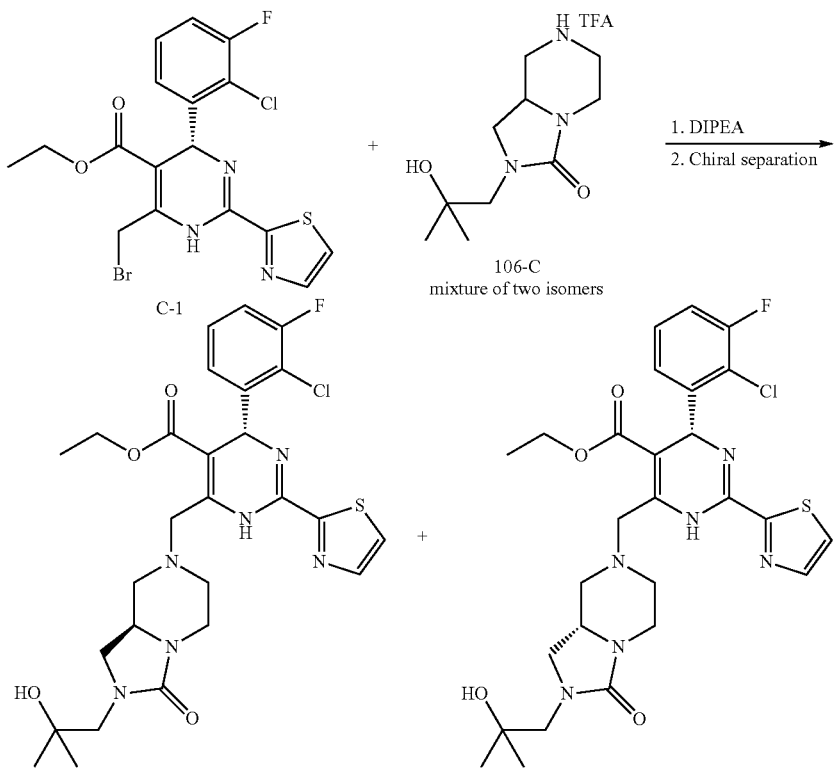

106A & 106B (2 single isomers)

The title two compounds were prepared in analogy to Example 82A-1 and 82B-1 by using 2-(2-hydroxy-2-methyl-propyl)-1,5,6,7,8,8a-hexahydroimidazo[1,5-a]pyrazin-3-one (compound 106-C) instead of trans-methyl 2-cyclopropyl-3-oxo-1,5,6,7,8,8a-hexahydroimidazo[1,5-a]pyrazine-8-carboxylate (compound 82-C).

Example 106A (faster eluting on ChiralPak AD-3 column with 30% isopropanol (0.05% DEA)/CO$_2$) was obtained as a light yellow solid (18 mg). $^1$H NMR (400 MHz, METHANOL-d$_4$) d ppm 7.96 (d, J=3.0 Hz, 1H), 7.76 (d, J=3.3 Hz, 1H), 7.33-7.24 (m, 2H), 7.15 (t, J=8.2 Hz, 1H), 6.25 (s, 1H), 4.14-4.01 (m, 3H), 3.97-3.88 (m, 2H), 3.80 (dd, J=2.0, 13.3 Hz, 1H), 3.75-3.69 (m, 1H), 3.36 (d, J=4.3 Hz, 1H), 3.24-3.15 (m, 2H), 3.13-3.07 (m, 1H), 3.01 (dd, J=2.9, 10.9 Hz, 1H), 2.76 (d, J=11.3 Hz, 1H), 2.36 (t, J=10.9 Hz, 1H), 2.22 (dt, J=3.1, 11.6 Hz, 1H), 1.22 (s, 6H), 1.13 (t, J=7.2 Hz, 3H). MS: calc'd 591 (MH$^+$), measured 591 (MH$^+$).

Example 106B (slower eluting on ChiralPak AD-3 column eluting with 30% isopropanol (0.05% DEA)/CO$_2$) was obtained as a light yellow solid (26 mg). $^1$H NMR (400 MHz, METHANOL-d$_4$) d ppm 7.97 (d, J=3.3 Hz, 1H), 7.76 (d, J=3.3 Hz, 1H), 7.34-7.24 (m, 2H), 7.16 (t, J=8.2 Hz, 1H), 6.24 (s, 1H), 4.13-4.01 (m, 3H), 3.96-3.84 (m, 3H), 3.66 (t, J=9.2 Hz, 1H), 3.30-3.16 (m, 3H), 3.14-3.03 (m, 1H), 2.95-2.83 (m, 2H), 2.36 (dt, J=3.4, 11.6 Hz, 1H), 2.22 (t, J=10.9 Hz, 1H), 1.21 (s, 6H), 1.13 (t, J=7.0 Hz, 3H). MS: calc'd 591 (MH$^+$), measured 591 (MH$^+$).

Preparation of 2-(2-hydroxy-2-methyl-propyl)-1,5,6,7,8,8a-hexahydroimidazo[1,5-a]pyrazin-3-one (Compound 106-C)

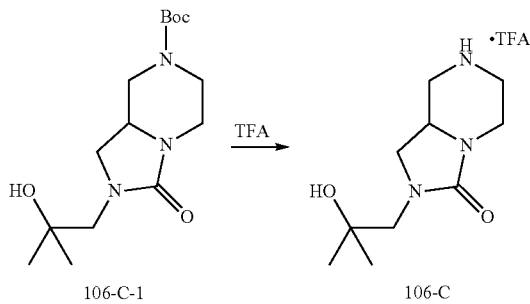 [SMILES: CC(C)(O)CN1CC2CN(C(=O)OC(C)(C)C)CCN2C1=O ; CC(C)(O)CN1CC2CNCCN2C1=O]

106-C-1          106-C tert-Butyl 2-(2-hydroxy-2-methyl-propyl)-3-oxo-5,6,8,8a-tetrahydro-1H-imidazo[1,5-a]pyrazine-7-carboxylate (compound 106-C-1) (1 mmol) was dissolved in CH$_2$Cl$_2$ (3 mL) followed by the slow addition of TFA (1 mL) at 0° C. After the reaction mixture was stirred at rt for 1 hour, the solvent was removed in vacuum to give the crude product 106-C, which was used directly in the next step.

Preparation of tert-butyl 2-(2,2-difluoroethyl)-3-oxo-5,6,8,8a-tetrahydro-1H-imidazo[1,5-a]pyrazine-7-carboxylate (Compound 106-C-1)

Compound 105-C-1 was prepared in analogy to Compound 67-D by using 1-amino-2-methyl-propan-2-ol instead of 2-aminoethanol.

Example 107

HBV Inhibition Assays

Cells and Culture Conditions:
HepG2.2.15 and HepDE19 are stably-transfected cell lines containing the HBV genome. Both cell lines are derived from the hepatoblastoma cell line Hep G2 (American Type Culture Collection, ATCC® HB-8065™) by the published procedures described in references: M A Selles et al. Proc. Natl. Acad. Sci. USA 1987, 84, 1005-1009 and H Guo et al. Journal of Virology 2007, 81, 12472-12484, respectively. Both cell lines were maintained in Dulbecco's modified Eagle's medium (DMEM)-F12 medium supplemented with 10% fetal bovine serum, 100 U/mL penicillin, 100 μg/mL streptomycin, and 0.5 mg/mL of G418.

While HepG2.2.15 cells constitutively support HBV replication and production of virus particles, HepDE19 cells are inducible by tetracycline. Addition of 1 μg/mL tetracycline in culture medium suppresses HBV replication in HepDE19 cells, whereas switching to tetracycline-free medium resumes this process.

Anti-HBV Activity In Vitro:

HepG2.2.15 cells were seeded into 96-well plates (3×10$^4$ cells in 100 μL media per well) and incubated overnight at 37° C. The test compounds were serially half-log diluted in DMSO, then diluted 100 times in culture media. 100 μL of diluted compounds were added into the plates to reach 0.5% final concentration of DMSO in every well. Five days after compound treatment, culture supernatant was collected for further analysis.

For quantitative PCR detection of extracellular HBV DNA, 100 μL of culture supernatant was collected and processed in MagNA Pure 96 Nucleic Acid Purification System (Roche Applied Science) for viral DNA extraction. The extracted samples were subjected to HBV DNA quantification by qPCR. The effective compound concentration at which HBV replication is inhibited by 50% (EC$_{50}$) was determined as shown in Table 1.

The compounds of the present invention were tested for their capacity to inhibit a HBV activity and activation as described herein. The Examples were tested in the above assays as described herein and found to have EC$_{50}$<0.2 μM in HepG2.2.15 assay. Particular compounds of formula (I) or other compounds of the present invention were found to have EC$_{50}$<0.02 μM in HepG2.2.15 assay.

TABLE 1

Anti-HBV activity data of particular compounds in HepG2.2.15 cells

| Example No. | EC$_{50}$ (μM) | Example No. | EC$_{50}$ (μM) |
|---|---|---|---|
| 1 | 0.104 | 2 | 0.054 |
| 3 | 0.023 | 4 | 0.003 |
| 5 | 0.159 | 6 | 0.014 |
| 7 | 0.014 | 8 | 0.011 |
| 9 | 0.064 | 10 | 0.057 |
| 11 | 0.001 | 12 | 0.149 |
| 13 | 0.066 | 14 | 0.002 |
| 15 | 0.110 | 16 | 0.041 |
| 17 | 0.039 | 18 | 0.108 |
| 19 | 0.003 | 20 | 0.052 |
| 21 | 0.016 | 22 | 0.003 |
| 23 | 0.003 | 24 | 0.001 |
| 25 | 0.002 | 26 | 0.002 |
| 27 | 0.003 | 28 | 0.030 |
| 29 | 0.007 | 30 | 0.095 |
| 31 | 0.100 | 32 | 0.199 |
| 33 | 0.030 | 34 | 0.008 |
| 35 | 0.011 | 36 | 0.006 |
| 37 | 0.017 | 38 | 0.005 |
| 39 | 0.030 | 40 | 0.034 |
| 41 | 0.014 | 42 | 0.006 |
| 43 | 0.006 | 44 | 0.016 |

TABLE 1-continued

Anti-HBV activity data of particular compounds in HepG2.2.15 cells

| Example No. | EC$_{50}$ (μM) | Example No. | EC$_{50}$ (μM) |
|---|---|---|---|
| 45 | 0.026 | 46 | 0.026 |
| 47 | 0.051 | 48 | 0.022 |
| 49 | 0.008 | 50 | 0.015 |
| 51 | 0.031 | 52 | 0.030 |
| 53 | 0.019 | 54 | 0.008 |
| 55 | 0.005 | 56 | 0.026 |
| 57 | 0.032 | 58 | 0.019 |
| 59 | 0.011 | 60 | 0.006 |
| 61 | 0.012 | 62 | 0.006 |
| 63 | 0.012 | 64 | 0.008 |
| 65 | 0.009 | 66 | 0.004 |
| 67 | 0.438 | 68 | 0.143 |
| 69 | 0.013 | 70 | 0.005 |
| 71 | 0.014 | 72 | 0.009 |
| 73 | 0.009 | 74 | 0.036 |
| 75 | 0.024 | 76 | 0.007 |
| 77 | 0.146 | 78 | 0.387 |
| 79 | 0.008 | 80 | 0.032 |
| 81 | 0.010 | 82A/82B | 0.145/0.002 |
| 83B | 0.009 | 84A/84B | 0.045/0.001 |
| 85A/85B | 0.259/0.006 | 86B | 0.004 |
| 87A/87B | 0.062/0.001 | 87B-1 | 0.004 |
| 88A/88B | 0.677/0.005 | 89 | 0.007 |
| 90A/90B | 0.096/0.300 | 91A/91B | 0.150/0.002 |
| 92A/92B | 0.078/0.0007 | 93 | 0.012 |
| 94 | 0.004 | 95 | 0.011 |
| 96 | 0.150 | 97A/97B | 0.037/0.0009 |
| 98 | 0.011 | 99 | 0.014 |
| 101A/101B | 0.040/0.0008 | 102A/102B | 0.147/0.014 |
| 103A/103B | 0.140/0.010 | 104A/104B | 0.131/0.004 |
| 105A/105B | 0.188/0.003 | 106A/106B | 0.032/0.003 |

Cytotoxicity and Selectivity Index:

HepDE19 cells were seeded into 96-well plates (5×10$^3$ cells per well) and treated with compounds for EC$_{50}$ determination. Five days after treatment, cell viability was measured by addition of 20 μL of CCK-8 reagent. Two hours after incubation at 37° C., the absorbance at wavelengths of 450 nm and 630 nm (OD$_{450}$ and OD$_{630}$) was recorded by a plate reader. The concentration results in the death of 50% of the host cells (CC$_{50}$) of each compound were determined.

The relative effectiveness of the compound in inhibiting viral replication compared to inducing cell death was defined as the selectivity index (CC$_{50}$ value/EC$_{50}$ value). Based on CC$_{50}$ and EC$_{50}$ data, selectivity indexes were determined.

Results of CC$_{50}$ and the corresponding selectivity index are given in Table 2.

TABLE 2

CC$_{50}$ and selectivity index of particular compounds

| Example No. | CC$_{50}$ (μM) | Selectivity index (CC$_{50}$/EC$_{50}$) | Example No. | CC$_{50}$ (μM) | Selectivity index (CC$_{50}$/EC$_{50}$) |
|---|---|---|---|---|---|
| 4 | 79 | 23872 | 11 | 52 | 30635 |
| 14 | 23 | 13016 | 19 | >100 | >30303 |
| 21 | >100 | >6211 | 22 | >100 | >34482 |
| 24 | 53 | 37857 | 26 | 28 | 18620 |
| 34 | 81 | 10655 | 35 | >100 | >9259 |
| 36 | >100 | >18181 | 38 | 100 | 21276 |
| 41 | >100 | >7194 | 42 | >100 | >15625 |
| 44 | >100 | >6369 | 54 | >100 | >12500 |
| 55 | >100 | >20000 | 59 | >100 | >9091 |
| 60 | 68 | 11333 | 61 | >100 | >8333 |
| 62 | >100 | >16667 | 63 | 91 | 7583 |
| 64 | 67 | 8375 | 65 | >100 | >11111 |
| 66 | 60 | 15000 | 70 | 63 | 12600 |
| 71 | >100 | >7143 | 73 | 70 | 7778 |
| 76 | >100 | >14286 | 79 | 52 | 6500 |
| 81 | 85 | 8500 | 82B | >100 | >50000 |
| 83B | >100 | >11111 | 84B | >100 | >100000 |
| 85B | >100 | >16667 | 86B | >100 | >25000 |
| 87B | >100 | >100000 | 88B | >100 | >20000 |
| 89 | 75 | 10714 | 91B | >100 | >50000 |
| 92B | 66 | 94285 | 93 | 86 | 7167 |
| 94 | 48 | 12000 | 97B | >100 | >100000 |
| 98 | 73 | 6636 | 99 | >100 | >7142 |
| 101B | >100 | >100000 | 102B | >100 | >7142 |
| 104B | 27 | >6750 | 105B | >100 | >33333 |
| 106B | 65 | 21666 | | | |

Example 108

Human Microsomal Metabolic Stability

Human Microsomes (BD Gentest) were preincubated with test compound for 10 minutes at 37° C. in 100 mM phosphate buffer, pH 7.4. The reactions were initiated by adding NADPH or NADPH regenerating system to give a final incubation volume of 400 μL. For NADPH system, the final incubations contained 1 μM test compound, 0.5 mg/mL liver microsomal protein, 1 mM NADPH in 100 mM phosphate buffer, pH 7.4. For the NADPH regenerating system, the final incubations contained 1 μM test compound, 0.5 mg/mL liver microsomal protein, 3 mM glucose 6-phosphate, 1 mM NADP, 3 mM MgCl$_2$ and 0.05 mg/mL glucose 6-phosphate dehydrogenase in 100 mM phosphate buffer, pH 7.4. After incubation times of 0, 3, 6, 9, 15 and 30 minutes at 37° C., 1 sample was obtained from each time point and 50 μL of each sample was removed and transferred to 150 μL of methanol solution which was maintained at 4° C. and contained 2 μM tolbutamide as internal standard. Following precipitation and centrifugation, the amount of compound remaining in the samples were determined by LC-MS/MS. Controls of no NADPH or no NADPH regenerating system at zero and 30 minutes were also prepared and analyzed.

Results of metabolic stability study in human microsome are given in Table 3.

TABLE 3

Metabolic stability in human microsome

| Example number | Human Microsomal Clearance (mL/min/kg) | Example number | Human Microsomal Clearance (mL/min/kg) |
|---|---|---|---|
| 19 | 0.4 | 20 | 0.1 |
| 21 | 2.7 | 25 | 0.4 |
| 28 | 4.4 | 29 | 0.3 |
| 30 | 1.7 | 31 | 0.3 |
| 32 | 1.6 | 33 | 2.5 |
| 34 | 1.8 | 35 | 0.3 |
| 36 | 4.4 | 37 | 2.5 |
| 38 | 2.0 | 39 | 0.4 |
| 41 | 2.0 | 42 | 2.0 |
| 43 | 3.1 | 44 | 1.7 |
| 45 | 0 | 46 | 0 |

TABLE 3-continued

Metabolic stability in human microsome

| Example number | Human Microsomal Clearance (mL/min/kg) | Example number | Human Microsomal Clearance (mL/min/kg) |
|---|---|---|---|
| 47 | 0 | 48 | 3.8 |
| 49 | 0 | 50 | 3.6 |
| 51 | 2.0 | 52 | 0.0 |
| 53 | 5.1 | 54 | 4.6 |
| 55 | 0.0 | 56 | 0.0 |
| 59 | 2.3 | 60 | 0.0 |
| 61 | 0.4 | 62 | 1.7 |
| 63 | 5.3 | 64 | 5.6 |
| 65 | 6.2 | 66 | 7.1 |
| 67 | 4.7 | 68 | 4.5 |
| 72 | 5.2 | 73 | 8.1 |
| 74 | 1.0 | 75 | 0.0 |
| 76 | 0.8 | 78 | 6.7 |
| 79 | 3.6 | 80 | 8.3 |
| 81 | 0.1 | 82A/82B | 1.7/2.7 |
| 83A/83B | 0.0/2.9 | 84A/84B | 0.0/3.6 |
| 85A/85B | 4.9/0 | 86B | 4.7 |
| 87B | 5.0 | 88B | 4.5 |
| 90A/90B | 0.3/0 | 91B | 5.8 |
| 99 | 6.1 | 101B | 6.1 |
| 102B | 6.2 | | |

Example 109

Lysa Solubility

Samples were prepared in duplicate from 10 mM DMSO stock solutions. After evaporation of DMSO with a centrifugal vacuum evaporator, the residue was solved in 0.05 M phosphate buffer (pH 6.5), stirred for one hour and shook for two hours. After one night, the solution was filtered using a microtiter filter plate. Then the filtrate and its 1/10 dilution were analyzed by direct UV measurement or by HPLC-UV. In addition a four-point calibration curve was prepared from the 10 mM stock solutions and used for the solubility determination of the compounds. The results were in µg/mL. In case the percentage of sample measured in solution after evaporation divided by the calculated maximum of sample amount was over 80%, the solubility was reported as higher than this value.

Results of Lysa are given in Table 4.

TABLE 4

Solubility data of particular compounds

| Example No. | Lysa (µg/mL) | Example No. | Lysa (µg/mL) |
|---|---|---|---|
| 19 | >727.0 | 20 | >780.0 |
| 21 | >786.0 | 28 | 337 |
| 30 | 610 | 31 | >775.0 |
| 32 | >701.0 | 33 | >748.0 |
| 34 | 326 | 35 | >754.0 |
| 36 | 485 | 37 | 422 |
| 38 | 627 | 39 | >770.0 |
| 41 | >804.0 | 42 | >785.0 |
| 44 | 207 | 45 | >690.0 |
| 46 | >744 | 47 | >767 |
| 48 | >807 | 49 | 312 |
| 50 | 339 | 51 | 589 |
| 53 | >723 | 54 | 387 |
| 55 | 470 | 56 | >740 |
| 59 | >685 | 60 | 436 |
| 61 | >742 | 62 | 374 |
| 63 | >751 | 64 | >669 |
| 65 | 194 | 67 | >794 |
| 68 | >794 | 71 | 232 |
| 72 | 551 | 73 | 564 |
| 74 | >716 | 75 | >774 |
| 76 | 565 | 78 | >793 |
| 79 | 180 | 80 | >616 |
| 81 | 279 | 82A/82B | >765/>760 |
| 83A/83B | >740/780 | 84A/84B | 570/770 |
| 85A/85B | >660/770 | 86B | >740 |
| 88B | >745 | 90A/90B | >730/>740 |
| 91B | >705 | 95 | 307 |
| 99 | >710 | 102B | >665 |

Example 110

Cytochrome P450 (Cyp450) Induction Screening Assay_mRNA Induction

Materials

Cell Culture

Human cryopreserved hepatocytes (Life Technologies, Carlsbad, USA) were thawed and cultured in collagen I coated 96-well plates with a density of 52,000 cells/well. After attachment, medium was changed and cells were pre-cultured overnight in hepatocyte maintenance medium (HMM; Lonza, Switzerland).

Test compounds were dosed to the cells next morning at an indicated concentration (up to 10 µM) in HMM culture media containing gentamycin and a constant 0.1% DMSO. Similarly, dilutions of the positive inducer compounds omeprazole (prototypical inducer of human CYP1A2; final concentrations: 1 and 10 µM), phenobarbital (prototypical inducer of human CYP2B6; final concentrations: 100 and 1000 µM) and rifampicin (prototypical inducer of human CYP3A4; final concentrations: 1 and 10 µM) were prepared from 1000 fold DMSO stock solutions in HMM containing gentamycin. Medium change was then performed and cells were exposed for 24 hours to test compounds, positive inducer compounds, or vehicle (0.1% DMSO), respectively.

At the end of the compound exposure period, medium was removed and cells lysed using 100 µL/well MagNA Pure LC RNA isolation tissue lysis buffer (Roche Diagnostics AG, Rotkreuz, Switzerland). Plates were then sealed and frozen at −80° C. until further workup.

mRNA Isolation, Processing and qRT-PCR mRNA isolation was performed using the MagNA Pure 96 system (Roche Diagnostics AG, Rotkreuz, Switzerland) and the respective cellular RNA large volume kit (Roche Diagnostics AG, Rotkreuz, Switzerland) from thawed samples diluted 1:1 with PBS. The volume of the cell lysis and an elution volume of 100 µL were used. 20 µL of the resulting mRNA suspension was then used for reverse transcription using 20 µL of the transcript or first stand cDNA synthesis kit (Roche prime Supply, Mannheim, Germany). The resulting cDNA was diluted with 40 µL of $H_2O$ before using for qRT-PCR. qRT-PCR was performed by using the forward and the reverse primer, the corresponding UPL (all from Microsynth, Balgach, Switzerland) and the Taqman Fast advanced master mix (Applied Biosystems), on an ABI 7900 machine (Applied Biosystems).

269

Calculations qRT-PCR Ct-values for the respective P450s were put into relation to the Ct-value of RN18S1 (microsynth, Balgach, Switzerland) of the same sample. Doing so, a respective Δct-value was calculated. Using the average of all Δct-values for the vehicle control samples, a ΔΔct-value was calculated for each sample (ΔΔct-value(sample)=Δct-value (sample)−average of Δct-value of all vehicle controls). The fold induction of the respective sample was calculated as 2^(−ΔΔct). The individual fold induction values were then averaged per treatment condition (usually n=3 biological replicates).

Relative induction values to the respective positive inducer compound condition (10 μM omeprazole for CYP1A2; 1000 μM Phenobarbital for CYP2B6; 10 μM rifampicin for CYP3A4) were then calculated from the fold induction values as follows:

Relative induction (%)=100×(T−V)/(P−V)

T: fold induction of test compound condition
P: fold induction of positive inducer compound
V: fold induction of vehicle controls Results of CYP3A4 induction are given in Table 5.

TABLE 5

Relative induction values of particular compounds to 10 μM rifampicin

| Example No. | % of Positive control (10 μM Rifampicin) |
|---|---|
| 11 | 17 |
| 19 | 1 |
| 21 | 2.4 |
| 22 | 0 |
| 25 | 0 |
| 27 | 0.2 |
| 30 | 7.3 |
| 34 | 0.2 |
| 36 | 6 |
| 38 | 0.2 |
| 42 | 0.6 |
| 43 | 0.2 |
| 45 | 20 |
| 54 | 0 |
| 55 | 0.1 |
| 59 | 2.2 |
| 62 | 0 |
| 73 | 0 |
| 76 | 1.3 |
| 82B | 6 |
| 86B | 11 |
| 87B | 4.0 |
| 88B | 3.7 |
| 91B | 1.7 |

270

The invention claimed is:
1. A compound of formula (I)

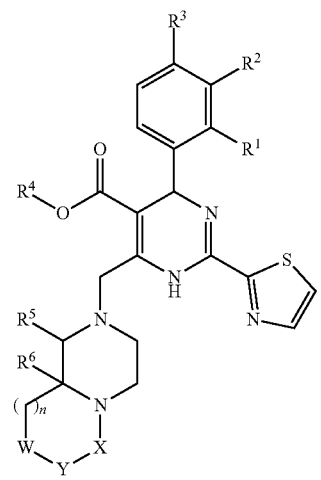

wherein
$R^1$ is hydrogen, halogen or $C_{1-6}$alkyl;
$R^2$ is hydrogen or halogen;
$R^3$ is hydrogen or halogen;
$R^4$ is $C_{1-6}$alkyl;
$R^5$ is hydrogen or carboxy;
$R^6$ is hydrogen, $C_{1-6}$alkoxycarbonyl or carboxy-$C_mH_{2m}$—;
X is carbonyl or sulfonyl;
Y is —$CH_2$—, —O— or —N($R^7$)—, wherein $R^7$ is hydrogen, $C_{1-6}$alkyl, $C_{3-7}$cycloalkyl, $C_{1-6}$alkoxycarbonyl-$C_mH_{2m}$—, —$C_mH_{2m}$—COOH, —($C_{1-6}$alkoxy)$C_{1-6}$alkyl-COOH, —$C_{1-6}$alkyl-O—$C_{1-6}$alkyl-COOH, —$C_{3-7}$cycloalkyl-$C_mH_{2m}$—COOH, —$C_mH_{2m}$—$C_{3-7}$cycloalkyl-COOH, hydroxy-$C_mH_{2m}$—, carboxyspiro[3.3]heptyl or carboxyphenyl-$C_mH_{2m}$—;
W is —$CH_2$—, —C($C_{1-6}$alkyl)$_2$-, —O— or carbonyl;
n is 0 or 1; and
m is 0-7;
or a pharmaceutically acceptable salts or enantiomer thereof.
2. A compound according to claim 1, wherein
$R^1$ is hydrogen, chloro, bromo or methyl;
$R^2$ is hydrogen or fluoro;
$R^3$ is hydrogen, chloro or fluoro;
$R^4$ is methyl or ethyl;
$R^5$ is hydrogen or carboxy;
$R^6$ is hydrogen, methyl-O-carbonyl or carboxymethyl;
X is carbonyl or sulfonyl;
Y is —$CH_2$—, —O—, —N($R^7$)—, wherein $R^7$ is hydrogen, methyl, isopropyl, t-butyl, cyclopropyl, methyl-O-carbonylisopropyl, carboxyethyl, carboxypropyl, carboxybutyl, carboxy(gemdimethyl)methyl, carboxy(gemdimethyl)ethyl, carboxy(gemdimethyl)propyl, carboxy(gemdimethyl)butyl, carboxy(methyl)ethyl, carboxy(ethyl)ethyl, carboxy(methoxy)ethyl, carboxycyclobutyl, carboxycyclobutylmethyl, carboxycyclopentyl, carboxycyclohexyl, carboxymethylcyclopropyl, carboxycyclopropylmethyl, carboxycyclobutylmethyl, carboxyspiro[3.3]heptyl, carboxymethoxyethyl, carboxymethoxypropyl, hydroxyethyl, hydroxymethyl(gemdimethyl)butyl, carboxyphenyl or carboxyphenylmethyl;

W is —CH$_2$—, —C(CH$_3$)$_2$—, —O— or carbonyl; and
n is 0 or 1;

or a pharmaceutically acceptable salt, or enantiomer thereof.

3. A compound of formula (IA) according to claim 1,

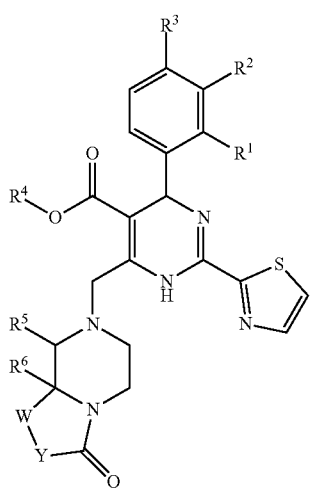

(IA)

wherein
R$^1$ is halogen or C$_{1-6}$alkyl;
R$^2$ is hydrogen or halogen;
R$^3$ is hydrogen or halogen;
R$^4$ is C$_{1-6}$alkyl;
R$^5$ is hydrogen or carboxy;
R$^6$ is hydrogen, C$_{1-6}$alkoxycarbonyl or carboxy-C$_m$H$_{2m}$—;
Y is —N(R$^7$)—, wherein R$^7$ is hydrogen, C$_{1-6}$alkyl, C$_{3-7}$cycloalkyl, C$_{1-6}$alkoxycarbonyl-C$_m$H$_{2m}$—, —C$_m$H$_{2m}$—COOH, —(C$_{1-6}$alkoxy)C$_{1-6}$alkyl-COOH, —C$_{1-6}$alkyl-O—C$_{1-6}$alkyl-COOH, —C$_{3-7}$cycloalkyl-C$_m$H$_{2m}$—COOH, —C$_m$H$_{2m}$—C$_{3-7}$cycloalkyl-COOH, hydroxy-C$_m$H$_{2m}$—, carboxyspiro[3.3]heptyl or carboxyphenyl-C$_m$H$_{2m}$—;
W is —CH$_2$— or carbonyl; and
m is 0-7;

or a pharmaceutically acceptable salt, or enantiomer thereof.

4. A compound according to claim 1, wherein
R$^1$ is chloro, bromo or methyl;
R$^2$ is hydrogen or fluoro;
R$^3$ is hydrogen, chloro or fluoro;
R$^4$ is methyl or ethyl;
R$^5$ is hydrogen or carboxy;
R$^6$ is hydrogen, methyl-O-carbonyl or carboxymethyl;
Y is —N(R$^7$)—, wherein R$^7$ is hydrogen, methyl, isopropyl, t-butyl, cyclopropyl, methyl-O-carbonylisopropyl, carboxyethyl, carboxypropyl, carboxybutyl, carboxy(gemdimethyl)methyl, carboxy(gemdimethyl)ethyl, carboxy(gemdimethyl)propyl, carboxy(gemdimethyl)butyl, carboxy(methyl)ethyl, carboxy(ethyl)ethyl, carboxy(methoxy)ethyl, carboxycyclobutyl, carboxycyclobutylmethyl, carboxycyclopentyl, carboxycyclohexyl, carboxymethylcyclopropyl, carboxycyclopropylmethyl, carboxycyclobutylmethyl, carboxyspiro[3.3]heptyl, carboxymethoxyethyl, carboxymethoxypropyl, hydroxyethyl, hydroxymethyl(gemdimethyl)butyl, carboxyphenyl or carboxyphenylmethyl; and
W is —CH$_2$— or carbonyl;

or a pharmaceutically acceptable salt or enantiomer thereof.

5. A compound of formula (IAA) according to claim 1,

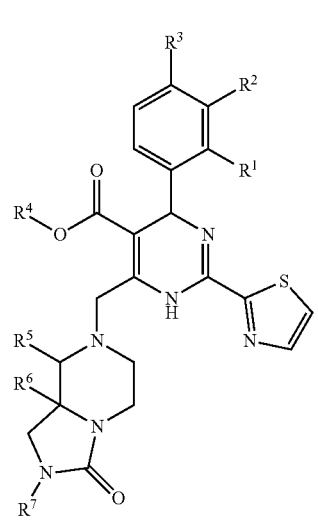

(IAA)

wherein
R$^1$ is halogen or C$_{1-6}$alkyl;
R$^2$ is hydrogen or halogen;
R$^3$ is hydrogen or halogen;
R$^4$ is C$_{1-6}$alkyl;
R$^5$ is hydrogen or carboxy;
R$^6$ is hydrogen;
R$^7$ is C$_{1-6}$alkyl, C$_{3-7}$cycloalkyl, —C$_m$H$_{2m}$—COOH, —C$_m$H$_{2m}$—C$_{3-7}$cycloalkyl-COOH or carboxyphenyl; and
m is 1-6;

or a pharmaceutically acceptable salt, or enantiomer thereof.

6. A compound according to claim 1, wherein
R$^1$ is chloro or methyl;
R$^2$ is hydrogen or fluoro;
R$^3$ is hydrogen or fluoro;
R$^4$ is methyl or ethyl;
R$^5$ is hydrogen or carboxy;
R$^6$ is hydrogen; and
R$^7$ is methyl, isopropyl, t-butyl, cyclopropyl, carboxy(gemdimethyl)ethyl, carboxy(gemdimethyl)propyl, carboxycyclopropylmethyl, carboxycyclobutylmethyl or carboxyphenyl;

or a pharmaceutically acceptable salt or enantiomer thereof.

7. A compound of formula (IB) according to claim 1,

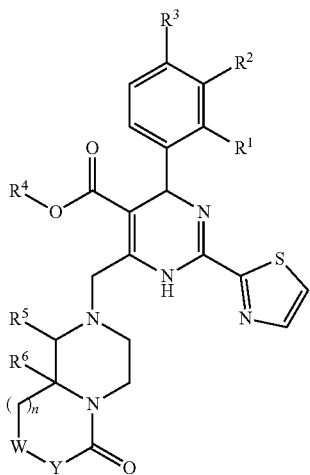

(IB)

wherein
R¹ is hydrogen or halogen;
R² is hydrogen or halogen;
R³ is hydrogen or halogen;
R⁴ is $C_{1-6}$alkyl;
R⁵ is hydrogen;
R⁶ is hydrogen or carboxymethyl;
Y is —CH₂— or —O—; W is —CH₂—, —C($C_{1-6}$alkyl)₂- or —O—;
n is 0 or 1;
or a pharmaceutically acceptable salt, or enantiomer thereof.

8. A compound according to claim 1, wherein
R¹ is hydrogen, chloro or bromo;
R² is hydrogen or fluoro;
R³ is hydrogen or fluoro;
R⁴ is methyl or ethyl;
R⁵ is hydrogen;
R⁶ is hydrogen or carboxymethyl;
Y is —CH₂— or —O—;
W is —CH₂—, —C(CH₃)₂— or —O—; and
n is 0 or 1;
or a pharmaceutically acceptable salt or enantiomer thereof.

9. A compound of formula (ID) according to claim 1,

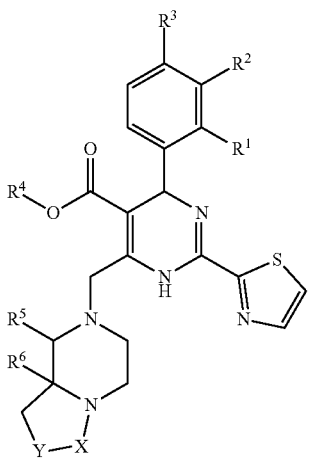

(ID)

wherein
R¹ is halogen or $C_{1-6}$alkyl;
R² is hydrogen or halogen;
R³ is hydrogen or halogen;
R⁴ is $C_{1-6}$alkyl;
R⁵ is hydrogen or carboxy;
R⁶ is hydrogen or $C_{1-6}$alkoxycarbonyl;
X is carbonyl;
Y is —O— or —N(R⁷)—, wherein R⁷ is hydrogen, $C_{1-6}$alkyl, $C_{3-7}$cycloalkyl, —$C_mH_{2m}$—COOH— $C_mH_{2m}$—$C_{3-7}$cycloalkyl-COOH, hydroxy-$C_mH_{2m}$—, carboxyspiro[3.3]heptyl or carboxyphenyl-$C_tH_{2t}$—;
m is 1-6; and
t is 0-6;
or a pharmaceutically acceptable salt, or enantiomer thereof.

10. A compound according to claim 1, wherein
R¹ is chloro, bromo or methyl;
R² is hydrogen or fluoro;
R³ is hydrogen or fluoro;
R⁴ is methyl or ethyl;
R⁵ is hydrogen or carboxy;
R⁶ is hydrogen or methyl-O-carbonyl;
X is carbonyl;
Y is —O—, —N(R⁷)—, wherein R⁷ is hydrogen, methyl, isopropyl, t-butyl, cyclopropyl, carboxy(gemdimethyl) ethyl, carboxy(methyl)ethyl, carboxycyclopropylmethyl, carboxyphenyl, carboxycyclopentyl, carboxycyclohexyl, carboxy(gemdimethyl)propyl, carboxy (gemdimethyl)butyl, carboxycyclobutylmethyl, carboxyspiro[3.3]heptyl, hydroxyethyl or carboxyphenylmethyl;
or a pharmaceutically acceptable salt or enantiomer thereof.

11. A compound of formula (IE) according to claim 1,

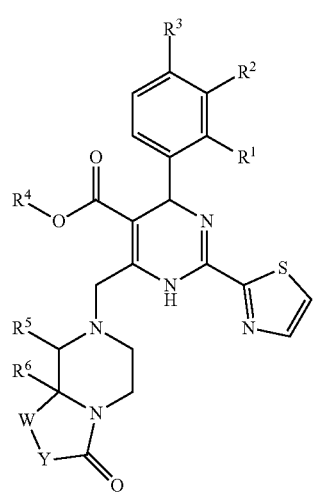

(IE)

wherein
R¹ is halogen or $C_{1-6}$alkyl;
R² is hydrogen or halogen;
R³ is hydrogen or halogen;
R⁴ is $C_{1-6}$alkyl;
R⁵ is hydrogen or carboxy;
R⁶ is hydrogen or carboxy-$C_mH_{2m}$—;
Y is —O— or —N(R⁷)—, wherein R⁷ is $C_{1-6}$alkyl, $C_{3-7}$cycloalkyl, —$C_mH_{2m}$—COOH, —$C_{3-7}$cycloalkyl-$C_mH_{2m}$—COOH, —$C_mH_{2m}$—$C_{3-7}$cycloalkyl-COOH, —(C$_{1-6}$alkoxy)C$_{1-6}$alkyl-COOH, —C$_{1-6}$alkyl-O—C$_{1-6}$alkyl-COOH, carboxyspiro[3.3]heptyl or carboxyphenyl-C$_m$H$_{2m}$—;
W is —CH$_2$— or —C(C$_{1-6}$alkyl)$_2$-; and
m is 0-6;
or a pharmaceutically acceptable salt, or enantiomer thereof.

12. A compound according to claim 1, wherein
R$^1$ is chloro or methyl;
R$^2$ is hydrogen or fluoro;
R$^3$ is hydrogen or fluoro;
R$^4$ is methyl or ethyl;
R$^5$ is hydrogen or carboxy;
R$^6$ is hydrogen or carboxymethyl;
Y is —O— or —N(R$^7$)—, wherein R$^7$ is isopropyl, methyl, t-butyl, cyclopropyl, carboxyethyl, carboxypropyl, carboxybutyl, carboxy(gemdimethyl)methyl, carboxy(gemdimethyl)ethyl, carboxy(methyl)ethyl, carboxycyclobutyl, carboxycyclopropylmethyl, carboxycyclopentyl, carboxycyclohexyl, carboxymethylcyclopropyl, carboxy(gemdimethyl)propyl, carboxy(ethyl)ethyl, carboxy(methoxy)ethyl, carboxycyclobutylmethyl, carboxyspiro[3.3]heptyl, carboxymethoxyethyl, carboxymethoxypropyl, carboxyphenylmethyl or carboxyphenyl;
W is —CH$_2$— or —C(CH$_3$)$_2$—;
or a pharmaceutically acceptable salt, or enantiomer thereof.

13. A compound of formula (IE) according to claim 1,

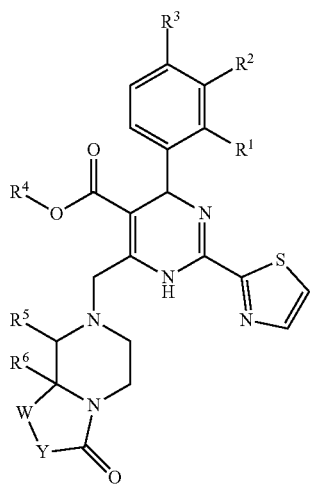

(IE)

wherein
R$^1$ is halogen or C$_{1-6}$alkyl;
R$^2$ is hydrogen or halogen;
R$^3$ is hydrogen or halogen;
R$^4$ is C$_{1-6}$alkyl;
R$^5$ is hydrogen or carboxy;
R$^6$ is hydrogen or carboxy-C$_m$H$_{2m}$—;
Y is —N(R$^7$)—, wherein R$^7$ is hydrogen, C$_{1-6}$alkyl, C$_{3-7}$cycloalkyl, —C$_m$H$_{2m}$—COOH, —C$_m$H$_{2m}$—C$_{3-7}$cycloalkyl-COOH or carboxyphenyl; and
m is 1-6;
or a pharmaceutically acceptable salt, or enantiomer thereof.

14. A compound according to claim 1, wherein
R$^1$ is chloro or methyl;
R$^2$ is hydrogen or fluoro;
R$^3$ is hydrogen or fluoro;
R$^4$ is methyl or ethyl;
R$^5$ is hydrogen or carboxy;
R$^6$ is hydrogen or carboxymethyl; and
Y is —N(R$^7$)—, wherein R$^7$ is hydrogen, methyl, t-butyl, cyclopropyl, carboxy(gemdimethyl)ethyl, carboxy(gemdimethyl)propyl, carboxy(methyl)ethyl, carboxycyclopropylmethyl, carboxycyclobutylmethyl or carboxyphenyl;
or a pharmaceutically acceptable salt or enantiomer thereof.

15. A compound that is 3-[(8aS)-3-oxo-1,5,6,7,8,8a-hexahydroimidazo[1,5-a]pyrazin-2-yl]-2,2-dimethyl-propanoic acid, or a pharmaceutically acceptable salt thereof.

16. A compound that is hexahydro-1-thia-2,5,7a-triazaindene 1,1-dioxide, or a pharmaceutically acceptable salt thereof.

17. A compound that is methyl 3-oxo-1,2,5,6,7,8-hexahydroimidazo[1,5-a]pyrazine-8a-carboxylate, or a pharmaceutically acceptable salt thereof.

18. A process for the preparation of a compound of claim 1, or a pharmaceutically acceptable salt thereof, comprising the reaction of:
(a) a compound of formula (A)

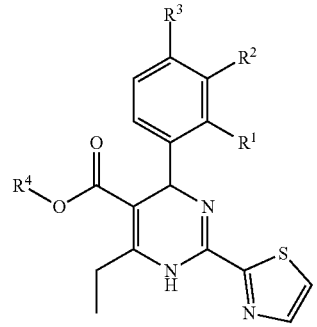

with

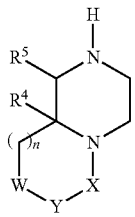

in the presence of a base.

19. A pharmaceutical composition comprising a compound according to claim 1, or a pharmaceutically acceptable salt thereof, and a therapeutically inert carrier.

20. A compound of claim 1, or a pharmaceutically acceptable salt thereof, when manufactured according to a process of claim 18.

21. A method for the treatment or prophylaxis of hepatitis B virus infection, which method comprises administering an effective amount of a compound according to claim 1, or a pharmaceutically acceptable salt thereof.

* * * * *